(12) United States Patent  
Frydman et al.

(10) Patent No.: US 7,279,502 B2  
(45) Date of Patent: Oct. 9, 2007

(54) POLYAMINE ANALOG CONJUGATES AND QUINONE CONJUGATES AS THERAPIES FOR CANCERS AND PROSTATE DISEASES

(75) Inventors: Benjamin Frydman, deceased, late of Madison, WI (US); by Linda Clifford, legal representative, Madison, WI (US); Laurence J. Marton, Palo Alto, CA (US)

(73) Assignee: Cellgate, Inc., Redwood City, CA (US)

( * ) Notice: Subject to any disclaimer, the term of this patent is extended or adjusted under 35 U.S.C. 154(b) by 0 days.

(21) Appl. No.: 10/970,089

(22) Filed: Oct. 20, 2004

(65) Prior Publication Data

US 2005/0233943 A1 Oct. 20, 2005

Related U.S. Application Data

(63) Continuation of application No. 10/385,224, filed on Mar. 10, 2003, now abandoned, which is a continuation of application No. 09/561,172, filed on Apr. 27, 2000, now Pat. No. 6,649,587.

(60) Provisional application No. 60/131,809, filed on Apr. 30, 1999.

(51) Int. Cl.
*A61K 31/131* (2006.01)
*A61K 31/132* (2006.01)
*C07K 211/13* (2006.01)
*C07K 211/17* (2006.01)

(52) U.S. Cl. ............... 514/659; 514/674; 564/455; 564/512

(58) Field of Classification Search ............ None
See application file for complete search history.

(56) References Cited

U.S. PATENT DOCUMENTS

| | | | |
|---|---|---|---|
| 2,440,724 A | 5/1948 | Morey et al. | |
| 3,956,502 A | 5/1976 | Slovinsky et al. | |
| 4,013,507 A | 3/1977 | Rembaum | |
| 4,035,174 A | 7/1977 | Grier et al. | 504/158 |
| 4,092,432 A | 5/1978 | Björklund et al. | 514/634 |
| 4,153,567 A | 5/1979 | Kluger et al. | 508/293 |
| 4,273,706 A | 6/1981 | Chapman et al. | 534/648 |
| 4,491,651 A | 1/1985 | Naiman | 525/187 |
| 4,537,601 A | 8/1985 | Naiman | 44/346 |
| 4,551,550 A | 11/1985 | Bey | |
| 4,577,636 A | 3/1986 | Spears | 424/1.53 |
| 4,590,288 A | 5/1986 | Klemann | 556/112 |
| 4,642,344 A | 2/1987 | Hajek et al. | 544/196 |
| 4,661,509 A | 4/1987 | Gordon et al. | |
| 4,698,446 A | 10/1987 | Lai et al. | 564/494 |
| 4,767,611 A | 8/1988 | Gordon | 424/932 |
| 4,849,207 A | 7/1989 | Sakata et al. | 424/1.65 |
| 4,868,219 A | 9/1989 | Thornfeldt | |
| 4,889,851 A | 12/1989 | Oku et al. | |
| 4,898,870 A | 2/1990 | Narutomi et al. | 514/292 |
| 4,935,449 A | 6/1990 | Bey et al. | 514/671 |
| 4,959,356 A | 9/1990 | Miura et al. | 424/1.81 |
| 4,963,565 A | 10/1990 | Gangadharam | 514/311 |
| 4,971,598 A | 11/1990 | Andress et al. | |
| 4,996,312 A | 2/1991 | Sakata et al. | 540/145 |
| 5,007,437 A | 4/1991 | Sterzer | 607/138 |
| 5,021,409 A | 6/1991 | Murrer et al. | 514/183 |
| 5,021,571 A | 6/1991 | Mease et al. | 544/166 |
| 5,080,998 A | 1/1992 | Irving et al. | 430/169 |
| 5,091,576 A | 2/1992 | Bergeron | |
| 5,120,843 A | 6/1992 | McCall et al. | 544/123 |
| 5,132,425 A | 7/1992 | Sotoya et al. | |
| 5,185,369 A | 2/1993 | Saccomano et al. | |
| 5,210,239 A | 5/1993 | Abe et al. | 552/307 |
| 5,217,964 A | 6/1993 | Edwards et al. | 514/104 |
| 5,242,684 A | 9/1993 | Merianos | |
| 5,283,367 A | 2/1994 | Babiarz et al. | |
| 5,284,647 A | 2/1994 | Niedballa et al. | 424/9.362 |
| 5,344,435 A | 9/1994 | Turner et al. | 607/101 |
| 5,354,782 A | 10/1994 | Edwards et al. | 514/655 |
| 5,354,858 A | 10/1994 | Morgan et al. | 540/145 |
| 5,374,658 A | 12/1994 | Lau | 514/557 |
| 5,385,942 A | 1/1995 | Abe et al. | 514/568 |
| 5,393,757 A | 2/1995 | Bergeron, Jr. et al. | |
| 5,401,443 A | 3/1995 | Nagano et al. | 264/4.7 |

(Continued)

FOREIGN PATENT DOCUMENTS

| | | |
|---|---|---|
| CA | 2321200 A1 | 9/1999 |
| CS | 252 771 B1 | 4/1989 |
| DE | 1 295 826 | 5/1969 |
| EP | 0 186 473 A2 | 7/1986 |
| EP | 0 186 473 A3 | 7/1986 |
| EP | 0 723 772 A1 | 7/1996 |

(Continued)

OTHER PUBLICATIONS

Akgun, N. et al. (1996). "Phototoxicity, Darktoxicity and Uptake Kinetics of Natural Hydrophilic and Hydrophobic Phorphyrins in Endothelial Cells," *Proc. SPIE-Int. Soc. Opt. Eng.* 2625:488-498.

Alfonso, I. et al. (1996). "Sequential Biocatalytic Resolution of (+)-trans-cyclohexane-1,2-diamine. Chemoenzymic Synthesis of an Optically Active Polyamine," *Chem. Commun.* 21:2471-2472.

Allolio, B. et al. (1989). "Treatment of Metastasizing Adrenal Carcinoma with Suramin," *Dtsch. Med. Woschenschr* 114(10):381-384. (In German; first page of document has English abstract).

(Continued)

*Primary Examiner*—Jeffrey Edwin Russel
(74) *Attorney, Agent, or Firm*—Morrison & Foerster LLP

(57) ABSTRACT

Peptide conjugates in which cytocidal and cytostatic agents, such as polyamine analogs or naphthoquinones, are conjugated to a polypeptide recognized and cleaved by enzymes such as prostate-specific antigen (PSA) and cathepsin B are provided, as well as compositions comprising these conjugates. Methods of using these conjugates in the treatment of prostate diseases are also provided.

6 Claims, 67 Drawing Sheets

U.S. PATENT DOCUMENTS

| | | | |
|---|---|---|---|
| 5,413,719 A | 5/1995 | Sivakumar et al. | 210/708 |
| 5,424,305 A | 6/1995 | Skalkos et al. | 514/185 |
| 5,434,145 A | 7/1995 | Edwards et al. | 514/108 |
| 5,498,522 A | 3/1996 | Porter | 435/6 |
| 5,512,559 A | 4/1996 | Skalkos et al. | 514/185 |
| 5,512,597 A | 4/1996 | Kyba et al. | |
| 5,516,807 A | 5/1996 | Hupe et al. | 514/673 |
| 5,530,092 A | 6/1996 | Meijer et al. | |
| 5,541,230 A | 7/1996 | Basu et al. | 514/642 |
| 5,563,262 A | 10/1996 | Morgan et al. | 540/145 |
| 5,587,394 A | 12/1996 | Morgan et al. | 514/185 |
| H1633 H | 2/1997 | Hiebert et al. | 528/373 |
| 5,599,686 A | 2/1997 | DeFeo-Jones et al. | 435/23 |
| 5,599,847 A | 2/1997 | Robins et al. | |
| 5,606,053 A | 2/1997 | Prashad et al. | 540/474 |
| 5,607,574 A | 3/1997 | Hart | 208/188 |
| 5,608,061 A | 3/1997 | Ciszewski et al. | 540/474 |
| 5,612,478 A | 3/1997 | Xu et al. | 540/474 |
| 5,627,215 A | 5/1997 | Frei et al. | 514/674 |
| 5,641,773 A | 6/1997 | Pardee et al. | 514/221 |
| 5,646,188 A | 7/1997 | Gilad et al. | 514/634 |
| 5,650,099 A | 7/1997 | Akhavan-Tafti et al. | |
| 5,654,287 A | 8/1997 | Prakash et al. | 514/49 |
| 5,654,484 A | 8/1997 | Prakash et al. | |
| 5,672,202 A | 9/1997 | Stirling et al. | 106/496 |
| 5,674,900 A | 10/1997 | Ubillas et al. | 514/557 |
| 5,677,349 A | 10/1997 | Gilad et al. | 514/634 |
| 5,677,350 A | 10/1997 | Frydman | 514/655 |
| 5,677,351 A | 10/1997 | Bergeron, Jr. | |
| 5,681,837 A | 10/1997 | Bergeron | 514/256 |
| 5,693,632 A | 12/1997 | Morgan et al. | 514/185 |
| 5,698,662 A | 12/1997 | Stoelwinder et al. | |
| 5,707,532 A | 1/1998 | Guerro et al. | 210/727 |
| 5,710,153 A | 1/1998 | Ohmoto et al. | |
| 5,719,193 A | 2/1998 | Bowlin et al. | |
| 5,736,297 A | 4/1998 | Roeschert et al. | |
| 5,744,453 A | 4/1998 | Mintz et al. | 514/26 |
| 5,750,788 A | 5/1998 | Haussling et al. | |
| 5,763,388 A | 6/1998 | Lightsey et al. | 523/212 |
| 5,763,625 A | 6/1998 | Boothman et al. | 549/390 |
| 5,776,458 A | 7/1998 | Angelucci et al. | 424/178.1 |
| 5,780,514 A | 7/1998 | Gutteridge et al. | 514/682 |
| 5,783,598 A | 7/1998 | Boyd et al. | 514/454 |
| 5,824,700 A | 10/1998 | Frydman et al. | 514/454 |
| 5,824,812 A | 10/1998 | Nantz et al. | |
| 5,843,865 A | 12/1998 | Del Corral et al. | |
| 5,843,959 A | 12/1998 | Bergeron, Jr. | 514/316 |
| 5,847,190 A | 12/1998 | Paulus et al. | |
| 5,849,259 A | 12/1998 | Hilger et al. | 424/1.65 |
| 5,866,016 A | 2/1999 | Jaquess et al. | |
| 5,866,679 A | 2/1999 | DeFeo-Jones et al. | 530/322 |
| 5,869,522 A | 2/1999 | Boyd et al. | 514/456 |
| 5,877,165 A | 3/1999 | Miura et al. | 514/64 |
| 5,880,161 A | 3/1999 | Basu et al. | 514/642 |
| 5,883,270 A | 3/1999 | Frydman et al. | 552/292 |
| 5,886,050 A | 3/1999 | Bergeron, Jr. | |
| 5,886,051 A | 3/1999 | Bergeron, Jr. et al. | |
| 5,886,173 A | 3/1999 | Hemmi et al. | 540/472 |
| 5,889,061 A | 3/1999 | Frydman et al. | 514/674 |
| 5,906,996 A | 5/1999 | Murphy | |
| 5,912,241 A | 6/1999 | Gottlieb et al. | 424/529 |
| 5,932,201 A | 8/1999 | de Labbey et al. | |
| 5,958,397 A | 9/1999 | Smerbeck et al. | |
| 5,962,533 A | 10/1999 | Bergeron, Jr. | 514/674 |
| 5,969,163 A | 10/1999 | Frydman et al. | 514/389 |
| 5,977,187 A | 11/1999 | Frydman et al. | 514/717 |
| 5,985,331 A | 11/1999 | Gottlieb et al. | 424/529 |
| 5,998,362 A | 12/1999 | Feng et al. | 514/2 |
| 6,001,573 A | 12/1999 | Roelant | 435/6 |
| 6,025,351 A | 2/2000 | Morgan et al. | 514/185 |
| 6,034,129 A | 3/2000 | Mandeville, III et al. | |
| 6,046,282 A | 4/2000 | Starner et al. | |
| 6,051,611 A | 4/2000 | Kyba et al. | |
| 6,066,628 A | 5/2000 | Stojiljkovic et al. | 514/185 |
| 6,068,835 A | 5/2000 | Franzke et al. | |
| 6,083,479 A | 7/2000 | Platzek et al. | 424/1.65 |
| 6,100,430 A | 8/2000 | Yamamoto et al. | 564/455 |
| 6,103,666 A | 8/2000 | Del Corral et al. | |
| 6,130,204 A | 10/2000 | DeFeo-Jones et al. | 514/16 |
| 6,143,864 A | 11/2000 | DeFeo-Jones et al. | 530/322 |
| 6,174,858 B1 | 1/2001 | Brady et al. | 514/12 |
| 6,177,561 B1 | 1/2001 | Sinn et al. | 540/145 |
| 6,184,232 B1 | 2/2001 | Bergeron, Jr. | |
| 6,235,794 B1 | 5/2001 | Bergeron, Jr. | |
| 6,265,540 B1 | 7/2001 | Isaacs et al. | 530/326 |
| 6,274,630 B1 | 8/2001 | Bergeron, Jr. | |
| 6,307,102 B1 | 10/2001 | Tokumoto et al. | |
| 6,319,956 B1 | 11/2001 | Iwata | |
| 6,342,534 B1 | 1/2002 | Bergeron, Jr. | |
| 6,384,097 B1 | 5/2002 | Tokumoto et al. | |
| 6,384,177 B1 | 5/2002 | Tokumoto et al. | |
| 6,399,662 B1 | 6/2002 | Bergeron | |
| 6,444,707 B1 | 9/2002 | Lampe et al. | |
| 6,528,048 B1 | 3/2003 | Koike et al. | |
| 6,531,512 B1 | 3/2003 | Kramer et al. | |
| 6,605,645 B2 | 8/2003 | Iwata | |
| 6,641,655 B1 | 11/2003 | McElhinney et al. | |
| 6,649,587 B1* | 11/2003 | Frydman et al. | 514/2 |
| 6,664,270 B2 | 12/2003 | Bergeron, Jr. | |
| 6,673,890 B1 | 1/2004 | Boeckh et al. | |
| RE38,417 E | 2/2004 | Bergeron, Jr. | |
| 6,706,922 B2 | 3/2004 | Wolff et al. | |
| 2002/0004031 A1 | 1/2002 | Dinkelborg et al. | 424/1.69 |
| 2002/0045780 A1 | 4/2002 | Bergeron, Jr. | |
| 2002/0061287 A1 | 5/2002 | Wolff et al. | |
| 2002/0061926 A1 | 5/2002 | Phillips | |
| 2002/0094990 A1 | 7/2002 | Bergerson | |
| 2002/0143068 A1 | 10/2002 | Bergeron, Jr. | |
| 2003/0045674 A1 | 3/2003 | Higley | |
| 2003/0055113 A1 | 3/2003 | Wang et al. | |
| 2003/0100615 A1 | 5/2003 | Bergeron, Jr. | |
| 2003/0130356 A1 | 7/2003 | Frydman et al. | |
| 2003/0130534 A1 | 7/2003 | Golden | |
| 2003/0143713 A1 | 7/2003 | Aghajari et al. | |
| 2003/0158262 A1 | 8/2003 | Ramesh et al. | |
| 2003/0185778 A1 | 10/2003 | Fahl et al. | |
| 2003/0232799 A1 | 12/2003 | Wang et al. | |
| 2004/0006049 A1 | 1/2004 | Frydman et al. | |
| 2004/0006055 A1 | 1/2004 | Winchell | |
| 2004/0019043 A1 | 1/2004 | Coucouvanis et al. | |
| 2004/0019087 A1 | 1/2004 | Ternansky et al. | |
| 2004/0039057 A1 | 2/2004 | Perlmutter et al. | |
| 2004/0047844 A1 | 3/2004 | Shepard | |
| 2004/0133013 A1 | 7/2004 | Frydman et al. | |
| 2005/0080144 A1 | 4/2005 | Frydman et al. | |

FOREIGN PATENT DOCUMENTS

| | | |
|---|---|---|
| EP | 0 723 772 B1 | 7/1996 |
| EP | 0 255 679 A2 | 2/1998 |
| EP | 0 255 679 A3 | 2/1998 |
| EP | 0 255 679 B1 | 2/1998 |
| EP | 0 889 112 A1 | 1/1999 |
| JP | 45-30077 | 9/1970 |
| JP | 05-032902 | 2/1993 |
| JP | 7-228589 A | 8/1995 |
| JP | 07-277964 A | 10/1995 |
| JP | 09-235280 A | 9/1997 |
| JP | 2000-026320 A | 1/2000 |
| JP | 2001-0131449 A | 5/2001 |
| WO | 93/04036 A1 | 3/1993 |
| WO | 94/07480 A1 | 4/1994 |
| WO | WO94/07894 | 4/1994 |
| WO | WO94/08578 A2 | 4/1994 |

| | | | |
|---|---|---|---|
| WO | WO95/18091 A1 | 7/1995 |
| WO | 95/20580 A1 | 8/1995 |
| WO | WO96/22962 A1 | 8/1996 |
| WO | WO96/33988 A1 | 10/1996 |
| WO | 96/38528 A1 | 12/1996 |
| WO | WO96/40096 A1 | 12/1996 |
| WO | WO97/02027 A1 | 1/1997 |
| WO | WO97/02030 A1 | 1/1997 |
| WO | 97/07674 A1 | 3/1997 |
| WO | WO97/08162 A1 | 3/1997 |
| WO | WO97/29199 A2 | 8/1997 |
| WO | WO97/29199 A3 | 8/1997 |
| WO | WO97/30022 A1 | 8/1997 |
| WO | WO97/31611 A2 | 9/1997 |
| WO | WO97/31611 A3 | 9/1997 |
| WO | WO97/31936 A2 | 9/1997 |
| WO | WO97/31936 A3 | 9/1997 |
| WO | WO-98/10651 A1 | 3/1998 |
| WO | 98/14190 A1 | 4/1998 |
| WO | WO98/17624 A1 | 4/1998 |
| WO | WO98/25884 A1 | 6/1998 |
| WO | WO98/25885 A1 | 6/1998 |
| WO | WO98/32729 A1 | 7/1998 |
| WO | WO98/33503 | 8/1998 |
| WO | WO98/37057 | 8/1998 |
| WO | 98/51660 A1 | 11/1998 |
| WO | WO98/52966 A1 | 11/1998 |
| WO | WO-98/56425 A1 | 12/1998 |
| WO | WO99/13920 | 3/1999 |
| WO | 99/17802 A1 | 4/1999 |
| WO | WO99/16474 | 4/1999 |
| WO | WO99/16757 | 4/1999 |
| WO | WO99/21542 A2 | 5/1999 |
| WO | WO99/21542 A3 | 5/1999 |
| WO | 99/43752 A1 | 9/1999 |
| WO | WO99/54283 A1 | 10/1999 |
| WO | WO99/62512 | 12/1999 |
| WO | WO 00/01419 A1 | 1/2000 |
| WO | 00/09634 A1 | 2/2000 |
| WO | WO 00/05235 | 2/2000 |
| WO | WO 00/17205 | 3/2000 |
| WO | WO 00/18439 | 4/2000 |
| WO | 00/66175 A2 | 11/2000 |
| WO | 00/66175 A3 | 11/2000 |
| WO | WO 00/66528 A2 | 11/2000 |
| WO | WO 00/66528 A3 | 11/2000 |
| WO | WO 00/66587 A2 | 11/2000 |
| WO | WO 00/66587 A3 | 11/2000 |
| WO | 01/64779 A2 | 9/2001 |
| WO | 01/64779 A3 | 9/2001 |
| WO | 01/79329 A1 | 10/2001 |
| WO | 02/22584 A1 | 3/2002 |
| WO | 02/38105 A2 | 5/2002 |
| WO | 02/38105 A3 | 5/2002 |
| WO | 02/062341 A1 | 8/2002 |
| WO | 02/091989 A2 | 11/2002 |
| WO | 02/091989 A3 | 11/2002 |
| WO | 03/033455 A1 | 4/2003 |

OTHER PUBLICATIONS

Ashraf, W. et al. (1994). "Comparative Effects of Intraduodenal Psyllium and Senna on Canine Small Bowel Motility," *Aliment. Pharmacol. Ther.* 8:329-336.

Bachrach, U. et al. (1971). "Antivirus Action of Acrolein, Glutaraldehyde and Oxidized Spermine" *J. Gen. Virol.* 13:415-422.

Bachrach, U. and Don, R. (1971). "Inactivation of Myxoviruses by Oxidized Polyamines" *J. Gen. Virol.* 11:1-9.

Bachrach, U. and Rosenkovitch, E. (Feb. 1972). "Effect of Oxidized Spermine and Other Aldehydes on the Infectivity of Vaccinia Virus" *Appl. Microbiol.* 23(2):232-235.

Baez et al. (1997). "Glutathione Transferases Catalyse the Detoxication of Oxidized Metabolites (o-Quinones) of Catecholamines and May Serve as an Antioxidant System Preventing Degenerative Cellular Processes," *Biochem. J.* 324:25-28.

Bailey, S.M. et al. (1997). "Involvement of DT-Diaphorase (EC 1.6.99.2). in the DNA Cross-Linking and Sequence Selectivity of the Bioreductive Anti-Tumour Agent EO9," *Br. J. Cancer* 76(12):1596-1603.

Basu, H.S. et al. (1990). "Effects of Variation in the Structure of Spermine on the Association with DNA and the Induction of DNA Conformational Changes" *Biochem. J.* 269:329-334.

Begleiter, A. et al. (1997). "Induction of DT-Diaphorase in Cancer Chemoprevention and Chemotherapy," *Oncol. Res.* 9:371-382.

Behe, M. and Felsenfeld, G. (Mar. 1981). "Effects of Methylation on a Synthetic Polynucleotide: the B --- Z Transition in Poly(dG-m$^5$dC).Poly(dG-m$^5$dC)," *Proc. Natl. Acad. Sci. USA* 78(3):1619-1623.

Berchtold, C.M. et al. (1998). "Inhibition of Cell Growth in CaCO2 Cells by Polyamine Analogue N$^1$,N$^{12}$-bis(ethyl)Spermine is Preceded by a Reduction in MYC Oncoprotein Levels," *J. Cell. Physiol.* 174:380-386.

Bernacki, R.J. et al. (May 1, 1992). "Antitumor Activity of N,N'-Bis(Ethyl)Spermine Homologues Against Human MALME-3 Melanoma Xenografts," *Cancer Res.* 52:2424-2430.

Blokhin, Andrei V. et al., "Novel Quinones As Disease Therapies", U.S. Appl. No. 10/139,978, filed May 6, 2002.

Bloomfield, V.A. and Wilson, R.W. (1981). "Interactions of Polyamines with Polynucleotides," Chapter 10 in *Polyamines in Biology and Medicine*. Morris, D.R. and Marton, L.J., eds., Marcel Dekker, New York, pp. 183-206.

Boveris, A. et al. (1978). "Superoxide Anion Production and Trypanocidal Action of Naphthoquinones on Trypanosoma Cruzi," *Comp. Biochem. Physiol.* 61C:327-329.

Bressoud, D., et al. (1992). "Dark Induction of Haem Oxygenase Messenger RNA by Haematoporphyrin Derivative and Zinc Phthalocyanine; Agents for Photodynamic Therapy," *J. Photochem. Photobiol. B: Biol.* 14:311-318.

Broder, S. et al. (Sep. 21, 1985). "Effects of Suramin on HTLV-III/LAV Infection Presenting as Kaposi's Sarcoma or AIDS-Related Complex: Clinical Pharmacology and Suppression of Virus Replication In Vivo," *Lancet* 2:627-630.

Bullock, F.J. et al. (Jan. 1970). "Antiprotozoal Quinones. II. Synthesis of 4-amino-1,2-naphthoquinones and Related Compounds as Potential Antimalarials," *J. Med. Chem.* 13:97-103.

Byers, T.L. and Pegg, A.E. (1990). "Regulation of Polyamine Transport in Chinese Hamster Ovary Cells," *J. Cellular Physiol.* 143:460-467.

Chang, B.K. et al. (1992). "Antitumor Effects of N-Alkylated Polyamine Analogues in Human Pancreatic Adenocarcinoma Models," *Cancer Chemother. Pharmacol.* 30:179-182.

Chang, B.K. et al. (1992). "Regulatory and Antiproliferative Effects of N-Alkylated Polyamine Analogues in Human and Hamster Pancreatic Adenocarcinoma Cell Lines," *Cancer Chemother. Pharmacol.* 30:183-188.

Chang, B.K. et al. (Oct. 1993). "Effects of Diethyl Spermine Analogues in Human Bladder Cancer Cell Lines in Culture," *J. Urol.* 150:1293-1297.

Christensson, A. et al. (1990). "Enzymatic Activity of Prostate-Specific Antigen and its Reactions with Extracellular Serine Proteinase Inhibitors," *Eur. J. Biochem.* 194:755-763.

Chung, J. et al. (1996). "Acceleration of the Alcohol Oxidation Rate in Rats with Aloin, a Quinone Derivative of Aloe," *Biochem. Pharmacol.* 52:1461-1468.

Clarys, P. and Barel, A. (1998). "Efficacy of Topical Treatment of Pigmentation Skin Disorders with Plant Hydroquinone Glucosides as Assessed by Quantitative Color Analysis," *J. Dermatol.* 25:412-414.

Cortelli, P. et al. (1997). "Clinical and Brain Bioenergetics Improvement with Idebenone in a Patient with Leber's Hereditary Optic Neuropathology: A Clinical and $^{31}$P-MRS Study," *J. Neurol. Sci.* 148:25-31.

Cote, P. and Goodman, L. (1973). "Glucopyranosides Derived from 2-hydroxy-1,4-naphthoquinones," *Carbohyd. Res.* 26:247-251.

Creaven, P.J. et al. (1997). "Unusual Central Nervous System Toxicity in a Phase I Study of $N^1N^{11}$ Diethylnorspermine in Patients with Advanced Malignancy," *Invest. New Drugs* 15:227-234.

Davidson, N.E. et al. (May 1, 1993). "Growth Inhibition of Hormone-Responsive and -Resistant Human Breast Cancer Cells in Culture by $N^1$, $N^{12}$-Bis(Ethyl)Spermine," *Cancer Res.* 53:2071-2075.

De Groot, F.M.H. et al. (1999). "Synthesis and Biological Evaluation of Novel Prodrugs of Anthracyclines for Selective Activation by the Tumor-Associated Protease Plasmin," *J. Med. Chem.* 42(25):5277-5283.

DeFeo-Jones, D. et al. (Nov. 2000). "A Peptide-Doxorubicin 'Prodrug' Activated by Prostate-Specific Antigen Selectively Kills Prostate Tumor Cells Positive for Prostate-Specific Antigen In Vivo," *Nat. Med.* 6(11):1248-1252.

Dekant, W. (1993). "Bioactivation of Nephrotoxins and Renal Carcinogens by Glutathione S-Conjugate Formation," *Toxicol. Lett.* 67:151-160.

Denmeade S.R. et al. (Mar. 2000). "Enzymatic Activation of a Thapsigargin Prodrug by Prostate Specific Antigent (PSA) as Treatmnent for Metastic Prostate Cancer," *Proceedings of the American Association for Cancer Research 91st Annual Meeting*(Apr. 1-5, 2000) 41:46 (Abstract #292).

Denmeade S.R. et al. (May 1998). "Enzymatic Activation of Prodrugs by Prostate-Specific Antigen: Targeted Therapy for Metastatic Prostate Cancer," *Cancer Journal From Scientific American* 4(Suppl.1):S15-S21.

Denmeade, S.R. et al. (Nov. 1997). "Specific and Efficient Peptide Substrates for Assaying the Proteolytic Activity of Prostate-specific Antigen," *Cancer Res.* 57:4924-4930.

Denmeade, S.R. et al. (Jun. 15, 1998). "Enzymatic Activation of a Doxorubicin-Peptide Prodrug by Prostate-Specific Antigen," *Cancer Res.* 58:2537-2540.

Dolan, M.E. et al. (1998). "Effects of 1,2-naphthoquinones on Human Tumor Cell Growth and Lack of Cross-Resistance with Other Anticancer Agents," *Anticancer Drugs* 9:437-448.

Driscoll et al. (Apr. 1974), "Structure Antitumor Activity Relationships Among Quinone Derivatives", Cancer Chemot. Reports 4(2):1-362.

Dubowchik, G.M. and Firestone, R.A. (1998). "Cathepsin B-Sensitive Dipeptide Prodrugs. 1. A Model Study of Structural Requirements for Efficient Release of Doxorubicin," *Bioorg. Med. Chem. Lett.* 8:3341-3346.

Dunn, W.J. III et al. (1980). "Structure-Activity Analyzed by Pattern Recognition: The Asymmetric Case," *J. Med. Chem.* 23(6): 595-599.

Dunzendorfer, U. (1985). "Polyamines, Polyamine Antimetabolites and Urogenital Tumors. State of Research and Clinical Results," *Urol. Int.* 40:241-250. (In German, first page of document has English abstract).

Eyer, P. (Oct. 1994). "Reactions of Oxidatively Activated Arylamines with Thiols: Reaction Mechanisms and Biologic Implications. An Overview," *Environ. Health Persp.* 102(Suppl. 6):123-132.

Fernández, C.O. et al. (1994). "Interactions Between Polyamine Analogs with Antiproliferative Effects and tRNA: a $^{15}$N NMR Analysis," *Cell Mol. Biol.* 40(7):933-944.

Feuerstein, B.G. et al. (1991). "Implications and Concepts of Polyamine-Nucleic Acid Interactions" *J. Cell. Biochem.* 46:37-47.

Fiedler, W.J. and Hesse, M. (1993). "Synthese Von Selektiv N-funktionalisierten Polyamin-Derivaten," *Helv. Chim. Acta* 76:1511-1519. (In German—first page of document has English abstract).

Fischer, H.A. (1975. "Synthesis of $^3$H-Spermine," *J. Labelled Compd.* 11(1):141-143. (In German—Chemical Abstracts "CAPlus" record attached).

Fowler, L.M. et al. (1991). "Nephrotoxicity of 4-Aminophenol Glutathione Conjugate," *Hum. Exp. Toxicol.* 10:451-459.

Freitas, I. and Novarina, A. (1987). "Dark Effects of Hematoporphyrin Derivative on Lactate Dehydrogenase Activity and Distribution in HeLa Cells: Cytochemical Evaluation," *Photochemistry and Photobiology* 46(5):699-706.

Freitas, I. et al. (1988). "Dark Effects of Porphyrins on the Activity and Subcellular Distribution of Dehydrogenases in Yoshida Hepatoma Cells: Cytochemical Evaluations," *Medicine Biologie Environment* 16:97-109.

Frydman, B. and Valasinas, A. (1999). "Polyamine-Based Chemotherapy of Cancer," *Exp. Opin. Ther. Patents* 9(8): 1055-1068.

Frydman, B. et al. (Feb. 15, 1997). "Induction DNA Topoisomerase II-Mediated DNA Cleavage by Beta-Lapachone and Related Naphthoquinones," *Cancer Res.* 57:620-627.

Frydman, L. et al. (Oct. 1992). "Interactions Between Natural Polyamines and tRNA: an $^{15}$N NMR Analysis," *Proc. Natl. Acad. USA* 89:9186-9190.

Gantchev, T.G. and Hunting, D.J. (1997). "Inhibition of the Topoisomerase II-DNA Cleavable Complex by the Ortho-Quinone Derivative of the Antitumor Drug Etoposide (VP-16)," *Biochem. Biophys. Res. Comm.* 237(1):24-27.

Gosule, L.C. and Schellman, J.A. (1978). "DNA Condensation with Polyamines I. Spectroscopic Studies," *J. Mol. Biol.* 121:311-326.

Goto, M. et al. (Feb. 1969). "Stereochemical Studies of Metal Chelates. III. Preparation and Stereochemistry of Cobalt (III) Complexes with C-Substituted Triethylenetetramines at the Central Ethylenediamine Bridge," *Inorg. Chem.* 8(2):358-366.

Hafner, E.W. et al. (Dec. 25, 1979). "Mutants of *Escherichia coli* that do not Contain 1,4-Diaminobutane (Putrescine) or Spermidine," *J. Biol. Chem.* 254(24):12419-12426.

Herr, H.W. et al. (Mar. 15, 1984). "Potentiation of Methylglyoxal-Bis-Guanylhydrazone by Alpha-Difluoromethylornithine in Rat Prostate Cancer," *Cancer* 53(6):1294-1298.

Hinson, J.A. and Forkert, P. (1995). "Phase II Enzymes and Bioactivation," *Can. J. Physiol. Pharmacol.* 73:1407-1413.

Hondo, H. (1988). "Anti-Tumor Effect of Hyperthermia Plus Hematoporphyrin Derivative on Malignant Brain Tumor," *Brain and Nerve* 40(5):477-484. (BIOSIS English language abstract only).

Horn, Y. et al. (1987). "Phase I-II Clinical Trial with Alpha-Difluoromethylornithine—an Inhibitor of Polyamine Biosynthesis," *Eur. J. Cancer Clin. Oncol.* 23(8):1103-1107.

Horoszewicz, J.S. et al. (Apr. 1983). "LNCaP Model of Human Prostatic Carcinoma," *Cancer Res.* 43:1809-1818.

Igarashi, K. et al. (Oct. 30, 1990). "Spermine-Like Functions of $N^1$, $N^{12}$-Bis(Ethyl)Spermine: Stimulation of Protein Synthesis and Cell Growth and Inhibition of Gastric Ulceration," *Biochem. Biophys. Res. Commun.* 172(2):715-720.

Inouye, H. et al. (Feb. 1975). "Quinones and Related Compounds in Higher Plants. II. On the Naphthoquinones and Related Compounds from Catalpa Wood," *Chem. Pharm. Bull.* 23(2):384-391.

Iwata, M. and Kuzuhara, H. (1989). "Efficient Synthetic Method for Differentially Protected Naturally Occurring Acyclic Polyamines," *Bull. Chem. Soc. Japan* 62(4):1102-1106.

Jain, S. et al. (1989). "Base Only Binding of Spermine in the Deep Groove of the A-DNA Octamer d(GTGTACAC)," *Biochem.* 28(6):2360-2364.

James, D. A. et al. (1994). "Potency and Selective Toxicity of Tetra(Hydroxyphenyl)- and Tetrakis(dihydroxyphenyl)porphyrins in Human Melanoma Cells, With and Without Exposure to Red Light," *Photochemistry and Photobiology* 59(4):441-447.

Jänne, J. et al. (1978). "Polyamines in Rapid Growth and Cancer," *Biochim.Biophys. Acta.* 473:241-293.

Jeffers, L. et al. (1997). "Effects of the Polyamine Analogues BE-4-4-4-4, BE-3-7-3, and BE-3-3-3 on the Proliferation of Three Prostate Cancer Cell Lines," *Cancer Chem. Pharm.* 40:172-179.

Jeong, J.K. et al. (Sep. 1996). "Quinone Thioether-Mediated DNA Damage, Growth Arrest, and Gadd153 Expression in Renal Proximal Tubular Epithelial Cells," *Mol. Pharmacol.* 50(3):592-598.

Kanter, P.M. et al. (1994). "Preclinical Toxicologic Evaluation of DENSPM ($N^1$, $N^{11}$-diethylnorspermine) in Rats and Dogs," *Anticancer Drugs* 5:448-456.

Khanum, F. and Jain, V. (1989). "Effects of Hematoporphyrin Derivative on the Cellular Energy Metabolism in the Absence and Presence of Light," *Photochem. and Photobiol.* 50(5):647-648, 650-651.

Kobiro, K. et al. (1992). "Synthesis and Molecular Structures of Nickel (II) Alkyl-Substituted Cyclam Complexes," *Inorg. Chem.* 31(4):676-685.

Koningsberger, J. C. et al. (1995). "Exogenous Protoporphyrin Inhibits Hep G2 Cell Proliferation, Increases the Intracellular Hydrogen Peroxide Concentration and Causes Ultrastructural Alterations," *J. Hepatology* 22:57-65.

Koningsberger, J. C. (1992). "Toxic Dark Effects of Protoporphyrin," *Digestive Disease Week and The 93rd Annual Meeting of the American Gastroenterological Association San Franscisco*, California Supplement to *Gastroenterology* . 102(4): A835. (Abstract only).

Kramer, D. et al. (Feb. 3, 1995). "Stable Amplification of the S-Adenosylmethionine Decarboxylase Gene in Chinese Hamster Ovary Cells," *J. Biol. Chem.* 270(5):2124-2132.

Kramer, D.L. et al. (1993). "Regulation of Polyamine Transport by Polyamines and Polyamine Analogs," *J. Cell. Physiol.* 155:399-407.

Kramer, D.L. et al. (Dec. 1, 1997). "Effects of Novel Spermine Analogues on Cell Cycle Progression and Apoptosis in MALME-3M Human Melanoma Cells," *Cancer Res.* 57:5521-5527.

Li, C.J. et al. (Sep. 1, 1995). "Induction of Apoptosis by beta-Lapachone in Human Prostate Cancer Cells," *Cancer Res.* 55:3712-3715.

Lilja, H. et al. (Nov. 1985) "A Kallikrein-like Serine Protease in Prostatic Fluid Cleaves the Predominant Seminal Vesicle Protein," *J. Clin. Invest.* 76(5):1899-1903.

Lovaas, E. (1997). "Antioxidative and Metal-Chelating Effects of Polyamine," *Adv. Pharmacol.* 38:119-149.

Mahadik, S.P. and Scheffer, R.E. (1996). "Oxidation Injury and Potential Use of Antioxidants in Schizophrenia," *Prostaglandins Leukot. Essent. Fatty Acids* 55(1&2):45-54.

Mamont, P.S. et al. (Mar. 15, 1978). "Anti-Proliferative Properties of DL-Alpha-Difluoromethyl Ornithine in Cultured Cells. A Consequence of the Irreversible Inhibition of Ornithine Decarboxylase," *Biochem. Biophys. Res. Commun.* 81(1):58-66.

Marton, L.J. and Pegg, A.E. (1995). "Polyamines as Targets for Therapeutic Intervention," *Ann. Rev. Pharm. Toxicol.* 35:55-91.

Matsumoto, T. et al. (1969). "α-Caryopterone, A New Pyranojuglone from Caryopteris Clandonensis," *Helv. Chim. Acta* 52(3):808-812 (In German—Chemical Abstracts English-language record attached).

Mazzoni, A. et al. (1986). "Comparative Distribution of Free Doxorubicin and Poly-L-aspartic Acid Liked Doxorubicin in MS-2 Sarcoma Bearing Mice," *Cancer Drug Deliv.* 3(3):163-172.

Mertens, J.J.W.M. et al. (1991). "Inhibition of γ-Glutamyl Transpeptidase Potentiates the Nephrotoxicity of Glutathione-Conjugated Chlorohydroquinones," *Toxicol. Appl. Pharmacol.* 110:45-60.

Mi, Z. et al. (1998). "Human Prostatic Carcinoma Cell Lines Display Altered Regulation of Polyamine Transport in Response to Polyamine Analogs and Inhibitors," *Prostate* 34:51-60.

Monks, T.J. (1995). "Modulation of Quinol/Quinone-Thioether Toxicity by Intramolecular Detoxication," *Drug Metab. Rev.* 27(1 &2):93-106.

Monks, T.J. et al. (1994). "Oxidation and Acetylation as Determinants of 2-Bromocystein-S-ylhydroquinone-Mediated Nephrotoxicity," *Chem. Res. Toxicol.* 7(4):495-502.

Mordente, A. et al. (1998). "Antioxidant Properties of 2,3-Dimethoxy-5-Methyl-6-(10-Hydroxydecyl)-1,4-Benzoquinone (Idebenone)," *Chem. Res. Toxicol.* 11(1):54-63.

Morgan, D.M.L. and Christensen, J. (1983). "Polyamine Oxidation and the Killing of Intracellular Parasites," *Adv. Polyamine Res.* 4:169-174.

Morgan, D.M.L. (1998). "Polyamines. An Introduction," *Methods. Mol. Biol.* 79:3-30.

Morgan, D.M.L. et al. (1986). "The Effect of Purified Aminoaldehydes Produced by Polyamine Oxidation on the Development in Vitro of Plasmodium Falciparum in Normal and Glucose-6-Phosphate-Dehydrogenase-Deficient Erythrocytes," *Biochem. J.* 236:97-101.

Mukhopadhyay, R. and Madhubala, R. (1995). "Effects of Bis(benzyl)Polyamine Analogs on Leishmania Donovani Promastigotes," *Exp. Parasitol.* 81:39-46.

Müller-Lissner, S.A. (1993). "Adverse Effects of Laxatives: Fact and Fiction," *Pharmacol.* 47(Suppl. 1):138-145.

Nagarajan, S. and Ganem, B. (1987). "Chemistry of Naturally Occurring Polyamines. II. Unsaturated Spermidine and Spermine Derivatives," *J. Org. Chem.* 52(22):5044-5046.

Nanji, A.A. and Tahan, S.R. (1996). "Association Between Endothelial Cell Proliferation and Pathologic Changes in Experimental Alcoholic Liver Disease," *Toxicol. Appl. Pharmacol.* 140:101-107.

Neder, K. et al. (1998). "Reaction of β-Lapachone and Related Maphthoquinones with 2-Mercaptoethanol: A Biomimetic Modes of Topoisomerase II Poisoning by Quinones," *Cell and Mol. Biol.* 44(3):465-474.

Nelson, W.L. et al. (1984). "The 3,4-Catechol Derivative of Propranolol, a Minor Dihydroxylated Metabolite," *J. Med. Chem.* 27(7):857-861.

Nishimura, K. et al. (1971). "Phagocidal Effects of Acrolein," *Biochim: Biophys. Acta* 247:153-156.

Novarina, A. et al. (1988). "Quantative Histochemistry of Lactate Dehydrogenase in Tumor Cells. Dark Effects of Porphyrin Drugs," Proceedings of the Eigth International Congress of Histochemistry and Cytochemistry and the Thirty-ninth Annyal Meeting of the Histochemical Society *J. Histochemistry and Cytochemistry* 36(7a):941. Abstract 404.

O'Brien, P.J. (1991). "Molecular Mechanisms of Quinone Cytotoxicity," *Chem. Biol. Interactions* 80:1-41.

O'Sullivan, M.C. et al. (1997). "Polyamine Derivatives as Inhibitors of Trypanothione Reductase and Assessment of Their Trypanocidal Activities," *Bioorg. Med. Chem.* 5(12):2145-2155.

Pegg, A.E. and McCann, P.P. (1982). "Polyamine Metabolism and Function," *Am. J. Physiol.* 243 (Cell Physiol. 12):C212-C221.

Pershin, G.N. et al. (1975). "Bonaphthon-A New Antiviral Chemotherapeutic Agent," *Farmakol. Toksikol* (1975) 38(1):69-73. (In Russian; Chemical Abstracts English-language abstract attached).

Planchon, S.M. et al. (Sep. 1, 1995). "β-Lapachone-Mediated Apoptosis in Human Promyelocytic Leukemia (HL-60) and Human Prostate Cancer Cells: A p53-Independent Response," *Cancer Res.* 55:3706-3711.

Planchon, S.M. et al. (1999). "Bcl-2 Protects Against Beta-Lapachone-Mediated Caspase 3 Activation and Apoptosis in Human Myeloid Leukemia (HL-60) Cells," *Oncol. Rep.* 6:485-492.

Pohjanpelto, P. et al. (Oct. 8, 1981). "Polyamine Starvation Causes Disappearance of Actin Filaments and Microtubules in Polyamine-Auxotrophic CHO Cells," *Nature* 293:475-477.

Porter, C.W. et al. (Jun. 1, 1987). "Relative Abilities of Bis(Ethyl) Derivatives of Putrescine, Spermidine, and Spermine to Regulate Polyamine Biosynthesis and Inhibit L1210 Leukemia Cell Growth," *Cancer Res.* 47:2821-2825.

Porter, C.W. and Bergeron, R.J. (1988). "Enzyme Regulation as an Approach to Interference with Polyamine Biosynthesis—An Alternative to Enzyme Inhibition," *Advances in Enzyme Regulation* 27:57-79.

Porter, C.W. and Bergeron, R.J. (1988). "Regulation of Polyamine Biosynthetic Activity by Spermidine and Spermine Analogs—A Novel Antiproliferative Strategy," *Adv. Exp. Med. Biol.* 250:677-690.

Porter, C.W. et al. (Jul. 15, 1991). "Correlations Between Polyamine Analogue-Induced Increases in Spermidine/Spermine $N^1$-Acetyltransferase Activity, Polyamine Pool Depletion, and Growth Inhibition in Human Melanoma Cell Lines," *Cancer Res.* 51:3715-3720.

Puckett-Vaughn, D.L. et al. (1993). "Enzymatic Formation and Electrochemical Characterization of Multiply Substituted Glutathione Conjugates of Hydroquinone," *Life Sci.* 52(14):1239-1247.

Rainwater, L.M. et al. (Aug. 1990). "Prostate-Specific Antigen Testing in Untreated and Treated Prostatic Adenocarcinoma," *Mayo Clinic Proc.* 65:1118-1126.

Rao, D.N.R. and Cederbaum, A.I. (1997). "A Comparative Study of the Redox-Cycling of a Quinone (Rifamycin S). and a Quinonimine (Rifabutin) Antibiotic by Rat Liver Microsomes," *Free Radic. Biol. Med.* 22(3):439-446.

Redd, M.J. et al. (Apr. 25, 1997). "A Complex Composed of Tup1 and Ssn6 Represses Transcription in Vitro," *J. Biol. Chem.* 272(17):11193-11197.

Reddy, V.K. et al. (1998). "Conformationally Restricted Analogues of $^1$N, $^{12}$N-bisethylspermine: Synthesis and Growth Inhibitory Effects on Human Tumor Cell Lines," *J. Med. Chem.* 41(24):4723-4732.

Redgate, E.S. et al. (1995). "Polyamines in Brain Tumor Therapy," *J. Neuro-Oncol.* 25:167-179.

Řihová, B. et al. (1993). "Targetable Photoactivatable Drugs. 3. In Vitro Efficacy of Polymer Bound Chlorin $E_6$ Toward Human Hepatocarcinoma Cell Line (PLC/PRF/5) Targeted with Galactosamine and to Mouse Splenocytes Targeted with Anti-Thy 1.2 Antibodies," *J. Controlled Release* 25:71-87.

Saito, T. (Mar. 1988). "Ten Years of Anticancer Drug-Carboquone," *Jpn. J. Cancer Chemother.* 15(3):549-554. (English abstract included on last page of document).

Shappell, N.W. et al. (1992). "Differential Effects of the Spermine Analog, $N^1$, $N^{12}$-Bis(Ethyl)-Spermine, on Polyamine Metabolism and Cell Growth in Human Melanoma Céll Lines and Melanocytes," *Anticancer Res.* 12:1083-1089.

Sharma, A. et al. (Aug. 1997). "Antitumor Efficacy of $N^1$, $N^{11}$-Diethylnorspermine on a Human Bladder Tumor Xenograft in Nude Athymic Mice," *Clin. Cancer Res.* 3:1239-1244.

Sicuro, T. et al. (1987). "Dark- and Light-Interaction of Porphyrins with Malignant Cell Compartment," *Medicine Biologie Environnement* 15:67-70.

Singh, S. et al. (Nov. 15, 1996). "Capsaicin (8-Methyl-N-Vanillyl-6-Nonenamide) is a Potent Inhibitor of Nuclear Transcription Factor-Kappa B Activation by Diverse Agents," *J. Immunol.* 157(10):4412-4420.

Sinha, A.A. et al. (1995). "Cathepsin B in Angiogenesis of Human Prostate: An Immunohistochemical and Immunoelectron Microscopic Analysis," *Anat. Rec.* 241:353-362.

Sinha, A.A. et al. (1995). "Immunohistochemical Localization of Cathepsin B in Neoplastic Human Prostate," *Prostate* 26:171-178.

Snyder, R.D. et al. (May 15, 1991). "Effects of Polyamine Analogs on the Extent and Fidelity of In Vitro Polypeptide Synthesis," *Biochem. Biophys. Res. Commun.* 176(3):1383-1392.

Snyder, R.D. et al. (1994). "Anti-Mitochondrial Effects of Bisethyl Polyamines in Mammalian Cells," *Anticancer Res.* 14:347-356.

Splinter, T.A.W. et al. (1986). "Phase I Study of Alpha-difluoromethylornithine and Methyl-GAG," *Eur. J. Cancer Clin. Oncol.* 22(1):61-67.

Sun, J.S. et al. (1998). "A Preparative Synthesis of Lapachol and Related Naphthoquinones," *Tetrahedron Letters* 39:8221-8224.

Takenaka, S. et al. (1996). "Construction of a Dimeric DNA-Binding Peptide Model by Peptide-Anthraquinone Conjugation," *Int. J. Pept. Prot. Res.* 48(5):397-400.

Takuwa, A. et al. (Sep. 1986). "The Addition of Alcohol to 1,2-naphthoquinone Promoted by Metal Ions. Facile Synthesis of 4-alkoxy-1,2-naphthoquinones," *Bull. Chem. Soc. Jpn.* 59(9):2959-2961.

Takuwa, A. et al. (1986). "Structural Influences on the Isomerization of 4-benzyl- and 4-allyl-1,2-naphthoquinones to Quinonemethides and their Stereochemistry," *J. Chem. Soc.* 1:1627-1631.

Vonarx-Coinsman, V. et al. (1995). "HepG2 Human Hepatocarcinoma Cells: an Experimental Model for Photosensitization by Endogenous Porphyrins," *J. Photochem. and Photobiol. B:Biology*, 30:201-208.

Watt, K.W.K. et al. (May 1986). "Human Prostate-Specific Antigen: Structural and Functional Similarity with Serine Proteases," *Proc. Natl. Acad. Sci. USA* 83:3166-3170.

Woodburn, K. W. (1992). "Evaluation of Porphyrin Characteristics Required for Photodynamic Therapy," *Photochemistry and Photobiology* 55(5):697-701, 703-704.

Wunz, T.P. et al. (1987). "New Antitumor Agents Containing the Anthracene Nucleus," *J. Med. Chem.* 30(8):1313-1321.

Yan, S. et al. (Feb. 1998). "Cathepsin B and Human Tumor Progression," *Biol. Chem.* 379:113-123.

Yuan, Z.M. et al. (1994). "Cytotoxic Activity of $N^1$- and $N^8$-Aziridinyl Analogs of Spermidine," *Biochem. Pharmacol.* 47(9):1587-1592.

Zagaja, G.P. et al. (1998). "Effects of Polyamine Analogues on Prostatic Adenocarcinoma Cells in Vitro and in Vivo," *Cancer Chemother. Pharmacol.* 41(6):505-512.

U.S. Appl. No. 09/179,383, filed Oct. 26, 1998.

Bacchi, C.J. et al. (Jan. 2002). "Novel Synthetic Polyamines are Effective in the Treatment of Experimental Microsporidiosis, and Opportunistic AIDS-Associated Infection," *Antimicrobial Agents and Chemotherapy* 46(1):55-61.

Huang, Y. et al. (Jul. 2003). "A Novel Polyamine Analog Inhibits Growth and Induces Apoptosis in Human Breast Cancer Cells," *Clinical Cancer Research* 9:2769-2777.

Reddy, V.K. et al. (2001). "*Cis*-Unsaturated Analogues of 3,8,13,18,23-Pentaazapentacosane (BE-4-4-4-4): Synthesis and Growth Inhibitory Effects on Human Prostate Cancer Cell Lines," *J. Med. Chem.* 44(3):404-417.

Valasinas, A. et al. (2001). "Conformationally Restricted Analogues of $^1$N, $^{14}$N-Bisethylhomospermine (BE-4-4-4): Synthesis and Growth Inhibitory Effect on Human Prostate Cancer Cells," *J. Med. Chem.* 44(3):390-403.

Valasinas, A. et al. (2003). "Long-Chain Polyamines (Oligoamines) Exhibit Strong Cytotoxicities Against Human Prostate Cancer Cells," *Biorganic & Medicinal Chemistry* 11:4121-4131.

Caplus. (Apr. 28, 1990). "Reaction Products of Higher Saturated and/or Unsaturated Carboxylic Acids with Amines," Accession No. 1990:164044, eight pages.

Aragó, J. et al. (Jan. 1992). "Macrocyclic Effect on Anion Binding. A Potentiometric and Electrochemical Study of the Interaction of 21- and 21-Membered Polyazaalkanes with $[Fe(CN_6]^{4-}$ and $[Co(CN_6]^{3-}$," *J. Chem. Soc. Dalton Trans* (1):319-324.

Bacchi, C.J. et al. (2001). "SL-11158, A Synthetic Oligoamine, Inhibits Polyamine Metabolism of *Encephalitozoon cuniculi*," *J. Eukaryot. Microbiol.*, pp. 92S-94S.

Baker, L.A. et al. (May 20, 2002). "Synthesis and Catalytic Properties of Imidazole-Functionalized Poly(propylene imine) Dendrimers," *Bulletin Of The Korean Chemical Society* 23(5):647-654.

Bazzicalupi, C. et al. (1998). "Palladium (II) Co-ordination by Linear N-methylated Polyamines: A Solution and Solid-State Study," *J. Chem. Soc. Dalton Trans.*, pp. 1625-1631.

Bruice, T.C. et al. (1997). "A Microgonotropen Branched Decaaza Decabutylamine and its DNA and DNA/Transcription Factor Interactions," *Bioorganic & Medicinal Chemistry* 5(4):685-692.

Cabani, S.et al. (Jan.-Feb. 1999). "Molecular Dioxygen Binding to Co(II) Complexes With Open-Chain and Macrocyclic Polyazaalkanes in Aqueous Solutions," *Annali Di Chimica (Societa Chimica Italiana)* 89(1-2):99-106.

Caplus Abstract of EP 186473, Chemical Abstracts Accession No. 1986:517956, one page (1986).

Caplus Abstract of JP 45-30077, Chemical Abstracts Accession No. 1971:143260, one page (1971).

Casero, R.A., Jr. et al. (Jan. 4, 2001). "Terminally Alkylated Polyamine Analogues as Chemotherapeutic Agents," *J. Med. Chem.* 44(1):1-26.

Derwent World Patent Index Abstract of WO 99/43752, two pages (1999).

Dubowchik, G.M. et al. (1996). "Lipophilic Polyamino-Bolaamphiphile Designed to Dissipate pH Gradients Across a Bilayer Membrane: Synthesis and Proton Transport," *Tetrahedron Letters* 37(36):6465-6468.

Krakowiak, K.E. et al. (1996). "Thermal Removal of BOC-Protecting Groups During Preparation of Open-Chain Polyamines," *Synthetic Communications* 26(21):3999-4004.

Kröger, N. et al. (Dec. 19, 2000). "Species-Specific Polyamines From Diatoms Control Silica Morphology", *Proc. Natl. Acad. Sci. USA* 97(26):14133-14138.

Lange, P. et al. (Jan. 31, 1996). "Dendrimer-Based Multinuclear Gold (1) Complexes," *Inorg. Chem.* 35(3):637-642.

Mitchell, J.L.A. et al. (Sep. 1, 2002). "Antizyme Induction by Polyamine Analogues as a Factor of Cell Growth Inhibition," *Biochem. J.* 366(2):663-671.

Office Action mailed Apr. 1, 2004 for U.S. Appl. No. 10/272,269 filed Oct. 16, 2002, five pages.

Office Action mailed Nov. 3, 2006 for U.S. Appl. No. 10/957,105 filed Oct. 1, 2004.

Office Action mailed Apr. 12, 2007 for U.S. Appl. No. 10/957,105 filed Oct. 1, 2004, five pages.

Sakai, N. et al. (1997). "Transmembrane Ion Transport Mediated by Amphiphilic Polyamine Dendrimers," *Tetrahedron Letters* 38(15):2613-2616.

Salmon, A. et al. (2001). "Water Soluble Ferrocenyl and Polyferrocenyl Compounds: Synthesis and Electrochemistry," *Journal Of Organometallic Chemistry* 637-639:595-608.

Satz, A.L. et al. (Feb. 2002). "Recognition in the Minor Groove of Double-Stranded DNA by Microgonotropens," *Accounts of Chemical Research*.35(2):86-95.

Tasaki, K. et al. (Sep. 2001). "Computer Simulation a $LiPF_6$ Salt Association in Li-Ion Battery Electrolyte in the Presence of an Anion Trapping Agent," *Journal of The Electrochemical Society* 148(9):A984-A988.

Tsiorvas, D. et al. (Jul. 30, 2002). "Liquid Crystals Derived from Cholesterol Functionalized Poly(propylene imine) Dendrimers," *Macromolecules* 35(16):6466-6469.

esp@cenet family record for EP 723 772, two pages (1996).

* cited by examiner

Figure 33
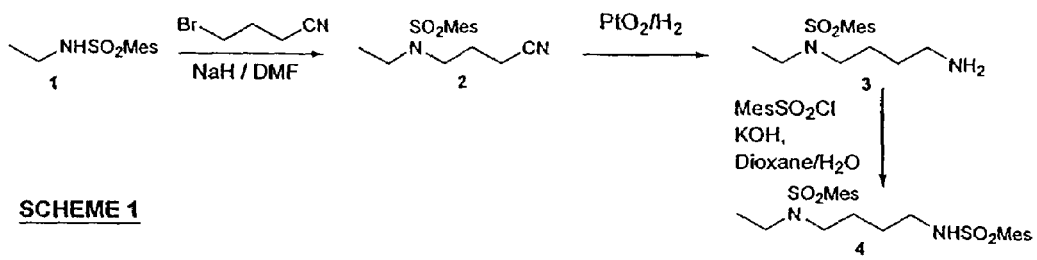
SCHEME 1
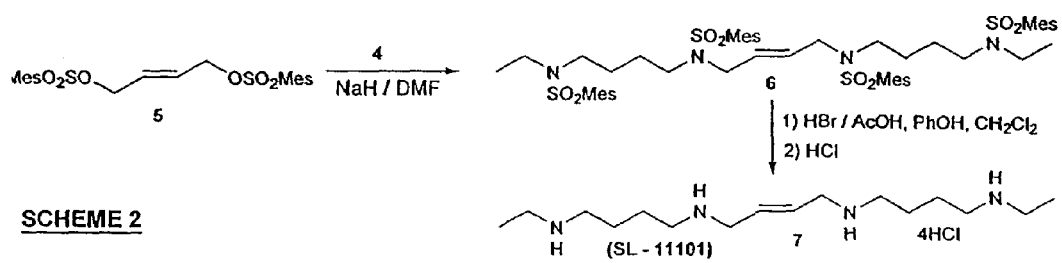
SCHEME 2
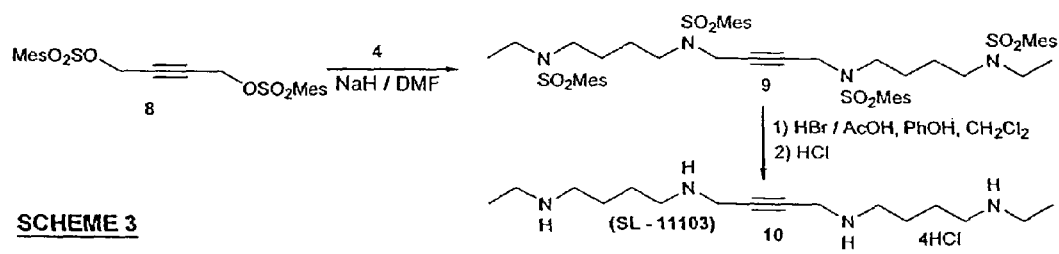
SCHEME 3
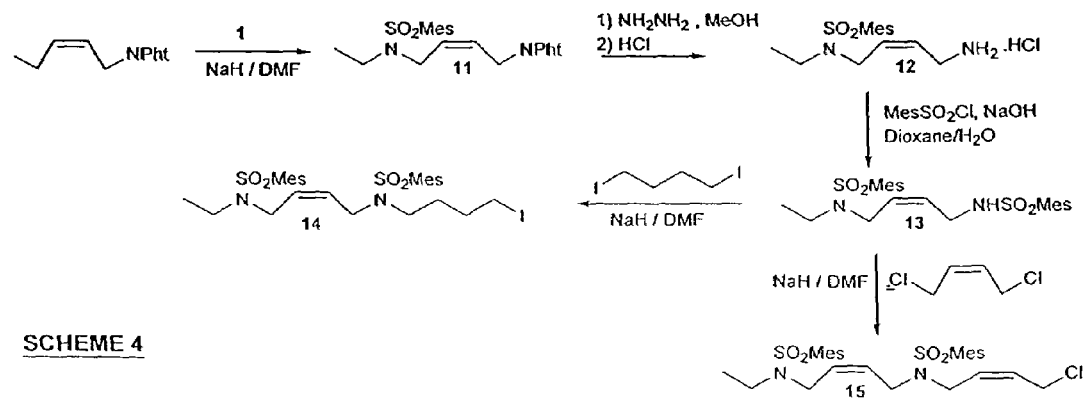
SCHEME 4

Figure 34
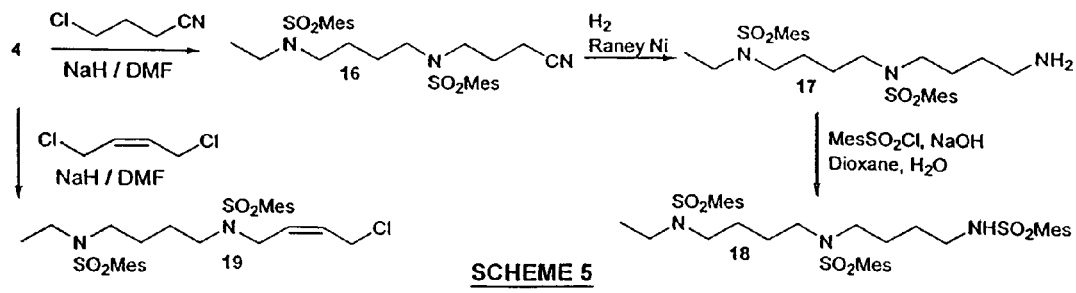
SCHEME 5
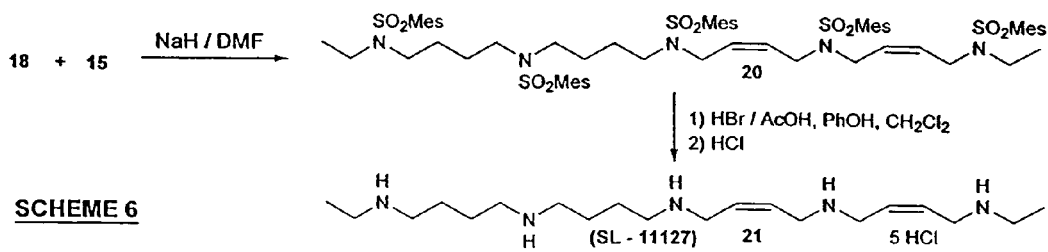
SCHEME 6
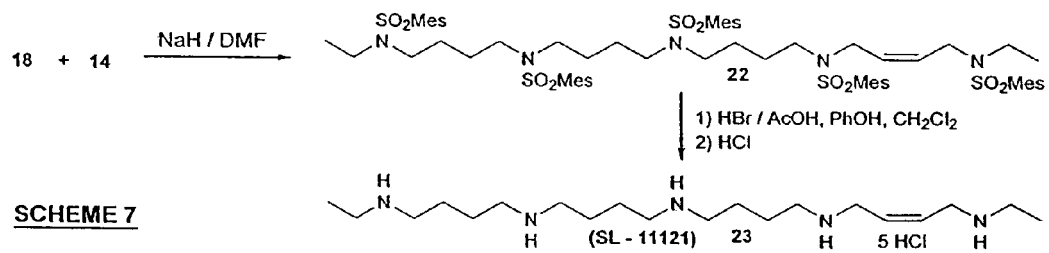
SCHEME 7
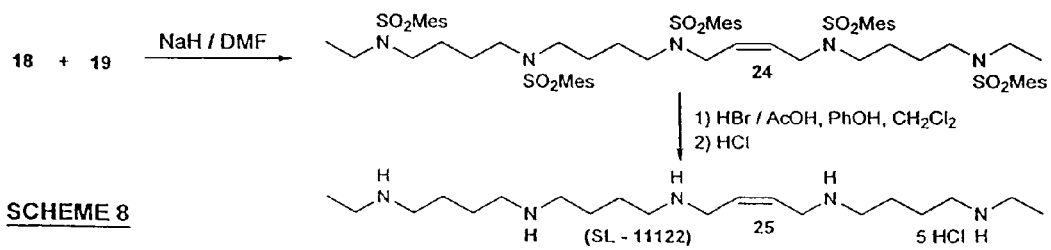
SCHEME 8
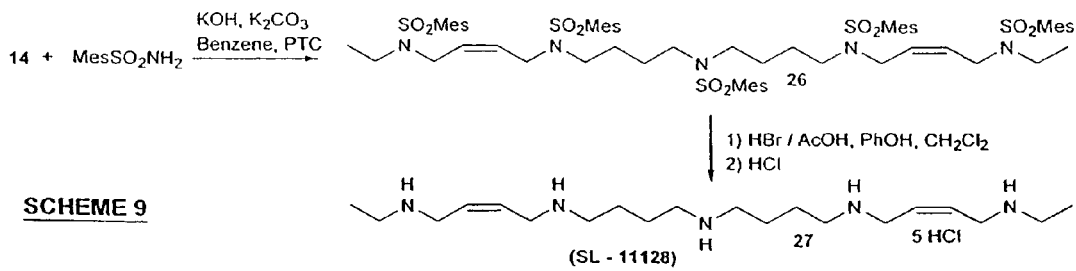
SCHEME 9

Figure 35
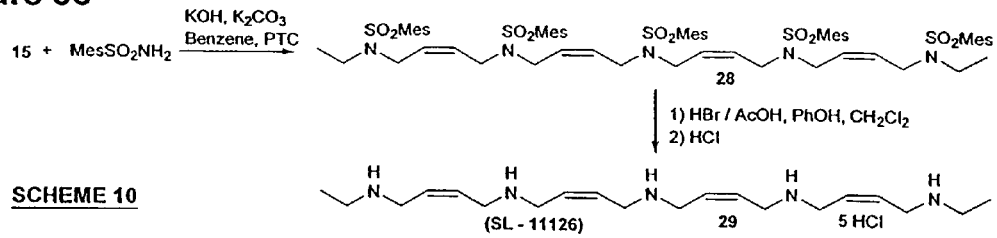
SCHEME 10
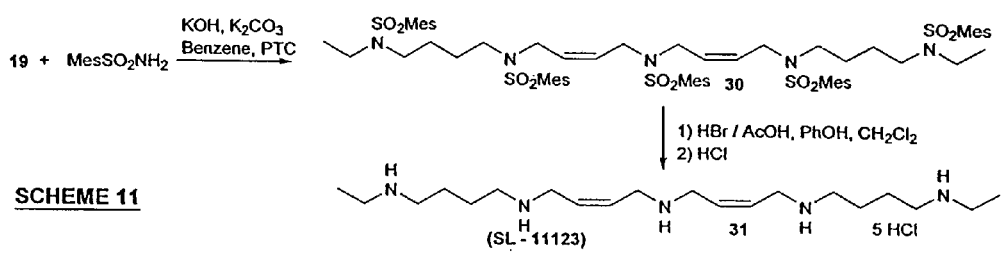
SCHEME 11
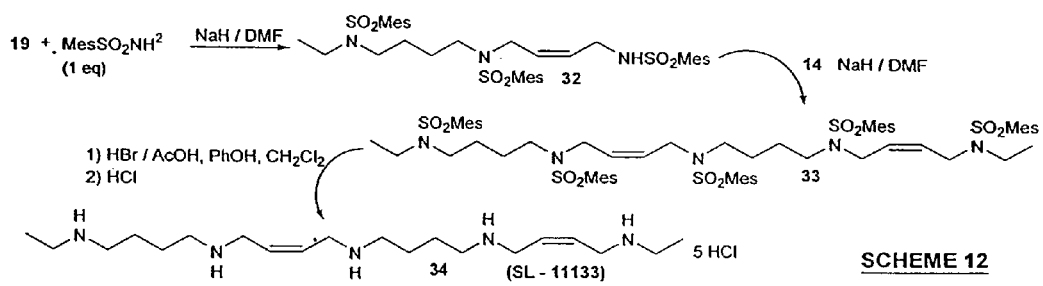
SCHEME 12
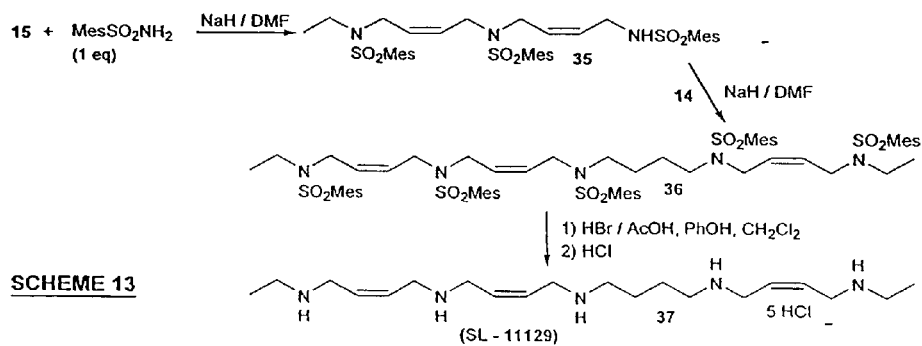
SCHEME 13
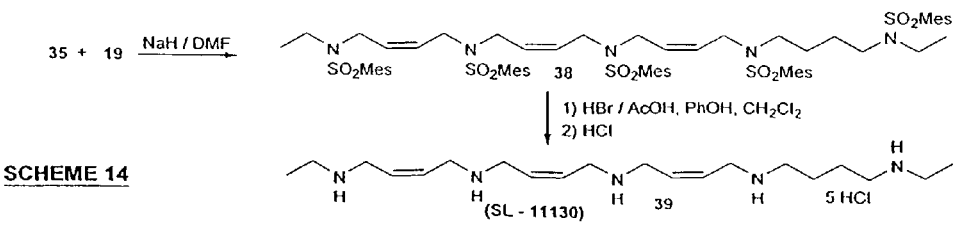
SCHEME 14

Figure 36
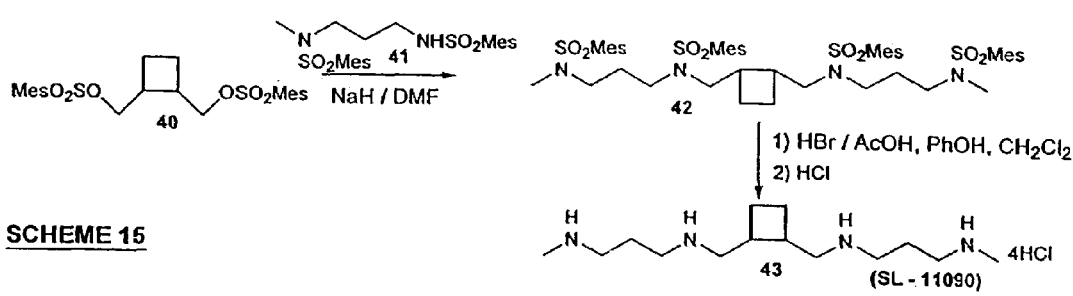
SCHEME 15
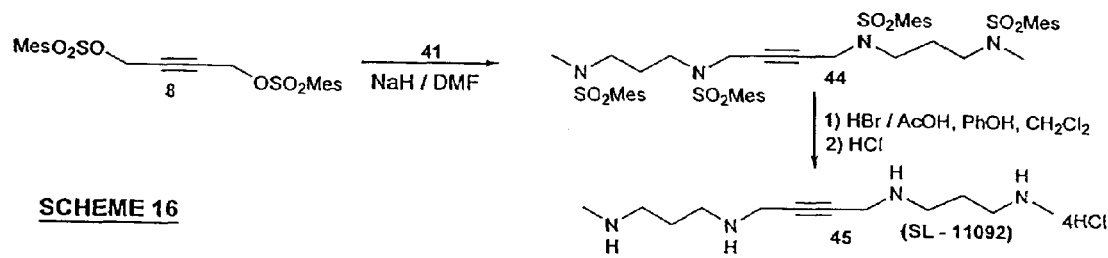
SCHEME 16
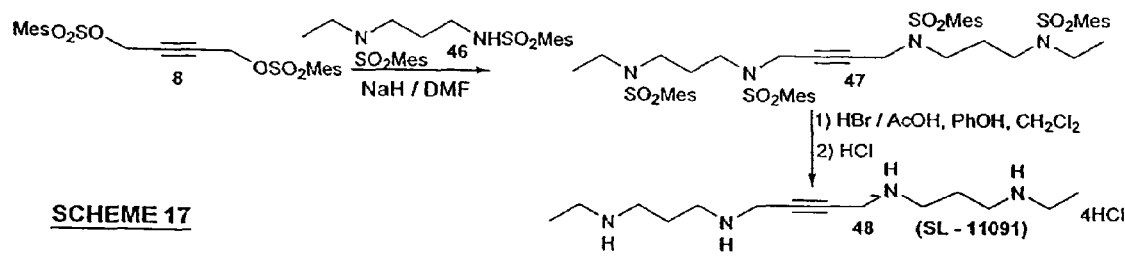
SCHEME 17

Figure 37
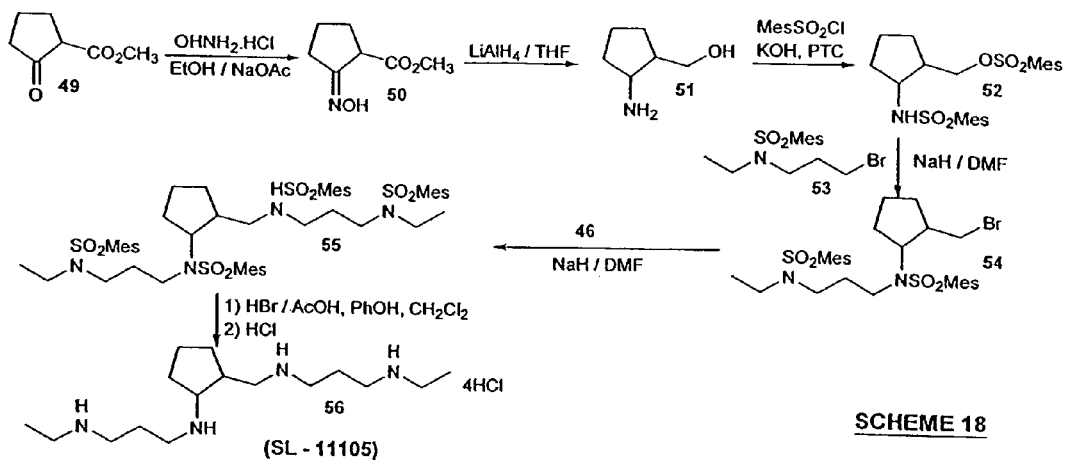
SCHEME 18
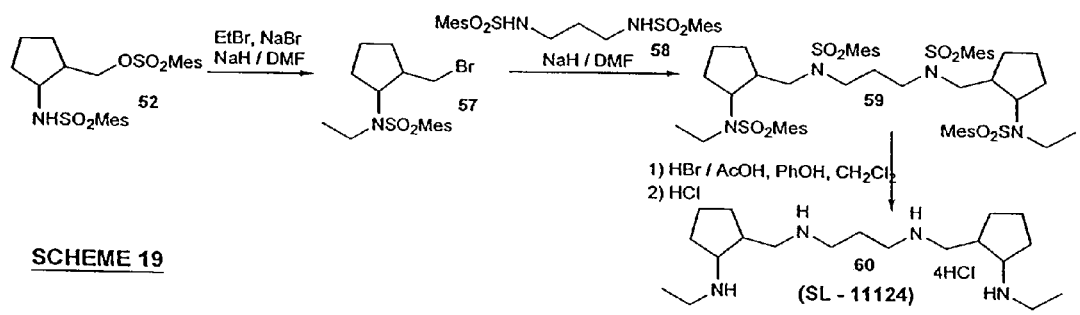
SCHEME 19
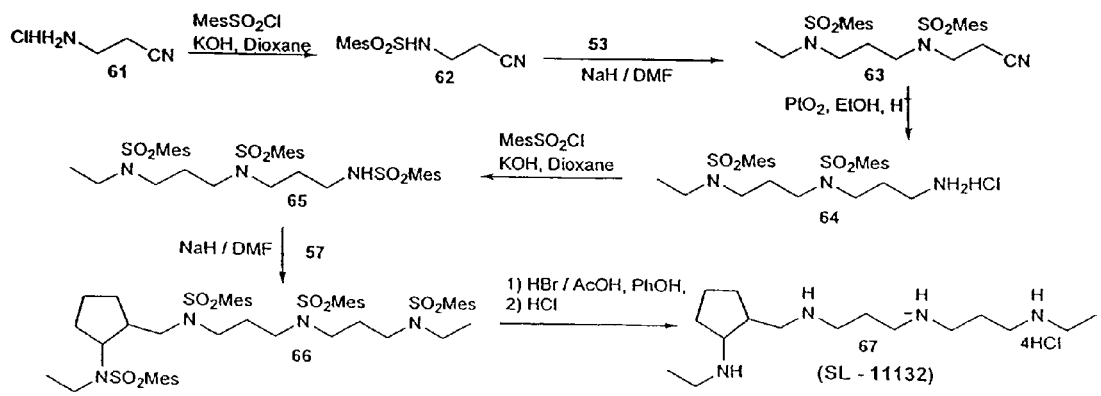
SCHEME 20

SCHEME 21

Figure 39
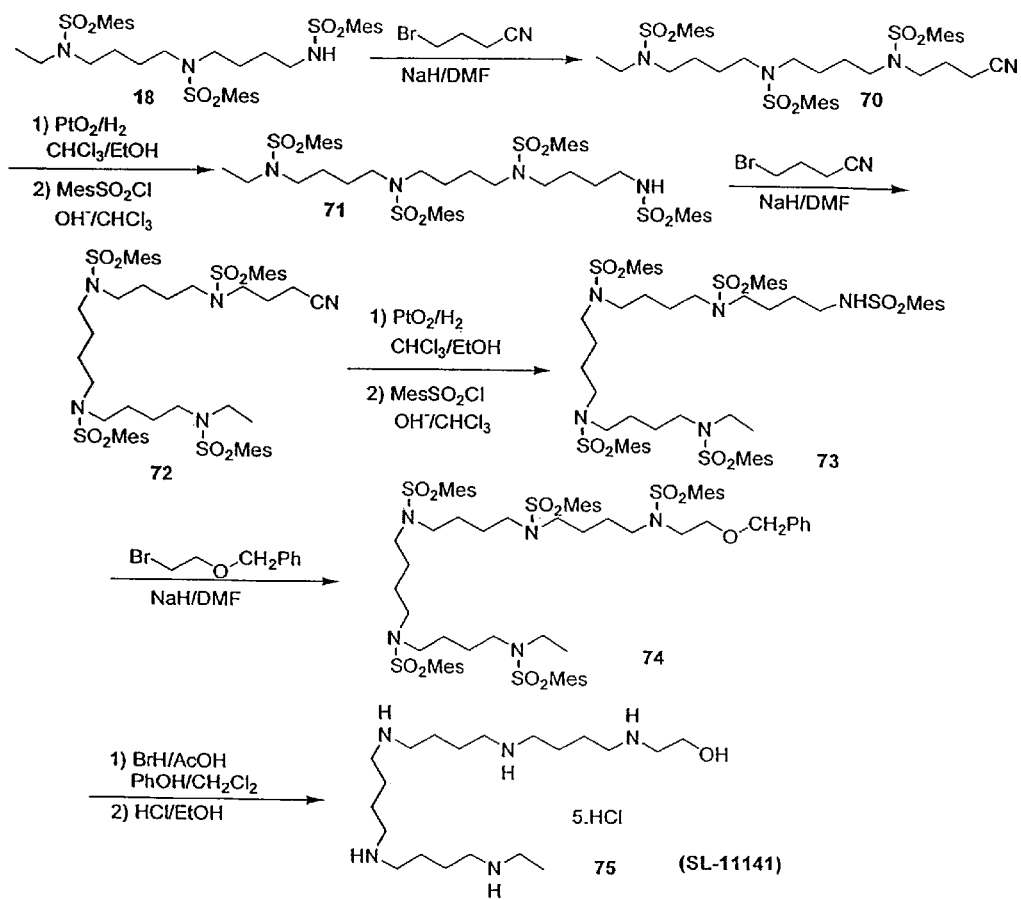
SCHEME 22
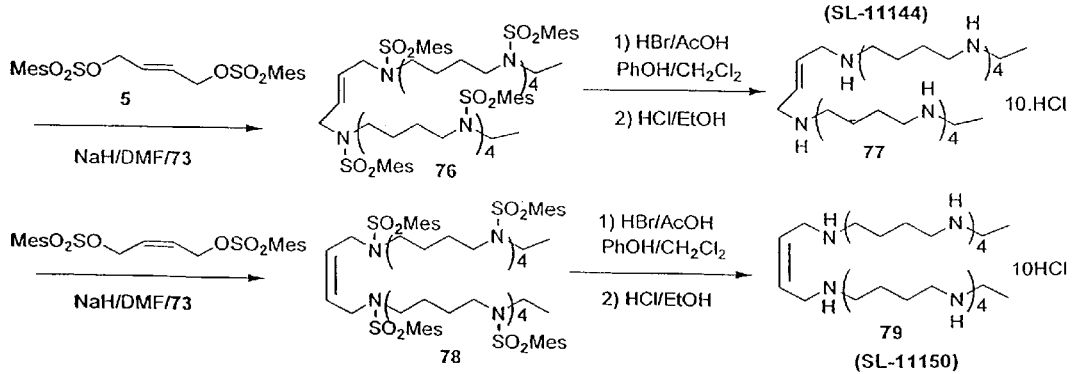
SCHEME 23

SCHEME 24

Scheme 502
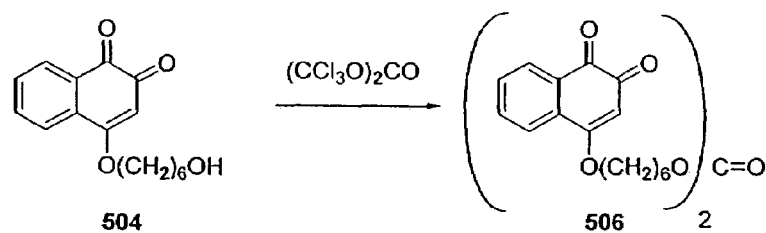
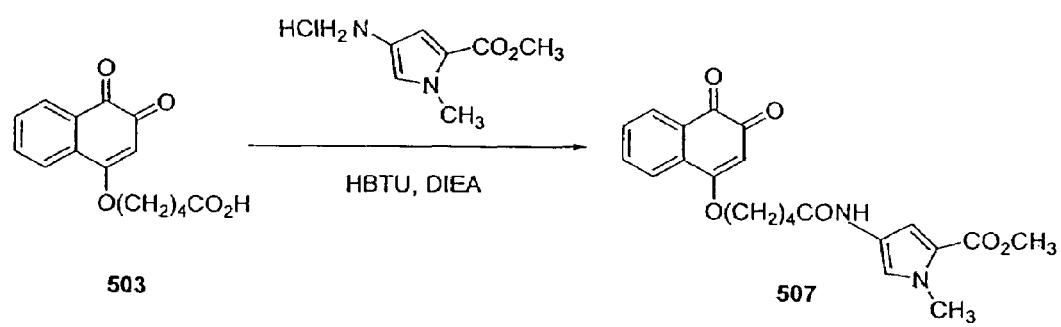
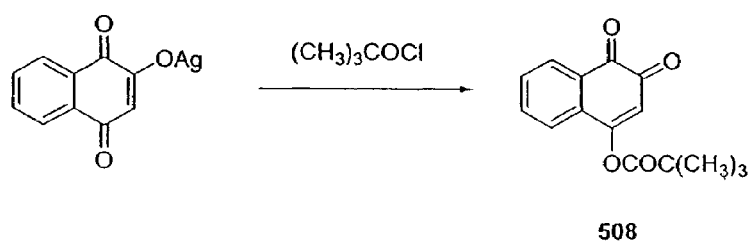
FIGURE 42

Scheme 503
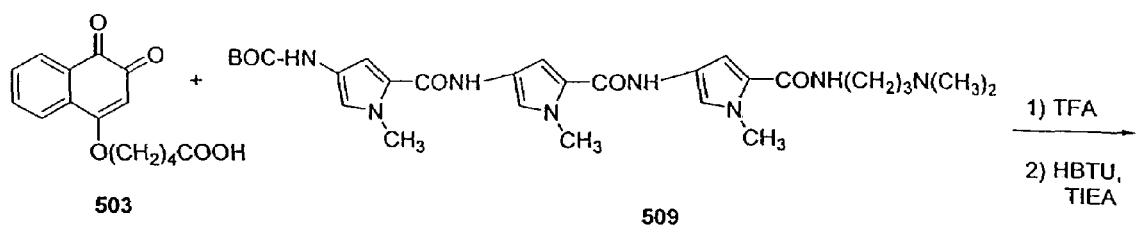
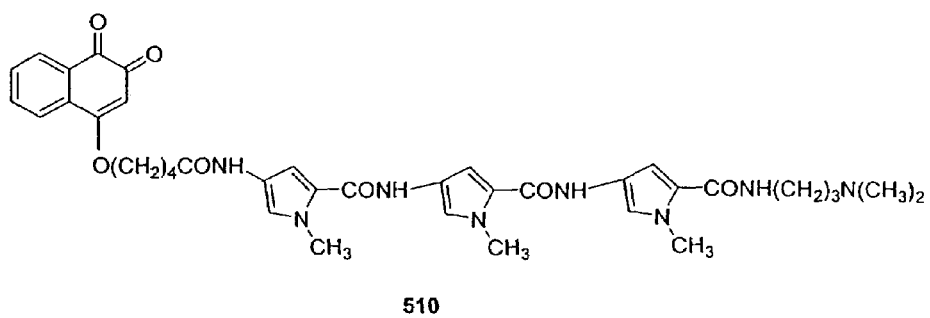
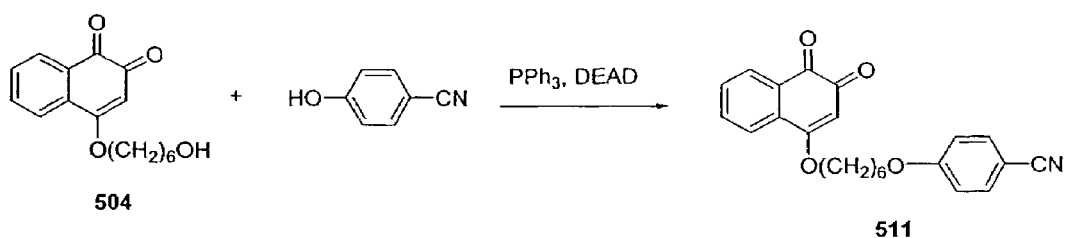
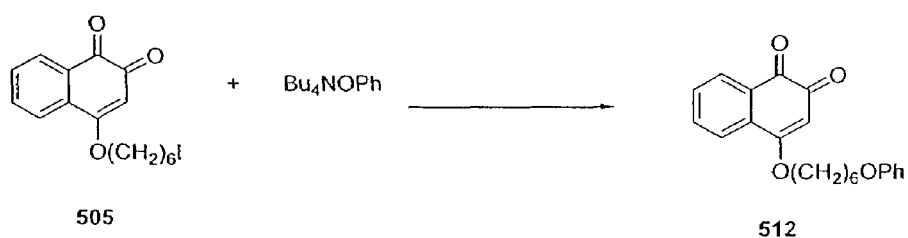
FIGURE 43

Scheme 504

Scheme 505

Scheme 506

Scheme 507

Scheme 508

Scheme 509

Scheme 510

Scheme 511

Scheme 512

Scheme 513

Boc-Gln + β-Ala-β-Lapachone → Boc-Gln-β-Ala-β-Lapachone →

Gln-β-Ala-β-Lapachone → Boc-Leu-Gln-β-Ala-β-Lapachone →

Leu-Gln-β-Ala-β-Lapachone → Nα-Boc-Lys(Nε-Cbz)-Leu-Gln-β-Ala-β-Lapachone

→ Lys(Nε-Cbz)-Leu-Gln-β-Ala-β-Lapachone → morpholino-Ser(OBn)-Lys(Nε-Cbz)-Leu-Gln-β-Ala-β-Lapachone → morpholino-Ser-Lys-Leu-Gln-β-Ala-β-Lapachone

N-Fmoc-Ser(OBn) → N-Fmoc-Ser(OBn)-OtBu → Ser(OBn)-OtBu →
morpholino-Ser(OBn)-OtBu → morpholino-Ser(OBn)

FIG. 53

Scheme 514

Boc-Leu + β-Lapachone → Boc-Leu-β-Lapachone → Leu-β-Lapachone →

Boc-Gln-Leu-β-Lapachone → Gln-Leu-β-Lapachone →

Boc-Leu-Gln-Leu-β-Lapachone → Leu-Gln-Leu-β-Lapachone →

Boc-Lys(Nε-Cbz)-Leu-Gln-Leu-β-Lapachone →

Lys(Nε-Cbz)-Leu-Gln-Leu-β-Lapachone → morpholino-Ser(OBn)-Lys(Nε-Cbz)-Leu-Gln-Leu-β-Lapachone → morpholino-Ser-Lys-Leu-Gln-Leu-β-Lapachone

SL-11154

SCHEME 26

Figure 57
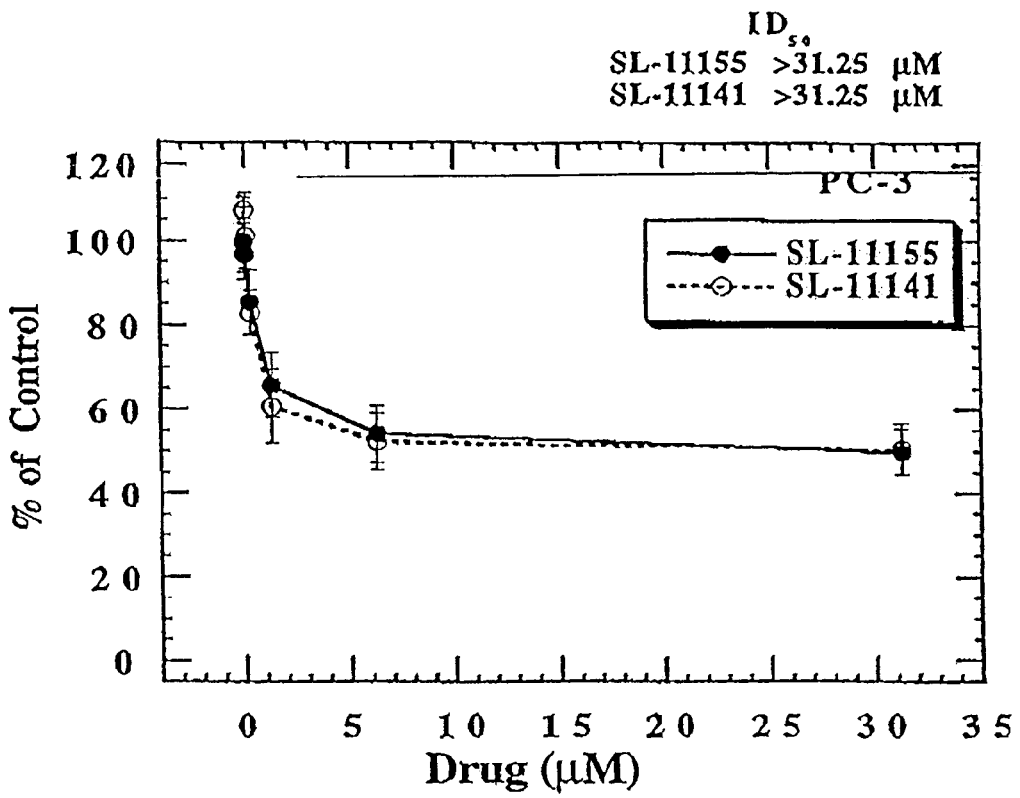
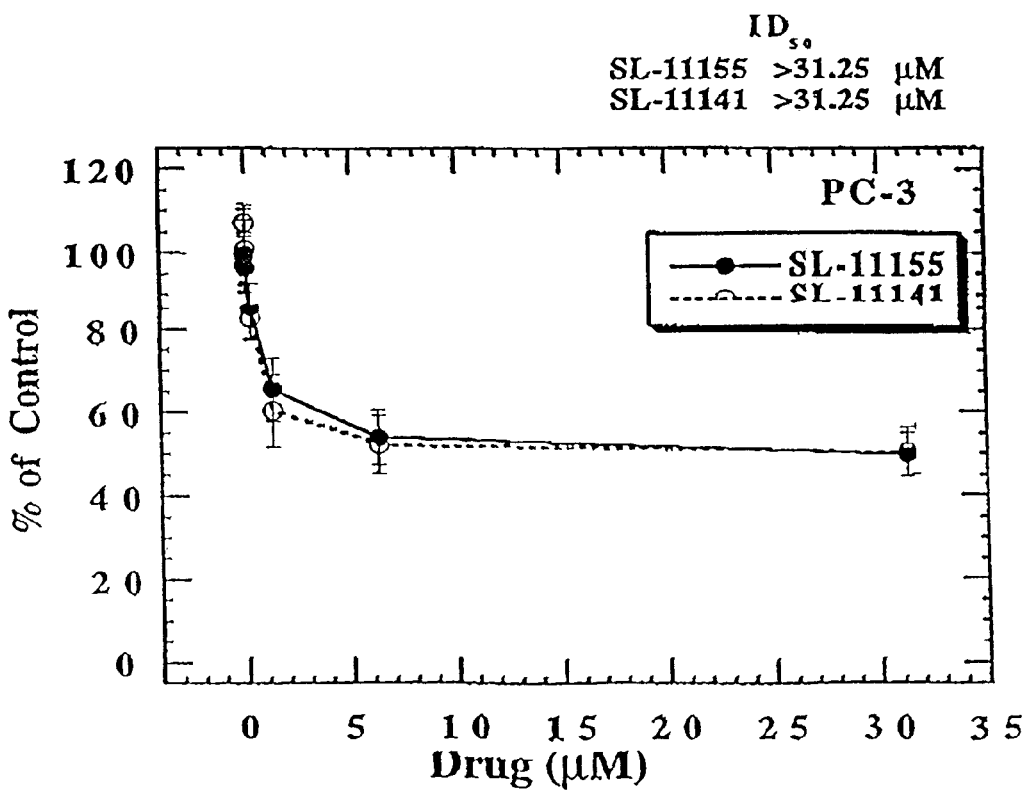

Figure 58
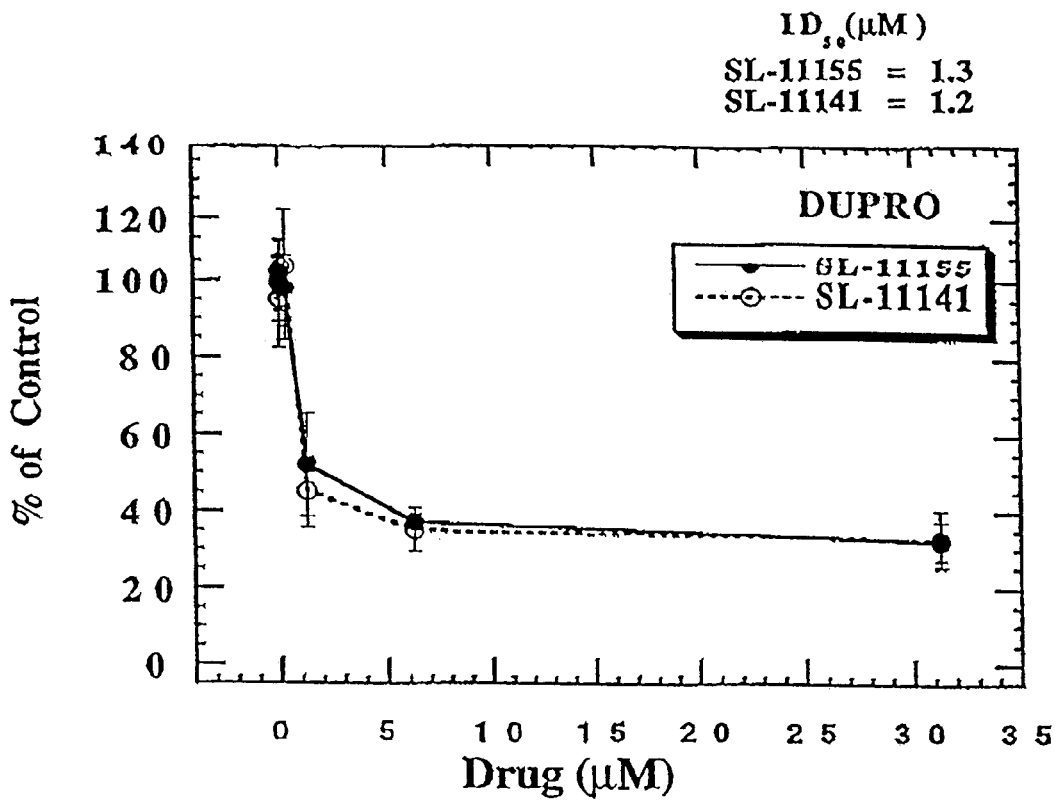
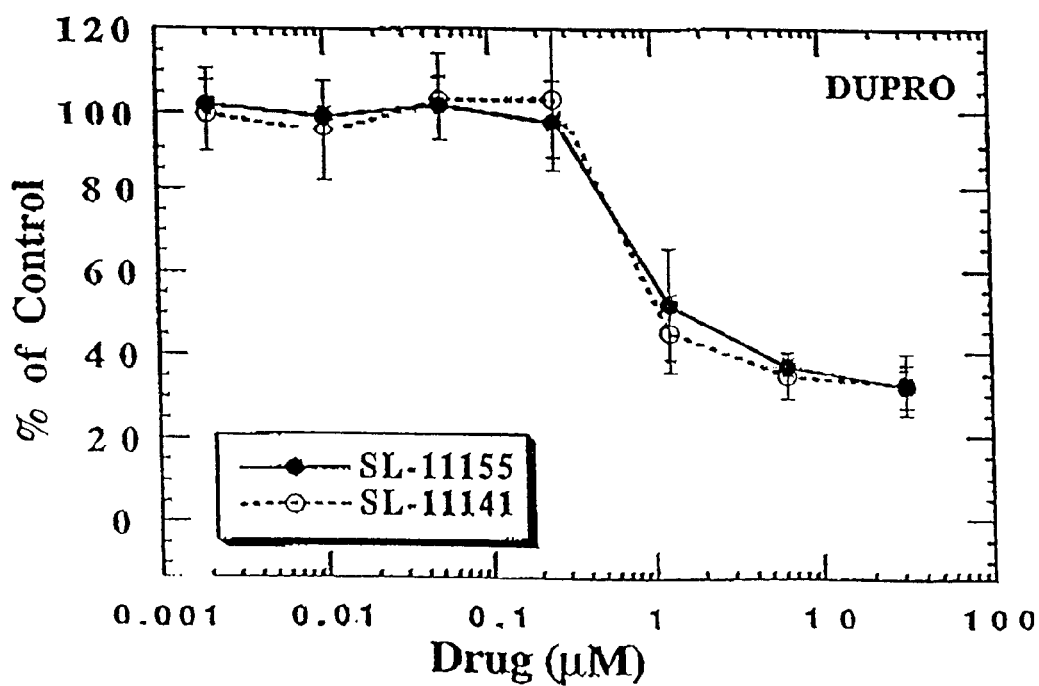

Figure 59
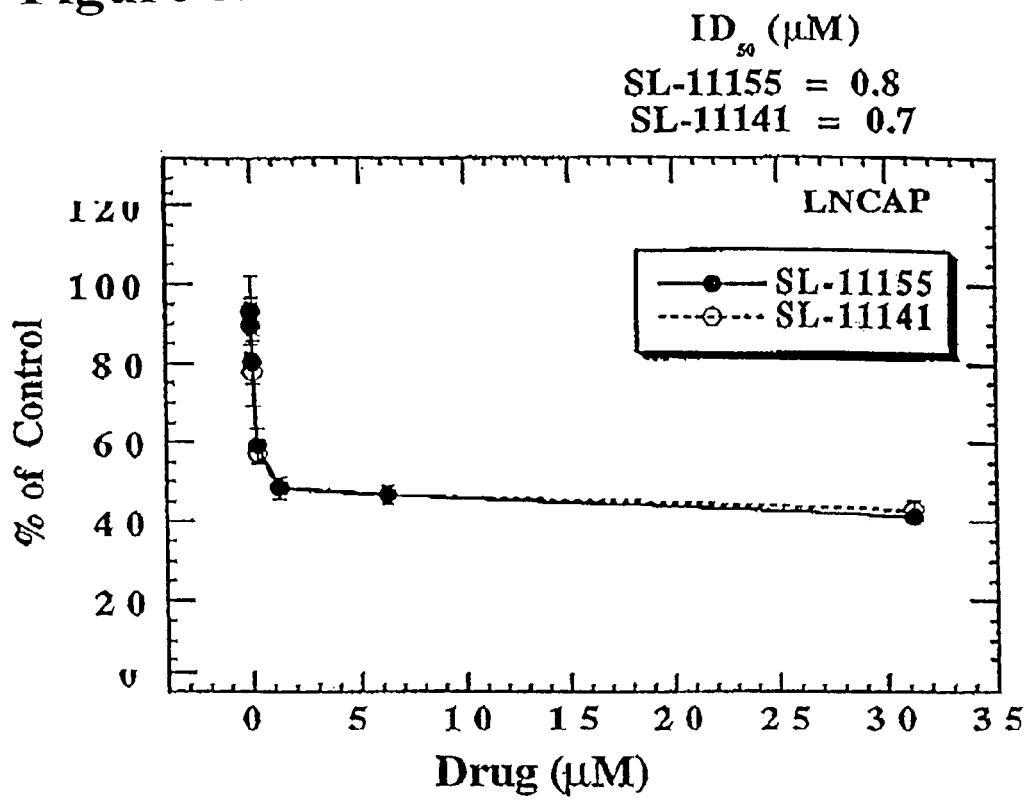
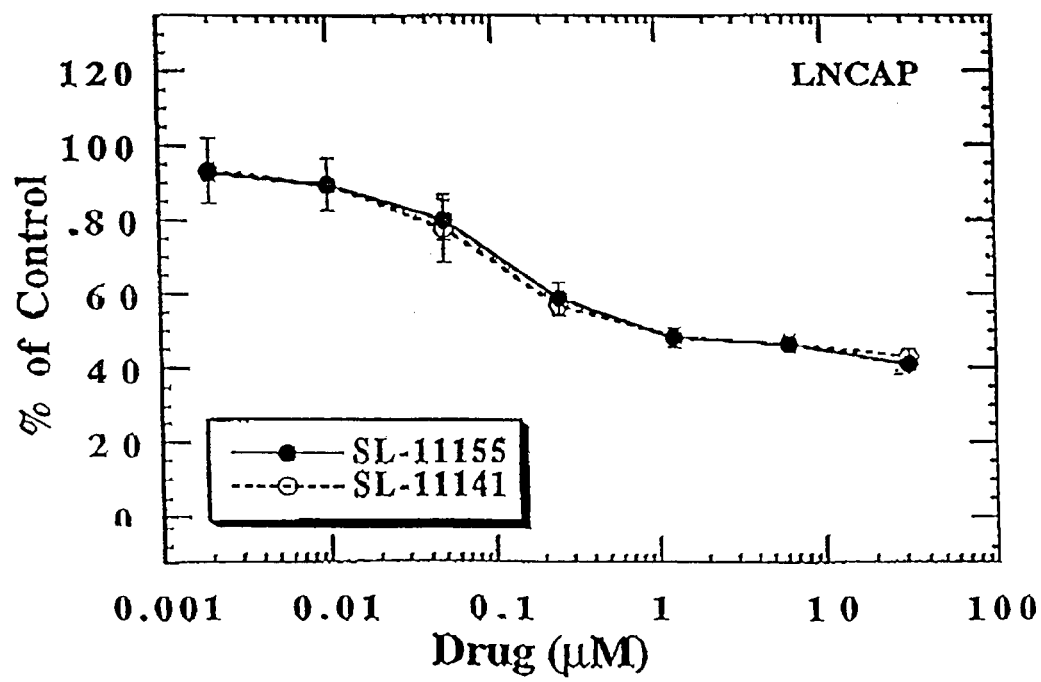

Figure 60
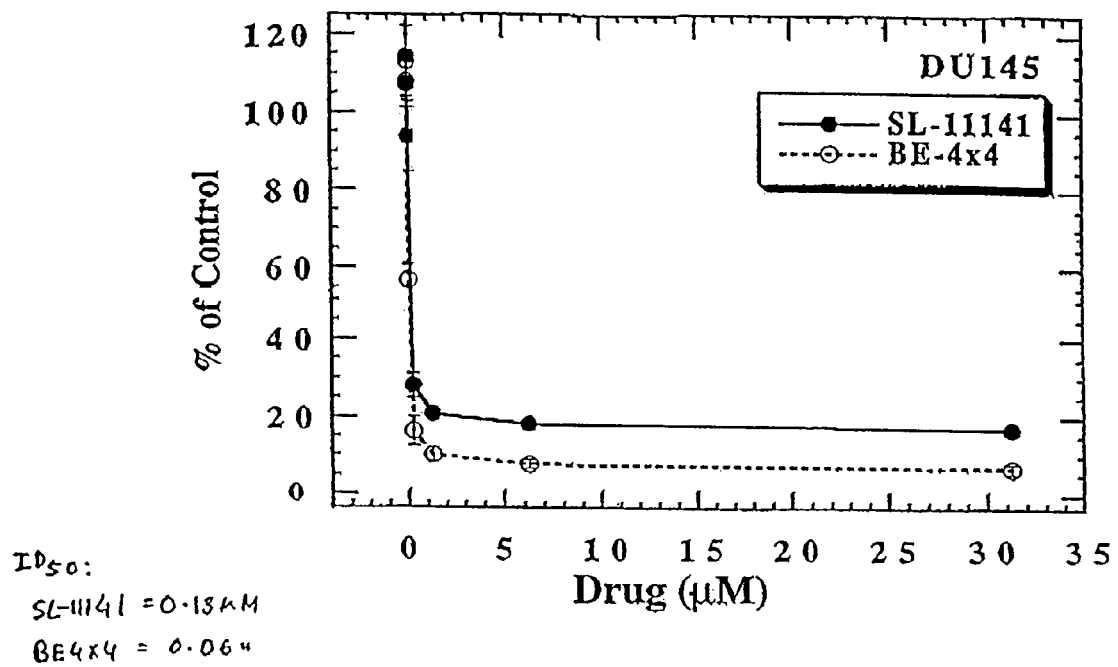
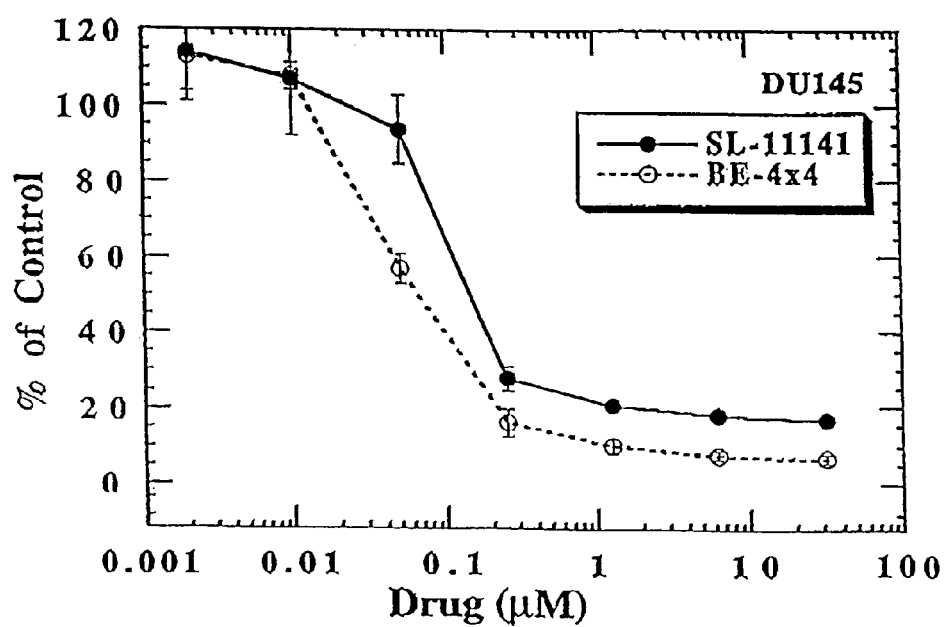

SEQUENCE LISTING

```
<160> NUMBER OF SEQ ID NOS: 14

<210> SEQ ID NO 1
<211> LENGTH: 6
<212> TYPE: PRT
<213> ORGANISM: Artificial Sequence
<220> FEATURE:
<223> OTHER INFORMATION: Synthesized peptide substrate for prostate
      specific antigen

<400> SEQUENCE: 1

His Ser Ser Lys Leu Gln
1               5

<210> SEQ ID NO 2
<211> LENGTH: 5
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 5
<223> OTHER INFORMATION: Xaa = Beta-Alanine

<400> SEQUENCE: 2

Ser Lys Leu Gln Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Synthesized peptide substrate for prostate
      specific antigen

<400> SEQUENCE: 3

Ser Lys Leu Gln Leu
1               5

<210> SEQ ID NO 4
```

```
<211> LENGTH: 4
<212> TYPE: PRT
<213> ORGANISM: Artificial Sequence
<220> FEATURE:
<223> OTHER INFORMATION: Synthesized peptide substrate for prostate
      specific antigen

<400> SEQUENCE: 4

Ser Lys Leu Gln
1

<210> SEQ ID NO 5
<211> LENGTH: 4
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 1
<223> OTHER INFORMATION: Xaa = N-alpha-Boc-Lys(N-epsilon-Cl-Cbz)
<220> FEATURE:
<221> NAME/KEY: VARIANT
<222> LOCATION: 4
<223> OTHER INFORMATION: Xaa = beta-Ala-beta-lapachone

<400> SEQUENCE: 5

Xaa Leu Gln Xaa
1

<210> SEQ ID NO 6
<211> LENGTH: 4
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 1
<223> OTHER INFORMATION: Xaa = Lys(N-epsilon-Cl-Cbz)
<220> FEATURE:
<221> NAME/KEY: VARIANT
<222> LOCATION: 4
<223> OTHER INFORMATION: Xaa = Leu-(beta-lapachone)

<400> SEQUENCE: 6

Xaa Leu Gln Xaa
1

<210> SEQ ID NO 7
<211> LENGTH: 5
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 1
<223> OTHER INFORMATION: Xaa = morpholino-Ser-(OBn)
<220> FEATURE:
<221> NAME/KEY: VARIANT
<222> LOCATION: 2
<223> OTHER INFORMATION: Xaa = Lys(N-epsilon-Cl-Cbz)
<220> FEATURE:
<221> NAME/KEY: VARIANT
<222> LOCATION: 5
<223> OTHER INFORMATION: Xaa = beta-Ala-beta-lapachone

<400> SEQUENCE: 7
```

```
Xaa Xaa Leu Gln Xaa
 1               5

<210> SEQ ID NO 8
<211> LENGTH: 5
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 1
<223> OTHER INFORMATION: Xaa = morpholino-Ser
<220> FEATURE:
<221> NAME/KEY: VARIANT
<222> LOCATION: 5
<223> OTHER INFORMATION: Xaa = beta-Ala-beta-lapachone

<400> SEQUENCE: 8

Xaa Lys Leu Gln Xaa
 1               5

<210> SEQ ID NO 9
<211> LENGTH: 4
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 1
<223> OTHER INFORMATION: Xaa = Boc-Lys-(N-epsilon-Cl-Cbz)
<220> FEATURE:
<221> NAME/KEY: VARIANT
<222> LOCATION: 4
<223> OTHER INFORMATION: Xaa = Leu-beta-lapachone

<400> SEQUENCE: 9

Xaa Leu Gln Xaa
 1

<210> SEQ ID NO 10
<211> LENGTH: 4
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 1
<223> OTHER INFORMATION: Xaa = Lys(N-epsilon-Cl-Cbz)
<220> FEATURE:
<221> NAME/KEY: VARIANT
<222> LOCATION: 4
<223> OTHER INFORMATION: Xaa = Leu-beta-lapachone

<400> SEQUENCE: 10

Xaa Leu Gln Xaa
 1

<210> SEQ ID NO 11
<211> LENGTH: 5
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
```

```
<222> LOCATION: 1
<223> OTHER INFORMATION: Xaa = morpholino-Ser(OBn)
<220> FEATURE:
<221> NAME/KEY: VARIANT
<222> LOCATION: 2
<223> OTHER INFORMATION: Xaa = Lys(N-epsilon-Cl-Cbz)
<220> FEATURE:
<221> NAME/KEY: VARIANT
<222> LOCATION: 5
<223> OTHER INFORMATION: Xaa = Leu-beta-lapachone

<400> SEQUENCE: 11

Xaa Xaa Leu Gln Xaa
 1               5

<210> SEQ ID NO 12
<211> LENGTH: 5
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 1
<223> OTHER INFORMATION: Xaa = morpholino-Ser
<220> FEATURE:
<221> NAME/KEY: VARIANT
<222> LOCATION: 5
<223> OTHER INFORMATION: Xaa = Leu-beta-lapachone

<400> SEQUENCE: 12

Xaa Lys Leu Gln Xaa
 1               5

<210> SEQ ID NO 13
<211> LENGTH: 4
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 1
<223> OTHER INFORMATION: Xaa = morpholino-Ser

<400> SEQUENCE: 13

Xaa Lys Leu Gln
 1

<210> SEQ ID NO 14
<211> LENGTH: 4
<212> TYPE: PRT
<213> ORGANISM: Artificial Sequence
<220> FEATURE:
<223> OTHER INFORMATION: Synthesized peptide substrate for prostate
      specific antigen
<220> FEATURE:
<221> NAME/KEY: VARIANT
<222> LOCATION: 1
<223> OTHER INFORMATION: Xaa = Morpholino-Ser
<220> FEATURE:
<221> NAME/KEY: VARIANT
<222> LOCATION: 4
<223> OTHER INFORMATION: Xaa = Gln-Quin

<400> SEQUENCE: 14

Xaa Lys Leu Xaa
 1
```

POLYAMINE ANALOG CONJUGATES AND QUINONE CONJUGATES AS THERAPIES FOR CANCERS AND PROSTATE DISEASES

CROSS-REFERENCE TO RELATED APPLICATIONS

This application is a continuation of U.S. patent application Ser. No. 10/385,224 filed Mar. 10, 2003 (now abandoned), which is a continuation of U.S. patent application Ser. No. 09/561,172 filed Apr. 27, 2000 (now U.S. Pat. No. 6,649,587) which in turn claims priority to U.S. Provisional Patent Application Ser. No. 60/131,809 filed Apr. 30, 1999 (now abandoned). The contents of those applications are hereby incorporated by reference herein in their entireties.

STATEMENT OF RIGHTS TO INVENTIONS MADE UNDER FEDERALLY SPONSORED RESEARCH

Not applicable

TECHNICAL FIELD

This invention relates to therapeutic compositions in which a cytostatic or cytocidal compound, such as a polyamine analog or a quinone, is conjugated to a polypeptide recognized and cleaved by enzymes such as prostate specific antigen (PSA) and cathepsin B. This invention also relates to medicinal uses of these conjugates, such as uses in treating cancer, and uses in treating prostate diseases such as prostate cancer, prostatitis and benign prostatic hyperplasia (BPH).

BACKGROUND OF THE INVENTION

Despite advances in early diagnosis, prostate cancer remains a disease with high and increasing annual incidence and mortality. Prostate cancer is now the most frequently diagnosed cancer in men. This cancer is often latent; many men carry prostate cancer cells without overt signs of disease. Autopsies of individuals dying of other causes show prostate cancer cells in 30% of men at age 50; by age 80, the prevalence is 60%. Further, prostate cancer can take up to 10 years to kill the patient after initial diagnosis. Prostate cancer is newly diagnosed in over 180,000 men in the U.S. each year, of which over 39,000 will die of the disease. In early stage cancers, metastasis occurs to lymph nodes. In late stage, metastasis to bone is common and often associated with uncontrollable pain.

In addition to cancer, two other significant diseases of the prostate are BPH and prostatitis. The cost of treating these three diseases is immense. The annual treatment of prostatic diseases in the U.S. requires about 4.4 million physician visits and 850,000 hospitalizations, and costs billions of dollars. Although treatments for prostatic diseases exist, these are generally only partially or temporarily effective and/or produce unacceptable side effects.

Benign prostatic hyperplasia (BPH) causes urinary obstruction, resulting in urinary incontinence. It occurs in almost 80% of men by the age of 80. BPH is often treated surgically with a transurethral resection of the prostate (TURP). This procedure is very common: 500,000 TURPs are performed in the U.S. each year and BPH is the second most common cause of surgery in males. Unfortunately, a side-effect of TURP is the elimination of the ejaculatory ducts and the nerve bundles of the penis, resulting in impotence in 90% of patients.

An alternative therapy for prostate cancer involves radiation therapy. A catheter has been developed which squeezes prostate tissue during microwave irradiation; this increases the therapeutic temperature to which the prostate tissue more distal to the microwave antennae can be heated without excessively heating nearby non-prostate tissue. U.S. Pat. No. 5,007,437. A combination of a radiating energy device integrated with a urinary drainage Foley type catheter has also been developed. U.S. Pat. No. 5,344,435. However, cancerous prostatic cells generally demonstrate a slow growth rate; few cancer cells are actively dividing at any one time. As a result, prostate cancer is generally resistant to radiation therapy.

This slow growth rate also makes prostate cancer resistant to chemotherapy, although several such methods are now in use or in development. Pharmacotherapy for the treatment of BPH is currently aimed at relaxing prostate smooth muscle (alpha$_1$ blockade) and decreasing prostate volume (androgen suppression). Clinical trials have been undertaken to evaluate selective alpha$_1$ blockers, antiandrogens, and 5-alpha reductase inhibitors for the treatment of BPH. Finasteride, a 5-alpha reductase inhibitor, has shown an ability to cause regression of the hyperplastic prostate gland in a majority of patients. Mocellini et. al. (1993) *Prostate* 22:291; and Marberger (1998) *Urology* 51:677-86.

Additional therapeutic techniques for prostate cancer include using chemical forms of medical castration by shutting down androgen production in the testes, or directly blocking androgen production in the prostate. For the treatment of prostate cancer oral estrogens and luteinizing releasing hormone analogs are used as well as surgical removal of glands that produce androgens (orchiectomy or adrenalectomy). However, estrogens are no longer recommended because of serious, even lethal, cardiovascular complications. Luteinizing hormone releasing hormone (LHRH) analogs are used instead. However, hormonal therapy invariably fails with time with the development of hormone-resistant tumor cells. Furthermore, since 20% of patients fail to respond to hormonal therapy, it is believed that hormone-resistant cells are present at the onset of therapy.

Estramustine, a steroidal nitrogen mustard derivative, was originally thought to be suitable for targeted drug delivery through conjugation of estrogen to toxic nitrogen mustard. Clinical trials, however, have been disappointing when survival is used as an endpoint. Finasteride, a 4-aza steroid (Proscar® from Merck & Co.), inhibits the enzyme responsible for the intracellular conversion of testosterone to dihydrotestosterone, the most potent androgen in the prostate. Casodex® (bicalutamide, Zeneca, Ltd.), a non-steroidal anti-androgen, is thought to inhibit cellular uptake of testosterone by blocking androgen receptors in the nucleus. However, almost all advanced cancer prostate cells fail to respond to androgen deprivation.

An additional method for treating prostatic diseases involves administration of inhibitors of polyamine synthesis. Dunzendorfer (1985) *Urol. Int.* 40:241-250. Naturally-produced polyamines include spermidine and spermine and their precursor, diamine putrescine, which are secreted by the prostate gland and are abundant in the seminal fluid. Polyamines are required for cell division, and probably for differentiation. Spermine apparently stabilizes the DNA, which is tightly packed in the heads of sperm cells. Polyamines may be essential for stability of actin filament bundles and microtubules. However, polyamine biosynthesis inhibitors such as alpha-difluoromethylornithine (DFMO) cause toxicities, including severe hearing loss, these toxicities sometimes forcing the cessation of treatment. Splinter et al. (1986) *Eur. J. Cancer Clin. Oncol.* 22:61-67; and Horn et al. (1987) *Eur. J. Cancer Clin. Oncol.* 23:1103-1107. Another inhibitor, methylglyoxal-bis-guanyl-hydrazone (MGBG), caused side effects so extreme that, in one study, drug deaths occurred in over half of treated animals. Dunzendorfer (1985); and Herr et al. (1984) *Cancer* 53:1294-1298.

A related type of therapy for prostate cancer involves using polyamine analogs, such as DENSPM (N1,N11-diethylnorspermine or BE-333). Mi et al. (1988) *Prostate* 34:51-60. While the precise role(s) of naturally-produced polyamines have not been clearly defined, interactions with DNA and RNA have been convincingly implicated. Since the nature of these interactions is highly structure-dependent, polyamine analogs have been designed to effectively disrupt polyamine function by competition with naturally-occurring polyamines. Several polyamine analogs have been developed that exert marked inhibition of human tumor cell growth both in culture and in nude mice xenografts. Polyamine analogs such as BE-4444 [1,19-bis(ethylamino)-5,10,15-triazanonadecane], BE-373 [N,N'-bis(3-ethylamino) propyl)-1,7-heptane diamine], and BE-333 are particularly effective in inhibiting prostate xenograft tumors in nude mice. Zagaja et al. (1998) *Cancer Chem. Pharm.* 41:505-512; Jeffers et al. (1997) *Cancer Chem. Pharm.* 40:172-179; Feuerstein et al. (1991) *J. Cell. Biochem.* 46:37-47; and Marton et al. (1995) *Ann. Rev. Pharm. Toxicol.* 35:55-91. However, polyamine analogs can cause systemic toxicity. BE-333, for example, causes side effects such as headache, nausea and vomiting, unilateral weakness, dysphagia, dysarthria, numbness, paresthesias, and ataxia. Creaven et al. (1997) *Invest. New Drugs* 15:227-34. In one test, administration of BE-333 caused labored breathing, convulsive movements and acute death in rats. Kanter et al. (1994) *Anticancer Drugs* 5:448-56. This toxicity limits many polyamine analogs to a small therapeutic window.

None of the above techniques for treating prostate diseases has been universally successful. Following localized therapy, up to 40% of patients with advanced disease, and a large proportion of all patients, eventually develop metastatic disease. Treatment for advanced disease initially involving hormonal manipulations and palliative radiotherapy have demonstrated symptomatic relief, but not long-term disease-free survival. The use of cytotoxic agents in the management of hormone-resistant advanced prostate cancer remains poorly defined. A few single agents have become "standard therapy", although demonstration of their efficacy, by contemporary standards, is lacking. Combinational chemotherapy is frequently employed, although its contribution to overall patient management is largely unsubstantiated, especially when critical assessment of efficacy parameters are used. Newer approaches using chemohormonal therapy and hormonal priming therapies have failed. High-dose chemotherapy with transplant regimens are not well-tolerated in an elderly population, to which most victims of prostate cancer belong. A growth factor inhibitor, suramin, has shown promising initial results, but also many side effects. Allolio et al. (1989) *Dtsch. Med. Woschenschr.* 114:381-4; and Broder et al. (1985) *Lancet* 2:627-30. However, no therapy to date has been demonstrated to improve overall survival in patients with advanced hormone refractory prostate cancer.

Approximately one out of every four males above the age of 55 suffers from a prostate disease. Due to the aging U.S. population, the incidence of BPH, prostatitis and prostate cancer is likely to increase and to become an even more severe problem.

It would be advantageous to develop a new treatment of prostate cancer which retains the potency of chemotherapy without being subject to the various side effects and disadvantages of current therapies.

All references cited herein are hereby incorporated by reference in their entirety.

SUMMARY OF THE INVENTION

The invention provides therapeutic compositions in which a cytostatic or cytocidal agent is conjugated to a polypeptide, where the polypeptide is cleaved from the agent by an enzyme.

In one embodiment, the cytostatic or cytocidal agent is a polyamine analog. The polyamine analog can be linked to the peptide at the carboxy terminus of the peptide by an amide linkage to a primary or secondary amine group of the polyamine. The polyamine analog can contain a hydroxy group, and can be linked to the peptide at the carboxy terminus of the peptide by an ester linkage through the hydroxy group. In another embodiment, the polyamine analog is conformationally restricted.

In another embodiment of the invention, the polyamine analog linked to the polypeptide is of the formula:

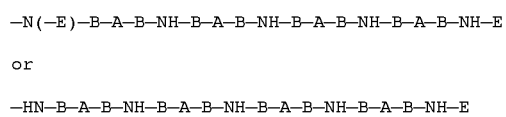

wherein each A is independently selected from the group consisting of a single bond, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; each B is independently selected from the group consisting of: a single bond, $C_1$-$C_6$ alkyl, and $C_2$-$C_6$ alkenyl; and each E is independently selected from the group consisting of H, $C_1$-$C_6$ alkyl, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; and any salt or stereoisomer thereof In another embodiment of the invention, the polyamine analog linked to the polypeptide is of the formula:

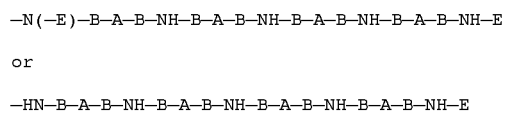

wherein each A is independently selected from the group consisting of a single bond, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; each B is independently selected from the group consisting of: a single bond, $C_1$-$C_6$ alkyl, and $C_2$-$C_6$ alkenyl; and each E is independently selected from the group consisting of H, $C_1$-$C_6$ alkyl, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; with the proviso that either at least one A moiety is selected from the group consisting of $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl, or at least one B moiety is selected from the group consisting of $C_2$-$C_6$ alkenyl; and any salt or stereoisomer thereof.

In another embodiment of the invention, the polyamine analog linked to the polypeptide is of the formula:

$$-N(-E)-B-A-B-NH-B-A-B-NH-B-A-B-NH(-B-A-B-NH)_x-E$$

or $$-HN-B-A-B-NH-B-A-B-NH-B-A-B-NH(-B-A-B-NH)_x-E$$

wherein each A is independently selected from the group consisting of: a single bond, $C_6$-$C_2$ alkyl, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; each B is independently selected from the group consisting of: a single bond, $C_1$-$C_6$ alkyl, and $C_2$-$C_6$ alkenyl; each E is independently selected from the group consisting of H, $C_1$-$C_6$ alkyl, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; and x is an integer from 2 to 16; and any salt or stereoisomer thereof.

In another embodiment of the invention, the polyamine analog linked to the polypeptide is of the formula:

$$-N(-E)-B-A-B-NH-B-A-B-NH-B-A-B-NH(-B-A-B-NH)_x-E$$

or $$-HN-B-A-B-NH-B-A-B-NH-B-A-B-NH(-B-A-B-NH)_x-E$$

wherein each A is independently selected from the group consisting of: a single bond, $C_6$-$C_2$ alkyl, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; each B is independently selected from the group consisting of: a single bond, $C_1$-$C_6$ alkyl, and $C_2$-$C_6$ alkenyl; each E is independently selected from the group consisting of H, $C_1$-$C_6$ alkyl, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; and x is an integer from 2 to 16; with the proviso that either at least one A moiety is selected from the group consisting of $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl, or at least one B moiety is selected from the group consisting of $C_2$-$C_6$ alkenyl; and any salt or stereoisomer thereof.

In another embodiment of the invention, the polyamine analog linked to the polypeptide is of the formula:

$$E-NH-B-A-B-NH-B-A-B-NH-B-A-B-NH(-B-A-B-NH)_x-E$$

wherein each A is independently selected from the group consisting of: a single bond, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; each B is independently selected from the group consisting of: a single bond, $C_1$-$C_6$ alkyl, and $C_2$-$C_6$ alkenyl; each E is independently selected from the group consisting of $C_1$-$C_6$ alkyl, $C_1$-$C_6$ alkanol, $C_3$-$C_6$ cycloalkanol, and $C_3$-$C_6$ hydroxyaryl, and the peptide is linked to the polyamine via an ester linkage at one and only one E group hydroxy; and x is an integer from 0 to 16; and any salt or stereoisomer thereof.

In another embodiment of the invention, the polyamine analog linked to the polypeptide is of the formula:

$$E-NH-B-A-B-NH-B-A-B-NH-B-A-B-NH(-B-A-B-NH)_x-E$$

wherein each A is independently selected from the group consisting of: a single bond, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; each B is independently selected from the group consisting of: a single bond, $C_1$-$C_6$ alkyl, and $C_2$-$C_6$ alkenyl; each E is independently selected from the group consisting of $C_1$-$C_6$ alkyl, $C_1$-$C_6$ alkanol, $C_3$-$C_6$ cycloalkanol, and $C_3$-$C_6$ hydroxyaryl, with the proviso that at least one E moiety be selected from the group consisting of $C_1$-$C_6$ alkanol, $C_3$-$C_6$ cycloalkanol, and $C_3$-$C_6$ hydroxyaryl, and the peptide is linked to the polyamine via an ester linkage at one and only one E group hydroxy; and x is an integer from 0 to 16; and any salt or stereoisomer thereof.

In another embodiment of the invention, the polyamine analog linked to the polypeptide is of the formula:

$$-N(-E)-D-NH-B-A-B-NH-D-NH-E$$

or $$-NH-D-NH-B-A-B-NH-D-NH-E$$

wherein A is selected from the group consisting of $C_2$-$C_6$ alkynyl; each B is independently selected from the group consisting of: a single bond, $C_1$-$C_6$ alkyl, and $C_2$-$C_6$ alkenyl; each D is independently selected from the group consisting of $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkenyl, and $C_3$-$C_6$ cycloaryl; and each E is independently selected from the group consisting of H, $C_1$-$C_6$ alkyl, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; and any salt or stereoisomer thereof.

In another embodiment of the invention, the polyamine analog linked to the polypeptide is of the formula:

$$-N(-E)-B-A-B-NH-F-NH-B-A-B-NH-E$$

or $$-NH-B-A-B-NH-F-NH-B-A-B-NH-E$$

wherein F is selected from the group consisting of $C_1$-$C_6$ alkyl; each A is independently selected from the group consisting of: a single bond, $C_1$-$C_6$ alkyl; $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; each B is independently selected from the group consisting of: a single bond, $C_1$-$C_6$ alkyl, and $C_2$-$C_6$ alkenyl; and each E is independently selected from the group consisting of H, $C_1$-$C_6$ alkyl, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; and any salt or stereoisomer thereof.

In another embodiment of the invention, the polyamine analog linked to the polypeptide is of the formula:

$$-N(-E)-B-A-B-NH-F-NH-B-A-B-NH-E$$

or $$-NH-B-A-B-NH-F-NH-B-A-B-NH-E$$

wherein F is selected from the group consisting of $C_1$-$C_6$ alkyl; each A is independently selected from the group consisting of: a single bond, $C_1$-$C_6$ alkyl; $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; each B is independently selected from the group consisting of: a single bond, $C_1$-$C_6$ alkyl, and $C_2$-$C_6$ alkenyl; and each E is independently selected from the group consisting of H, $C_1$-$C_6$ alkyl, $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl; with the proviso that either at least one A moiety is selected from the group consisting of $C_2$-$C_6$ alkenyl, $C_2$-$C_6$ alkynyl, $C_3$-$C_6$ cycloalkyl, $C_3$-$C_6$ cycloaryl, and $C_3$-$C_6$ cycloalkenyl, or at least one B moiety is selected from the group consisting of $C_2$-$C_6$ alkenyl; and any salt or stereoisomer thereof.

In another embodiment, the cytostatic or cytocidal agent is a quinone, such as a naphthoquinone. In one embodiment, the naphthoquinone contains a hydroxy group and is linked to the peptide by the hydroxy group. In another embodiment, the naphthoquinone contains a primary or secondary amino group and is linked to the peptide by the amino group.

In another embodiment of the invention, the quinone linked to the polypeptide is selected from compounds of the formula

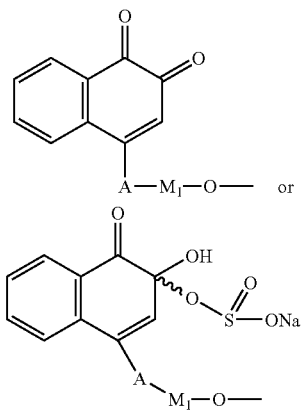

wherein A is —CH2-, —O—, —C(=O)—O—, or —O—C(=O)—, and $M_1$ is $C_1$-$C_8$ alkyl, $C_1$-$C_8$ branched alkyl, $C_3$-$C_8$ cycloalkyl, or $C_3$-$C_8$ cycloaryl.

In another embodiment of the invention, the quinone linked to the polypeptide is selected from compounds of the formula

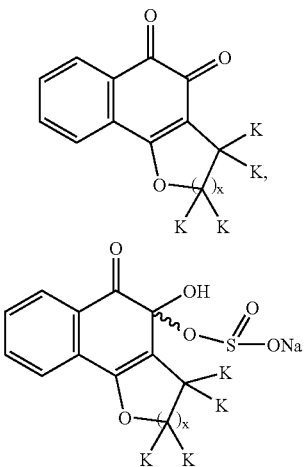

wherein x is 1 or 2; and each K is independently selected from the group consisting of H, OH, $C_1$-$C_8$ alkyl, $C_1$-$C_8$ alkenyl, $C_1$-$C_8$ alkanol, $C_1$-$C_8$ alkoxy, and

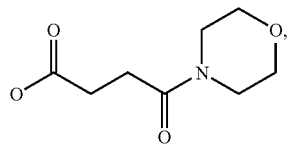

with the proviso that one and only one K is selected from the group consisting of OH and $C_1$-$C_8$ alkanol, the peptide being conjugated to the terminal hydroxy group of the alcohol; and where zero or two, but no more than two, vicinal K's in the molecule represent single electrons which form a pi bond, thus forming a double bond together with the existing sigma bond between the two adjacent carbons bearing the two vicinal K's.

In another embodiment of the invention, the quinone linked to the polypeptide is selected from compounds of the formula

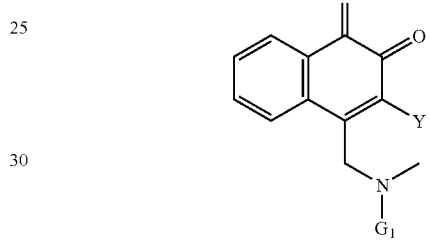

wherein Y is selected from the group consisting of —H, —F, —Br, —Cl, and —I; and wherein $G_1$ is selected from the group consisting of H, $C_1$-$C_8$ alkyl,

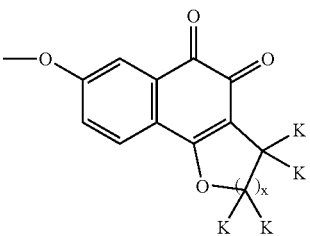

and —C(=O)—$CH_nX_{3-n}$, where n is an integer from 0 to 3 and X is selected from the group consisting of F, Cl, Br, and I; and the peptide is conjugated to the quinone via the amino group bearing G1.

In another embodiment of the invention, the quinone linked to the polypeptide is selected from compounds of the formula wherein x is 1 or 2; and each K is independently selected from the group consisting of H, $C_1$-$C_8$ alkyl, $C_1$-$C_8$ alkenyl, $C_1$-$C_8$ alkoxy, and

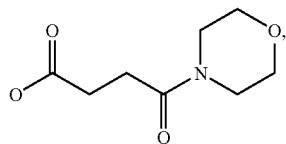

and where zero or two, but no more than two, vicinal K's in the molecule represent single electrons which form a pi bond, thus forming a double bond together with the existing sigma bond between the two adjacent carbons bearing the two vicinal K's.

In one embodiment of the invention, the cytostatic or cytocidal agent is conjugated to a polypeptide recognized and cleaved by prostate-specific antigen (PSA). In one embodiment, the polypeptide is recognized and cleaved by PSA and comprises less than about 25 amino acids. Preferably, the polypeptide comprises less than about 10 amino acids. More preferably, the polypeptide comprises the sequence HSSKLQ (SEQ ID NO:1). More preferably, the polypeptide comprises or consists of the sequence SKLQ-β-alanine (SEQ ID NO:2) or SKLQL, (SEQ ID NO:3) or comprises or consists of the sequence SKLQ (SEQ ID NO:4).

In another embodiment, the cytostatic or cytocidal agent is conjugated to a polypeptide recognized and cleaved by cathepsin B. In one embodiment, the peptide sequence is X—P2-P1, where X is hydrogen, an amino-protecting group, or an amino-capping group attached to the N-terminus of P2; where P2 is the N-terminal amino acid and P1 is the C-terminal amino acid; and where P2 is a hydrophobic amino acid and P1 is a basic or polar amino acid. In another embodiment, the peptide sequence is X—P2-P1-Y, where X is hydrogen, an amino-protecting group, or an amino-capping group attached to the N-terminus of P2; P2 is a hydrophobic amino acid; P1 is a basic or polar amino acid; and where Y is leucine, β-alanine, or a nonentity. In a further embodiment, X is a 4-morpholinocarbonyl group. In yet another embodiment, P2 is selected from the group consisting of leucine, isoleucine, valine, methionine, and phenylalanine; and P1 is selected from the group consisting of lysine, arginine, glutamine, asparagine, histidine and citrulline.

The invention also comprises compositions where the cytostatic or cytocidal agent conjugated to a polypeptide is combined with a pharmaceutically acceptable excipient.

The invention also provides methods of treating cancers and other diseases characterized by cell proliferation, for example prostate cancer, in an individual comprising administering to the individual an effective amount of a composition comprising a therapeutic amount of a cytostatic or cytocidal agent conjugated to a polypeptide. These conjugates include polyamine analog conjugates or quinone conjugates of the present invention, for example, a polyamine analog or a quinone conjugated to a polypeptide recognized and cleaved by an enzyme such as prostate-specific antigen (PSA) or cathepsin B. The disease can be prostatitis, benign prostate hyperplasia (BPH), or prostate cancer, and can include suppression of the proliferation of metastatic tumors. The individual can be a mammal, and is preferably a human.

$ED_{50}$ of BE-4444=0.6 μM, SL-11121=0.52 μM, SL-11122>31.25 μM, SL-11123>31.25 μM, SL-11126=0.2 μM SL-11127>31.25 μM, SL-11128=0.5 μM, SL-11129=1.7 μM, SL-11130>31.25 μM, and SL-11133>31.25 μM.

Figure 1:
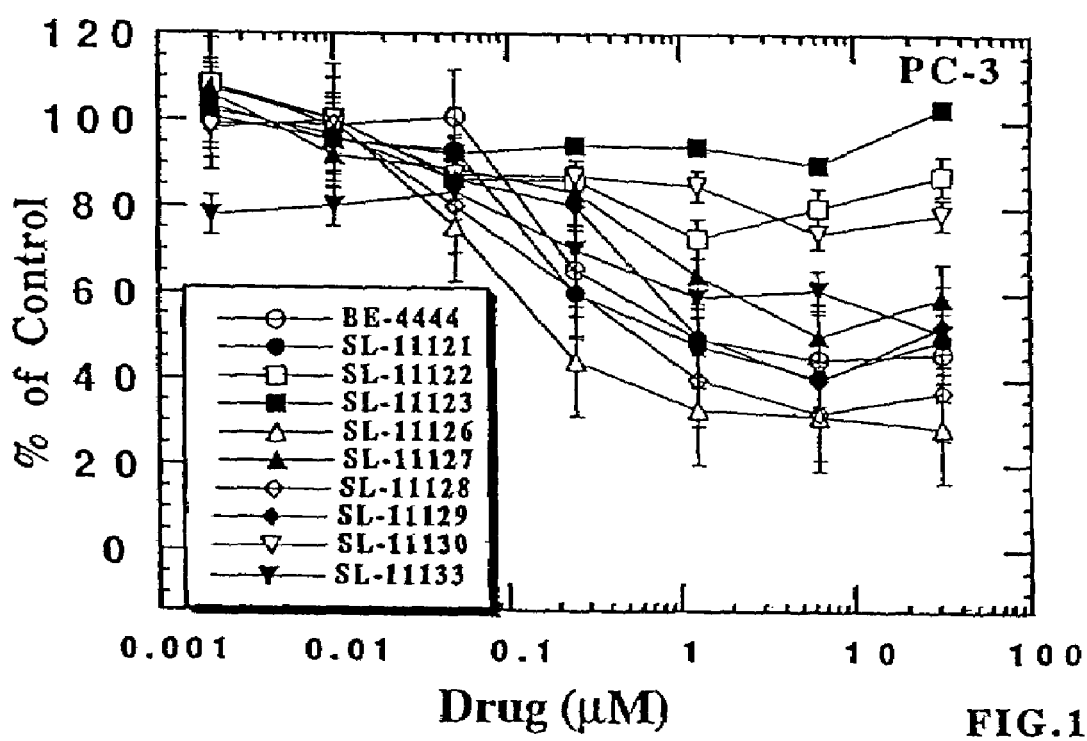
FIG. 1 is a graph depicting the in vitro effect of increasing concentrations of BE-4444 (○), SL-11121 (●), SL-11122 (□), SL-11123 (■), SL-11126 (Δ), SL-11127 (▲), SL-11128 (◇), SL-11129 (♦), SL-11130 (▽), SL-11133 (▼) on the survival of cultured human prostate cancer cells PC3.
Figure 2:
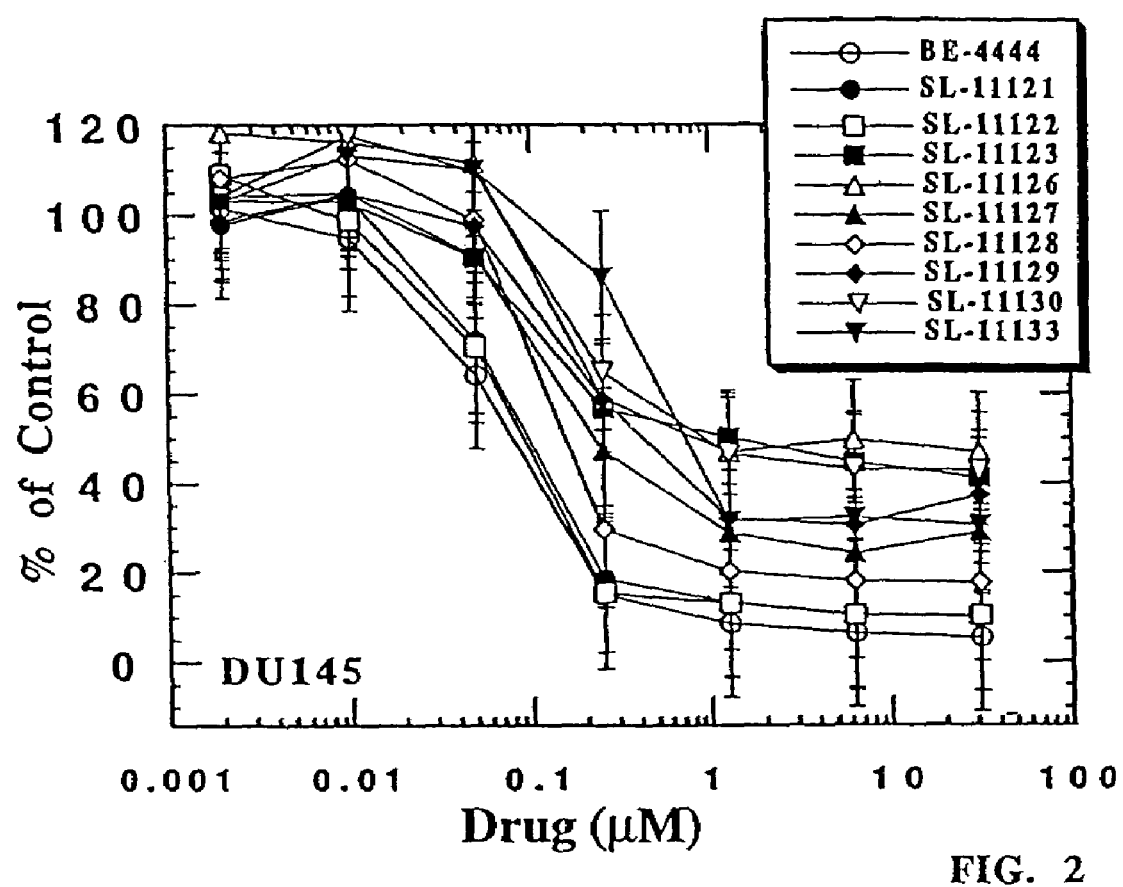

FIG. 2 is a graph depicting the in vitro effect of increasing concentrations of BE-4444 (○), SL-11121 (●), SL-11122 (□), SL-11123 (■), SL-11126 (Δ), SL-11127 (▲), SL-11128 (◇), SL-11129 (♦), SL-11130 (▽), and SL-11133 (▼) on the survival of cultured human prostate cancer cells DU145.

$ED_{50}$ of BE-4444=0.07 μM, SL-11121=0.08 μM, SL-11122=0.08 μM, SL-11123=0.51 μM, SL-11126=0.51 μM SL-11127 0.22 μM, SL-11128=0.14 μM, SL-11129=0.32 μM, SL-11130=0.43 μM, and SL-11133=0.34 μM.

Figure 3:
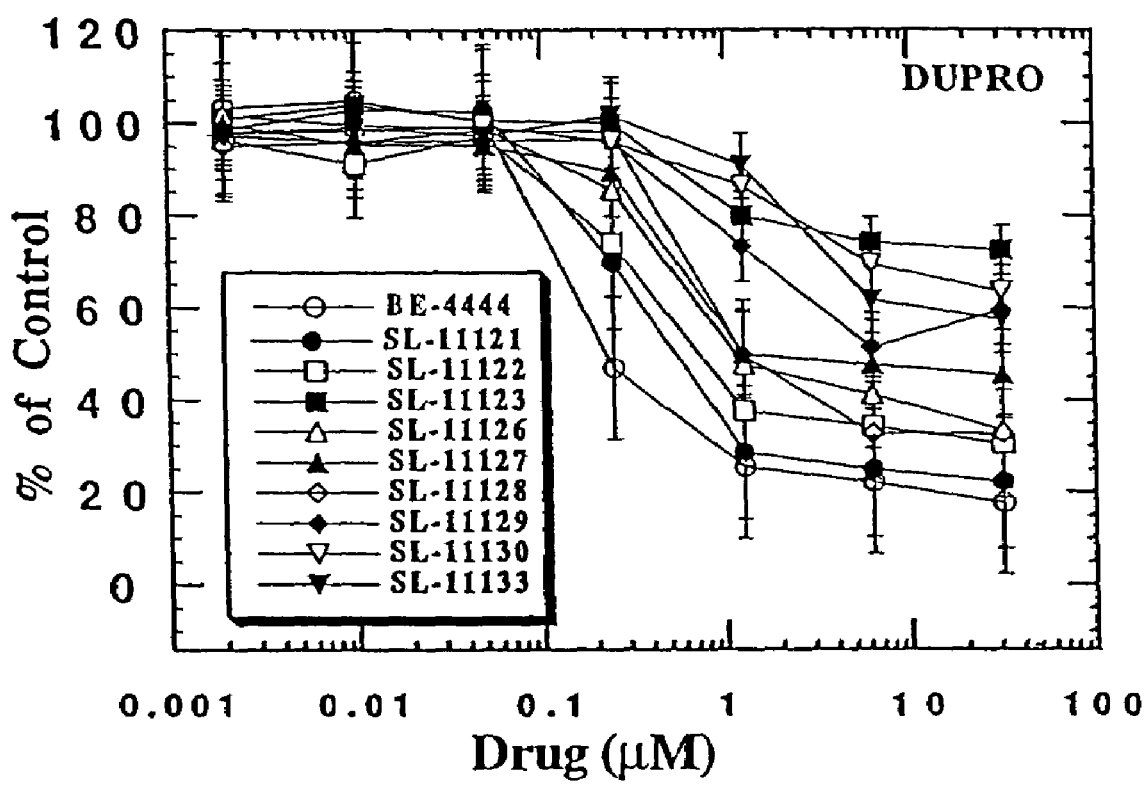

FIG. 3 is a graph depicting the in vitro effect of increasing concentrations of BE-4444 (○), SL-11121 (●), SL-11122 (□), SL-11123 (■), SL-11126 (Δ), SL-11127 (▲), SL-11128 (◇), SL-11129 (♦), SL-11130 (▽), and SL-11133 (▼) on the survival of cultured human prostate cancer cells DUPRO.

$ED_{50}$ of BE-4444=0.2 μM, SL-11121=0.4 μM, SL-11122=0.56 μM, SL-11123>31.25 μM, SL-11126=1.1 μM, SL-11127 1.3 μM, SL-11128=1.28 μM, SL-11129>31.25 μM, SL-11130>31.25 μM, and SL-11133=31.25 μM.

Figure 4:
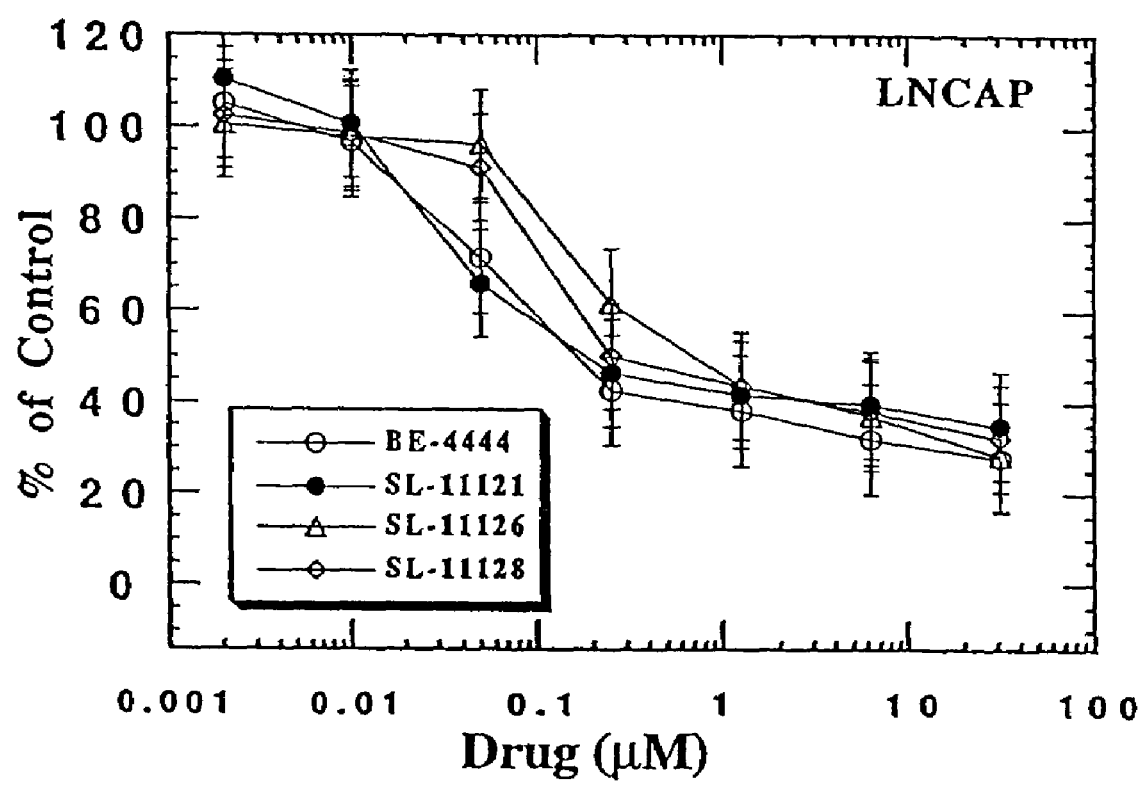

FIG. 4 is a graph depicting the in vitro effect of increasing concentrations of BE-4444 (○), SL-11121 (●), SL-11126 (Δ), SL-11128 (◇), on the survival of cultured human prostate cancer cells LNCAP.

$ED_{50}$ of BE-4444=0.14 μM, SL-11121=0.14 μM, SL-11126=0.55 μM and SL-11128=0.3 μM.

Figure 5:
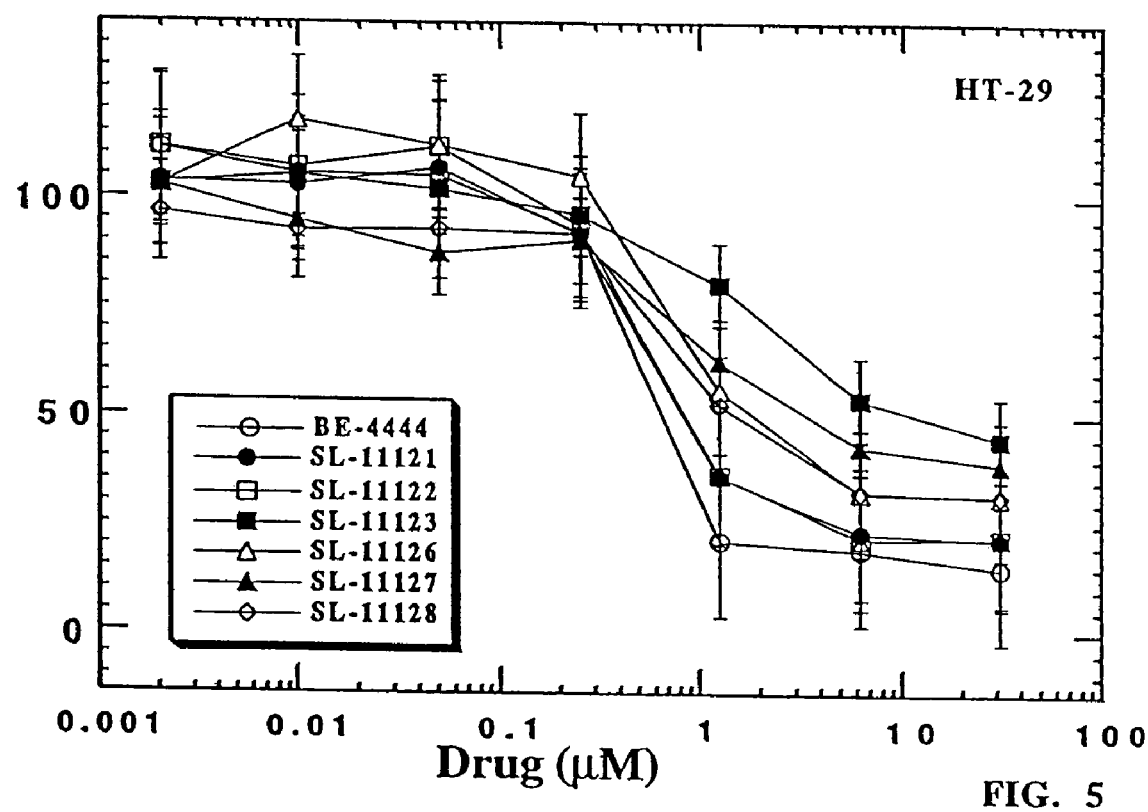

FIG. 5 is a graph depicting the in vitro effect of increasing concentrations of BE-4444 (○), SL-11121 (●), SL-11122 (□), SL-11123 (■), SL-11126 (Δ), SL-11127 (▲), and SL-11128 (◇) on the survival of cultured human colon cancer cells HT29.

$ED_{50}$ of BE-4444=0.5 μM, SL-11121=0.8 μM, SL-11122=0.8 μM, SL-11123=10.42 μM, SL-11126=1.5 μM, SL-11127=2.91 μM, and SL-11128=1.35 μM.

Figure 6:
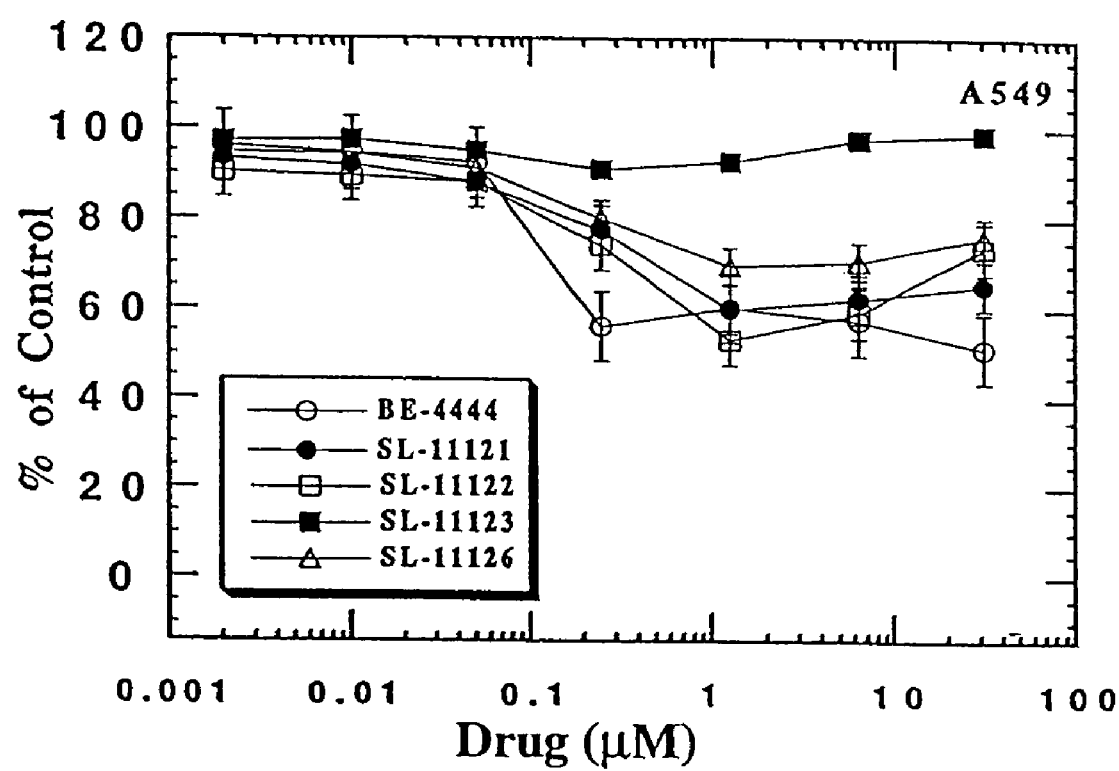

FIG. 6 is a graph depicting the in vitro effect of increasing concentrations of BE-4444 (○), SL-11121 (●), SL-11122 (□), SL-11123 (■), and SL-11126(Δ) on the survival of cultured human lung cancer cells A549.

$ED_{50}$ of BE-4444>31.25 μM, SL-11121>31.25 μM, SL-11122>31.25 μM, SL-11123>31.25 μM, and SL-11126>31.25 μM.

Figure 7:
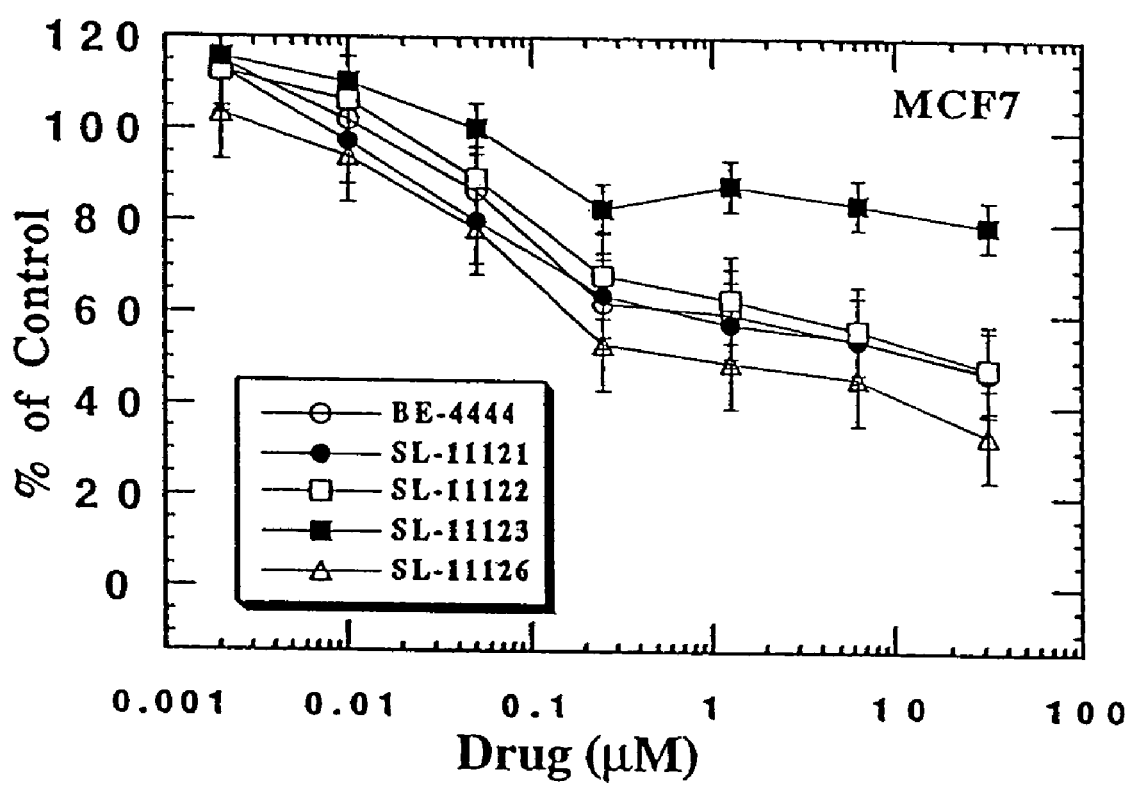

FIG. 7 is a graph depicting the in vitro effect of increasing concentrations of BE-4444 (○), SL-11121 (●), SL-11122 (□), SL-11123 (■), and SL-11126 (Δ) on the survival of cultured human breast cancer cells MCF7.

$ED_{50}$ of BE-4444>31.25 μM, SL-11121=17.0 μM, SL-11122>31.25 μM, SL-11123>31.25 μM, and SL-11126=0.7 μM.

Figure 8:
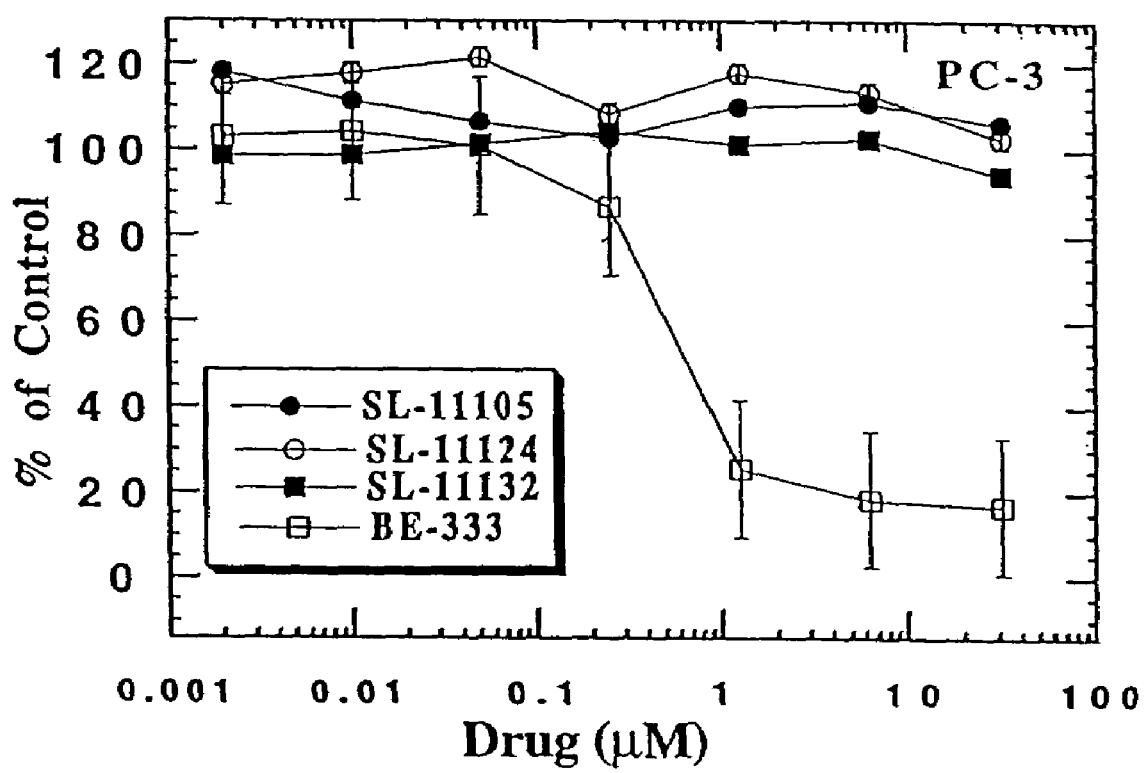

FIG. 8 is a graph depicting the in vitro effect of increasing concentrations of SL-11105 (●), SL-11124 (○), SL-11132 (■), and BE-333 (□) on the survival of cultured human prostate cancer cells PC3.

$ED_{50}$ of SL-11105>31.25 μM, SL-11124>31.25 μM, SL-11132>31.25 μM and BE-333=0.34 μM.

Figure 9:
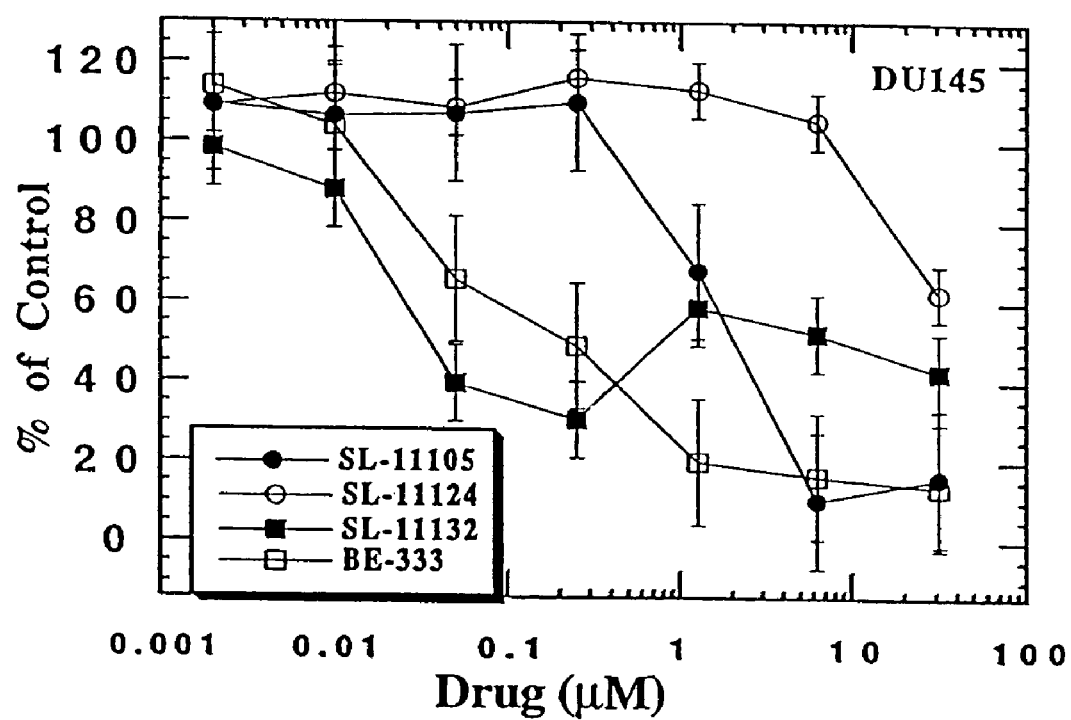

FIG. 9 is a graph depicting the in vitro effect of increasing concentrations of SL-11105 (●), SL-11124 (○), SL-11132 (■), and BE-333 (□) on the survival of cultured human prostate cancer cells DU145.

$ED_{50}$ of SL-11105=1.6 μM, SL-11124>31.25 μM, SL-11132=0.015 μM and BE-333=0.12 μM.

Figure 10:
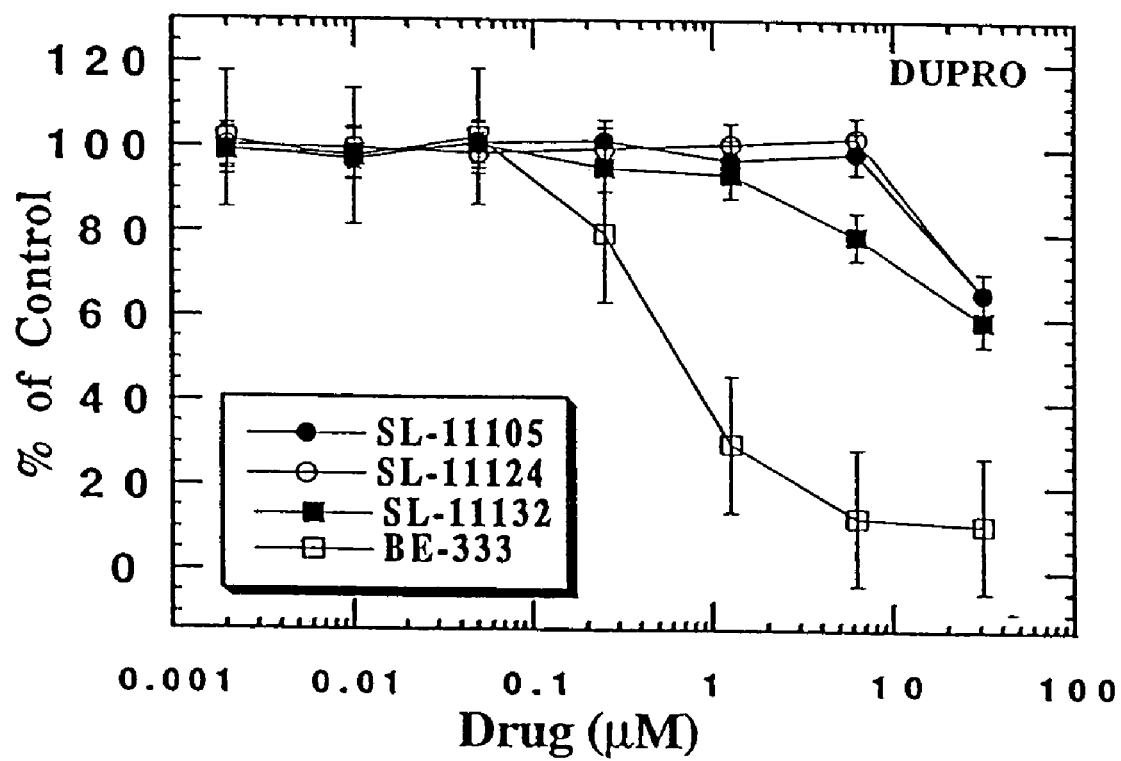

FIG. 10 is a graph depicting the in vitro effect of increasing concentrations of SL-11105 (●), SL-11124 (○), SL-11132 (■), and BE-333 (□) on the survival of cultured human prostate cancer cells DUPRO.

$ED_{50}$ of SL-11105=0.43 μM, SL-11124>31.25 μM, SL-11132>31.25 μM and BE-333=0.9 μM.

Figure 11:
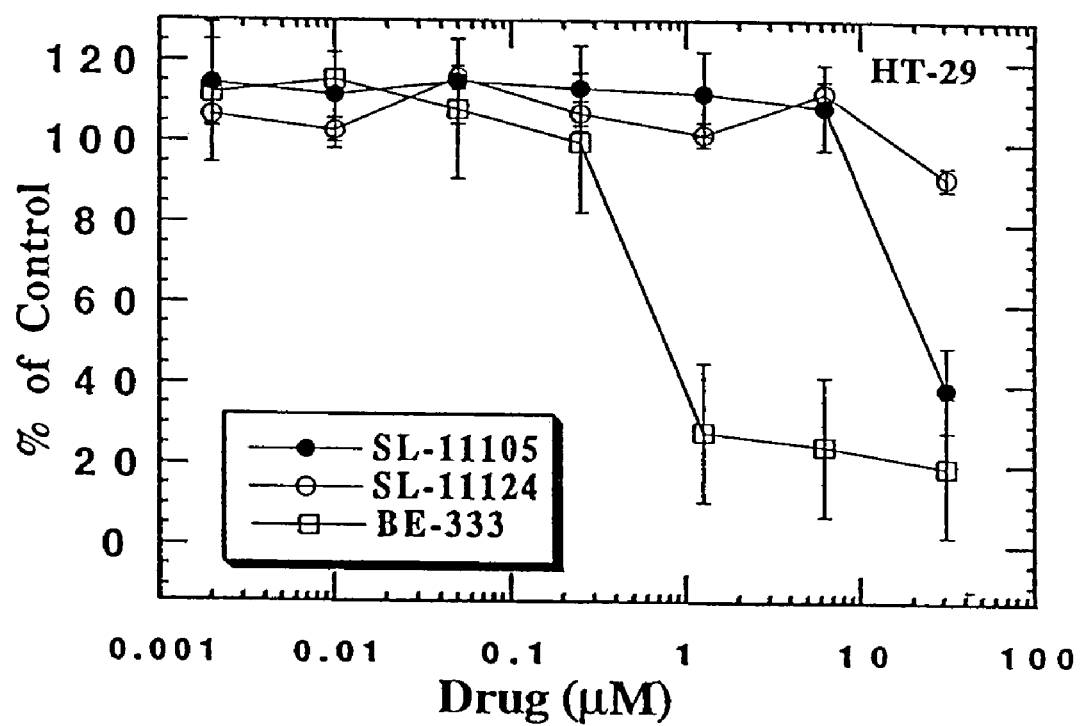

FIG. 11 is a graph depicting the in vitro effect of increasing concentrations of SL-11105 (●), SL-11124 (○), and BE-333 (□) on the survival of cultured human colon cancer cells HT29.

$ED_{50}$ of SL-11105=25.2 μM, SL-11124>31.25 μM, and BE-333=0.3 μM.

Figure 12:
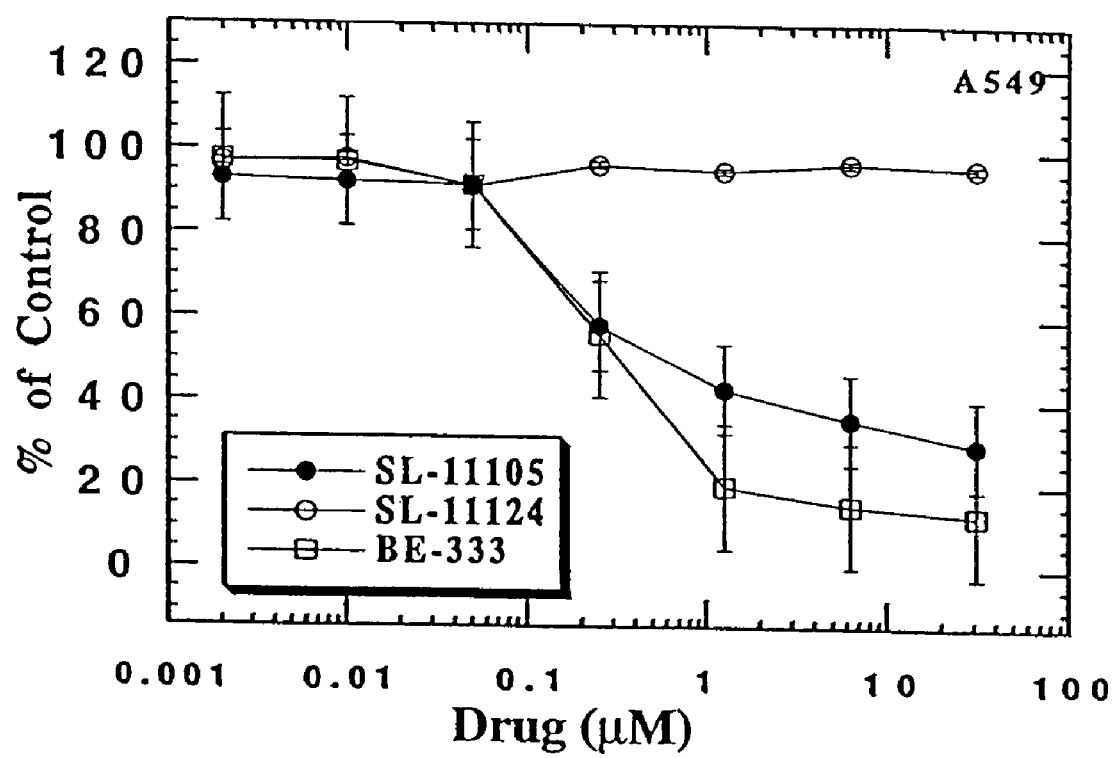

FIG. 12 is a graph depicting the in vitro effect of increasing concentrations of SL-11105 (●), SL-11124 (○), and BE-333 (□) on the survival of cultured human lung cancer cells A549.

$ED_{50}$ of SL-11105=0.43 μM, SL-11124>31.25 μM, and BE-333=0.3 μM.

Figure 13:
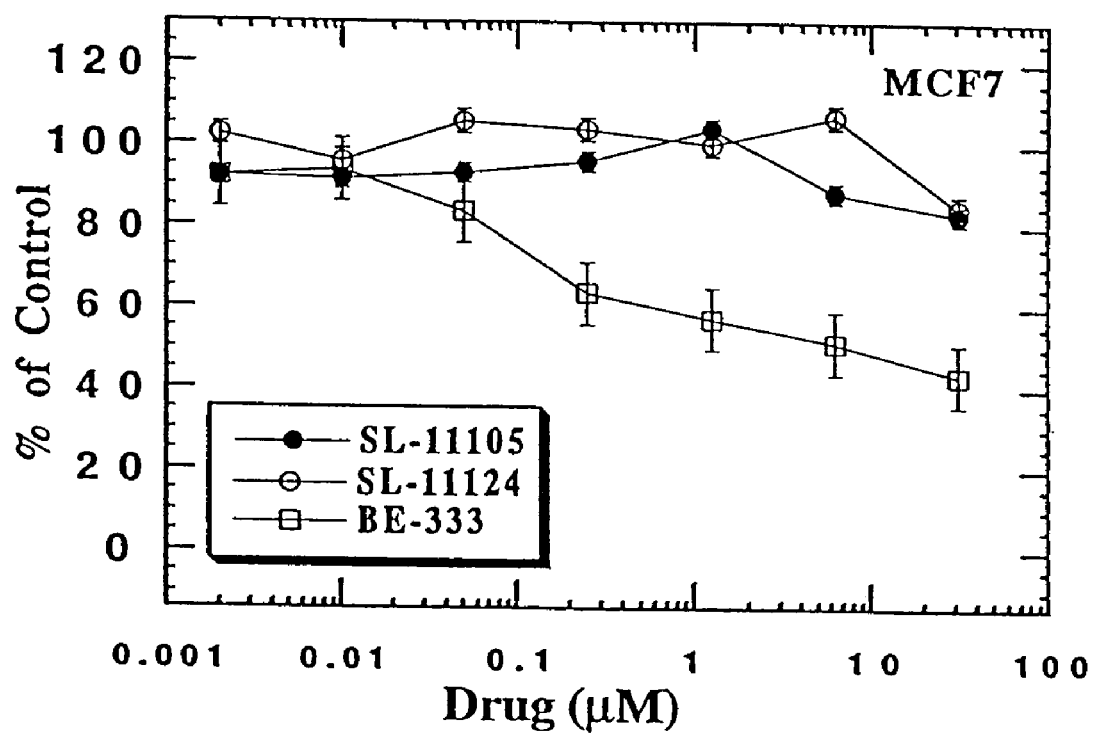

FIG. 13 is a graph depicting the in vitro effect of increasing concentrations of SL-11105 (●), SL-11124 (○), and BE-333 (□) on the survival of cultured human breast cancer cells MCF7.

$ED_{50}$ of SL-11105>31.25 μM, SL-11124>31.25 μM, and BE-333=3.7 μM.

Figure 14:
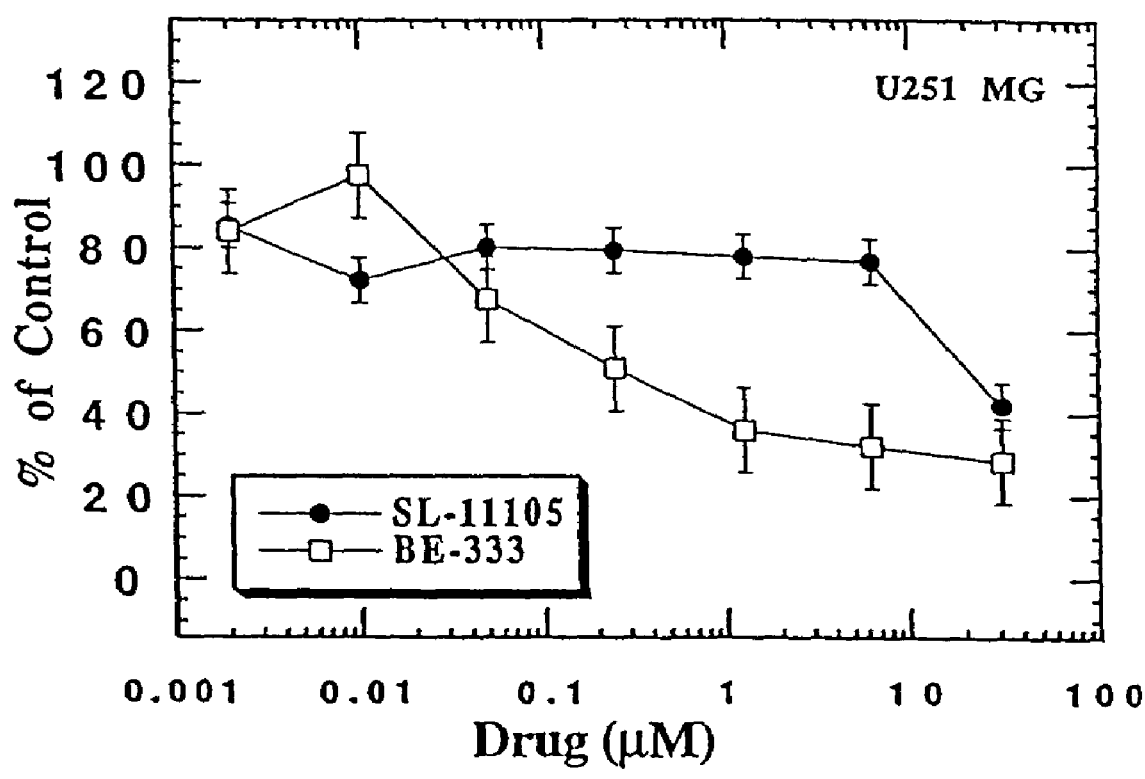

FIG. 14 is a graph depicting the in vitro effect of increasing concentrations of SL-11105 (●) and BE-333 (□) on the survival of cultured human brain tumor cells U251 MG NCI.

$ED_{50}$ of SL-11105=25.9 μM, and BE-333=0.23 μM.

Figure 15A:
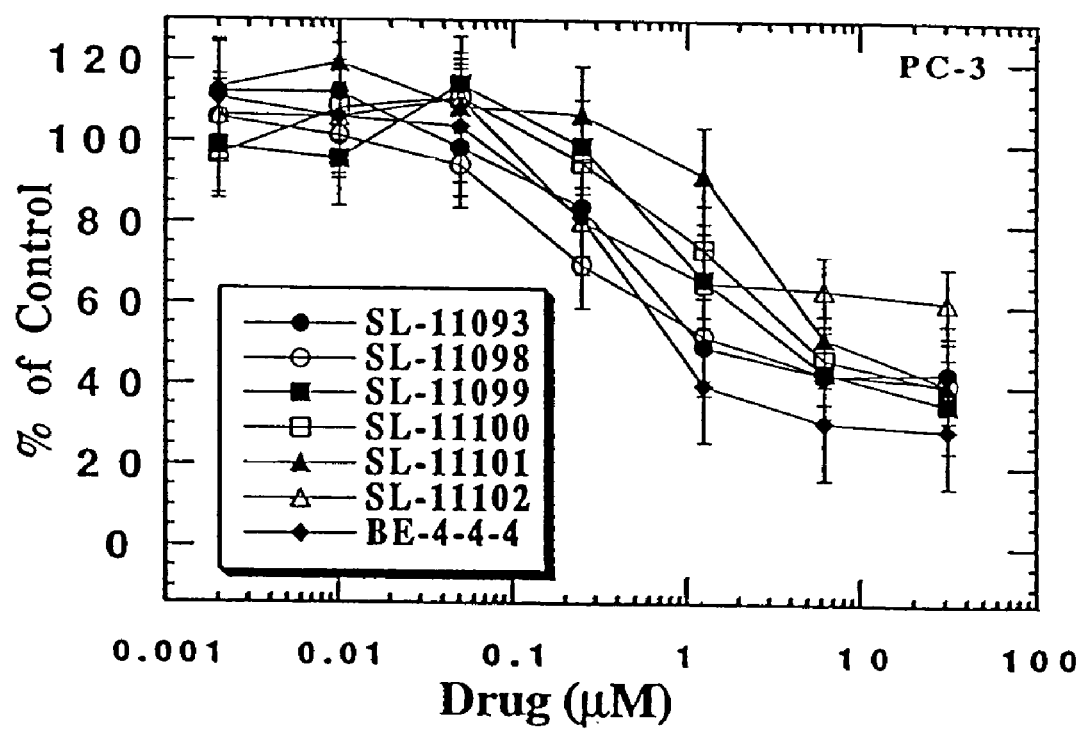

FIG. 15A is a graph depicting the in vitro effect of increasing concentrations of SL-11093 (●), SL-11098 (○), SL-11099 (■), SL-1100 (□), SL-11101 (▲), SL-11102 (Δ), and BE-444 (◆) on the survival of cultured human prostate cancer cells PC3.

$ED_{50}$ of SL-11093=1.6 μM, SL-11098=1.4 μM, SL-11099=2.5 μM, SL-11100=4.7 μM, SL-11101=7.7 μM, SL-11102>31.25 μM and BE-444=0.7 μM.

Figure 15B:
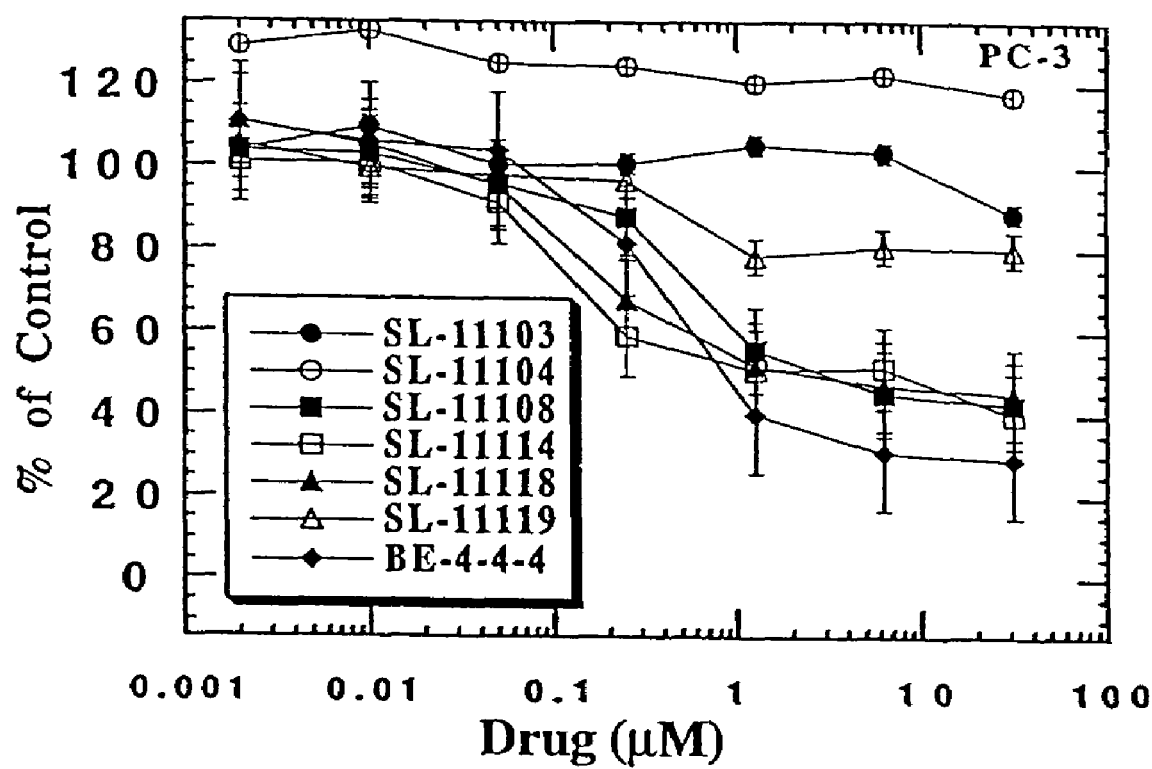

FIG. 15B is a graph depicting the in vitro effect of increasing concentrations of SL-11103 (●), SL-11104 (○), SL-11108 (■), SL-11114 (□), SL-11118 (▲), SL-11119 (Δ), and BE-444 (◆) on the survival of cultured human prostate cancer cells PC3.

Figure 16:
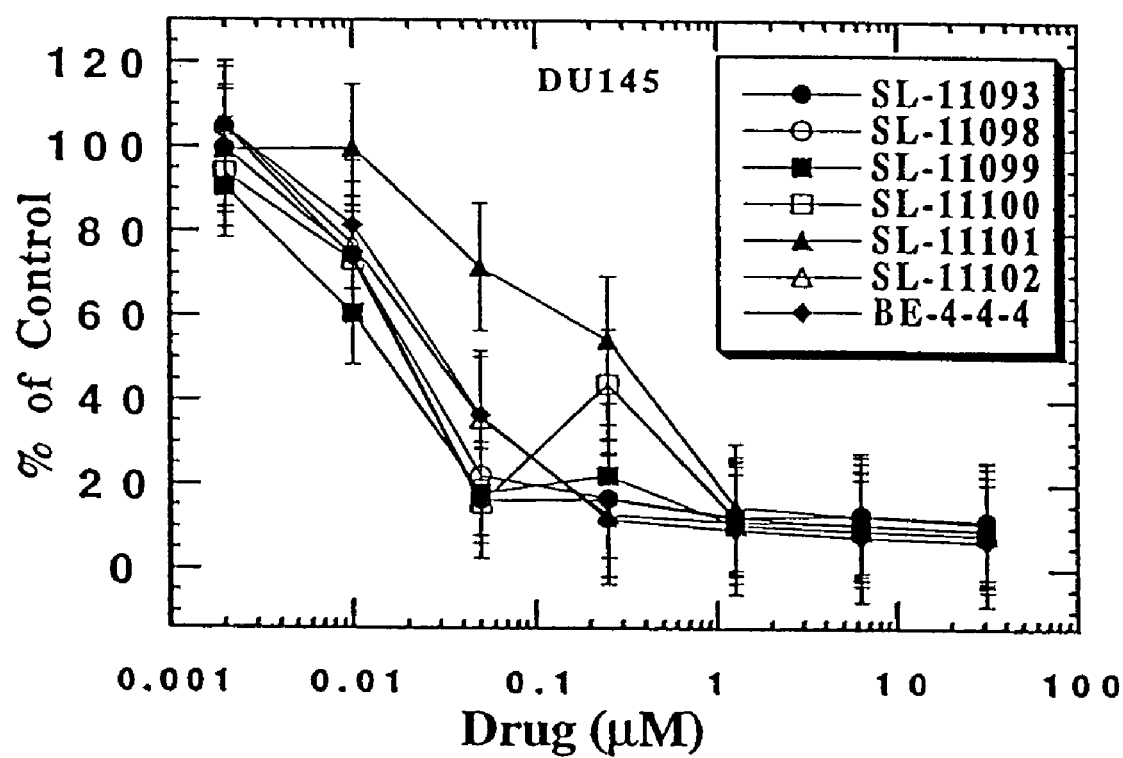
Figure 16:
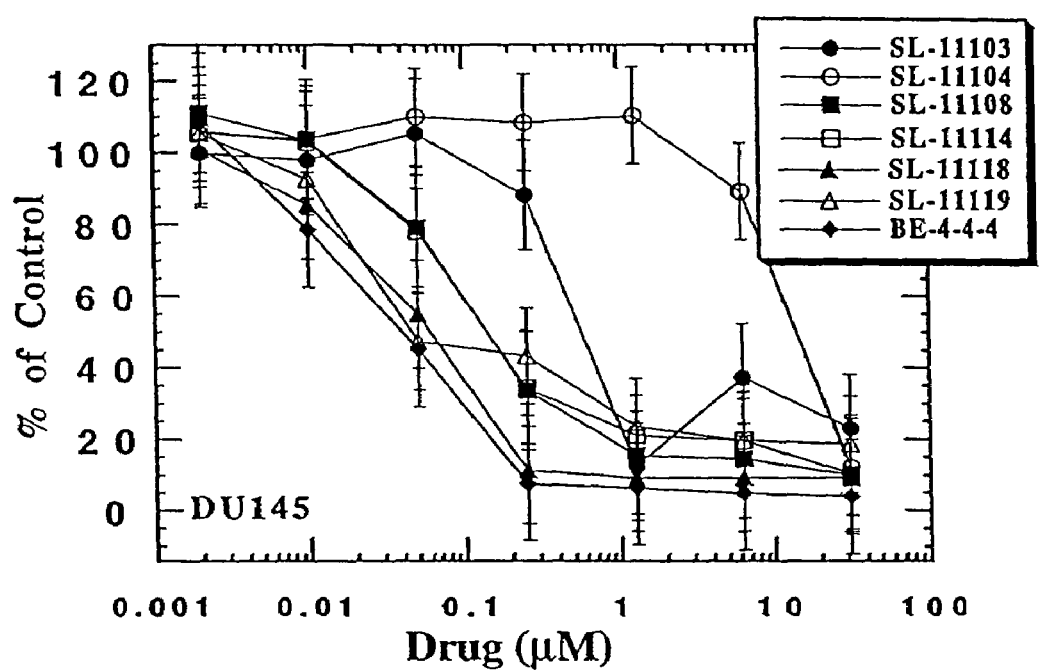

$ED_{50}$ of SL-11103>31.25 μM, SL-11104>31.25 μM, SL-11108=2.2 μM, SL-11114=0.7 μM, SL-11118=1.65 μM, SL-11119>31.25 μM and BE-444=0.7 μM FIG. 16A is a graph depicting the in vitro effect of increasing concentrations of SL-11093 (●), SL-11098 (○), SL-11099 (■), SL-1100 (□), SL-11101 (▲), SL-11102 (Δ), and BE-444 (◆) on the survival of cultured human prostate cancer cells DU145.

$ED_{50}$ of SL-11093=0.016 μM, SL-11098=0.02 μM, SL-11099=0.014 μM, SL-11100=0.021 μM, SL-11101=0.22 μM, SL-11102=0.03 μM and BE-444=0.03 μM.

FIG. 16B is a graph depicting the in vitro effect of increasing concentrations of SL-11103 (●), SL-11104 (○), SL-11108 (■), SL-11114 (□), SL-11118 (▲), SL-11119 (Δ), and BE-444 (◆) on the survival of cultured human prostate cancer cells DU145.

$ED_{50}$ of SL-11103=2.8 μM, SL-11104=9.4 μM, SL-11108=0.13 μM, SL-11114=0.13 μM, SL-11118=0.05 μM, SL-11119 0.08 μM and BE-444=0.03 μM.

Figure 17:
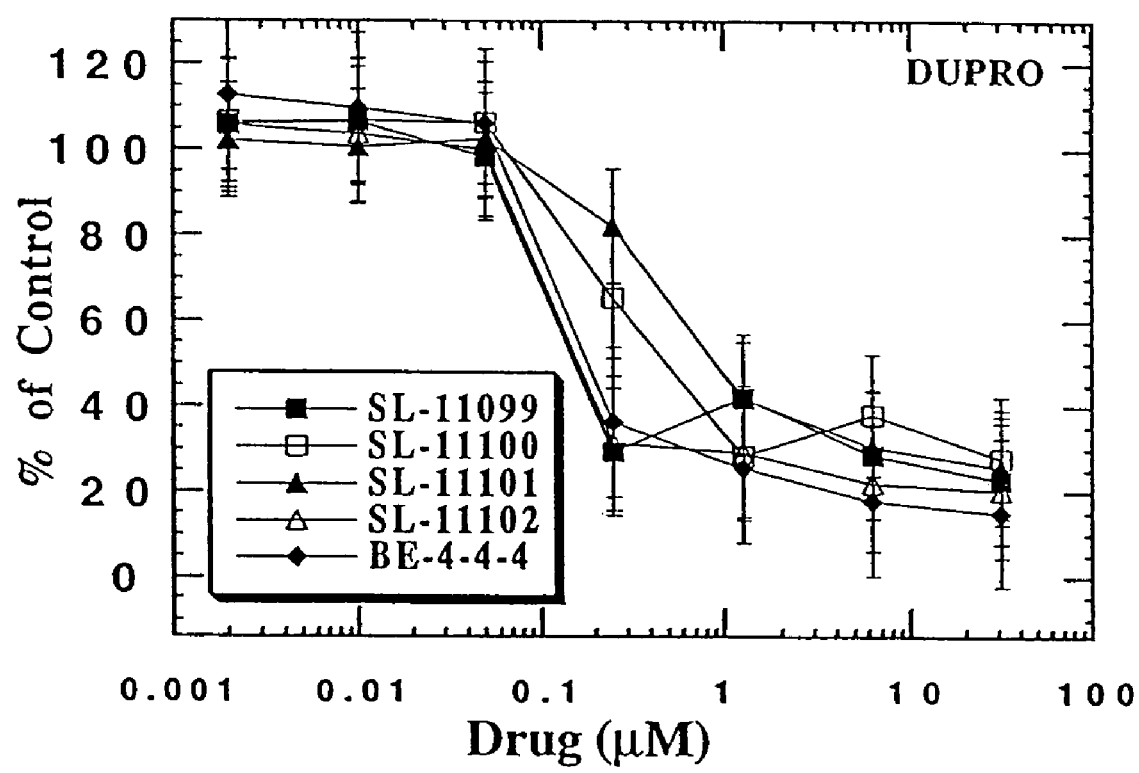
Figure 17:
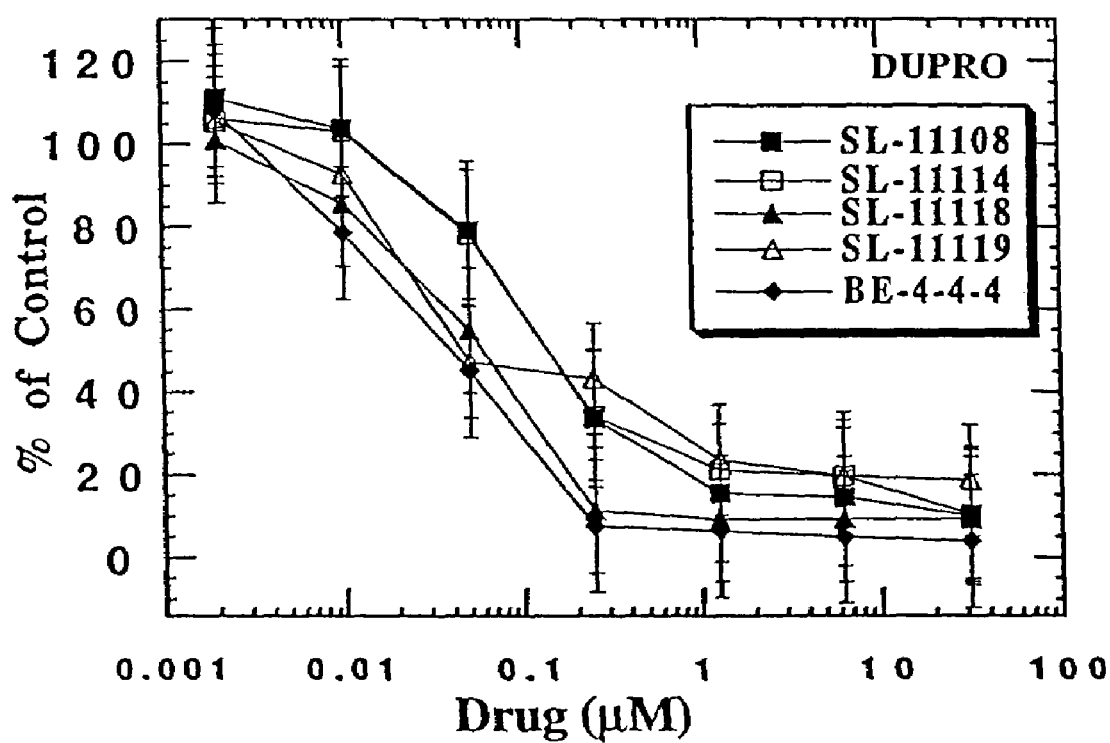

FIG. 17A is a graph depicting the in vitro effect of increasing concentrations of SL-11099 (■), SL-1100 (□), SL-11101 (▲), SL-11102 (Δ), and BE-444 (◆) on the survival of cultured human prostate cancer cells DUPRO.

$ED_{50}$ of =SL-11099=0.08 μM, SL-11100=0.3 μM, SL-11101=0.85 μM, SL-11102=0.15 μM and BE-444=0.2 μM.

FIG. 17B is a graph depicting the in vitro effect of increasing concentrations of SL-11108 (■), SL-11114 (□), SL-11118 (▲), SL-11119 (Δ), and BE-444 (◆) on the survival of cultured human prostate cancer cells DUPRO.

$ED_{50}$ of SL-11108=0.98 μM, SL-11114=0.64 μM, SL-11118=0.25 μM, SL-11119=0.44 μM and BE-444=0.2 μM.

Figure 18:
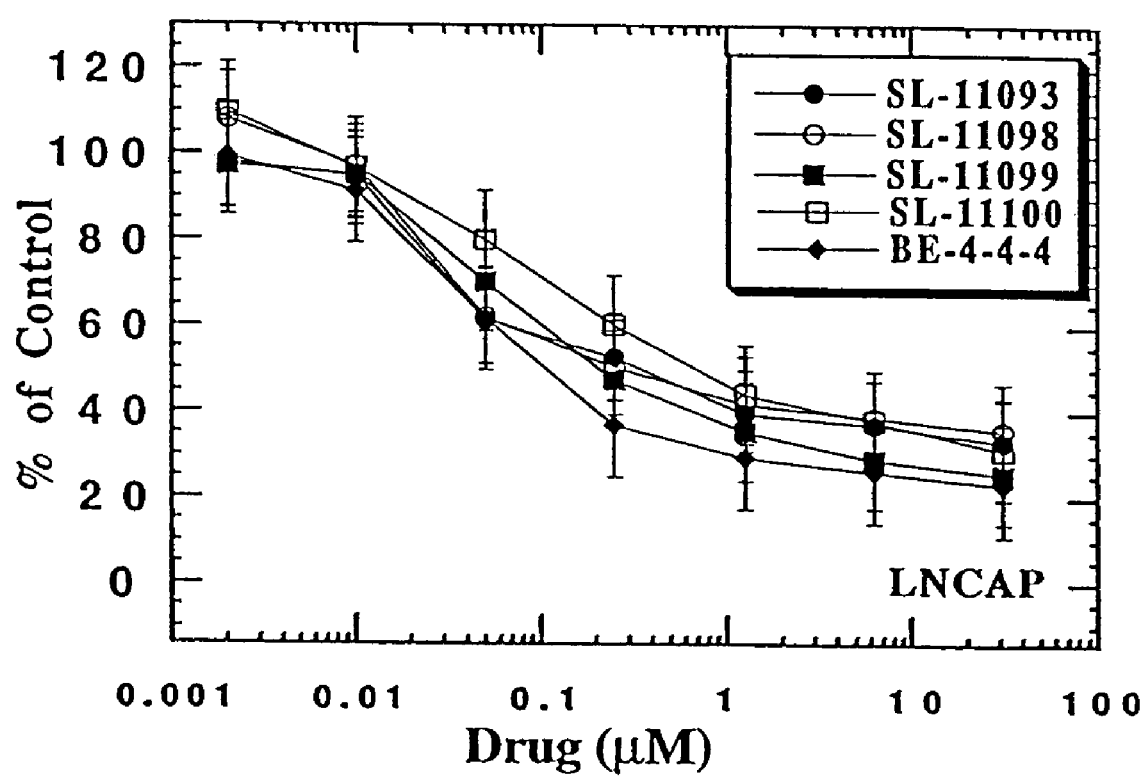
Figure 18:
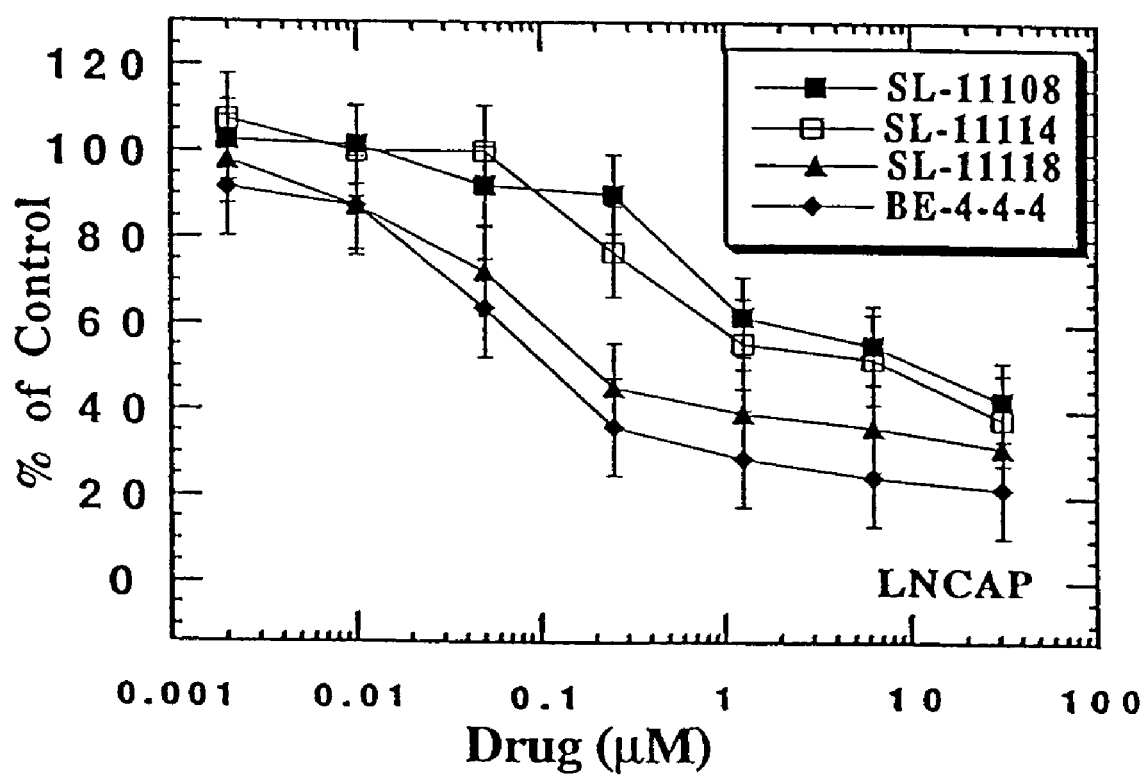

FIG. 18A is a graph depicting the in vitro effect of increasing concentrations of SL-11093 (●), SL-11098 (○), SL-11099 (■), SL-11100 (□), and BE-444 (◆) on the survival of cultured human prostate cancer cells LNCAP.

$ED_{50}$ of SL-11093=0.21 μM, SL-11098=0.17 μM, SL-11099=0.21 μM, SL-11100=0.7 μM, and BE-444=0.1 μM.

FIG. 18B is a graph depicting the in vitro effect of increasing concentrations of SL-11108 (■), SL-11114 (□), SL-11118 (▲), and BE-444 (◆) on the survival of cultured human prostate cancer cells LNCAP.

$ED_{50}$ of SL-11108=7.7 μM, SL-11114=3.0 μM, SL-11118=0.21 μM, and BE-444=0.1 μM.

Figure 19A:
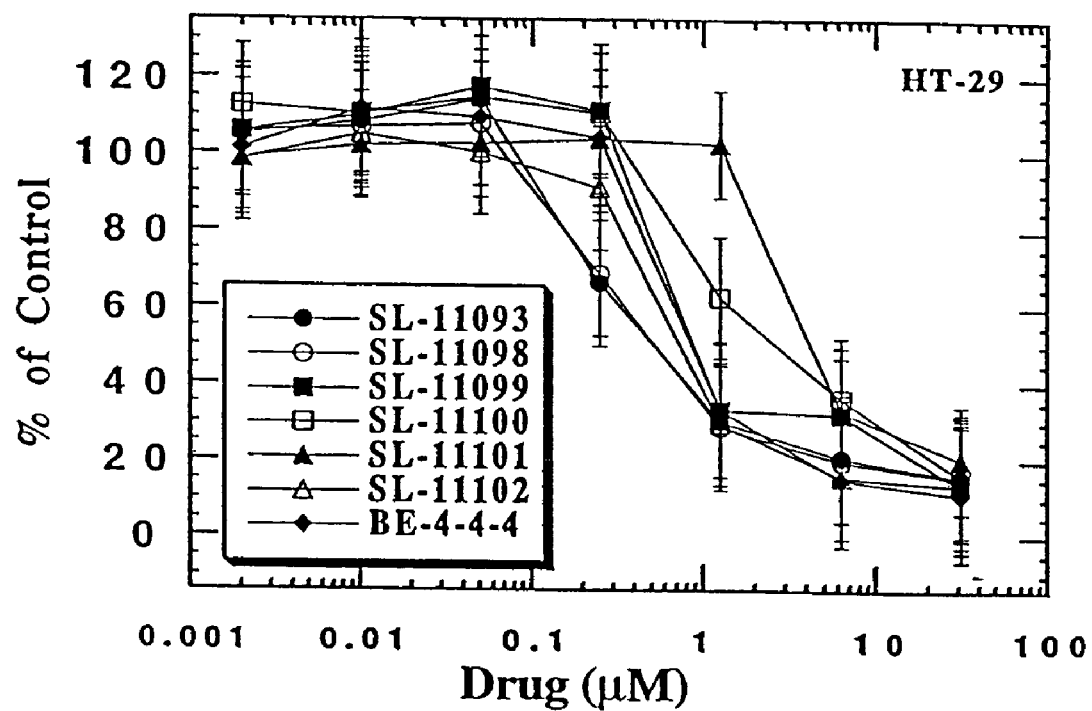

FIG. 19A is a graph depicting the in vitro effect of increasing concentrations of SL-11093 (●), SL-11098 (○), SL-11099 (■), SL-11110 (□), SL-11101 (▲), SL-11102 (Δ), and BE-444 (◆) on the survival of cultured human colon cancer cells HT29.

$ED_{50}$ of SL-11093=0.4 μM, SL-11098=0.4 μM, SL-11099=1.0 μM, SL-11100=2.0 μM, SL-11101=5.2 μM. SL-11102=0.73 μM and BE-444=0.93 μM.

Figure 19B:
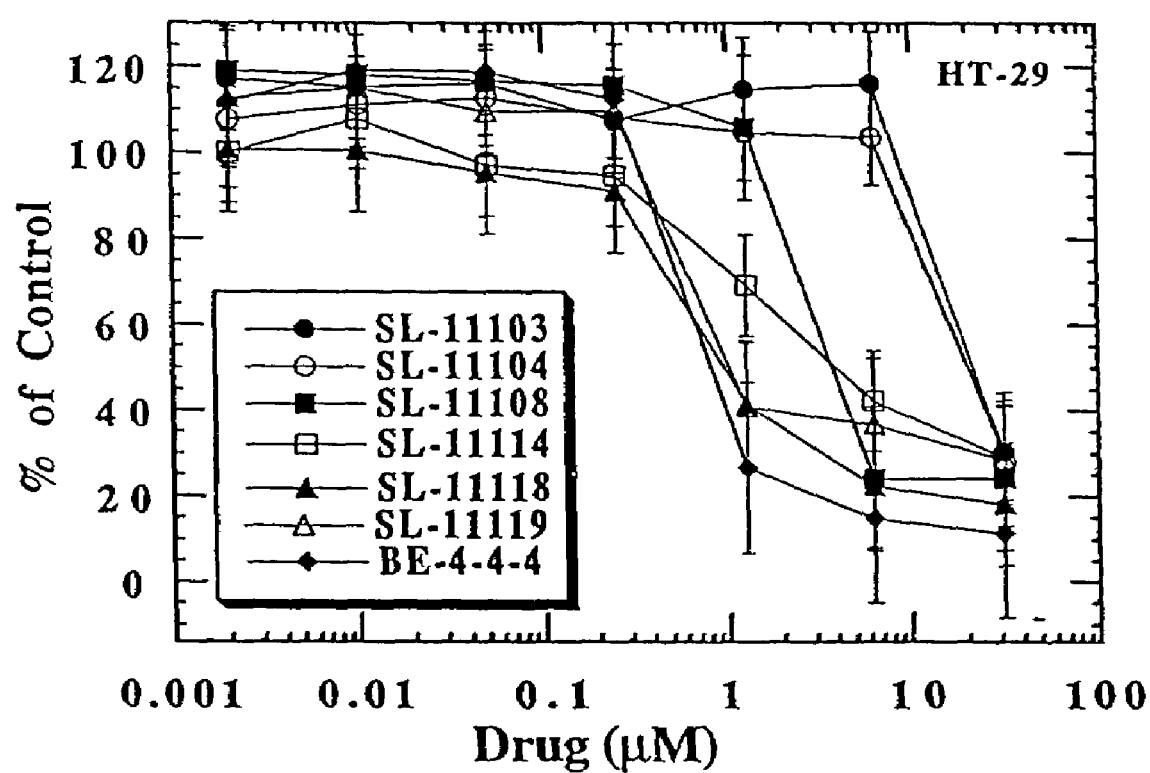

FIG. 19B is a graph depicting the in vitro effect of increasing concentrations of SL-11103 (●), SL-11104 (○), SL-11108 (■), SL-11114 (□), SL-11118 (▲), SL-11119 (Δ), and BE-444 (◆) on the survival of cultured human colon cancer cells HT29.

$ED_{50}$ of SL-11103=29.4 μM, SL-11104=25.8 μM, SL-11108=2.0 μM, SL-11114=3.6 μM, SL-11118=0.98 μM, SL-11119=0.97 μM and BE-444=0.93 μM.

Figure 20:
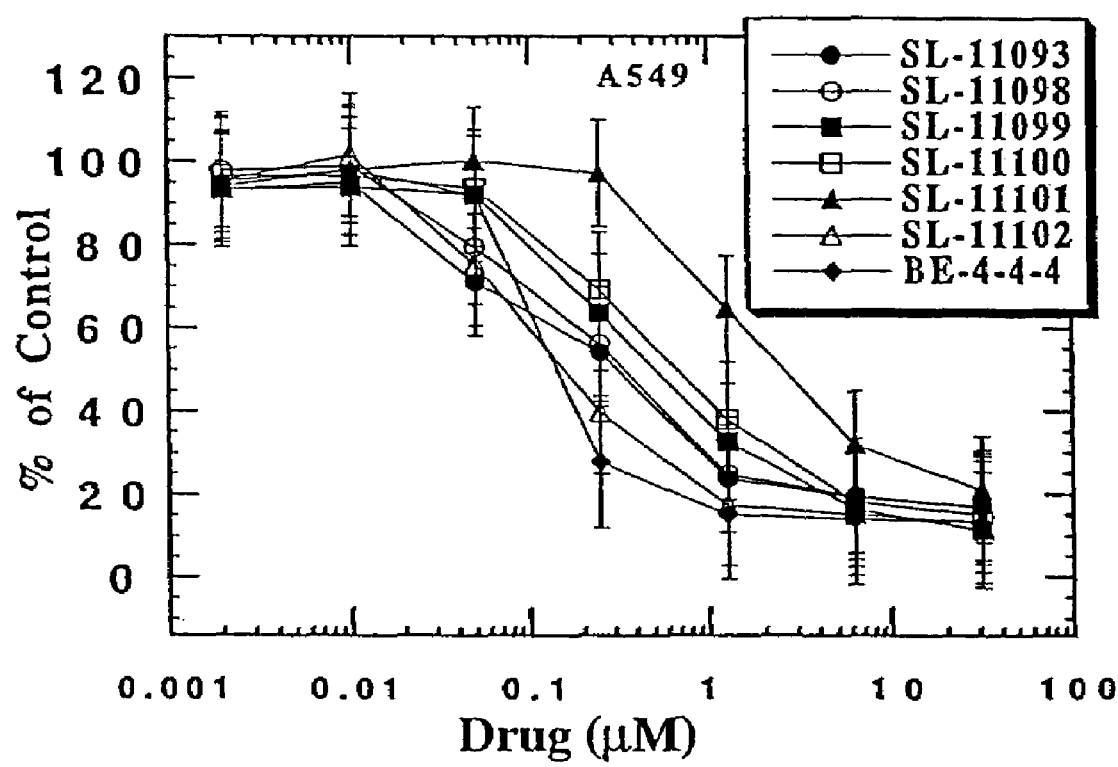
Figure 20:
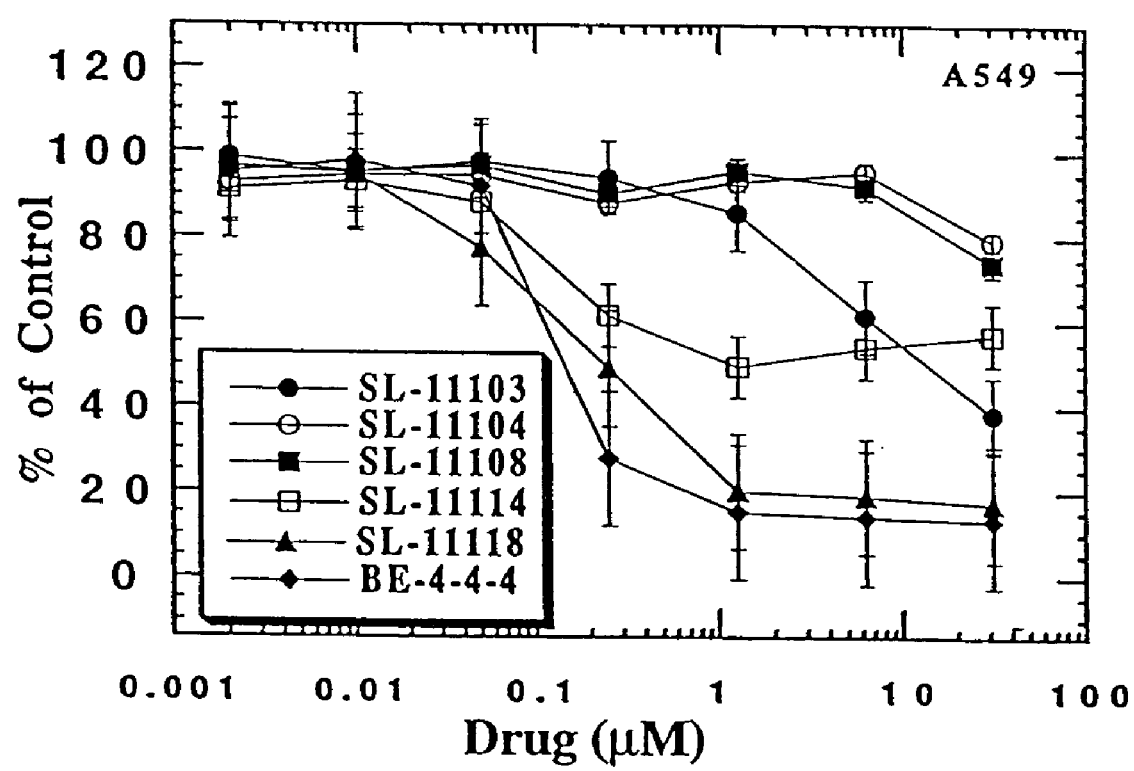

FIG. 20A is a graph depicting the in vitro effect of increasing concentrations of SL-11093 (●), SL-11098 (○), SL-11099 (■), SL-11100 (□), SL-11101 (▲), SL-11102 (Δ), and BE-444 (◆) on the survival of cultured human lung cancer cells A549.

$ED_{50}$ of SL-11093=0.26 μM, SL-11098=0.29 μM, SL-11099=0.51 μM, SL-11100=0.65 μM, SL-11101=2.2 μM, SL-11102=0.15 μM and BE-444=0.15 μM.

FIG. 20B is a graph depicting the in vitro effect of increasing concentrations of SL-11103 (●), SL-11104 (○), SL-11108 (■), SL-11114(□), SL-11118 (▲), and BE-444 (◆) on the survival of cultured human lung cancer cells A549.

$ED_{50}$ of SL-11103=12.4 μM, SL-11104>31.25 μM, SL-11108>31.25 μM, SL-1114>31.25 μM, SL-11118=0.214 μM and BE-444=0.15 μM.

Figure 21:
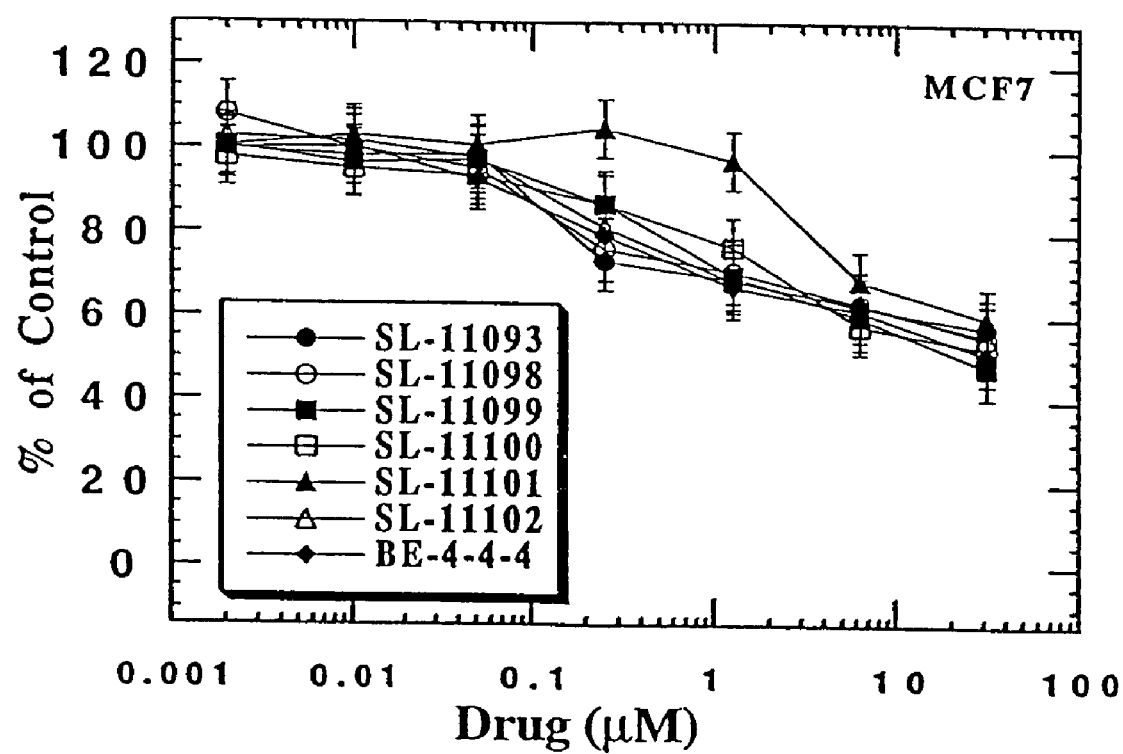
Figure 21:
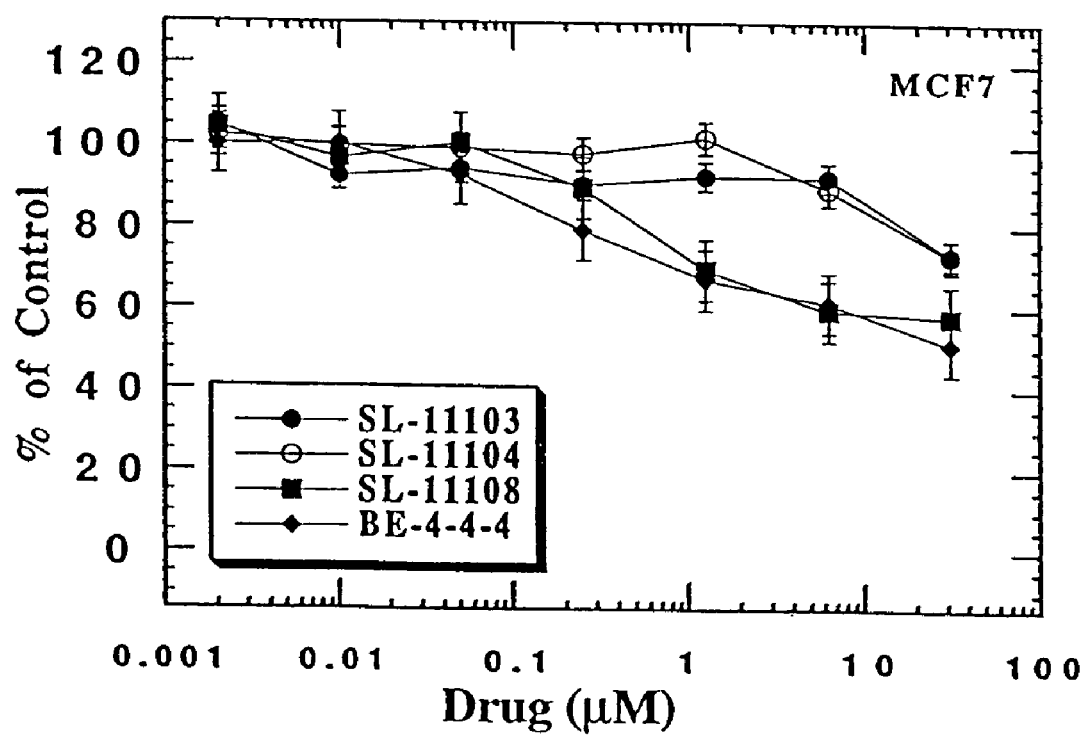

FIG. 21A is a graph depicting the in vitro effect of increasing concentrations of SL-11093 (●), SL-11098(○), SL-11099(■), SL-11100(□), SL-11101 (▲), SL-11102 (Δ), and BE-444 (♦) on the survival of cultured human breast cancer cells MCF7.

ED$_{50}$ of SL-11093=0.66 μM, SL-11098>31.25 μM, SL-11099=26.3 μM, SL-11100>31.25 μM, SL-11101>31.25 μM SL-11102>31.25 μM and BE-444>31.25 μM.

FIG. 21B is a graph depicting the in vitro effect of increasing concentrations of SL-11103 (●), SL-11104 (○), SL-11108 (■), and BE-444 (♦) on the survival of cultured human breast cancer cells MCF7.

ED$_{50}$ of SL-11103>31.25 μM, SL-11104>31.25 μM, SL-11108>31.25 μM, and BE-444>31.25 μM.

Figure 22:
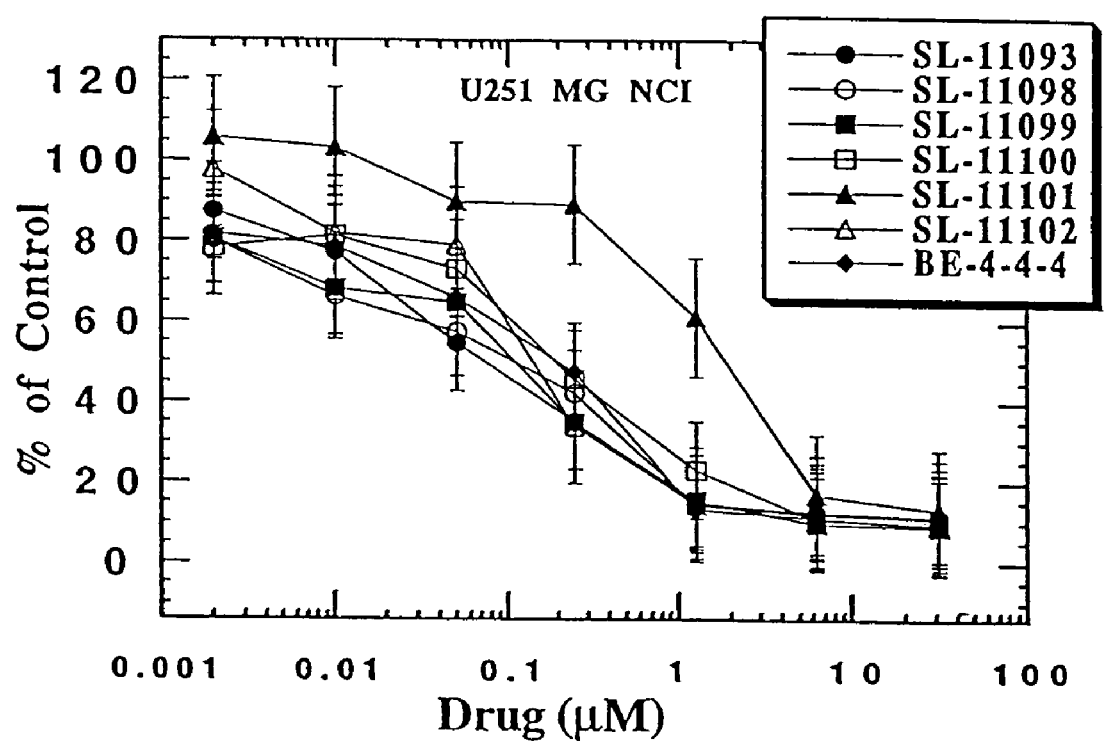
Figure 22:
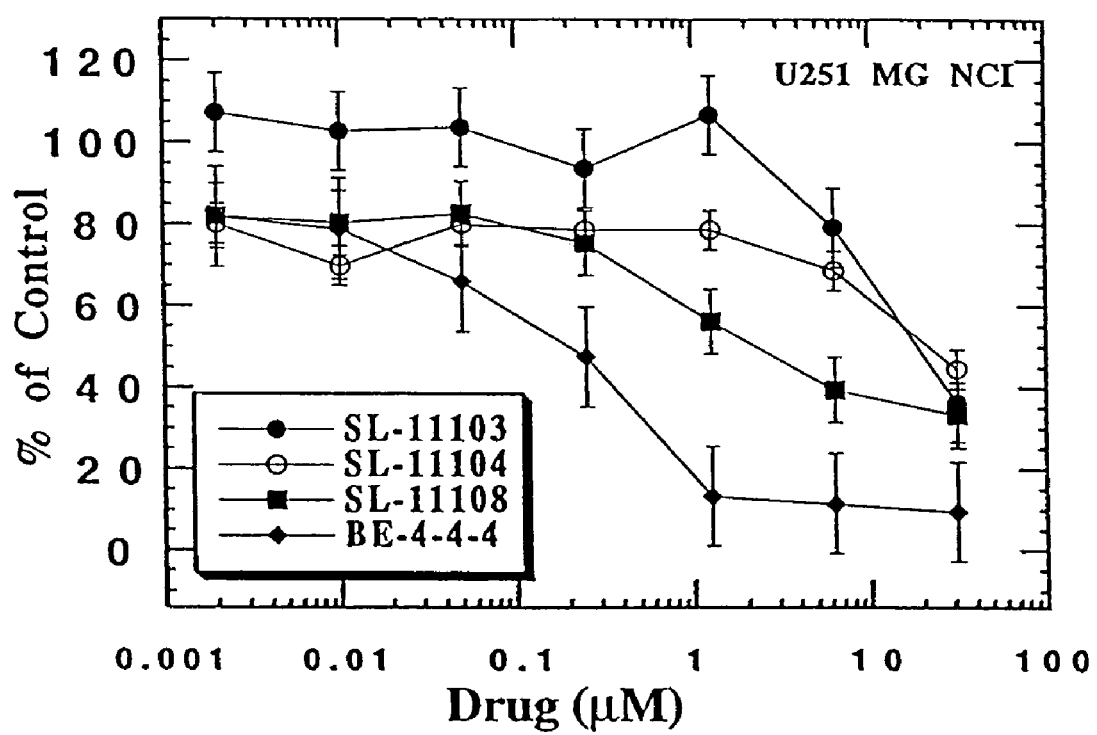

FIG. 22A is a graph depicting the in vitro effect of increasing concentrations of SL-11093 (●), SL-11098 (○), SL-11099 (■), SL-11100 (□), SL-11101 (▲), SL-11102 (Δ), and BE-444 (♦) on the survival of cultured human brain tumor cells U251 MG NCI.

ED$_{50}$ of SL-11093=0.07 μM, SL-11098=0.1 μM, SL-11099=0.11 μM, SL-11100=0.22 μM, SL-11101=1.7 μM, SL-11102=0.15 μM and BE-444=0.2 μM.

FIG. 22B is a graph depicting the in vitro effect of increasing concentrations of SL-11103 (●), SL-11104 (○), SL-11108 (■), and BE-444 (♦) on the survival of cultured human brain tumor cells U251 MG NCI.

ED$_{50}$ of SL-11103=9.5 μM, SL-11104=14.71 μM, SL-11108=2.0 μM, and BE-444=0.2 μM.

Figure 23:
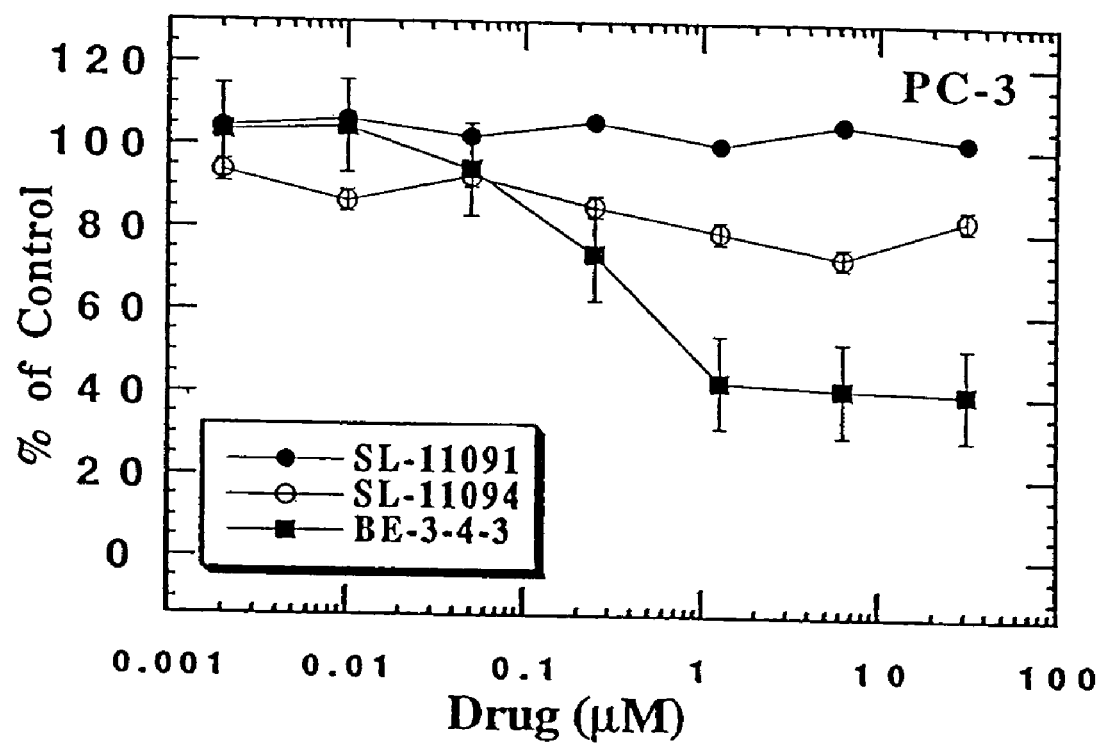

FIG. 23 is a graph depicting the in vitro effect of increasing concentrations of SL-11091 (●), SL-11094 (○), and BE-343 (■) on the survival of cultured human prostate cancer cells PC3.

ED$_{50}$ of SL-11091>31.25 μM, SL-11094>31.25 μM, and BE-343=0.24 μM.

Figure 24:
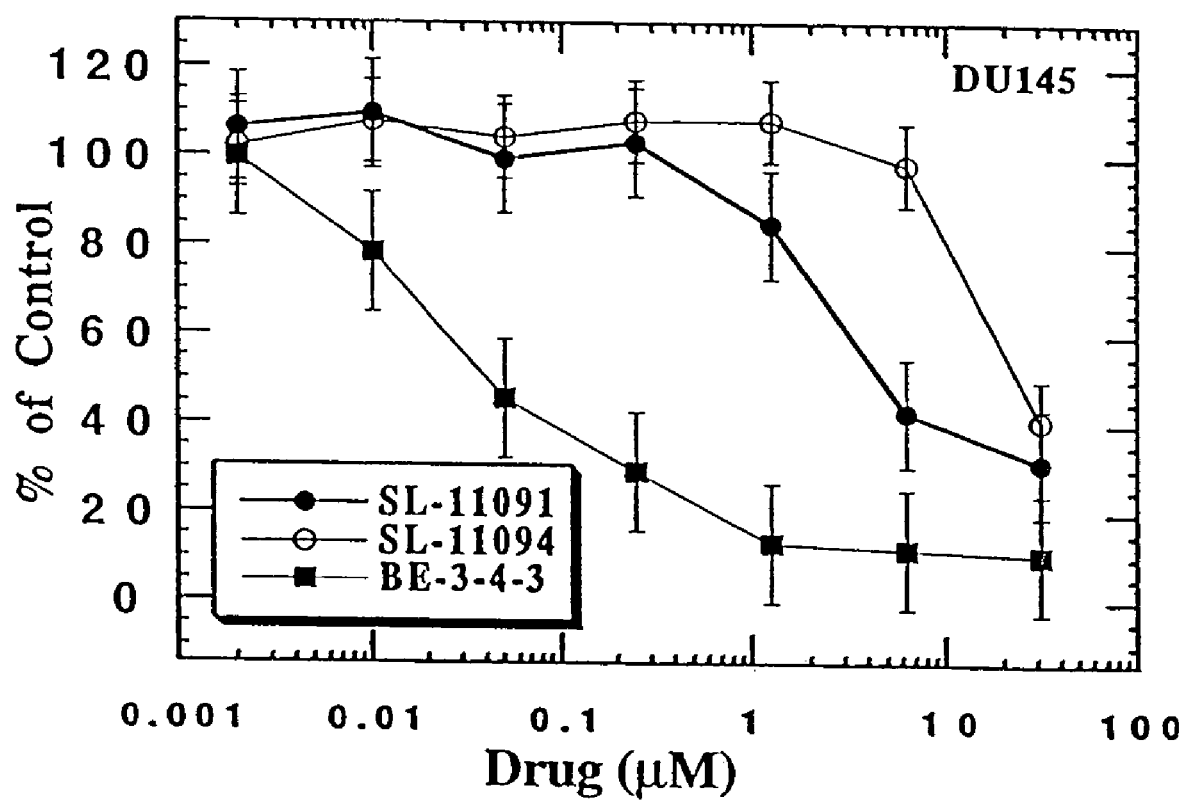

FIG. 24 is a graph depicting the in vitro effect of increasing concentrations of SL-11091 (●), SL-11094 (○), and BE-343 (■) on the survival of cultured human prostate cancer cells DU145.

ED$_{50}$ of SL-11091=4.33 μM, SL-11094=15.4 μM, and BE-343=0.044 μM.

Figure 25:
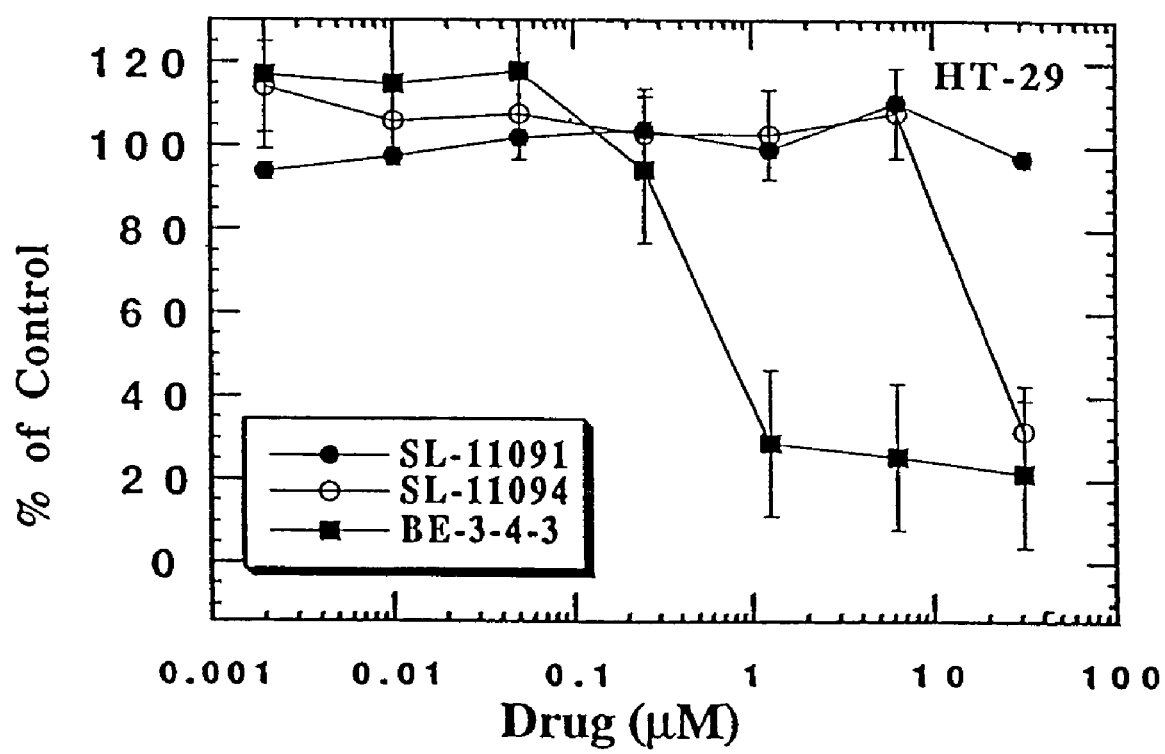

FIG. 25 is a graph depicting the in vitro effect of increasing concentrations of SL-11091 (●), SL-11094 (○), and BE-343 (■) on the survival of cultured human colon cancer cells HT29.

ED$_{50}$ of SL-11091>31.25 μM, SL-11094=28.8 μM, and BE-343=0.6 μM.

Figure 26:
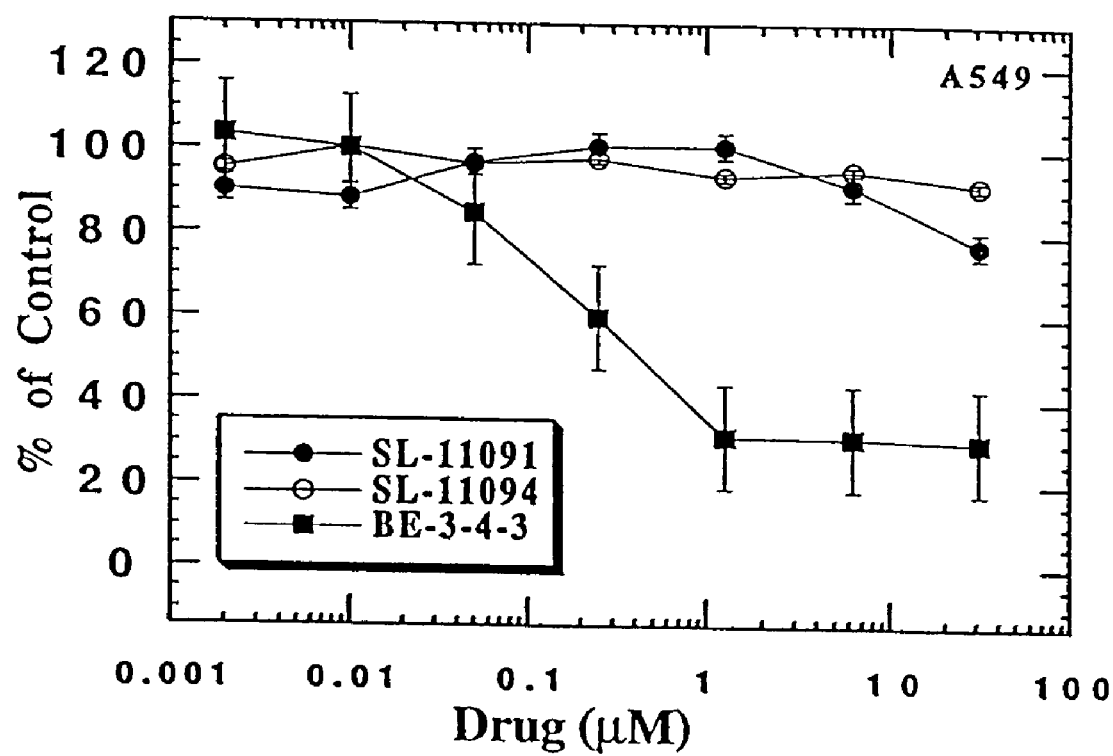

FIG. 26 is a graph depicting the in vitro effect of increasing concentrations of SL-11091 (●), SL-11094 (○), and BE-343 (■) on the survival of cultured human lung cancer cells A549.

ED$_{50}$ of SL-11091>31.25 μM, SL-11094>31.25 μM, and BE-343=0.2 μM.

Figure 27:
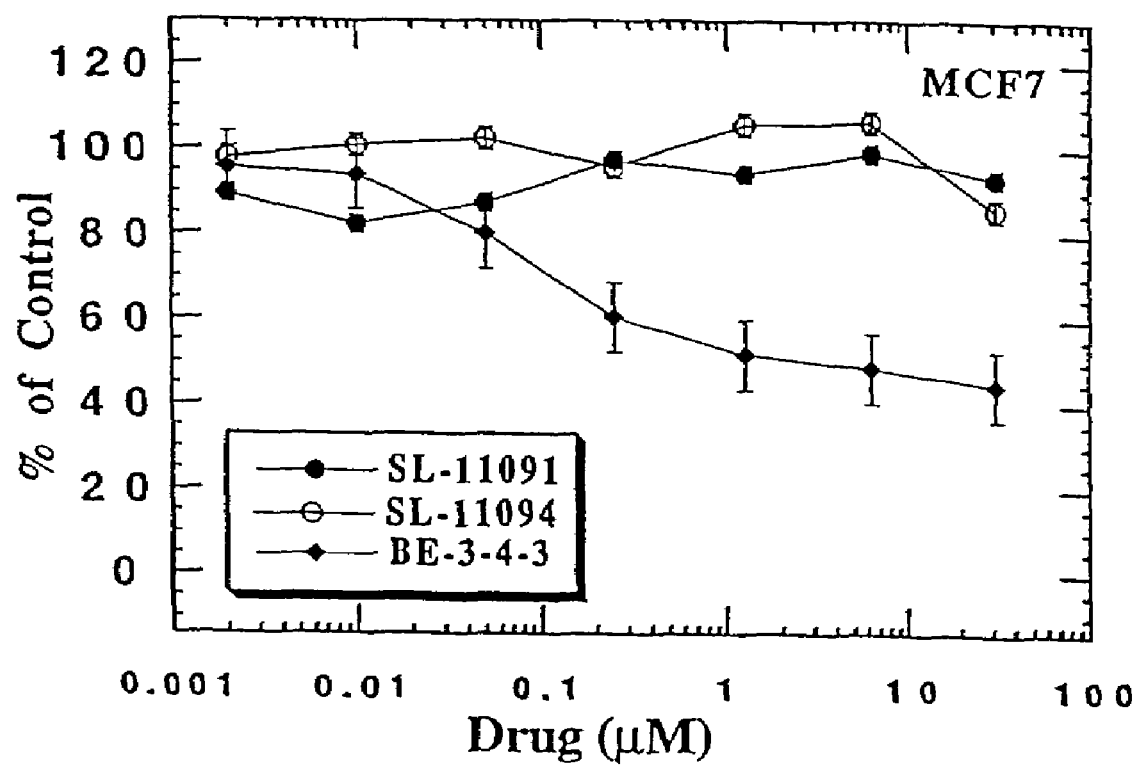

FIG. 27 is a graph depicting the in vitro effect of increasing concentrations of SL-11091 (●), SL-11094 (○), and BE-343 (♦) on the survival of cultured human breast cancer cells MCF7.

ED$_{50}$ of SL-11091>31.25 μM, SL-11094>31.25 μM, and BE-343=0.5 μM.

Figure 28:
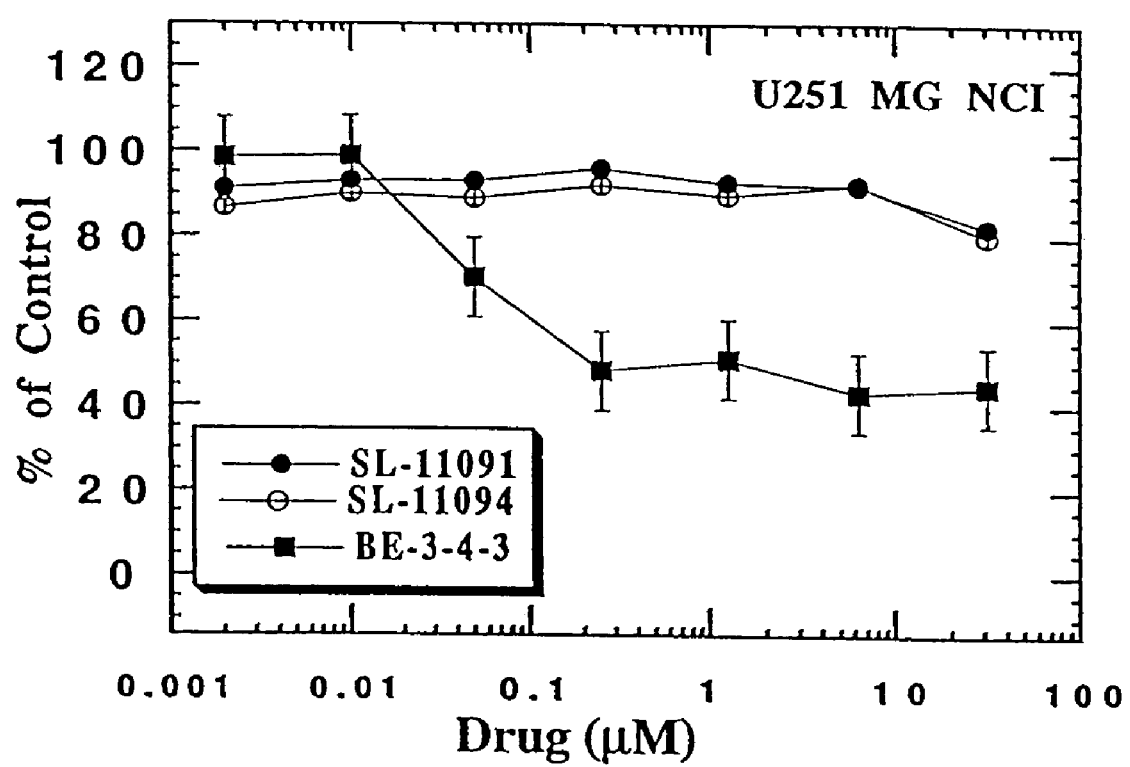

FIG. 28 is a graph depicting the in vitro effect of increasing concentrations of SL-11091 (●), SL-11094 (○), and BE-343 (■) on the survival of cultured human brain tumor cells U251 MG NCI.

ED$_{50}$ of SL-11091>31.25 μM, SL-11094>31.25 μM, and BE-343=0.14 μM.

Figure 29:
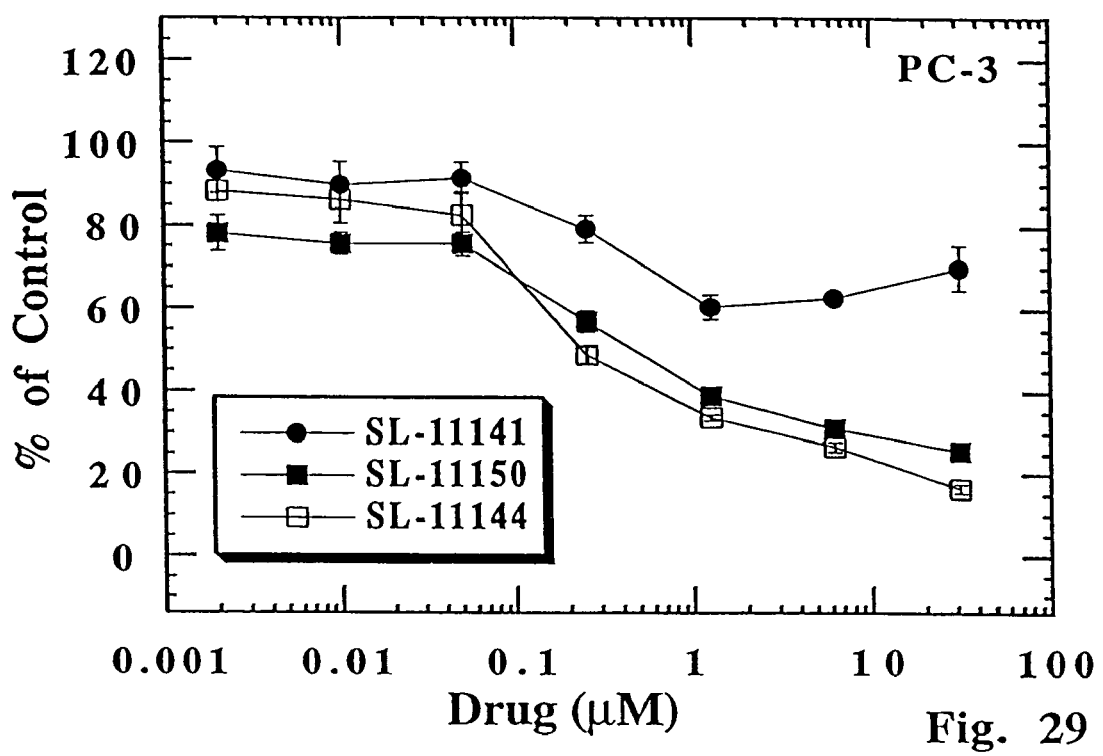

FIG. 29 is a graph depicting the in vitro effect of increasing concentrations of SL-11141 (●), SL-11144 (□), SL-11150 (■) on the survival of cultured human prostate cancer cells PC3.

ED$_{50}$ of SL-11141>31.25 μM, SL-11144=0.3 μM, and SL-11150=0.5 μM.

Figure 30:
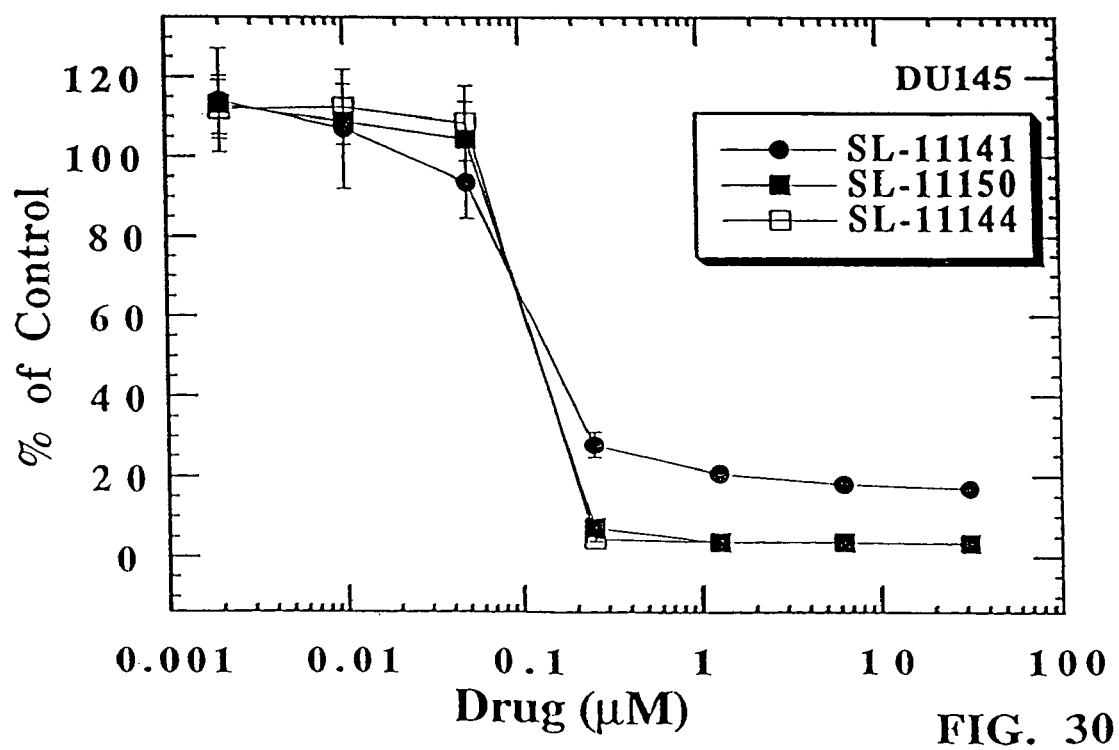

FIG. 30 is a graph depicting the in vitro effect of increasing concentrations of SL-11141 (●), SL-11144 (□), SL-11150 (■) on the survival of cultured human prostate cancer cells DU145.

ED$_{50}$ of SL-11141=0.13 μM, SL-11144=0.1 μM, and SL-11150=0.11 μM.

Figure 31:
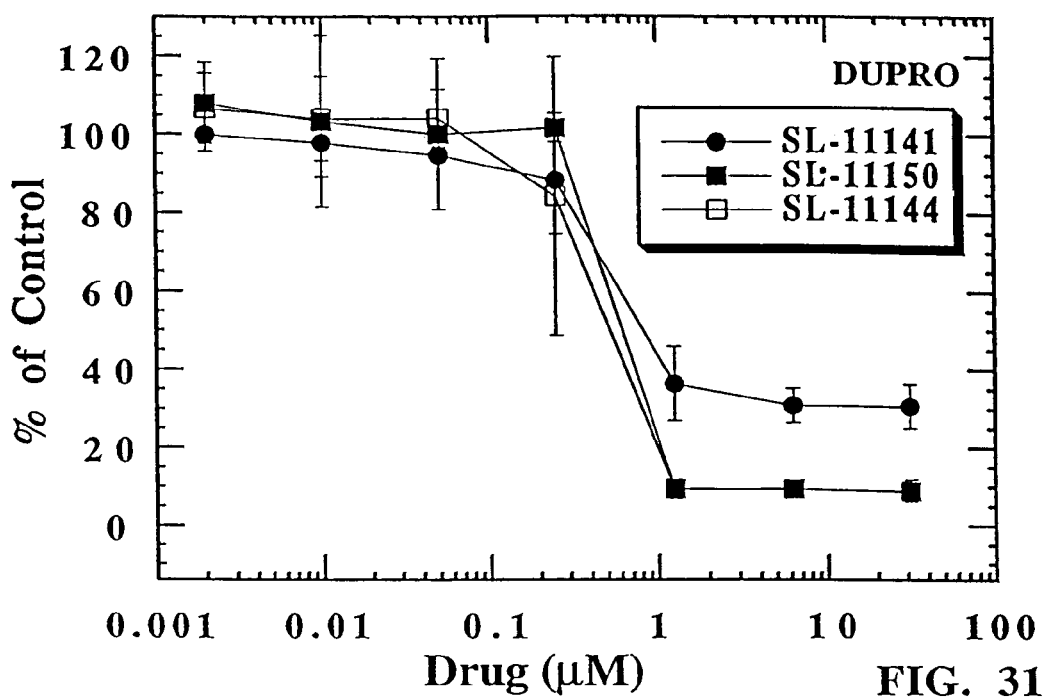

FIG. 31 is a graph depicting the in vitro effect of increasing concentrations of SL-11141 (●), SL-11144 (□), SL-11150 (■) on the survival of cultured human prostate cancer cells DUPRO.

ED$_{50}$ of SL-11141=0.71 μM, SL-11144=0.36 μM, and SL-11150=0.48 μM.

Figure 32:
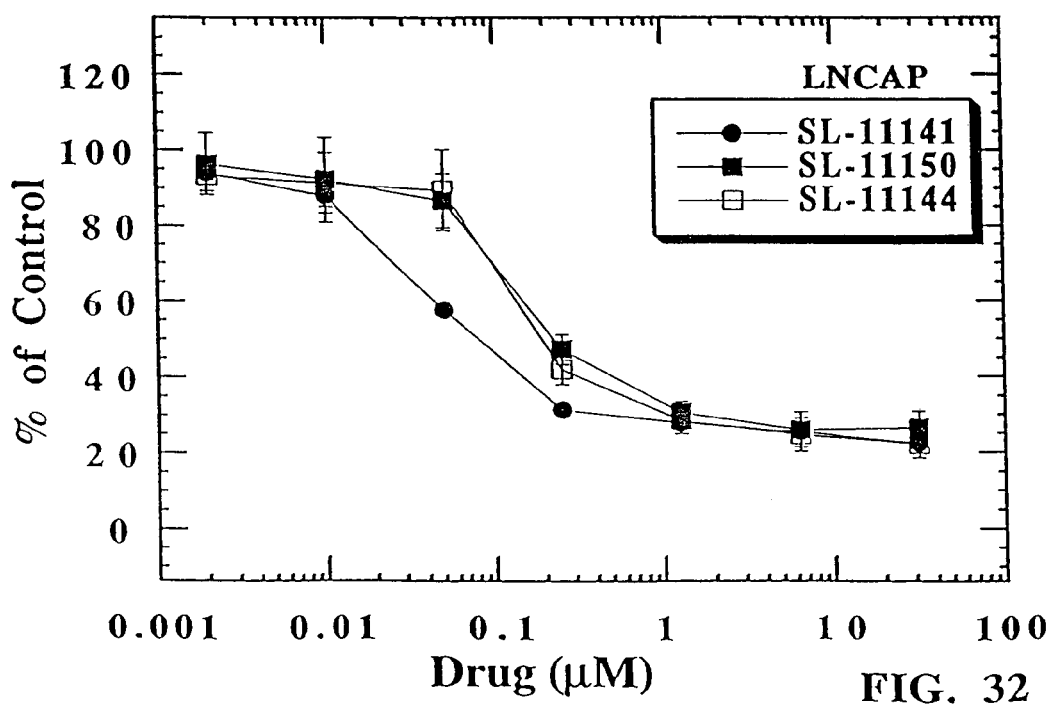

FIG. 32 is a graph depicting the in vitro effect of increasing concentrations of SL-11141 (●), SL-11144 (□), SL-11150 (■) on the survival of cultured human prostate cancer cells LNCAP.

ED$_{50}$ of SL-11141=0.07 μM, SL-11144=0.20 μM, and SL-11150=0.23 μM.

FIG. 33 illustrates synthetic methodology used to prepare polyamine compounds useful in the invention.

FIG. 34 illustrates additional synthetic methodology used to prepare polyamine compounds useful in the invention.

FIG. 35 illustrates additional synthetic methodology used to prepare polyamine compounds useful in the invention.

FIG. 36 illustrates additional synthetic methodology used to prepare polyamine compounds useful in the invention.

FIG. 37 illustrates additional synthetic methodology used to prepare polyamine compounds useful in the invention.

Figure 38:
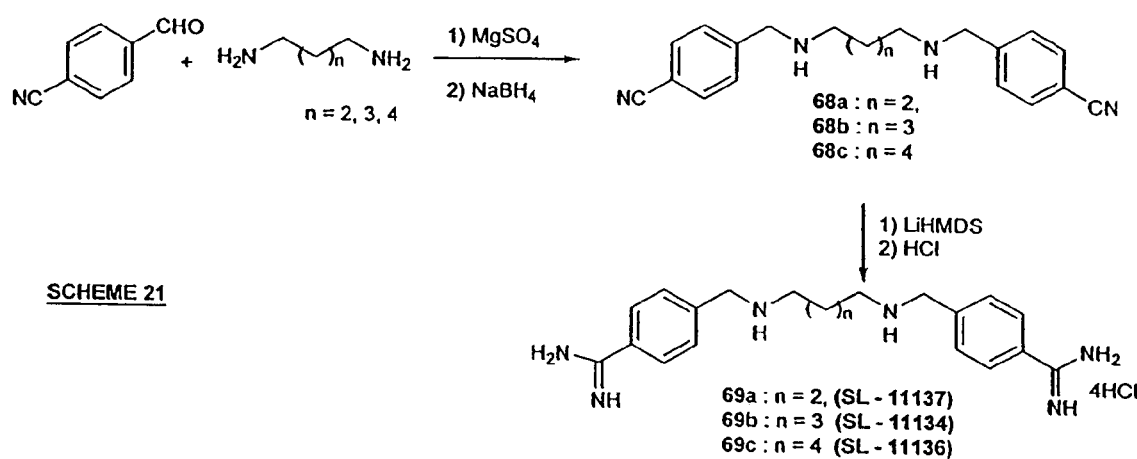

FIG. 38 illustrates additional synthetic methodology used to prepare polyamine compounds useful in the invention.

FIG. 39 illustrates additional synthetic methodology used to prepare polyamine compounds useful in the invention.

Figure 40A:
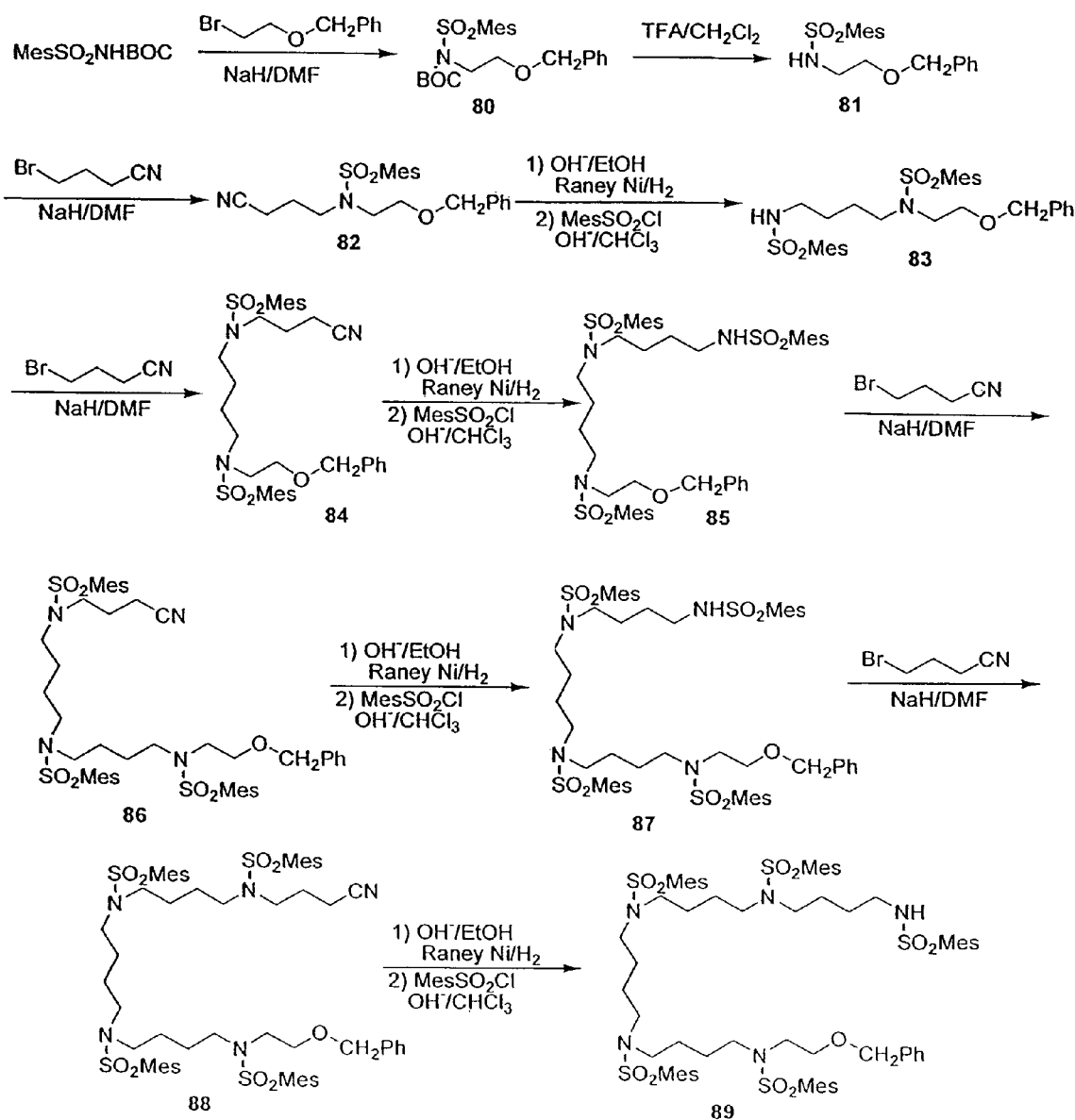

FIG. 40A illustrates additional synthetic methodology used to prepare polyamine compounds useful in the invention.

Figure 40B:
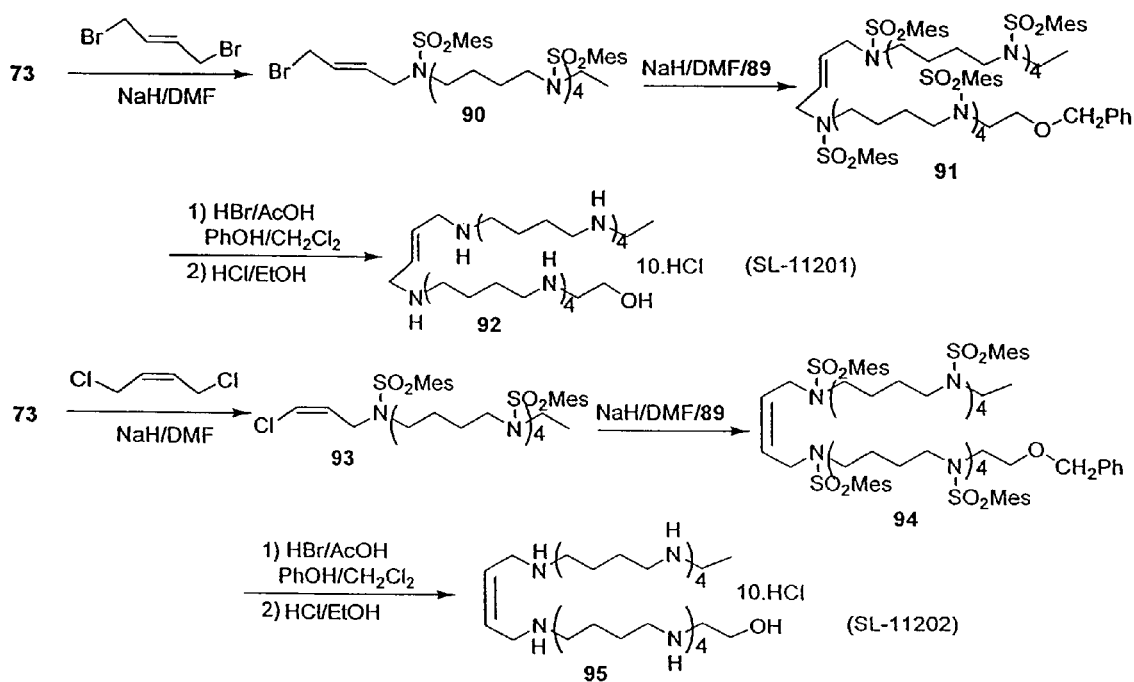

FIG. 40B illustrates additional synthetic methodology used to prepare polyamine compounds useful in the invention.

Figure 41:
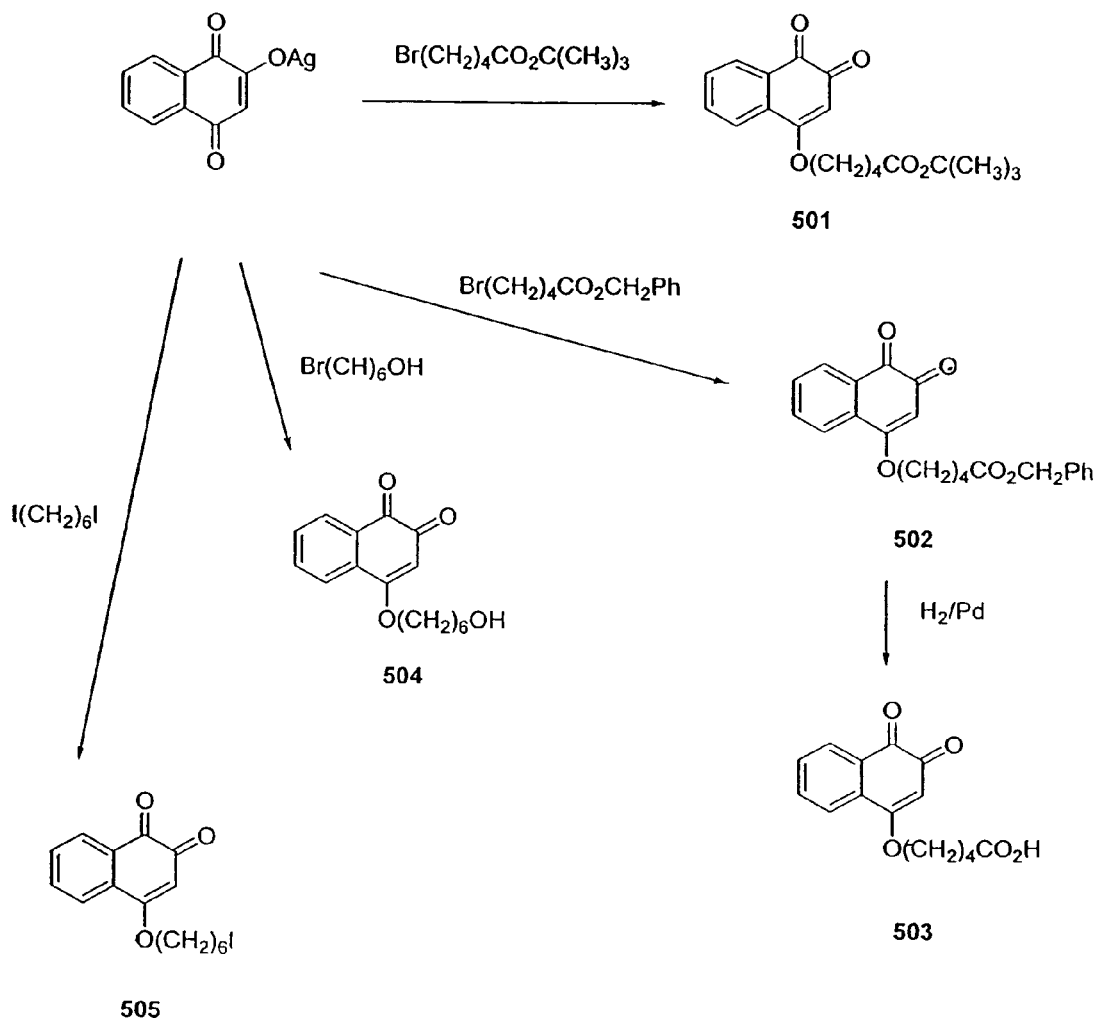

FIG. 41 depicts Scheme 501, illustrating the synthetic preparation of quinone compounds useful in the invention.

FIG. 42 depicts Scheme 502, illustrating the synthetic preparation of additional quinone compounds useful in the invention.

FIG. 43 depicts Scheme 503, illustrating the synthetic preparation of additional quinone compounds useful in the invention.

Figure 44:
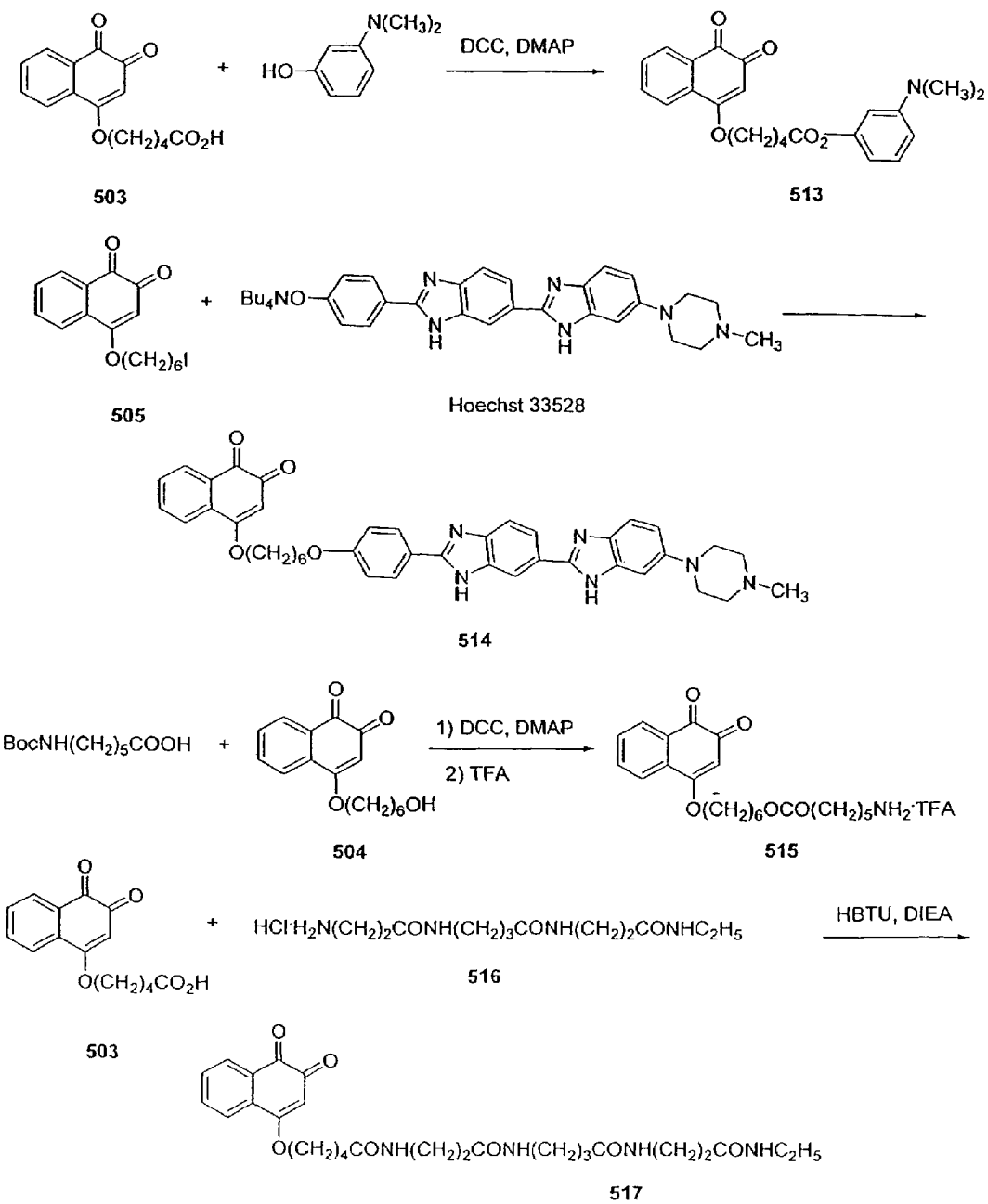

FIG. 44 depicts Scheme 504, illustrating the synthetic preparation of additional quinone compounds useful in the invention.

Figure 45:
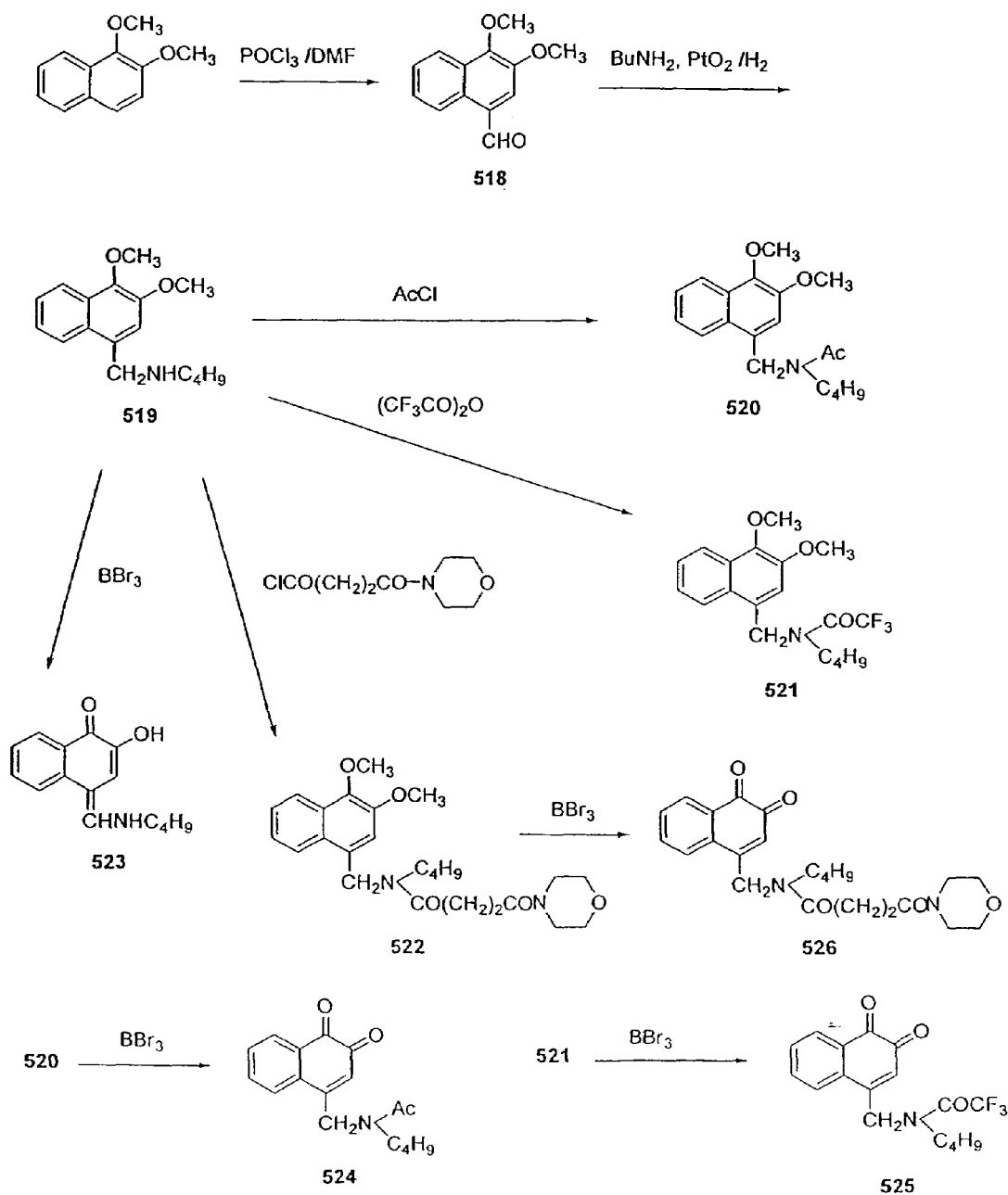

FIG. 45 depicts Scheme 505, illustrating the synthetic preparation of additional quinone compounds useful in the invention.

Figure 46:
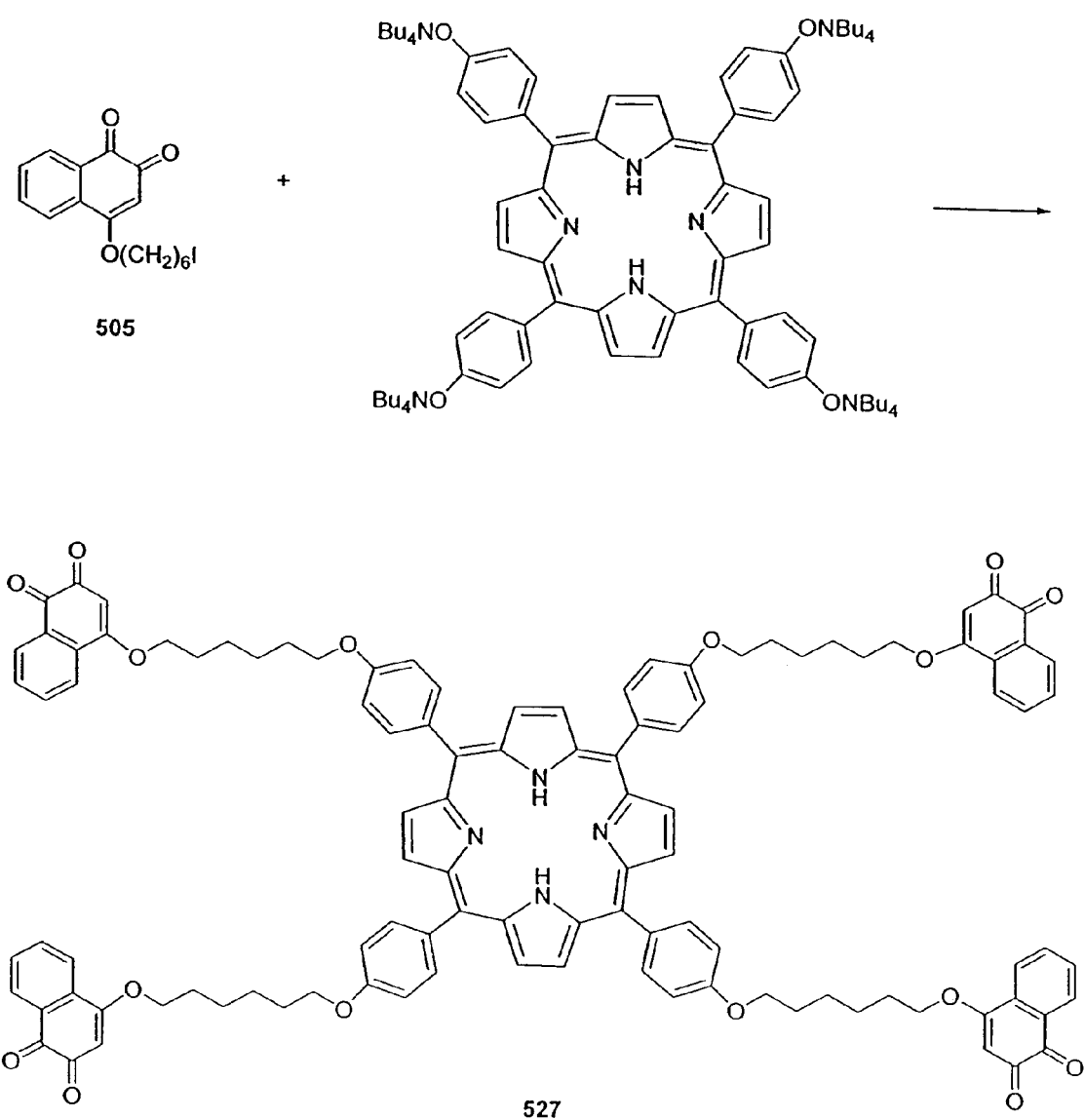

FIG. 46 depicts Scheme 506, illustrating the synthetic preparation of additional quinone compounds useful in the invention.

Figure 47:
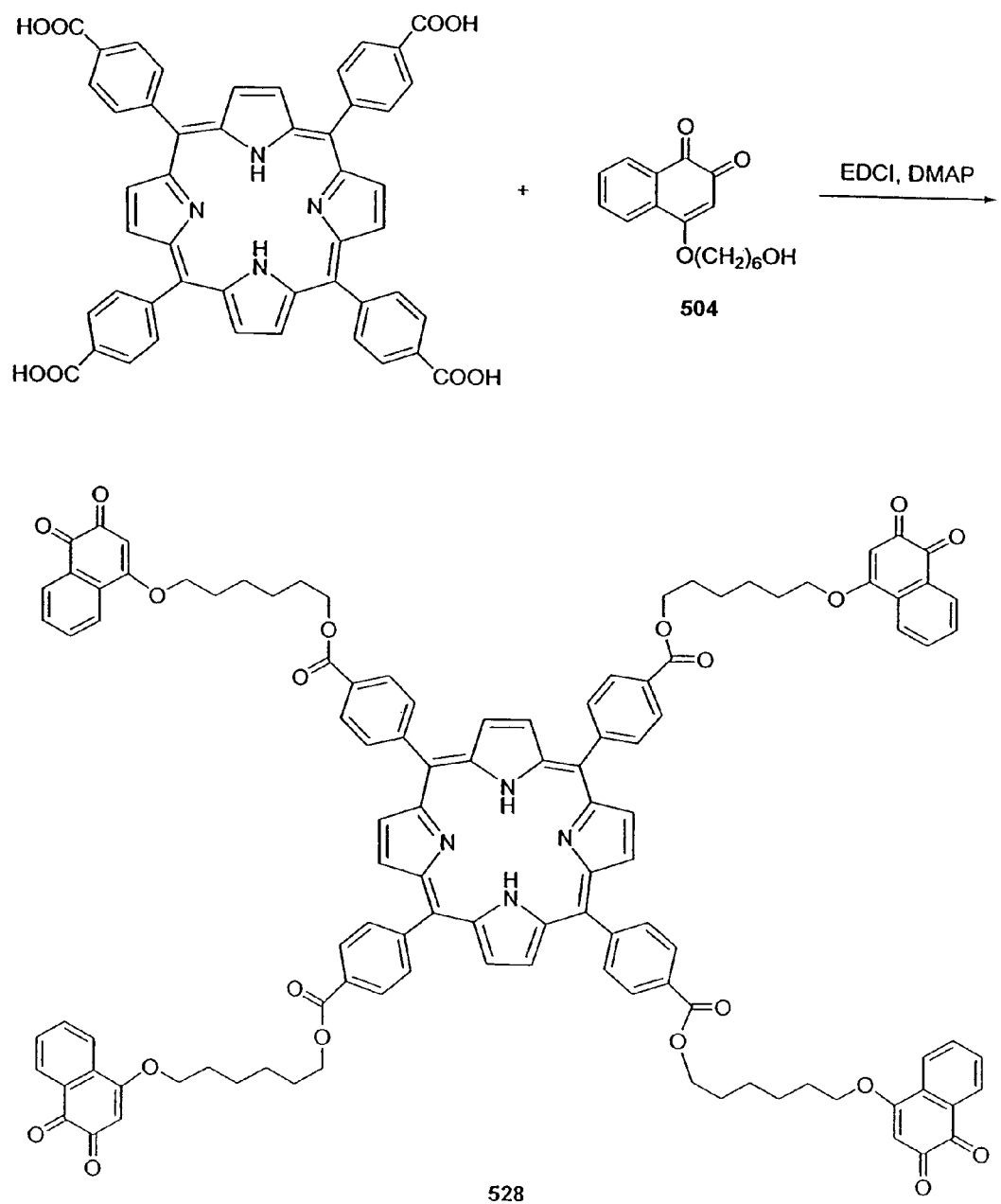

FIG. 47 depicts Scheme 507, illustrating the synthetic preparation of additional quinone compounds useful in the invention.

Figure 48:
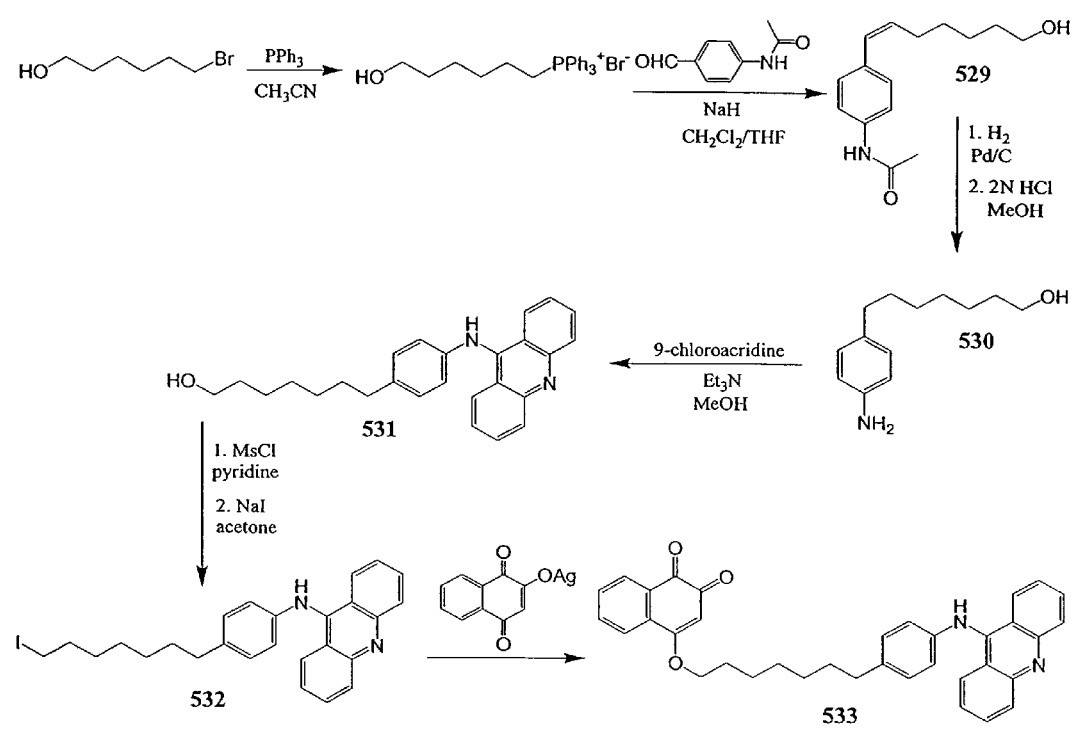

FIG. 48 depicts Scheme 508, illustrating the synthetic preparation of additional quinone compounds useful in the invention.

Figure 49:
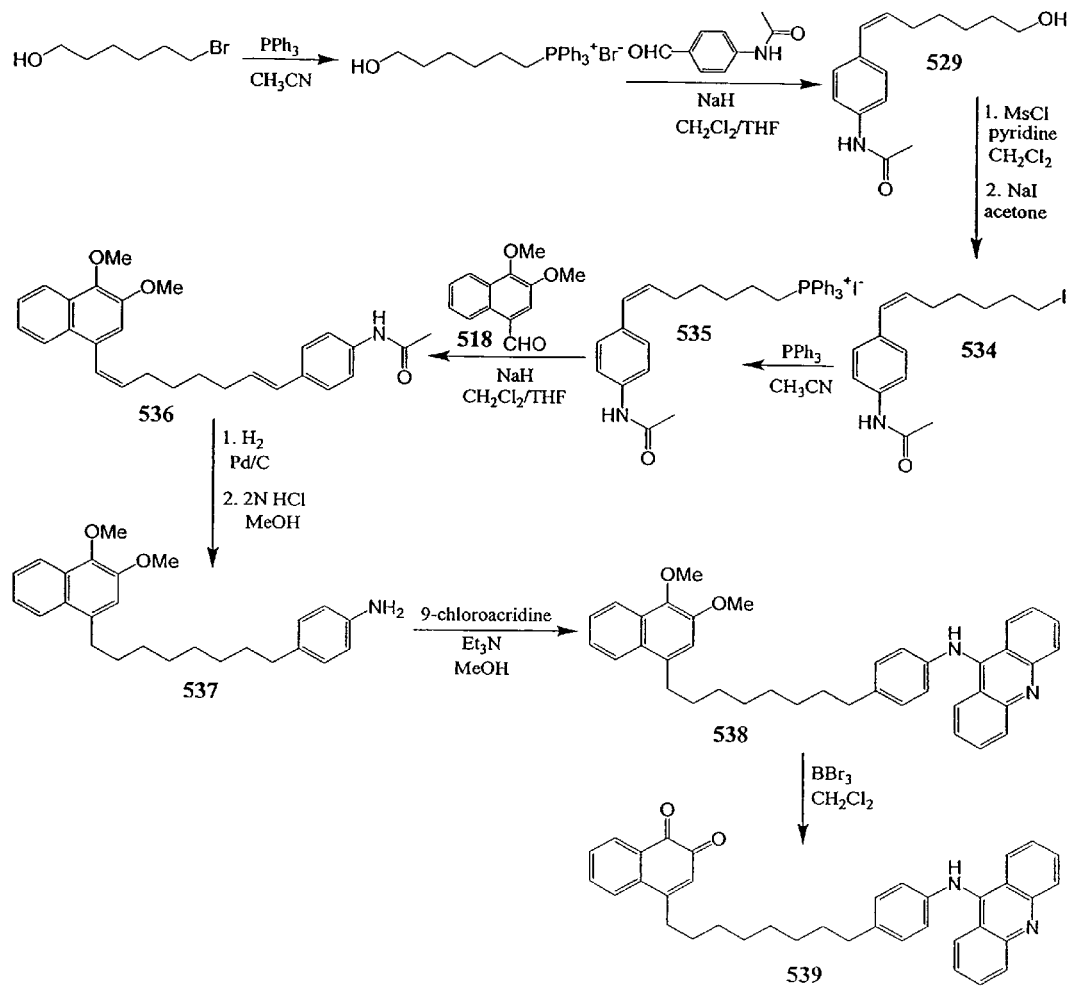

FIG. 49 depicts Scheme 509, illustrating the synthetic preparation of additional quinone compounds useful in the invention.

Figure 50:
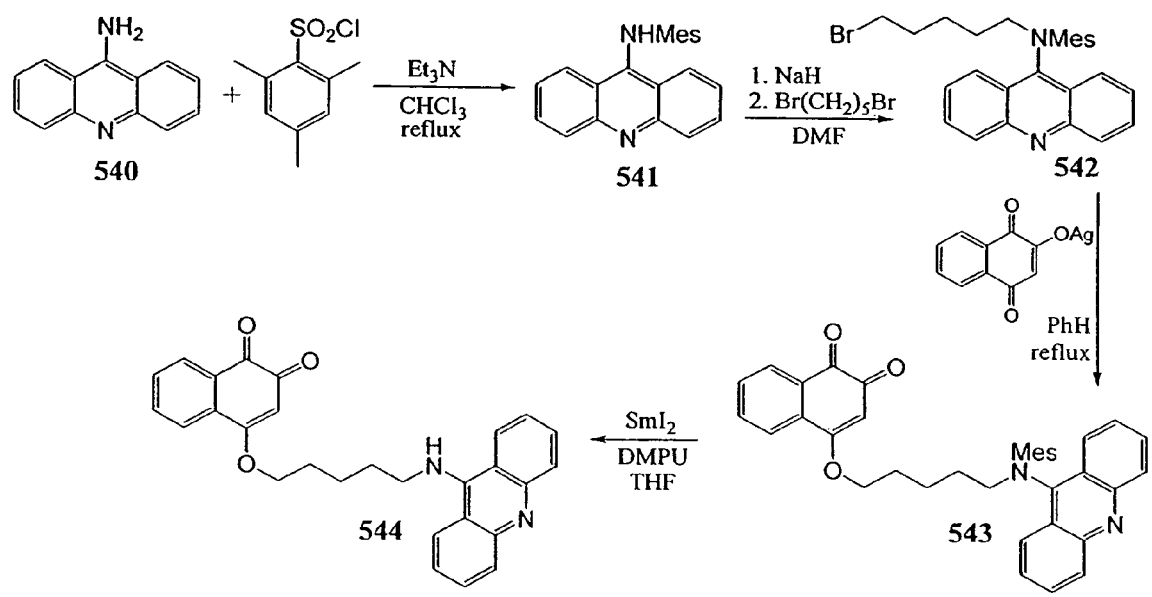

FIG. 50 depicts Scheme 510, illustrating the synthetic preparation of additional quinone compounds useful in the invention.

Figure 51:
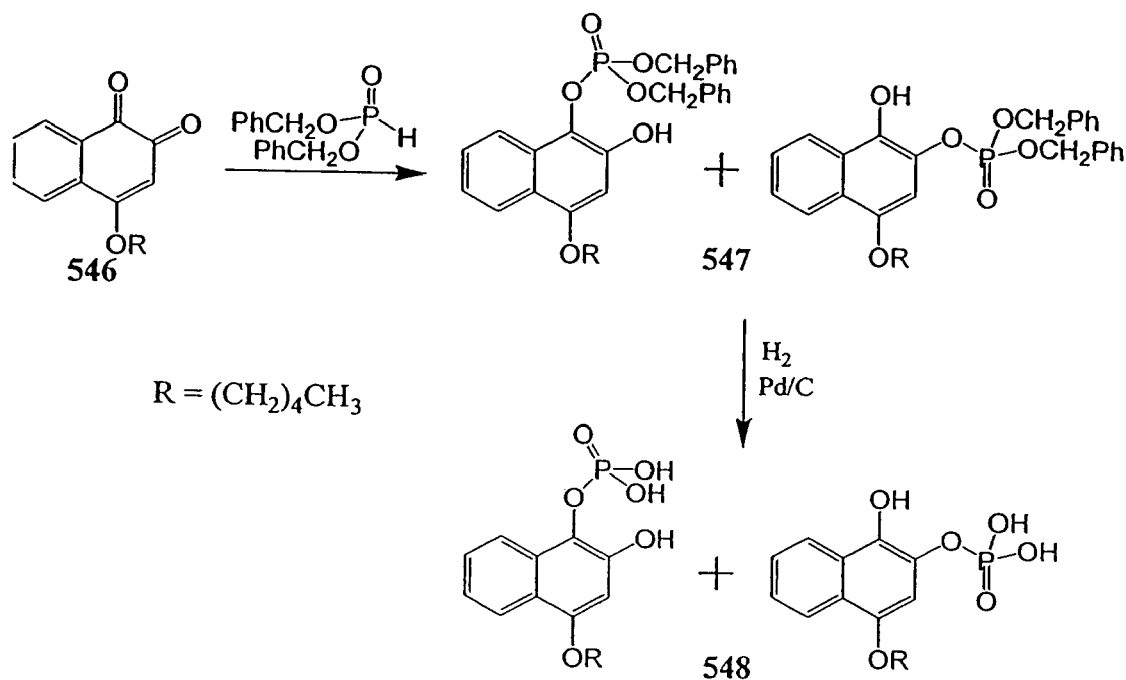

FIG. 51 depicts Scheme 511, illustrating the synthetic preparation of additional quinone compounds useful in the invention.

Figure 52:
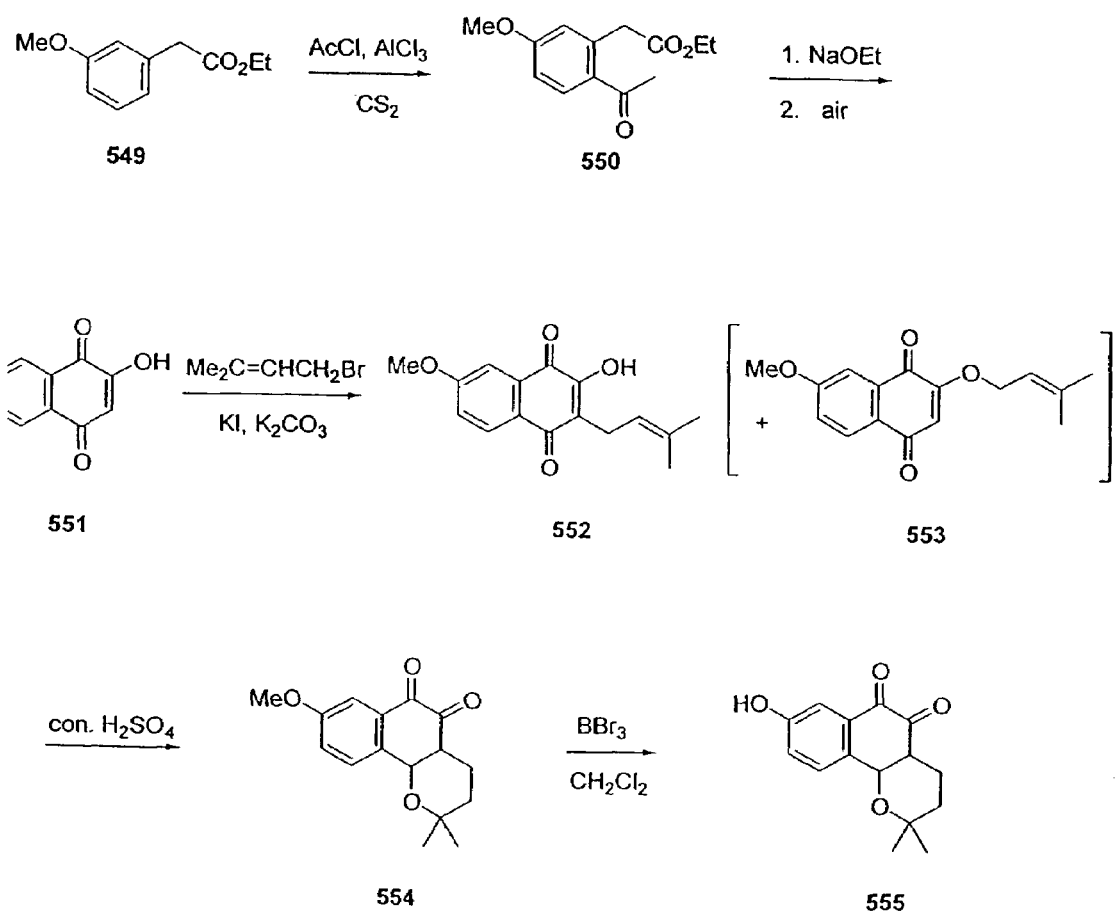

FIG. 52 depicts Scheme 512, illustrating the synthetic preparation of additional quinone compounds useful in the invention.

FIG. 53 depicts Scheme 513, illustrating synthetic preparation of peptides conjugated to certain quinone compounds (SEQ ID NOS:2, 5-8).

Figure 54:
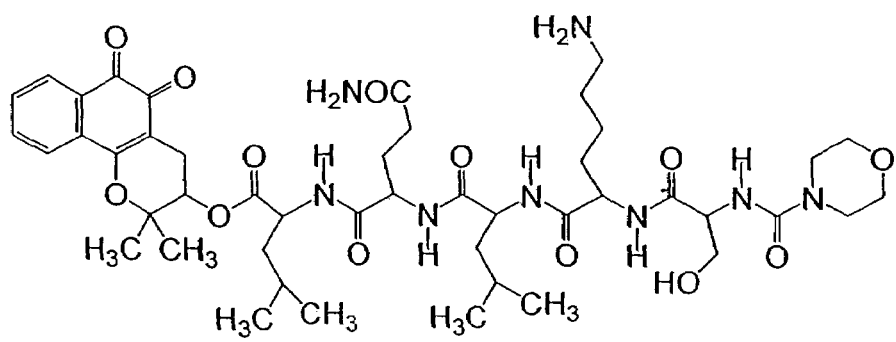

FIG. 54 depicts Scheme 514, illustrating additional synthetic preparation of peptides conjugated to certain quinone compounds (SEQ ID NOS:3, 9-12).

Figure 55:
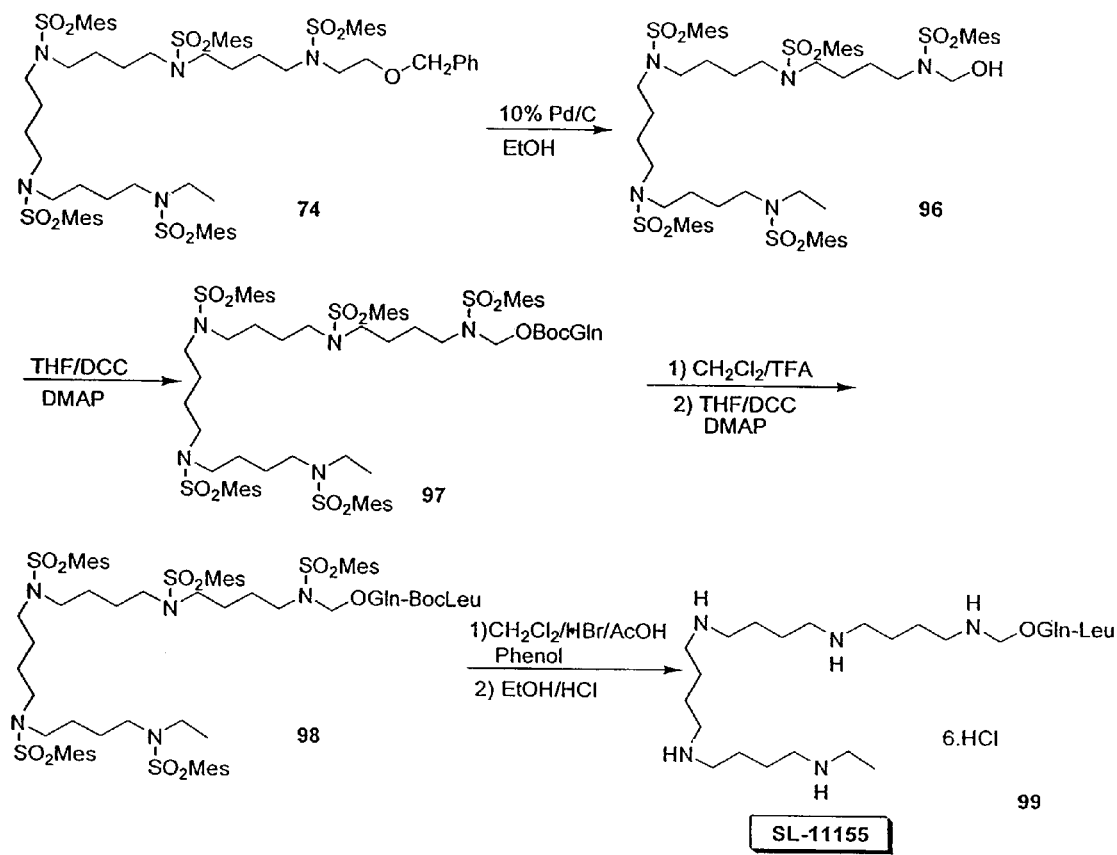

FIG. 55 depicts Scheme 25, illustrating the synthesis of a dipeptide conjugated to a polyamine alchohol via an ester linkage.

Figure 56:
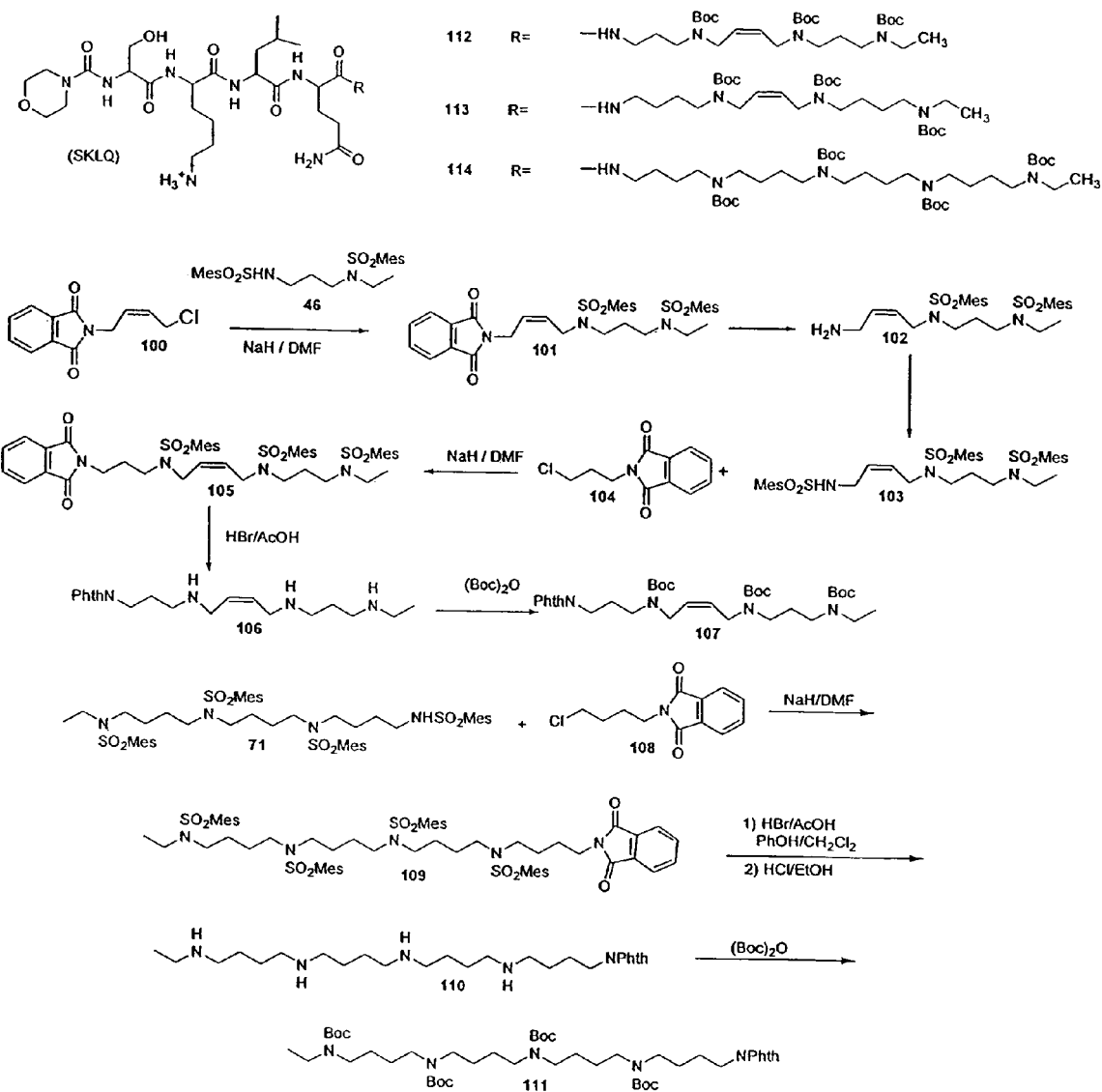

FIG. 56 depicts Scheme 26, illustrating the synthesis of a tetrapeptide conjugated to various polyamines via an amide linkage (SEQ ID NO:13).

FIG. 57 is a graph depicting the in vitro effects of increasing concentrations of SL-11141 (○) and SL-11155 (●) on the survival of cultured human prostate cancer cells PC3.

FIG. 58 is a graph depicting the in vitro effects of increasing concentrations of SL-11141 (○) and SL-11155 (●) on the survival of cultured human prostate cancer cells DUPRO.

FIG. 59 is a graph depicting the in vitro effects of increasing concentrations of SL-11141 (○) and SL-11155 (●) on the survival of cultured human prostate cancer cells LNCAP.

FIG. 60 is a graph depicting the in vitro effects of increasing concentrations of SL-11141 (●) and BE 4×4 (○) and SL-11155 on the survival of cultured human prostate cancer cells DU145.

MODES FOR CARRYING OUT THE INVENTION

The present invention encompasses polyamine analog and quinone conjugates in which a polyamine analog or a quinone is conjugated to a polypeptide to form an inactive prodrug. The conjugates of the invention are useful in treating cancers and other diseases characterized by cell proliferation. The polyamine analog conjugates of the present invention are particularly useful in suppression of proliferation of prostate cells.

The polypeptides are preferably enzyme substrates, designed to be specifically recognized and cleaved by enzymes overexpressed by, or expressed exclusively by, cancerous cells or cells of the target tissue. Prostate specific antigen (PSA), for example, is produced in large amounts only by prostate tissues. A peptide substrate for PSA can thus be bound to a polyamine analog to form a prodrug. When the polypeptide moiety of the conjugate is removed by PSA, the prodrug becomes active and the polyamine analog can inhibit proliferation of the prostate cell. This proliferation inhibition is useful in treating a variety of prostatic diseases.

PSA is a protease expressed in the highly specialized apically-superficial layer of secretory (luminal) cells of the prostate gland, as well as at other sites of the urogenital tract, frequently coinciding with glucosamine glucans, glycoproteins and numerous enzyme proteins. PSA is found in seminal fluid in its free form and in serum, where it occurs in an inactive complex form with alpha$_1$-chymotrypsin. PSA has chymotrypsin-like substrate specificity. Lilja et al. (1985) *J. Clin. Invest.* 76:1899-1903; Watt et al. (1986) *Proc. Natl. Acad. Sci. USA* 83:3166-3170; and Christensson et al. (1990) *J. Biochem.* 194:755-765. PSA specifically recognizes and cleaves polypeptides, including those of sequences HSSKLQ (SEQ ID NO:1) and SKLQ (SEQ ID NO:4), which are not recognized by abundant serum proteases. Denmeade et al. (1997) *Cancer Res.* 57:4924-30; and Denmeade et al. (1998) *Cancer Res.* 58:2537-40. While both normal and cancerous prostate tissues produce PSA [Denmeade et al. (1997)], PSA levels in the seminal fluid and blood serum increase many-fold in patients with prostate tumors. Increased PSA levels are also detected in patients with BPH or prostatitis. Rainwater et al. (1990) *Mayo Clinic Proc.* 65:11118-26. In addition, even when blood serum PSA levels increase up to 1000 ng/ml in patients with advanced prostate cancer, PSA in the blood serum is inactive. Denmeade et al. (1997).

Conjugation of the polyamine analogs with a polypeptide cleaved by PSA decreases the danger of toxicity of the polyamine analog in two ways. First, the polypeptide moiety reduces biological activity of the polyamine analog outside of the target tissues. Second, because the polypeptides are recognized by PSA and thus target the prodrug to the prostate, a lower dosage of polyamine analog can be administered. As discussed below, the polyamine analog can be any polyamine analog, including, but not limited to, 1, 12-Me$_2$-SPM, SL-11027, SL-11028, SL-11029, SL-11033, SL-11034, SL-11037, SL-11038, SL-11043, SL-11044, SL-11047, SL-11048, SL-11050, SL-11090, SL-11091, SL-11092, SL-11093, SL-11094, SL-11098, SL-11099, SL-11100, SL-11101, SL-11102, SL-11103, SL-11104, SL-11105, SL-11108, SL-11114, SL-11118, SL-11119, SL-11121, SL-11122, SL-11123, SL-11124, SL-11126, SL-11127, SL-11128, SL-11129, SL-11130, SL-11132, SL-11133, SL-11134, SL-11136, SL-11137, SL-11141, SL-11144, SL-11150, SL-11201, and SL-11202. Preferably, the polyamine analog is conformationally restricted.

Definitions

By "polyamine analog" is meant an organic cation structurally similar but non-identical to polyamines such as spermine and/or spermidine and their precursor, diamine putrescine. By a "polyamine" is meant any of a group of aliphatic, straight-chain amines derived biosynthetically from amino acids; polyamines are reviewed in Marton et al. (1995) *Ann. Rev. Pharm. Toxicol.* 35:55-91. Polyamines cadaverine and putrescine are diamines produced by decarboxylation of lysine or ornithine, respectively. Putrescine is converted to spermidine, and spermidine to spermine, by the addition of an aminopropyl group. This group is provided by decarboxylated S-adenosyl methionine. Polyamine analogs, which can be branched or un-branched, include, but are not limited to, BE-4444 [1,19-bis(ethylamino)-5,10,15-triazanonadecane]; BE-333 [N1,N11-diethylnorspermine; DENSPM; 1,11-bis(ethylamino)-4,8-diazaundecane; thermine; Warner-Parke-Davis]; BE-33 [N1,N7-bis(ethyl)norspermidine]; BE-34 [N1,N8-bis(ethyl)spermidine]; BE-44 [N1,N9-bis(ethyl)homospermidine]; BE-343 [N1,N12-bis(ethyl)spermine; diethylspermine-N1-N12; DESPM]; BE-373 [N,N'-bis(3-ethylamino)propyl)-1,7-heptane diamine, Merrell-Dow]; BE-444 [N1,N14-bis(ethyl)homospermine; diethylhomospermine-N1-N14]; BE-3443 [1,17-bis(ethylamino)-4,9,14-triazaheptadecane]; BE-4334 [1,17- bis(ethylamino)-5,9,13-triazaheptadecane]; 1,12-Me$_2$-SPM [1,12-dimethylspermine]; various polyamine analogs disclosed in WO 98/17624 and U.S. Pat. No. 5,889,061; and the various novel polyamine analogs illustrated in the Figures and described herein, including, but not limited to, compounds designated SL-11027, SL-11028, SL-11029, SL-11033, SL-11034, SL-11037, SL-11038, SL-11043, SL-11044, SL-11047, SL-11048, SL-11050, SL-11090, SL-11091, SL-11092, SL-11093, SL-11094, SL-11098, SL-11099, SL-11100, SL-11101, SL-11102, SL-11103, SL-11104, SL-11105, SL-11108, SL-11114, SL-11118, SL-11119, SL-11121, SL-11122, SL-11123, SL-11124, SL-11126, SL-11127, SL-11128, SL-11129, SL-11130, SL-11132, SL-11133, SL-11134, SL-11136, SL-11137, SL-11141, SL-11144, SL-11150, SL-11201, and SL-11202. Additional polyamine analogs useful for this invention are known in the art, such as O'Sullivan et al. (1997) *Bioorg. Med. Chem.* 5:2145-2155; and Mukhopadhyaya et al. (1995) *Exp. Parasit.* 81:39-46; and U.S. Pat. No. 4,935,449.

By "conformationally restricted" is meant that, in a polyamine analog, at least two amino groups are locked or limited in spatial configuration relative to each other. The relative movement of two amino groups can be restricted, for example, by incorporation of a cyclic or unsaturated moiety between them (exemplified, but not limited to, a ring, such as a three-carbon ring, four-carbon ring, five-carbon-ring, six-carbon ring, or a double or triple bond, such as a double or triple carbon bond). Groups restricting conformational flexibility by means of steric hindrance, yet structurally favorable to the anti-proliferative effects, can also be used according to the invention. A "conformationally restricted" polyamine analog can comprise at least two amino groups which are conformationally restricted relative to each other, but can also further comprise amino groups which are not conformationally restricted relative to each other. Flexible molecules such as spermine and BE-444 can have a myriad of conformations and are therefore not conformationally restricted.

By "cancer" is meant the abnormal presence of cells which exhibit relatively autonomous growth, so that they exhibit an aberrant growth phenotype characterized by a significant loss of cell proliferation control. One embodiment of the present invention comprises methods of treating prostate cancer.

By "prostate" is meant the muscular, glandular organ which surrounds the urethra of males at the base of the bladder. The prostate is a non-essential organ.

For purposes of this invention, "PSA" includes any functionally-preserved variant, derivative and/or fragment of PSA, including amino acid sequence variants and proteins differing in post-translational modification, which retain the sequence-specific proteolytic ability of PSA.

For purposes of this invention, "cathepsin B" includes any functionally-preserved variant, derivative and/or fragment of cathepsin B, including amino acid sequence variants and proteins differing in post-translational modification, which retain the sequence-specific proteolytic ability of cathepsin B.

The terms "polypeptide", "polypeptide moiety", "protein", and the like are used interchangeably herein to refer to any polymer of amino acid residues of any length. The polymer can be linear or non-linear (e.g., branched), it can comprise modified amino acids or amino acid analogs, and it can be interrupted by chemical moieties other than amino acids. The terms also encompass an amino acid polymer that has been modified naturally or by intervention; for example, by disulfide bond formation, glycosylation, lipidation, acetylation, phosphorylation, or any other manipulation or modification, such as, conjugation with a labeling or bioactive component. The polypeptide components of the conjugates of the present invention are recognized and cleaved by enzymes such as prostate-specific antigen (PSA) or cathepsin B. Preferably, the specificity of cleavage is such that the polypeptide is cleaved to produce a free polyamine analog or free quinone with biological activity or a polyamine analog or free quinone with a very short residual polypeptide or single amino acid attached, which residual polypeptide or single amino acid does not interfere with the desired biological activity of the polyamine analog or quinone.

By "conjugation" is meant the process of forming a covalent linkage, with or without an intervening linker, between two moieties, such as a polyamine analog and a polypeptide moiety. The conjugation can be performed by any method known in the art, such as those described in Wong, *Chemistry of Protein Conjugation and Cross-linking*, 1991, CRC Press, Boca Raton, and described herein. Suitable methods include using strategies incorporating protecting groups such as the t-butyloxycarbonyl (BOC) protecting group (reagents for introducing the BOC group are available from Sigma, St. Louis, Mo., and other suppliers). Other suitable protecting groups which can be used in the conjugation reactions are described in Greene et al., *Protective Groups in Organic Synthesis*, 2nd Edition, 1991, Wiley, New York. Preferably, the polypeptide moiety is conjugated to the polyamine analog moiety or quinone moiety such that (1) the presence of the polypeptide moiety prevents the functionality of the polyamine analog or quinone; and (2) cleavage by an enzyme produces a free polyamine analog or free quinone, or a polyamine analog or quinone with such a small residual portion of the polypeptide moiety remaining attached, so that the polyamine analog is capable of effecting anti-proliferative activity. By "conjugate" is meant a chemical entity comprising two moieties which are covalently linked.

An "amino-capping group" or "amino-terminal capping group" is a group that covalently links to an amino group. Examples of amino-capping groups include, but are not limited to, 4-morpholinocarbonyl, acetyl, and trifluoroacetyl. An "amino-protecting group" or "amino-terminal protecting group" is a group that can be selectively removed from an amino group of a molecule without affecting the remainder of the molecule. Examples of amino-protecting groups include, but are not limited to, t-butyloxycarbonyl (BOC), 9-fluorenylmethoxycarbonyl (FMOC), benzyloxycarbonyl (CBZ), t-butyldimethylsilyl (TBDIMS), or suitable photolabile protecting groups such as 6-nitroveratryloxy carbonyl (Nvoc) and the like.

An "exterior nitrogen" or "exterior amino group" of a polyamine or polyamine analog is a nitrogen (amino) group which is flanked by only one other nitrogen group, while an "interior nitrogen" or "interior amino group" of a polyamine or polyamine analog is a nitrogen (amino) group which is flanked by two other nitrogen (amino) groups. For example, in a polyamine of the formula $R_1$—$N^1$H—$R_2$—$N^2$H—$R_3$—$N^3$H— . . . —$R_{(n-1)}$—$N^{(n-1)}$H—$N^n$H—$R_n$, where n is an integer, the nitrogens designated as $N^1$ and $N^n$ are the "exterior nitrogens" or "exterior amino groups," inasmuch as they are flanked by only one other nitrogen group, while $N^2$, $N^3$, etc., through $N^{(n-1)}$ are "interior nitrogens" or "interior amino groups," flanked by two other nitrogen (amino) groups.

An "individual" is a vertebrate, preferably a mammal, more preferably a human. Mammals include, but are not limited to, farm animals, sport animals, rodents, primates, and pets. Preferably, the individual is known or suspected to be afflicted by a prostate disease, such as BPH, prostatitis and/or prostate cancer. When the individual is not a human, a determination should be made of the specific amino acid sequence recognized and cleaved by the PSA of that individual's species. The polypeptide moiety of the polyamine analog conjugate should be suitably modified in sequence, if necessary, to be recognized and cleaved by the PSA present in that individual's species.

An "effective amount" or "therapeutic amount" is an amount sufficient to effect beneficial or desired clinical results. An effective amount can be administered in one or more administrations. For purposes of this invention, an effective amount of a polyamine analog conjugate is an amount that is sufficient to palliate, ameliorate, stabilize, reverse, slow or delay the progression of the disease state. A therapeutic amount of a polyamine analog conjugate of the present invention is an amount sufficient to inhibit proliferation of prostate cells. A polyamine analog conjugate is considered to be an effective agent for treating prostate diseases if it is effective against, for example, at least one type of prostate cancer cell line, even if it is not effective against a different prostate cell line.

As used herein, "treatment" is an approach for obtaining beneficial or desired clinical results, including, but not limited to, the suppression of proliferation of prostate cells. For purposes of this invention, beneficial or desired clinical results include, but are not limited to, alleviation of symptoms, diminishment of extent of disease, stabilization (i.e., not worsening) of state of disease, prevention of spread (i.e., metastasis) of disease, delay or slowing of disease progression, amelioration or palliation of the disease state, improvement in quality of enjoyment of life, and remission (whether partial or total), whether detectable or undetectable. "Treatment" can also mean prolonging survival as compared to expected survival if not receiving treatment.

By "suppressing proliferation of prostate cells" means that the proliferation of cells of the prostate gland, prostate-derived tumor cells, including metastatic tumors, or any cells expressing PSA is inhibited.

"Palliating" a disease means that the extent and/or undesirable clinical manifestations of a disease state are lessened and/or time course of the progression is slowed or lengthened, as compared to not administering polyamine analog conjugates of the present invention.

Polyamine Analogs Useful in the Invention

One embodiment of the present invention encompasses a polyamine analog conjugated to a polypeptide specifically recognized and cleaved by prostate-specific antigen (PSA). Another embodiment of the present invention encompasses a polyamine analog conjugated to a polypeptide specifically recognized and cleaved by cathepsin B. Other aspects of the invention encompass compositions comprising these conjugate(s). The polyamine analogs which may be used are as described below.

Generally, polyamine analog conjugates of the present invention can be produced by the following procedure. First, a polyamine analog is selected or a novel polyamine analog is designed. Without wishing to be bound by any particular theory explaining polyamine analog toxicity, it is believed that design of a novel polyamine analog can be based on the current knowledge of polyamine interaction with DNA and ability to induce structural changes in nucleic acids. Feuerstein et al. (1991); Gosule et al. (1978) *J. Mol. Biol.* 121:311-326; Behe et al. (1981) *Proc. Natl. Acad. Sci. USA* 78:1619-23; Jain et al. (1989) *Biochem.* 28:2360-2364; and Basu et al. (1990) *Biochem. J.* 269:329-334. Alternatively, a novel polyamine analog can be designed based on its likely ability to inhibit cell growth by suppressing natural polyamine synthesis or deplete the intracellular natural polyamine pool. Porter et al. (1988) in *Advances in Enzyme Regulation*, Pergamon Press, pp. 57-79. In the next step, the polyamine analog is tested in vitro for efficacy in inhibiting proliferation of prostate cells (such as LNCaP cells, PC-3 cells, or DUPRO cells). If it is efficacious, the polyamine analog is conjugated to a polypeptide. The polyamine analog conjugate can then be tested for its ability to be specifically recognized and cleaved by PSA, but not by other proteases, in a cell-free medium in vitro. If the polyamine analog conjugate passes this test, it can then be tested in animals, such as nude mice with prostate cancer xenografts. Testing can then proceed to human trials.

Conformationally Restricted Polyamine Analogs

Any polyamine analog (which has the requisite functional cytostatic or cytocidal property) may be used that has a pendant amino or hydroxyl group which can be conjugated to the C-terminus of the polypeptide moiety in an amide linkage or ester linkage, respectively, and examples are provided in the summary of the invention, the definition of "polyamine analogs" and in the synthetic schemes. Polyamine analogs used in the present invention are preferably conformationally restricted. Conformation is a determinant of the spatial arrangement of the pharmacophore or functional groups which interact with receptor binding sites. The latter prefer specific ligand conformations or a specific distribution of conformations. A flexible molecule such as spermine or BE-4444 can have a myriad of conformations. The conformer that binds to the macromolecule (e.g., DNA or RNA) may not necessarily be the one with the lowest energy as determined by spectroscopic methods or theoretically by molecular mechanics calculations. The binding energy of the polyamine analog binding to the nucleic acid may be overcome with formation of an unstable conformer. Conversely, in the presence of a conformationally rigid analog of a flexible molecule, the host macromolecule might change its overall conformation or the distances from one strand to the other. Hydrogen bonding is the main binding force of either spermine or spermidine associating with the helical region of a tRNA, and very likely also with DNA. Frydman et al. (1992) *Proc. Natl. Acad. Sci. USA* 89:9186-9191; and Fernandez et al. (1994) *Cell Mol. Biol.* 40: 933-944. The secondary amino groups present in the linear spermine analogs BE-4444 are the groups most directly involved in the formation of the hydrogen bonds with the paired bases of tRNA. While not wishing to limit the invention to any particular theory of operation, it is believed that those amino groups that usually flank the central four-carbon or three-carbon segment of the polyamine analog are most likely to function as the pharmacophore. When the nitrogens are separated by only a two-carbon segment they are not protonated at pH 7.4 and hence they do not form hydrogen bonds. If these amino groups are locked into various configurations by the incorporation of cyclic or unsaturated moieties into the polyamine analog molecule, a conformationally rigid analog is obtained. When such analogs bind to DNA or tRNA, they will very likely induce a change in the conformation of the nucleic acid strands or loops that may differ from the conformational changes induced by the natural polyamines.

Schemes 1-25 depict syntheses of various polyamine analogs which can be used in the invention. Examples of polyamine analogs which can be used in the invention are also given in U.S. Pat. Nos. 5,889,061 and 5,627,215, which describe tetraamino polyamine analogs. The synthesis of the polyamine analogs of those patents can be modified to introduce an amino-protecting group on the exterior nitrogens (i.e., representing the tetraamine as $R_1—N^1H—R_2—N^2H—R_3—N^3H—R_4—N^4H—R_5$, the nitrogens designated as $N^1$ and $N^4$ are the "exterior" nitrogens, inasmuch as they are flanked by only one other nitrogen group, while $N^2$ and $N^3$ are "interior" nitrogens, flanked by two other nitrogen groups) in place of the group that would ordinarily be attached at that point (in this example, a protecting group would be used instead of $R_1$ or $R_5$), and can be cleaved to yield a primary amino group at one of the exterior nitrogens, while maintaining amino-protecting groups on the other exterior nitrogen and the interior nitrogens. Scheme 26 depicts such a strategy of establishing a protecting group regimen which allows one of the exterior amino groups to be selectively deprotected, while maintaining the amino-protecting groups on the other exterior amino group and the interior amino groups. Examples of differential protection regimens of polyamines are also given in Fiedler et al. (1993) *Helv. Chim. Acta* 76:1511-1519 and Iwata et al. (1989) *Bull. Chem. Soc. Japan* 62:1102-1106.

TABLE 1

| No. | Structure |
|---|---|
| SL-11027 | 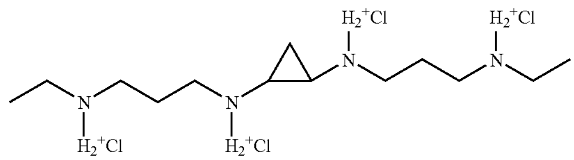 |
| SL-11028 | 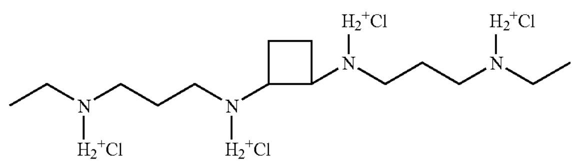 |
| SL-11029 | 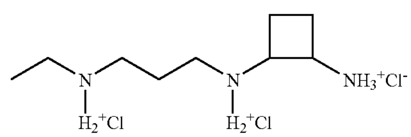 |
| SL-11033 | 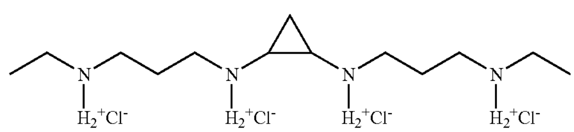 |
| SL-11034 | 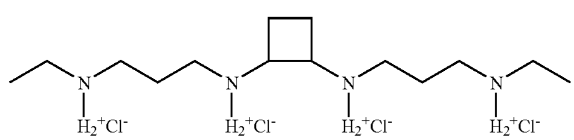 |
| SL-11035 | 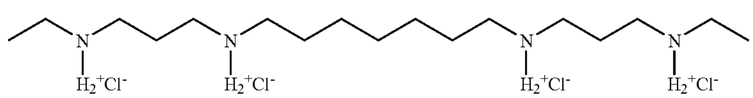 |
| SL-11036 | 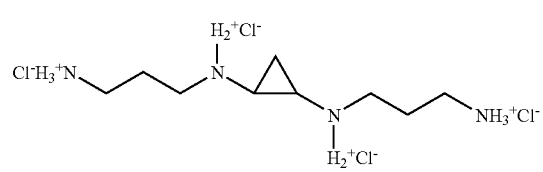 |
| SL-11037 | 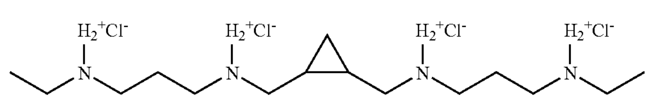 |
| SL-11038 | 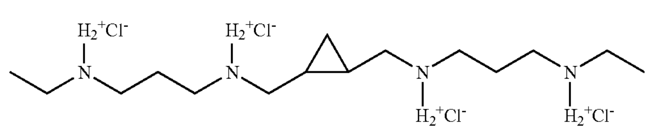 |

TABLE 1-continued

| No. | Structure |
|---|---|
| SL-11043 | (structure: EtNH-(CH₂)₃-NH-CH₂-cyclobutane-CH₂-NH-(CH₂)₃-NH-Et, all amines as H₂⁺Cl⁻) |
| SL-11044 | (structure: EtNH-(CH₂)₃-NH-CH₂-cyclobutane-CH₂-NH-(CH₂)₃-NH-Et, all amines as H₂⁺Cl⁻) |
| SL-11047 | (structure: EtNH-(CH₂)₃-NH-CH₂-CH=CH-CH₂-NH-(CH₂)₃-NH-Et, all amines as H₂⁺Cl⁻, cis-alkene) |
| SL-11048 | (structure: EtNH-(CH₂)₃-NH-CH₂-CH=CH-CH₂-NH-(CH₂)₃-NH-Et, all amines as H₂⁺Cl⁻, trans-alkene) |
| SL-11050 | BnNH(CH₂)₄NHBn•2HCl |
| SL-11061 | EtNH(CH₂)₄NH(CH₂)₄NH(CH₂)₄NH(CH₂)₄—NHEt•5HCl |
| SL-11090 | (structure: MeNH-(CH₂)₃-NH-CH₂-trans-cyclobutane-CH₂-NH-(CH₂)₃-NHMe •4HCl) |
| SL-11091 | (structure: EtNH-(CH₂)₃-NH-CH₂-C≡C-CH₂-NH-(CH₂)₃-NHEt •4HCl) |
| SL-11092 | (structure: MeNH-(CH₂)₃-NH-CH₂-C≡C-CH₂-NH-(CH₂)₃-NHMe •4HCl) |
| SL-11093 | (structure: EtNH-(CH₂)₃-NH-CH₂-cyclopropane-CH₂-NH-(CH₂)₄-NHEt •4HCl) |
| SL-11094 | (structure: EtNH-(CH₂)₃-NH-CH₂-(o-phenylene)-CH₂-NH-(CH₂)₃-NHEt •4HCl) |
| SL-11098 | (structure: EtNH-(CH₂)₄-NH-CH₂-cyclopropane-CH₂-NH-(CH₂)₄-NHEt •4HCl) |
| SL-11099 | (structure: EtNH-(CH₂)₄-NH-CH₂-cyclobutane-CH₂-NH-(CH₂)₄-NHEt •4HCl) |
| SL-11100 | (structure: EtNH-(CH₂)₄-NH-CH₂-cyclobutane-CH₂-NH-(CH₂)₄-NHEt •4HCl) |
| SL-11101 | (structure: EtNH-(CH₂)₄-NH-CH₂-CH=CH-CH₂-NH-(CH₂)₄-NHEt •4HCl) |

TABLE 1-continued
| No. | Structure |
|---|---|
| SL-11102 | 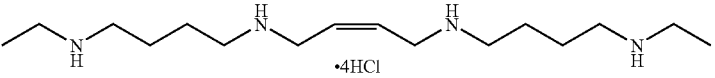 ·4HCl |
| SL-11103 |  ·4HCl |
| SL-11104 | 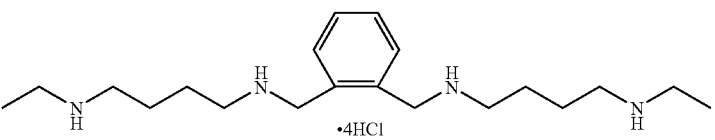 ·4HCl |
| SL-11105 | 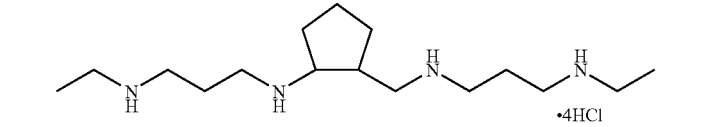 ·4HCl |
| SL-11108 | 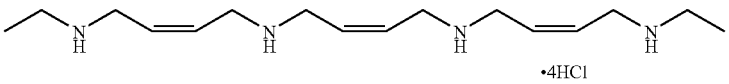 ·4HCl |
| SL-11114 | 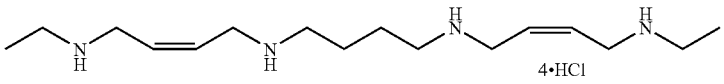 4·HCl |
| SL-11118 | 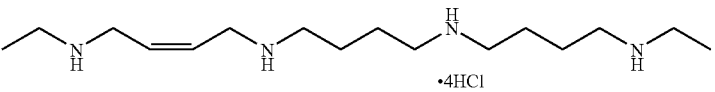 ·4HCl |
| SL-11119 | 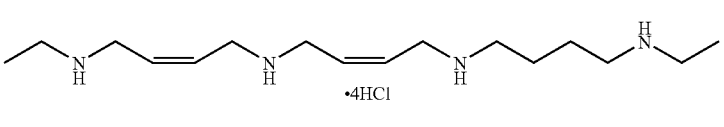 ·4HCl |
| SL-11121 | 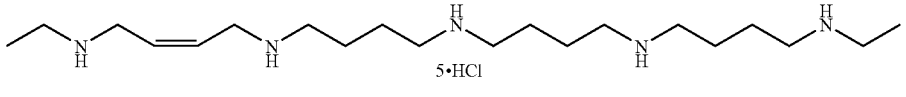 5·HCl |
| SL-11122 | 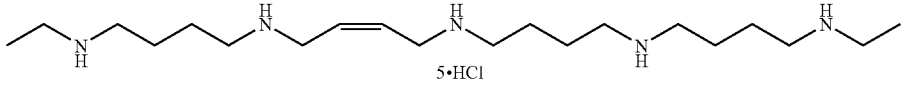 5·HCl |
| SL-11123 | 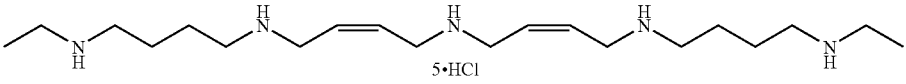 5·HCl |
| SL-11124 | 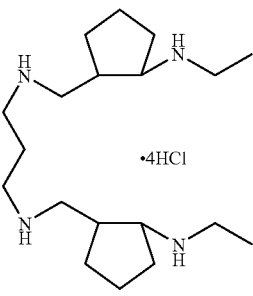 ·4HCl |

TABLE 1-continued
| No. | Structure |
|---|---|
| SL-11126 | 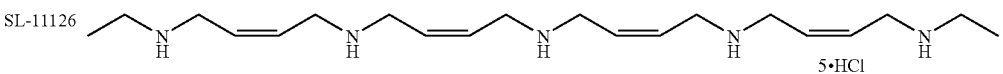 |
| SL-11127 | 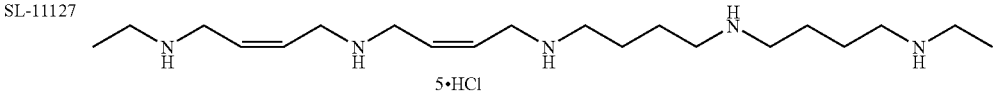 |
| SL-11128 | 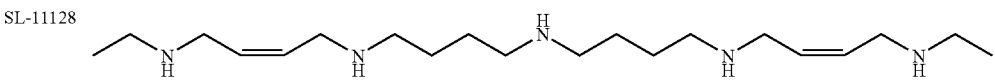 |
| SL-11129 | 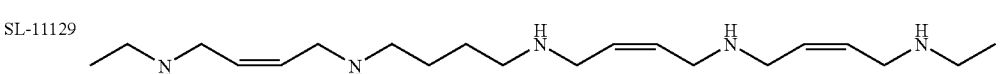 |
| SL-11130 | 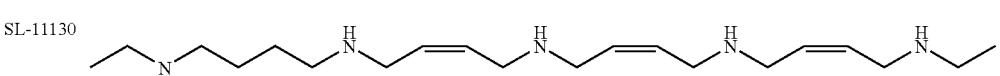 |
| SL-11132 | 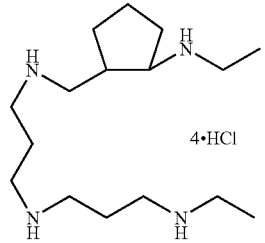 |
| SL-11133 | 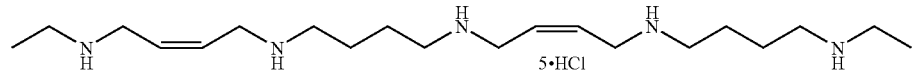 |
| SL-11134 | 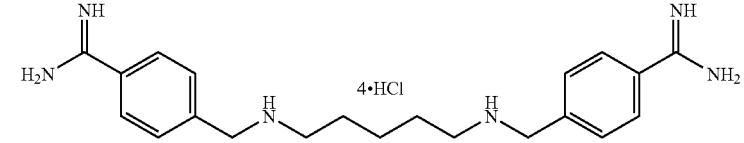 |
| SL-11135 | 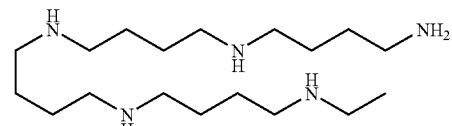 |
| SL-11136 | 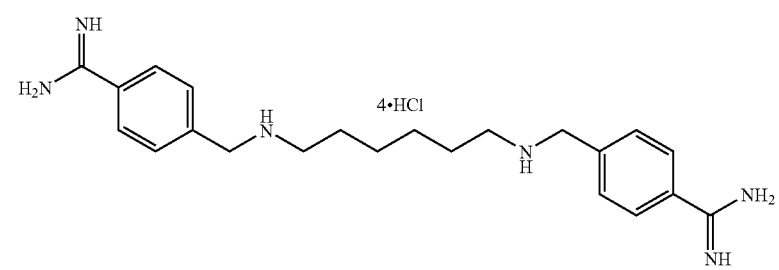 |

TABLE 1-continued

| No. | Structure |
|---|---|
| SL-11137 | (structure: 4-amidinobenzyl-NH-(CH2)4-NH-(CH2)3-NH-CH2-4-amidinobenzene, 4·HCl) |
| SL-11141 | (branched polyamine, 5·HCl, terminating in ethyl and 2-hydroxyethyl groups) |
| SL-11143 | (branched polyamine, 5·HCl, terminating in ethyl and β-alanylamide (−NHC(O)CH2CH2NH2) groups) |
| SL-11144 | (dimeric polyamine linked via cis/trans-but-2-ene, each arm = −NH−[(CH2)4−NH]4−Et, 10·HCl) |
| SL-11150 | (dimeric polyamine linked via cis-but-2-ene, each arm = −NH−[(CH2)4−NH]4−Et, 10·HCl) |
| SL-11155 | (branched polyamine, 6·HCl, one arm terminating in −NH−CH2CH2−O−Gln−Leu, other arm terminating in −NHEt) |
| SL-11157 | Et−NH−[(CH2)4−NH]3−CH2−CH=CH−CH2−NH−[(CH2)4−NH]3−Et, 8·HCl |
| SL-11158 | Et−NH−[(CH2)4−NH]3−CH2−CH=CH−CH2−NH−[(CH2)4−NH]3−Et (cis), 8·HCl |
| SL-11159 | Et−[NH−(CH2)4]9−NH−Et, 10·HCl |

TABLE 1-continued

| No. | Structure |
|---|---|
| SL-11160 | 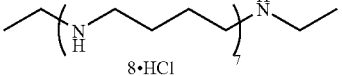<br>8·HCl |

Efficacy of Polyamine Analogs Against Tumor Cells In vitro

Novel polyamine analogs, once designed and constructed, are tested for efficacy in vitro against disease cells, such as prostate tumor cells. Known polyamines can also be tested in this way. Analogs found to be active against disease cells are particularly suitable for use in the conjugates and methods of the invention.

Quinones Useful in the Invention

Quinones useful in the invention include cytotoxic quinones with a pendant amino or hydroxyl group which can be conjugated to the C-terminus of the polypeptide moiety in an amide linkage or ester linkage, respectively. Syntheses of several quinones useful in the invention are presented below. Additional examples of quinones useful in the invention, along with methods for their preparation, are found in U.S. Pat. No. 5,763,625 (including, but not limited to, those compounds described at column 4, lines 40 to 52, where R is $(CH_2)_n$—$R_1$ and $R_1$ is a hydroxy or an amine); in U.S. Pat. No. 5,824,700 (including, but not limited to, those compounds of formula II at column 4, lines 20 to 48, which contain amino or hydroxy groups), and in U.S. Pat. No. 5,883,270 (including, but not limited to, those compounds of formula I at column 1, lines 49 to 67, which contain amino groups).

Preparation of Polypeptide Moiety of the Conjugates of the Invention

The polypeptide moiety of the conjugates of the invention, such as the polyamine analog conjugates or quinone conjugates of the present invention, should be specifically recognized and cleaved by enzymes present at high levels in the target tissue relative to levels in non-targeted tissues, or enzymes more readily accessible in the target tissue relative to non-targeted tissue. One example of such an enzyme is prostate specific antigen, which is present in high levels in the prostate. Another example of such an enzyme is cathepsin B, which is normally present primarily in lysosomes, but which has been found in some cancers to be associated with the extracellular face of the plasma membrane (as well as being overexpressed in cancer cells relative to normal cells). See Yan et al. (1998) *Biol. Chem.* 379:113-123. Cathepsin B is believed to play a role in degradation of the extracellular matrix, facilitating angiogenesis by tumors. Sinha et al. (1995) *Anat. Rec.* 241:353-362; Sinha et al. (1995) *Prostate* 26:171-178. Peptides attached to doxorubicin are disclosed in Dubowchik et al. (1998) *Bioorg. Med. Chem. Lett.* 8:3341-3346.

For use in targeting prostate tissue, the polypeptide components of the conjugates of the present invention comprise less than about 100 amino acids, preferably less than about 50 amino acids, more preferably less than about 25 amino acids, preferably less than about 10 amino acids, more preferably about seven or fewer amino acids, and more preferably, four or five amino acids. Preferably, the polypeptide comprises the amino acid sequence HSSKLQ, (SEQ ID NO:1) more preferably it comprises the sequence of tetrapeptide SKLQ (SEQ ID NO:4), and even more preferably it consists of SKLQ (SEQ ID NO:4). In another embodiment, the peptide comprises the sequence SKLQL (SEQ ID NO:3) or SKLQ-β-alanine, (SEQ ID NO:2) and in a more preferred embodiment, the peptide consists of SKLQL (SEQ ID NO:3) or SKLQ-β-alanine(SEQ ID NO:2). The peptide sequences can include N-terminal modifications, including, but not limited to, capping with amino-capping groups such as 4-morpholinocarbonyl and acetyl, or protection with protecting groups such as benzyloxycarbonyl (Cbz) or t-butyloxycarbonyl (Boc).

When cleavage of the polypeptide by cathepsin B is desired, the peptide will generally comprise less than about 10 amino acids, preferably less than about 4 amino acids. In preferred embodiments, the peptides comprise two or three amino acids. Preferred sequences include dipeptides of the sequence X—P2-P1, where P2 is the N-terminal amino acid and P1 is the C-terminal amino acid, where X is hydrogen, an amino-protecting group, or an amino-capping group; P2 is a hydrophobic amino acid; and P1 is a basic or polar amino acid. Another preferred sequence includes tripeptides of the form X—P2-P1-β-alanine or X—P2-P1-leucine, where P2 is the N-terminal amino acid and β-alanine or leucine is the C-terminal amino acid. A preferred embodiment for X is 4-morpholinocarbonyl. Preferred amino acids for P2 include leucine, isoleucine, valine, methionine, and phenylalanine. Preferred amino acids for P1 include lysine, arginine, glutamine, asparagine, histidine and citrulline. The peptide sequences may include N-terminal modifications, including, but not limited to, capping with amino-capping groups such as 4-morpholinocarbonyl and acetyl, or protection with protecting groups such as benzyloxycarbonyl (Cbz) or t-butyloxycarbonyl (Boc).

The polypeptides used in this invention can be made by procedures known in the art. The polypeptides can be produced by recombinant methods (i.e., single or fusion polypeptides) or by chemical synthesis. Polypeptides, especially shorter polypeptides up to about 50 amino acids, are conveniently made by chemical synthesis. See, for example, Atherton and Sheppard, *Solid Phase Peptide Synthesis: A Practical Approach*, New York: IRL Press, 1989; Stewart and Young: *Solid-Phase Peptide Synthesis 2nd Ed.*, Rockford, Ill.: Pierce Chemical Co., 1984; and Jones, *The Chemical Synthesis of Peptides*, Oxford: Clarendon Press, 1994. The polypeptides can be produced by an automated polypeptide synthesizer employing the solid phase method, such as those sold by Perkin Elmer-Applied Biosystems, Foster City, Calif., or can be made in solution by methods known in the art.

Polypeptides can also be made by expression systems, using recombinant methods. The availability of polynucleotides encoding polypeptides permits the construction of expression vectors encoding polypeptides. A polynucleotide encoding the desired polypeptide, whether in fused or mature form, and whether or not containing a signal sequence to permit secretion, may be ligated into expression vectors suitable for any convenient host. Both eukaryotic and prokaryotic host systems can be used. The polypeptide is then isolated from lysed cells or from the culture medium and purified to the extent needed for its intended use. Purification or isolation of the polypeptides expressed in host systems can be accomplished by any method known in the art. For example, cDNA encoding a polypeptide intact or a fragment thereof can be operatively linked to a suitable promoter, inserted into an expression vector, and transfected into a suitable host cell. The host cell is then cultured under conditions that allow transcription and translation to occur, and the desired polypeptide is recovered. Other controlling transcription or translation segments, such as signal sequences that direct the polypeptide to a specific cell compartment (i.e., for secretion), can also be used. Examples of prokaryotic host cells are known in the art and include, for example, *E. coli* and *B. subtilis*. Examples of eukaryotic host cells are known in the art and include yeast, avian, insect, plant, and animal cells such as COS7, HeLa, CHO and other mammalian cells.

A fusion protein may also be constructed that facilitates purification. Examples of components for these fusion proteins include, but are not limited to myc, HA, FLAG, His-6, glutathione S-transferase, maltose binding protein or the Fc portion of immunoglobulin. These methods are known in the art. See, for example, Redd et al. (1997) *J. Biol. Chem.* 272:11193-11197.

Preferably, especially if used for diagnostic purposes, the polypeptides are at least partially purified or isolated from other cellular constituents. Preferably, the polypeptides are at least 50% pure. In this context, purity is calculated as a weight percent of the total protein content of the preparation. More preferably, the proteins are 50-75% pure. More highly purified polypeptides may also be obtained and are encompassed by the present invention. For clinical use, the polypeptides are preferably highly purified, at least about 80% pure, and free of pyrogens and other contaminants. Methods of protein purification are known in the art and are not described in detail herein.

The polypeptide(s) must be cleavable by the enzyme targeted, such as PSA or cathepsin B. A polypeptide can be readily tested for this characteristic by determining whether cleavage has occurred when the polypeptide(s) is reacted under suitable conditions with PSA or cathepsin B. See, e.g., Denmeade et al. (1997).

Conjugation of Polyamine Analogs and Quinones to the Polypeptide Moiety

Any method known in the art can be used to conjugate (i.e., link) the polypeptide recognized and cleaved by enzymes such as PSA or cathepsin B to the polyamine analog or quinone, including, but not limited to, those disclosed herein. Suitable methods include using strategies incorporating protecting groups such as the t-butyloxycarbonyl (BOC) protecting group (reagents for introducing the BOC group are available from Sigma, St. Louis, Mo., and other suppliers). Other suitable protecting groups which can be used in the conjugation reactions are described in Greene et al., *Protective Groups in Organic Synthesis,* 2nd Edition, 1991, Wiley, New York. Preferably, the polypeptide moiety is conjugated to the polyamine analog moiety or quinone moiety such that (1) the presence of the polypeptide moiety prevents the functionality of the polyamine analog or quinone; and (2) cleavage by PSA produces a free polyamine analog or quinone, or a polyamine analog or quinone with such a small residual portion of the polypeptide moiety remaining attached, so that the polyamine analog or quinone is capable of effecting anti-proliferative activity.

The peptides are preferentially coupled via the α-COOH group of the C-terminal amino acid, although other linkages are possible, depending on the peptide sequence (e.g., the γ-carboxyl group of a glutamic acid residue can be used for linkage). When a polyamine is coupled, the linkage will be via an amino group of the polyamine (i.e., an amide linkage); when a polyamine alcohol is conjugated, the linkage can be via either an amino group or a hydroxy group of the polyamine alcohol (i.e., an amide linkage or ester linkage, respectively). When an amide linkage to a polyamine is used, the peptide is preferably coupled to an exterior nitrogen. When an ester linkage to a polyamine is used, the peptide is preferably coupled to a terminal hydroxy group. When a quinone containing an amino group is conjugated, the linkage to the peptide will be an amide linkage; when the quinone contains a hydroxy group, the linkage will be an ester linkage; and when the quinone contains both groups, either an amide linkage or an ester linkage can be employed.

In vitro and In vivo Testing of Polyamine Analog and Quinone Conjugates

When a polyamine analog or quinone has been shown to be effective in vitro, its conjugate can be constructed and also tested in vitro. Preferably, in vitro testing of polyamine analog or quinone conjugates should be performed with the same cell lines that demonstrated efficacy of the polyamine analogs or quinones themselves, e.g. human prostate cancer cell lines PC-3, DU-145 and DuPro. U.S. Pat. Nos. 5,883,270, 5,889,061, 5,763,625, and 5,824,700 all provide examples of protocols used to test compounds for biological activity.

Those conjugates shown to have efficacy in vitro are generally next tested in vivo. Prostate tumor xenografts can be grown in nude mice, for example, and polyamine analog conjugates or quinone conjugates administered to these test animals. Determination of efficacy can include measurement of effective dosage and monitoring of side effects.

Methods of Administration of Polyamine Analog Conjugates

The invention also provides methods of treatment and methods of suppressing cell proliferation or uncontrolled cell growth, especially prostate cell proliferation. The methods comprise administering an effective amount of any of the conjugates described herein. For treatment, an effective amount is an amount sufficient to palliate, ameliorate, stabilize, reverse, slow or delay the disease state; or for inhibition or suppression of proliferation of cells such as prostate cells.

Polyamine analog conjugates of the present invention can be administered to an individual via any route known in the art, including, but not limited to, those disclosed herein. Preferably administration of the polyamine analog conjugates is intravenous. Other methods of administration include but are not limited to, oral, intrarterial, intratumoral, intramuscular, transdermal or transcutaneous, subcutaneous, intraperitoneal, gastrointestinal, and directly to a specific or affected organ, e.g., the prostate.

The polyamine analog conjugates described herein are administratable in the form of tablets, pills, powder mixtures, capsules, injectables, solutions, suppositories, emulsions, dispersions, food premixes, and in other suitable forms. Additional methods of administration are known in the art. The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form may also contain non-toxic auxiliary substances such as emulsifying, preserving, or wetting agents, and the like. A suitable carrier is one which does not cause an intolerable side effect, but which allows the conjugates to retain its pharmacological activity in the body. Formulations for parenteral and nonparenteral drug delivery are known in the art and are set forth in *Remington's Pharmaceutical Sciences*, 19th Edition, Mack Publishing (1995). Solid forms, such as tablets, capsules and powders, can be fabricated using conventional tableting and capsule-filling machinery, which is well known in the art. Solid dosage forms can contain any number of additional non-active ingredients known to the art, including excipients, lubricants, dessicants, binders, colorants, disintegrating agents, dry flow modifiers, preservatives, and the like.

Liquid forms for ingestion can be formulated using known liquid carriers, including aqueous and non-aqueous carriers, suspensions, oil-in-water and/or water-in-oil emulsions, and the like. Liquid formulations can also contain any number of additional non-active ingredients, including colorants, fragrance, flavorings, viscosity modifiers, preservatives, stabilizers, and the like. For parenteral administration, polyamine analog or quinone conjugates can be administered as injectable dosages of a solution or suspension of the compound in a physiologically acceptable diluent or sterile liquid carrier such as water or oil, with or without additional surfactants or adjuvants. An illustrative list of carrier oils would include animal and vegetable oils (peanut oil, soy bean oil), petroleum-derived oils (mineral oil), and synthetic oils. In general, for injectable unit doses, water, saline, aqueous dextrose and related sugar solutions, and ethanol and glycol solutions such as propylene glycol or polyethylene glycol are preferred liquid carriers. The amount of conjugate administered per administration will vary, depending on the condition being treated and the individual's medical history.

The pharmaceutical unit dosage chosen is preferably fabricated and administered to provide a final concentration of drug at the point of contact with the cancer cell of from about 1 µM to about 10 mM. More preferred is a concentration of from about 1 µM to about 100 µM; still more preferred is a concentration of from about 1 µM to about 50 µM. As with all pharmaceuticals, the optimal effective concentration of a polyamine analog conjugate or quinone conjugate will need to be determined empirically and will depend on the type and severity of the disease, route of administration, disease progression and health and mass or body area of the patient. Such determinations are within the skill of one in the art. Polyamine analog conjugates or quinone conjugates can be administered as the sole active ingredient, or can be administered in combination with another active ingredient, including, but not limited to, cytotoxic agents, antibiotics, antimetabolites, nitrosourea, and vinca alkaloids.

Therapy may be monitored using standard methods in the art, such as determination of PSA levels in blood, biopsy, or imaging of the prostate or other tissue or organ.

The following examples are provided to illustrate but not limit the invention.

EXAMPLES

Synthesis of Conformationally-restricted Polyamine Analogs a) Spermine and Homospermine Analogs Containing a Conformational Restriction Scheme 2 exemplifies a $N^{\alpha}$, $N^{107}$-bisethyl homospermine analog 7 containing a central trans-unsaturated bond. Amide 4 was prepared as described in Scheme 1 by alkylation of amide 1 with bromobutyronitrile to give 2, followed by reduction of the nitrile to the amine 3 that was mesitylsulfonated to 4. Trans-allylic diester 5 was used to alkylate amide 4 and the tetramide 6 was obtained. Deprotection gave the trans-tetramide 7 (Scheme 2).

Introduction of a triple bond in the butane segment of homospermine also reduces its mobility. This was achieved by starting with the butyne diester 8 and following the sequence of reactions outlined above (Scheme 3). Schemes 15-20 are further examples of the synthesis of polyamine spermine and homospermine analogs of this type.

b) Synthesis of Pentamines with Conformational Restrictions.

Schemes 4-14 are outlines of the syntheses of conformationally restricted pentamines. Scheme 4 depicts the reaction of cis-1-chloro-4-phthalimido butene with amide 1 to give 11. Hydrazinolysis of 11 gave 12 which was amidated to 13. Reaction of the latter with 1,4-diiodobutane gave 14, while reaction with equimolar amounts of cis-1,4-dichlorobutene gave 15.

Amide 4 was alkylated with either 4-chlorobutyronitrile to give 16 or with cis-1,4-dichlorobutene to give 19. Nitrile 16 was reduced with hydrogen over Ni Raney to the amine 17 and the latter transformed in to the amide 18 (Scheme 5). Condensation of 18 with the chloroalkyl intermediate 15 gave the pentamide 20 that was deprotected to the pentamine 21 (Scheme 6). Condensation of 18 with the iodoalkyl derivative 14 gave 22 that was deprotected to the pentamine 23 (Scheme 7). Condensation of 18 and 19 gave pentamide 24 that was deprotected to the pentamine 25 (Scheme 8). Using 14 as the alkylating agent, mesitylenesulfonamide was dialkylated to give 26, and the latter deprotected to give 27 (Scheme 9). The analogous reaction carried out using 15 as alkylating agent, gave 28 and after deprotection led to the pentamine 29 (Scheme 10).

Alkylation of mesitylenesulfonamide with 19 gave the pentamide 30, which was deprotected to 31 (Scheme 11). When 19 was used to alkylate an equimolar amount of mesitylenesulfonamide then 32 was obtained. Alkylation of 32 with 14 gave 33, that was deprotected to give 34 (Scheme 12). When the chloroalkyl intermediate 15 was used to alkylate one equivalent of mesitylenesulfonamide, then the triamide 35 was obtained. Reaction of 35 with 14 gave 36 which was then deprotected to 37 (Scheme 13). Condensation of 35 and 19 gave the pentamide 38 that was deprotected to 39 (Scheme 14). The above mentioned Schemes describe the synthesis of cis-compounds. The same synthetic methodology can be used to obtain the trans-isomers, or cis and trans bonds in different segments within the same molecule.

c) Polyamine Analog with Diamidine Substituents.

A new class of polyamine analogs is shown in Scheme 21. They derive from 1,4-dibenzylputrescine, 1,5-dibenzylcadaverine, and 1,6-dibenzylhexanediamine. They are diamidine derivatives, where the diamidine residues are carrier groups that have been shown to be efficient in the transport of drugs into different protozoa. The general procedure of synthessis was based on the condensation of 4-cyanobenzaldehyde with the diaminoalkanes to give the Schiff bases, followed by reduction in situ to the corresponding dinitriles 68. The latter were converted to the diamidines 69 through their iminoethers.

d) Synthesis of Oligoamines.

Scheme 22 describes the synthesis of a N-2 hydroxyethyl derivative of a pentamine such as 75. Starting wtih 18, alkylation with 4-bromobutyronitrile gave 70. Reduction of the nitrile of 70 and mesitylenesulfonylation of the resulting amino group gave 71. It was alkylated again with 4-bromobutyronitrile to give 72, and again reduced and mesitylsulfonylated to give 73. The latter was then alkylated with the benzyl ester of 2-bromoethanol to give 74. Treatment with hydrobromic acid in acetic acid cleaved both the mesitylene sulfonyl protecting groups and the benzyl ether residue to give 75.

Scheme 23 reports the synthesis of a trans-decamine 77 and of a cis-decamine 79. Starting with the pentamide 73 (Scheme 22) and by reaction with trans-diester 5 (Scheme 2) the decamide 76 was prepared, which on deprotection gave 77 as a decahydrochloride. In an analogous manner, by condensation of 73 with the cis-1,4-dimesityleneoxy-2-butene, the decamide 78 was prepared, which on deprotection gave 79 as a decahydrochloride.

Scheme 24 outlines the synthesis of a N-2 hydroxyethyl trans-decamine 92 and a cis-2-hydroxyethyl decamine 95. The procedure repeats almost all the procedures described in the foregoing schemes. The synthesis of 80 proceeded by alkylating BOC-mesitylenesulfonamide with the benzyl ester of 2-bromoethanol. Cleavage of the BOC protecting group leads to 81, alkylation with 4-bromobutyronitrile then gave 82, and after reduction of the nitrile group and reaction with mesitylene sulfonyl chloride the diamide 83 was obtained. Again, alkylation with 4-bromobutyronitrile led to 84, reduction and mesitylsulfonylation gave 85, alkylation of 85 gave 86, reduction and mesitylsulfonylation gave 87, and alkylation, reduction and mesitylsulfonylation performed on 87 gave 89. Alkylation of 73 with trans-1,4-dibromo-2-butene gave 90. Alkylation of 89 with 90 gave 91, which after deprotection gave the trans-ω-hydroxy-decamine 92. Alkylation of 73 with cis-1,4-dichloro-2-butene gave 93. Alkylation of 89 with 93 gave 94. Deprotection of 94 gave the cis-ω-hydroxy-decamine 95, isomeric with 92.

e) Synthesis of Oligoamine Dipeptides.

Scheme 25 outlines the synthesis of a dipeptide derivative of 75 (SL-11141) that can be considered as a substrate of cathepsin B. Starting with 74, hydrogenolysis leads to 96, that is then is then esterified with N-BOC-glutamine to 97. The N-BOC residue is cleaved with TFA and N-BOC-leucine is coupled to the glutanine residue to give 98. Deprotection in acid media then affords the dipeptide 99 (SL-11155).

(f) Synthesis of Polyamine Conjugates of Peptides

Scheme 26 outlines the synthesis of polyamine conjugates of the N-morpholino derivative of tetrapeptide SKLQ (SEQ ID NO:4), the minimal structural requirement of a substrate of PSA. The protected form of the peptide (N-BOC residues) will be conjugated at its carboxy terminal with the polyamine residues corresponding to SL-11047, SL-11101, or BE-4-4-4-4 to give the conjugates 112, 113, and 114. The polyamine intermediates are constructed as follows. Chloride 100 is condensed with 46 to give 101. The phthalimido group is cleaved by hydrazinolysis to give 102, and the latter is mesitylated to 103 This amide is again alkylated with 104 to give 105. The mesitylene sulfonyl groups of 105 are then cleaved and 106 is obtained. It is protected using $(BOC)_2O$, and the resulting 102 is deprotected by hydrazinolysis to give the polyamine moiety of 112. In tandem, the known 74 (Scheme 17) was alkylated with 108 to give 109. Cleavage of the mesitylenesulfonyl groups gave 110. The free amino groups were reprotected with $(BOC)_2O$ to give 111. Cleavage of the phthalimido residue via hydrazinolysis using a procedure analogous to that for compound 12 below gave the aminopolyamine intermediate for the synthesis of 114.

Should a secondary amine be desired in place of the primary amino group of compounds 112-114 and analogous compounds, the primary amine can be readily alkylated under basic conditions with an alkyl halide to yield a secondary amine. As this amine remains unprotected, while the other amines are still protected by the BOC groups, coupling of the peptide to the secondary amine can be accomplished using the same protocol as given above for the primary amines; the reaction time for the coupling may need to be extended and the progress of the reaction can be readily monitored by HPLC or other methods.

Example 1

Synthesis of Polyamine Compounds

Compound 2: NaH (80%, 1.08 g, 36 mmol) was added to a solution of amide 1 (6.81 g, 30 mmol) in DMF (50 ml) in an ice-water bath under $N_2$. The mixture was stirred for 1 h and a solution of 4-bromobutyronitrile (4.88 g, 33 mmol) in DMF (10 ml) was added in portions. The mixture was stirred over night at 75° C. The solvent was distilled off, the residue taken up in chloroform washed with a saturated solution of ammonium chloride, dried ($Na_2SO_4$) and evaporated. The residue was purifid by flash chromatography on silica gel (hexane/ethyl acetate 3:1) to yield 8.0 g (90%) of 2 as a colorless oil. $^1$H-NMR ($CDCl_3$) δ 1.05 (t, 3H), 1.90 (m, 2H), 2.30 (b, m, 5H), 2.60 (s, 6H), 3.20 (q, 2H), 3.35 (t, 2H), 6.95 (s, 2H); $^{13}$C-NMR ($CDCl_3$): δ 12.50, 20.61, 22.43, 23.60, 31.05, 36.12, 40.39, 43.78, 118.62, 131.79, 132.67, 139.71, 142.41. MS-EI (m/z) 294 ($M^+$).

Compound 4: Nitrile 2 (7.8 g, 27 mmol) was dissolved in a mixture of ethanol (150 ml) and concentrated hydrochloric acid (1.5 ml). $PtO_2$ was added (700 mg) and the mixture was hydrogenated at 50 psi over night. The catalyst was filtered off and the solvent evaporated. The residue (78 g, 98%) was used in the next step without further purification. The free base gave $^1$H-NMR ($CDCl_3$) δ 1.00 (t, 3H), 1.55 (m, 4H), 2.25 (s, 3H), 2.80 (t, 2H), 3.20 (m, 4H), 6.95 (s, 2H); $^{13}$C-NMR ($CDCl_3$): δ 12.54, 20.69, 22.53, 24.72, 27.65, 39.92, 40.29, 44.59, 131.71, 133.21, 139.82, 142.09. FAB-MS (m/z) 299 ($M^+$+1). Mesitylenesulfonyl chloride (8.8 g, 40.5 mmol) in dioxane (30 ml) was added dropwise to a stirred mixture of compound 3 (7.8 g, 27 mmol) dissolved in dioxane (60 ml) and 50% KOH (30 ml) at 0° C. The reaction mixture was allowed to reach 20° C. and then kept over night. An excess of water was added and the mixture was extracted with chloroform, dried ($Na_2SO_4$) and evaporated. The oily residue was crystallized from ethyl acetate/hexane yielding 4; 10.9 g (82%); mp 71.5-72° C. $^1$H-NMR (CDCl$_3$) δ 1.00 (t, 3H), 1.10-1.50 (m, 4H), 2.30 (s, 6H), 2.55, 2.60 (s, 12H), 2.85 (q, 2H), 3.15 (m, 4H), 4.70 (t, 1H), 6.95, 7.00 (s, 4H); $^{13}$C-NMR (CDCl$_3$): δ 12.70, 20.92, 21.04, 22.73, 22.92, 24.58, 26.68, 40.04, 42.02, 44.42, 131.91, 133.31, 133.64, 138.99, 140.05, 142.15, 142.35. MS-FAB (m/z) 480 (M$^+$).

(E)-2-Butene-1,4-diyl bis[mesitylenesulfonate] (5): (E)-2-Butene-1,4-diol (1.76 g, 20 mmol), and benzyltriethylammonium bromide (270 mg, 1 mmol) were dissolved in 30 ml of a 50% potassium hydroxide solution and 30 ml of dioxane. The mixture was stirred at 5° C. and mesitylenesulfonyl chloride (8.72 g, 40 mmol) dissolved in 30 ml of dioxane was added dropwise. When the addition was over, stirring was continued for 1 h, water was then added, and the white precipitate was filtered and crystallized from chloroform-hexane to yield 5; 7.0 g (77%); mp 119-120° C. $^1$H-NMR (CDCl$^3$): δ 2.35 (s, 6H), 2.60 (s, 12H), 4.45 (d, 4H), 5.75 (b, 2H), 6.95 (s, 4H); $^{13}$C-NMR (CDCl$_3$): δ 20.96, 22.52, 67.96, 127.67, 131.69, 131.74, 139.79, 143.45. MS-EI (m/z), 452 (M$^+$), 253, 200, 183. Anal. Calcd for C$_{22}$H$_{28}$O$_6$S$_2$: C, 58.40; H, 6.19. Found: C, 58.35; H, 6.22.

Compound 6 was synthesized from 5 according to a procedure described elsewhere (Reddy et al., *J. Med. Chem.* 41:4723 (1998)) in 56% yield. $^1$H-NMR (CDCl$_3$): δ 0.95 (t, J=7.15 Hz, 6H, CH$_3$), 1.34 (m, 8H, CH$_2$), 2.29 (s, 12H, CH$_3$), 2.55 (s, 24H, CH$_3$), 3.09 (m, 12H, NCH$_2$), 3.72 (d, J=4.53 Hz, 4H, NCH$_2$), 5.48 (t, J=4.31 Hz, 2H, CH=CH), 6.92 (s, 4H, Ph), 6.93 (s, 4H, Ph); $^{13}$C-NMR (CDCl$_3$): δ 12.71, 20.90, 22.71, 22.76, 24.74, 40.04, 42.21, 44.56, 45.69, 128.45, 131.88, 132.02, 140.05, 140.16, 142.20, 142.58. MS-FAB (m/z) 1012.8 (M$^+$, 100%), 828.7, 646.7, 561, 176.

Compound 7 was obtained from 6 as described elsewhere (Reddy et al., *J. Med. Chem.* 41:4723 (1998)) in 75% yield, mp>230° C. $^1$H-NMR (D$_2$O): δ 1.26 (t, J=12.5 Hz, 6H, 2CH$_3$), 1.79 (m, 8H, CH$_2$), 3.12 (m, 12H, NCH$_2$), 3.80 (d, J=7.16, 4H, NCH$_2$), 6.10 (m, 2H, CH=CH); $^{13}$C-NMR (D$_2$O): δ 12.79, 25.10, 45.19, 48.53, 48.62, 50.36, 130.66. MS-MALDI (m/z): 285.3 (MH$^+$, 100%).

Compound 8 was obtained from the commercially available butyne diol. Mesitylenesulfonyl chloride (19.5 g, 90 mmol) in dioxane (30 ml) was added dropwise to a stirred and cooled mixture of butyne diol (2.58 g, 30 mmol), 50% potassium hydroxide (30 ml) and triethylbenzyne ammonium bromide (405 mg, 1.5 mmol). Once the addition was over, the mixture was stirred at room temperature for an additional 3 h. An excess of water was added and the white precipitate was cooled over night, filtered off and dried. Recrystallization from ethyl acetate/hexane afforded 8.6 g (63%) of 8; mp 105-106° C. $^1$H-NMR (CDCl$_3$): δ 2.30 (s, 6H), 2.60 (s, 12H), 4.50 (s, 4H), 6.95 (s, 4H); $^{13}$C-NMR (CDCl3): δ 20.93, 22.48, 56.13, 80.41, 130.65, 131.67, 139.98, 143.67. MS-EI (m/z) 450 (M$^+$).

Compound 9 was obtained following a procedure analogous to that described for compound 42 (see below). From 450 mg (1 mmol) of diester 8 and 1.05 g (2.2 mmol) of diamide 4, 570 mg (56%) of tetramide 9 was obtained. $^1$H-NMR (CDCl$_3$): δ 0.90 (t, 6H), 1.30 (bs, 8H), 2.20 (s, 12H), 2.45 (s, 24H), 3.05 (m, 12H), 3.75 (s, 4H), 6.87 (s, 8H); $^{13}$C-NMR (CDCl$_3$): δ 12.70, 20.78, 22.68, 34.65, 39.97, 44.46, 44.99, 78.62, 131.85, 131.98, 132.34, 140.14, 142.13, 142.55. MS-FAB (m/z) 1010 (M$^⊕$).

Compound 10 was obtained following a procedure analogous to that described for compound 43 (see below). From 500 mg (0.49 mmol) of tetramide 9, 160 mg (76%) of the tetrahydrochloride 25 was obtained; mp>280° C. (decomp).

$^1$H-NMR (D$_2$O): δ 1.30 (t, 6H), 1.80 (b, 8H), 2.90-3.25 (m, 12H), 4.05 (s, 4H); $^{13}$C-NMR (D$_2$O): δ 13.39, 25.64, 39.26, 45.72, 49.00, 49.20, 81.20. MS-MALDI 283 (M$^+$+1).

Compound 11: Mesitylenesulfonylethylamide 1 (3.1 g, 13.65 mmol) was dissolved in anhydrous DMF (30 ml) followed by the addition of NaH (85%, 0.423 g) in several portions. The mixture was stirred at room temperature for 1 h. N-(4-chloro-2-butenyl)-phthalimide (Aldrich, 3.06 g, 13 mmol) in 20 ml of DMF was added to the flask followed by stirring at 80° C. over night. The mixture was cooled to room temperature, quenched with H$_2$O (10 ml), and the solution was evaporated to dryness in vacuo. The solid residue was partitioned between 25 ml H$_2$O and 25 CHCl$_3$. The aqueous layer was extracted with CHCl$_3$ (3×25 ml), the organic layers were washed with brine (35 ml), dried (MgSO$_4$), the solvent was evaporated to afford a gum which solidified upon trituration with hexane to give 11. The $^1$H-NMR and $^{13}$C-NMR spectra showed that 11 was pure enough to be used in the next step without further purification, yield 4.75 g. $^1$H-NMR (CDCl$_3$): δ 1.16 (t, J=7.11 Hz, 3H, CH$_3$), 2.29 (s, 3H, CH$_3$), 2.63 (s, 6H, 2CH$_3$), 3.29 (q, J=7.11 Hz, 2H, CH$_2$), 4.06 (d, J=5.24 Hz, 2H, NCH$_2$), 4.26 (d, J=5.72 Hz, 2H, NCH$_2$), 5.59 (m, 2H, CH=CH), 6.95 (s, 2H, Ph), 7.71 (m, 2H, Ph), 7.83 (m, 2H, Ph); $^{13}$C-NMR (CDCl$_3$): δ 13.06, 20.89, 22.72, 34.35, 40.68, 42.01, 123.27, 126.69, 129.47, 131.90, 134.00, 140.24.

Compound 12: Amide 11 (20 g, 46.95 mmol) was dissolved in methanol, hydrazine monohydrate (5 ml, 98.52 mmol) was added and the solution stirred at 55° C. for 24 h. Initially it was a homogeneous solution; however, after several hours a white solid precipitated. The mixture was cooled to room temperature, 300 ml of conc. HCl were added slowly (exothermic reaction), and stirring at room temperature was continued for 12 h more. Methanol was evaporated, and the resulting solid was extracted with CHCl$_3$ (3×150 ml). The aqueous layer was neutralized with 50% NaOH, extracted again with CHCl$_3$ (3×100 ml), the combined organic layers were dried (MgSO$_4$); the solution was evaporated to afford a gum, which solidified under high vacuum to give 12; yield 9.0 g (65%). The compound was purified by column chromatography using hexane, ethyl acetate (7:3) as eluent; mp 167-169° C. $^1$H-NMR (CDCl$_3$): δ 1.0 (t, J=7.1 Hz, 3H, CH$_3$), 2.28 (s, 3H, CH$_3$), 2.56 (s, 6H, 2CH$_3$), 2.62 (br, NH$_2$), 3.12 (q, J=7.1 Hz, 2H, NCH$_2$), 3.73 (br, 2H, NCH$_2$), 3.94 (d, J=6.0 Hz, 2H, NCH$_2$), 5.80 (m, 2H, CH=CH), 6.92 (s, 2H, Ph); $^{13}$C-NMR (CDCl$_3$): δ 12.97, 20.93, 22.74, 36.43, 40.94, 42.08, 124.29, 131.89, 132.00, 132.62, 140.21, 142.67.

Compound 13 was obtained from 12 as described for 4 in 96% yield. It was purified by column chromatography using hexane and ethyl acetate (4:1.5) as eluants; mp 98-99° C.; $^1$H-NMR (CDCl$_3$): δ 0.93 (t, J=5.85 Hz, 3H, CH$_3$), 2.23 (s, 3H, CH$_3$), 2.24 (s, 3H, CH$_3$), 2.50 (s, 6H, 2CH$_3$), 2.56 (s, 6H, 2CH$_3$), 3.06 (q, J=7.15 Hz, 2H, NCH$_2$), 3.48 (t, J=5.99 Hz, 2H, NCH$_2$), 3.68 (d, J=5.72 Hz, 2H, NCH$_2$), 4.58 (t, J=6.24 Hz, 1H, NH), 5.44 (m, 2H, CH=CH), 6.87 (s, 2H, Ph), 6.89 (s, 2H, Ph); $^{13}$C-NMR (CDCl$_3$): δ 12.80, 20.89, 22.64, 22.89, 39.01, 40.59, 41.41, 128.14, 128.46, 131.91, 131.96, 139.08, 140.19, 142.26, 142.54. MS-FAB (m/z) 479.2 (M$^+$, 65%), 296.2, 279.1, 267.2, 183.1.

Compound 15: Amide 13 (4.79 g, 10 mmol) was dissolved in anhydrous DMF (40 ml) followed by addition of NaH (0.37 g) in several portions, the mixture stirred at room temperature for 2 h, cis-1,4-dichloro-2-butene (7.5 g, 60 mmol) in 10 ml DMF was added at once, and stirring was continued at 50° C. over night. The mixture was cooled to room temperature, quenched with 10 ml H$_2$O, the solvents were evaporated, and the contents were partitioned between H$_2$O (50 ml) and CHCl$_3$ (50 ml). The aqueous layer was extracted with CHCl$_3$ (3×50 ml), the pooled organic layers were dried (MgSO$_4$), evaporated, and 15 was purified by column chromatography using hexane, ethyl acetate (8.5: 1.5) as eluants; yield 5.5 g (97%), mp 106-108° C. $^1$H-NMR (CDCl$_3$): δ 1.03 (t, J=7.33 Hz, 3H, CH$_3$), 2.30 (s, 6H, 2CH$_3$), 2.57 (s, 12H, 4CH$_3$), 3.17 (q, J=7.31 Hz, NCH$_2$), 3.71 (m, 4H, NCH$_2$), 3.81 (d, J=6.87 Hz, 2H, NCH$_2$), 3.95 (d, J=7.70 Hz, 2H, CHCl$_2$), 5.50 (m, 3H, CH=CH), 5.74 (m, 1H, CH=CH), 6.93 (s, 2H, Ph), 6.95 (s, 2H, Ph); $^{13}$C-NMR (CDCl$_3$): δ 12.91, 22.70, 22.74, 38.20, 40.45, 41.60, 42.11, 42.33, 128.17, 128.95, 129.34, 129.40, 131.94, 132.08, 140.23, 140.34, 142.91. MS-FAB (m/z) 566.7 (M$^+$, 100%), 153.4, 96.3.

Compound 14 was prepared from 13 and 1,4-diiodobutane as described above for 15. The product was purified by column chromatography using hexanes and ethyl acetate (4:1) as eluant; yield 79%. $^1$H-NMR (CDCl$_3$): δ 1.04 (t, J=7.10 Hz, 3H, CH$_3$), 1.63 (m, 4H, CH$_2$), 2.30 (s, 6H, 2CH$_3$), 2.58 (s, 12H, 4CH$_3$), 3.04 (t, J=6.50 Hz, 2H, CH$_2$I), 3.16 (m, 4H, NCH$_2$), 3.78 (d, J=5.14 Hz, 4H, NCH$_2$), 5.55 (m, 2H, CH=CH), 6.94 (s, 2H, Ph), 6.95 (s, 2H, Ph); $^{13}$C-NMR (CDCl$_3$): δ 5.69, 12.92, 20.95, 22.72, 22.78, 28.25, 30.36, 40.47, 41.59, 42.11, 44.71, 128.34, 129.00, 131.94, 132.06, 132.60, 132.89, 140.15, 140.21, 142.50, 142.71.

Compound 16 was prepared from 4 and 4-bromobutyronitrile as described above for Compound 2 in 94% yield.

$^1$H NMR(CDCl$_3$): δ 0.97 (t, J=7.12 Hz, 3H, CH$_3$), 1.40 (m, 4H, 2CH$_2$), 1.85 (Pent., m, 2H, CH$_2$), 2.27 (t, J=7.17 Hz, 2H CH$_2$CN), 2.30 (s, 6H, 2CH$_3$), 2.57 (s, 6H, 2CH$_3$), 2.58 (s, 6H, 2CH$_3$), 3.13 (m, 6H, NCH$_2$), 3.28 (t, J=7.11 Hz, 2H, NCH$_2$), 6.94 (s, 2H, Ph), 6.96 (s, 2H, Ph); $^{13}$C NMR (CDCl$_3$): δ 12.55, 14.54, 20.84, 22.64, 22.73, 23.65, 24.43, 24.57, 39.88, 44.31, 44.54, 45.58, 118.69, 131.84, 132.05, 132.73, 133.36, 139.94, 142.20, 142.71.

Compound 17 was prepared from 16 as described above for Compound 3 in 93% yield. $^1$H NMR(CDCl$_3$): δ 1.00 (t, J=6.92 Hz, 3H, CH$_3$), 1.40 (m, 10H, 4CH$_2$, NH$_2$), 2.29 (s, 6H, 2CH$_3$), 2.57 (b, 14H, 4CH$_3$, CH$_2$N), 3.13 (m, 8H, 4CH$_2$N), 6.93 (s, 4H, 2 Ph); $^{13}$C NMR (CDCl$_3$): 12.72, 20.90, 22.72, 22.78, 24.67, 24.80, 30.80, 40.02, 41.61, 44.56, 45.10, 45.38, 131.87, 140.04, 142.21, 142.28; MS-FAB(M/Z) 552.3(M$^+$, 100%), 368.2, 299.1, 183.0, 154.0.

Compound 18 was prepared from 17 as described above for Compound 4.

$^1$H NMR(CDCl$_3$): δ 0.96 (t, J=7.13 Hz, 3H, CH$_3$), 1.38 (m, 8H, 4CH$_2$), 2.29 (s, 9H, 3CH$_3$), 2.55 (s, 6H, 2CH$_3$), 2.56 (s, 6H, 2CH$_3$); 2.59 (s, 6H, 2CH$_3$), 2.80 (m, 2H, CH$_2$N), 3.10 (m, 8H, NCH$_2$), 4.67(t, J=6.6 Hz, 1H, NH), 6.93 (s, 6H, 3 Ph); $^{13}$C NMR(CDCl$_3$): δ 12.56, 20.87, 22.70, 22.74, 22.84, 24.40, 26.45, 24.67, 26.62, 39.87, 41.88, 44.45, 45.02, 45.09, 131.86, 131.90, 131.92, 133.12, 133.32, 133.68, 138.91, 139.97, 142.02, 142.21, 142.38; MS-FAB(M/Z): 756.9(M+23(Na), 100%) 572.8, 390.7, 333.6, 305.6

Compound 19 was prepared from 4 and 1,4-dichloro-2-butene as described above for 15 in 99% yield. $^1$H-NMR (CDCl$_3$): δ 1.01 (t, J=7.11 Hz, 3H, CH$_3$), 1.38 (m, 4H, CH$_2$), 2.29 (s,3H), 2.30 (s,3H), 2.57 (s, 6H), 2.61 (s, 6H), 3.11 (m, 4H, NCH$_2$), 3.16 (q, J=7.15 Hz, 2H, NCH$_2$), 3.81 (d, J=7.17 Hz, 2H, NCH$_2$), 3.98 (d, J=8.05 Hz, 2H, CH$_2$Cl), 5.51 (m, 1H, CH=CH), 5.77 (m, 1H, CH—CH), 6.93 (s, 2H, Ph), 6.95 (s, 2H, Ph); $^{13}$C-NMR (CDCl$_3$): δ 12.76, 20.91, 22.71, 22.76, 24.74, 38.12, 40.08, 41.85, 44.59, 45.54, 129.14, 129.25, 131.88, 132.02, 140.09, 140.19, 142.21, 142.63. MS-FAB (m/z) 569.3 (M$^+$, 20%), 385.2, 240.1, 203.3, 183.0, 119 (100%).

Compound 20 was prepared from 18 and 15 following the procedure described above for 15. It was purified by column chromatography using hexanes-ethyl acetate (7:3) as eluant (78% yield). $^1$H-NMR (CDCl$_3$): δ 0.97 (t, J=7.10 Hz, 3H, CH$_3$), 0.99 (t, J=7.0 Hz, 3H, CH$_3$), 1.29 (m, 8H, CH$_2$), 2.29 (s, 15H, CH$_3$), 2.54, 2.55, 2.59 (s, 30H, CH$_3$), 3.06 (m, 12H, NCH$_2$), 3.65 (m, 8H, NCH$_2$), 5.48 (m, 4H, CH=CH), 6.92 (s, 10H, Ph); $^{13}$C-NMR (CDCl$_3$): δ 12.70, 12.83, 20.88, 20.91, 22.65, 22.68, 22.72, 22.74, 24.48, 24.72, 40.04, 40.47, 41.53, 42.07, 42.22, 42.34, 44.54, 44.96, 127.94, 128.27, 128.57, 129.20, 131.92, 132.05, 139.96, 140.00, 140.12, 140.16, 140.27, 142.19, 142.25, 142.47, 142.58, 142.87. MS-FAB (m/z) 1263.81 (M$^+$, 100%), 1080.01, 898.11, 714.81, 563.

Compound 21: Pentamide 20 (0.93 g, 0.735 mmol) was dissolved in 20 ml anhydrous CH$_2$Cl$_2$, phenol (3.46 g, 36.77 mmol) was added, followed by HBr in acetic acid (30%, 17.62 ml) and the mixture was stirred over night at 25° C. Water (10 ml) was added to the flask, the aqueous layer was separated, the organic layer was extracted with 5 ml H$_2$O, and the combined aqueous layers were washed with CH$_2$Cl$_2$ (6×15 ml). Water was evaporated under vacuum to afford a solid which was dissolved in 1 ml 1N NaOH followed by 1 ml of 50% KOH. This solution was extracted with CHCl$_3$ (10×5 ml). The combined organic layers were dried (MgSO$_4$), CHCl$_3$ was evaporated, and the residue dissolved in anhydrous diethyl ether. Anhydrous HCl gas was passed into the solution while cooling at 0° C. A white solid precipitated which was filtered and washed with ether. It was 21 (84%). $^1$H-NMR (D$_2$O): δ 1.29 (t, J=7.32 Hz, 3H, CH$_3$), 1.31 (t, J=7.24 Hz, 3H, CH$_3$), 1.79 (m, 8H, CH$_2$), 3.12 (m, 12H, NCH$_2$), 3.87 (m, 8H, NCH$_2$), 5.98 (m, 4H, CH=CH); $^{13}$C-NMR (D$_2$O): δ 13.36, 13.46, 25.66, 25.77, 45.44, 45.74, 46.24, 46.41, 46.84, 49.09, 49.41, 49.70, 129.02, 129.16, 129.47, 129.66. MS-MALDI (m/z) 354.36 (MH$^+$, 100%).

Compound 22 was prepared in 51% yield from 18 and 14 as described above for compound 15. $^1$H-NMR (CDCl$_3$): δ 0.97 (t, J=6.59 H, 3H, CH$_3$), 0.99 (t, J=7.02 Hz, 3H, CH$_3$), 1.29 (m, 12H, CH$_2$), 2.29 (s, 15H, CH$_3$), 2.55 (s), 2.56 (s), 2.57 (s), 3.10 (m, 16H, NCH$_2$), 3.70 (m, 4H, NCH$_2$), 5.47 (m, 2H, CH=CH), 6.93 (s, 10H, Ph); $^{13}$C-NMR (CDCl$_3$): δ 12.69, 12.83, 20.91, 22.69, 22.71, 22.76, 24.43, 24.70, 40.48, 41.11, 41.48, 44.50, 44.91, 128.13, 128.90, 131.88, 131.94, 132.01, 133.29, 139.95, 140.00, 140.15, 142.22, 142.29, 142.60. MS-FAB (m/z) 1265.91 (M$^+$, 100%), 1082.01, 900.11, 716.91, 563.81.

Compound 23 was prepared from 22 in 79% yield as described above for 21. $^1$H-NMR (D$_2$O): δ 1.29 (t, J=7.29 Hz, 3H, CH$_3$), 1.30 (t, J=7.30 Hz, 3H, CH$_3$), 1.78 (m, 12H, CH$_2$), 3.12 (m, 16H, NCH$_2$), 3.83 (m, 4H, NCH$_2$), 5.96 (m, 2H, CH=CH); $^{13}$C-NMR (D$_2$O): δ 13.31, 13.42, 25.62, 25.75, 45.38, 45.71, 46.18, 46.76, 49.07, 49.32, 49.69, 129.11, 129.39. MS-MALDI (m/z) 356.38 (MH$^+$, 100%).

Compound 24 was prepared from 18 (52% yield) as described. $^1$H-NMR (CDCl$_3$): δ 0.95 (m, 6H, 2CH$_3$), 1.32 (m, 12H, CH$_2$), 2.29 (s, 15H, CH$_3$), 2.55 (s, 30H, CH$_3$), 3.06 (m, 16H, NCH$_2$), 3.70 (m, 4H, NCH$_2$), 5.47 (m, 2H, CH=CH), 6.92 (s, 10H, Ph); $^{13}$C-NMR (CDCl$_3$): δ 12.67, 20.90, 22.71, 22.76, 24.43, 24.68, 39.97, 42.08, 44.48, 44.90, 45.61, 128.28, 128.45, 131.87, 131.93, 132.01, 139.96, 140.00, 140.12, 142.21, 142.28, 142.58. MS-FAB (m/z) 1265.91 (M$^+$, 100%), 1082.01, 900.11.

Compound 25 was prepared from 24 in 96% yield as described above for 21. $^1$H-NMR (D$_2$O): δ 1.28 (t, J-7.29

Hz, 6H, 2CH$_3$), 1.78 (m, 12H, CH$_2$), 3.09 (m, 16H, NCH$_2$), 3.84 (m, 4H, NCH$_2$), 5.96 (m, 2H, CH═CH); $^{13}$C-NMR (D$_2$O): δ 13.31, 25.61, 25.73, 45.70, 46.79, 49.05, 49.36, 49.65, 129.19. MS-MALDI (m/z) 356.4 (MH$^+$).

Compound 26: A mixture of KOH (0.25 g), K$_2$CO$_3$ (0.25 g) and tetra-n-butyl-ammonium hydrogen bromide (0.05 g) were suspended in 15 ml benzene. Mesitylenesulfonylamide (0.199 g, 1 mmol) was added to the suspension and the mixture was heated to 50° C. Iodide 14 (1.98 g, 3 mmol) in 10 ml benzene was added to the flask, the mixture heated under reflux over night, then cooled to room temperature; the inorganic solids were filtered off and washed with benzene (2×20 ml). The combined organic layers were washed several times with water until the washings were neutral. The benzene was dried (MgSO$_4$), evaporated and the residue purified by column chromatography using hexanes and ethyl acetate (7.5:2.5) as eluant; 25% yield (0.948 g). $^1$H-NMR (CDCl$_3$): δ 1.00(t, J=7.18 Hz, 6H, CH$_3$), 1.28 (m, 8H, CH$_2$), 2.29 (s, 15H, CH$_3$), 2.53 (s), 2.55 (s), 2.57 (s), 3.03 (m, 8H, NCH$_2$), 3.12 (q, J=7.13 Hz, 4H, NCH$_2$), 3.70 (m, 8H, NCH$_2$), 5.47 (m, 4H, CH═CH), 6.93 (s, 10H, Ph); $^{13}$C-NMR (CDCl$_3$): δ 12.78, 20.85, 22.63, 22.69, 24.32, 24.58, 40.41, 41.43, 42.00, 44.76, 45.43, 128.08, 128.83, 131.88, 131.95, 132.77, 132.85, 133.23, 139.90, 140.04, 140.08, 142.22, 142.43, 142.53. MS-FAB (m/z) 1263.81 (M$^+$, 100%), 1081, 898.11, 815.01, 561.81, 418.81.

Compound 27 was prepared from 26 in 57% yield as described above for 21. $^1$H-NMR (D$_2$O): δ 1.31 (t, J=7.31 Hz, 6H, CH$_3$), 1.78 (m, 8H, CH$_2$), 3.15 (m, 12H, NCH$_2$), 3.83 (m, 8H, NCH$_2$), 5.96 (m, 4H, CH═CH); $^{13}$C-NMR (CDCl$_3$): δ 13.43, 25.64, 25.76, 45.39, 46.19, 46.77, 49.35, 49.72, 129.11, 129.41. MS-MALDI (m/z) 354.3 (MH$^+$, 100%).

Compound 28 was prepared from 15 and mesitylenesulfonylamide in 24% yield as described above for 26; mp 57.7° C. $^1$H-NMR (CDCl$_3$): δ 0.99 (t, J=7.09 Hz, 6H, CH$_3$), 2.29 (s, 15H, CH$_3$), 2.53 (s), 2.55 (s), 3.12 (q, J=7.09 Hz, 4H, NCH$_2$), 3.63 (m, 16H, NCH$_2$), 5.49 (m, 8H, CH═CH), 6.93 (s, 10H, Ph); $^{13}$C-NMR (CDCl$_3$): δ 12.85, 20.89, 20.92, 22.66, 40.47, 41.53, 42.19, 128.00, 128.47, 128.58, 129.11, 131.92, 132.05, 140.17, 140.30, 142.46, 142.87. MS-FAB (m/z) 1259.81 (M$^+$, 60%), 1075.91, 894.01, 306.51, 153.4 (100%).

Compound 29 was prepared from 28 in 81% yield as described above for 21. $^1$H-NMR (D$_2$O): δ 1.31 (t, J=7.29 Hz, 6H, CH$_3$), 3.15 (q, J=7.31 Hz, 4H, NCH$_2$), 3.84 (m, 4H, NCH$_2$), 3.90 (m, 12H, NCH$_2$), 5.98 (m, 8H, CH═CH); $^{13}$C-NMR (D$_2$O): δ 13.42, 45.41, 46.22, 46.44, 129.07, 129.37, 129.42, 129.58. MS-MALDI (m/z) 350.31 (MH$^+$).

Compound 30 was prepared from 19 in 25% yield as described above for 26; mp 62.3° C. $^1$H-NMR (CDCl$_3$): δ 0.95 (5, J=7.17 Hz, 6H, CH$_3$), 1.33 (m, 8H, CH$_2$), 2.29 (s, 15H, CH$_3$), 2.54 (s), 2.55 (s), 3.07 (m, 12H, NCH$_2$), 3.65 (m, 8H, NCH$_2$), 5.48 (m, 4H, CH═CH), 6.92 (s, 10H, Ph); $^{13}$C-NMR (CDCl$_3$): δ 12.69, 20.90, 22.69, 22.73, 24.70, 40.03, 42.13, 42.30, 44.53, 45.59, 128.11, 128.79, 131.87, 132.00, 140.02, 140.14, 140.28, 142.17, 142.58, 142.85. MS-FAB (m/z) 1263.81 (M$^+$, 100%), 1080.01, 898.11, 714.01, 153.

Compound 31 was prepared from 30 in 87% yield as described above for 21. $^1$H-NMR (D$_2$O): δ 1.28 (t, J=7.32 Hz, 6H, CH$_3$), 1.79 (m, 8H, CH$_2$), 3.10 (m, 12H, NCH$_2$), 3.87 (m, 8H, NCH$_2$), 5.98 (m, 4H, CH═CH), $^{13}$C-NMR (D$_2$O): δ 12.70, 25.00, 25.13, 45.10, 45.81, 46.21, 48.44, 48.78, 128.44, 128.85. MS-MALDI (m/z) 354.3 (MH$^+$).

Compound 32: Mesitylenesulfonylamide (1.47 g, 7.38 mmol) was dissolved in 50 ml anhydrous DMF, and NaH (85%, 0.3 g) was added to it under a nitrogen atmosphere. The mixture was stirred at room temperature and 19 (1.40 g, 2.46 mmol) in 25 ml DMF were added. Heating at 65° C. continued over night. The mixture was cooled to room temperature, and 10 ml of H$_2$O were added. The solvents were evaporated and the solid residue was partitioned between 40 ml H$_2$O and 40 ml CHCl$_3$. The aqueous layer was extracted with CHCl$_3$ (2×30 ml), the combined organic layers were washed with H$_2$O (3×50 ml), dried (MgSO$_4$), and evaporated. The residue was purified by column chromatography using hexanes-ethyl acetate (7.5:2.5). 1.7 g (97%) of 32 as a white solid was obtained. $^1$H-NMR (CDCl$_3$): δ 0.94 (t, J=7.10 Hz, 3H, CH$_3$), 1.30 (m, 4H, CH$_2$), 2.29 (s), 2.30 (s), 2.55 (s, 12H, CH$_3$), 2.65 (s, 6H, CH$_3$), 3.11 (m, 6H, NCH$_2$), 3.52 (m, 1H, NCH), 3.65 (m, 2H, NCH$_2$), 3.71 (m, 1H, NCH$_2$), 4.82 (br, 1H, NH), 5.47 (m, 2H, CH═CH), 6.93 (s, 4H, Ph), 6.96 (s, 2H, Ph); $^{13}$C-NMR (CDCl$_3$): δ 12.50, 20.91, 22.71, 22.76, 22.83, 22.91, 24.66, 38.98, 39.85, 42.15, 42.26, 44.50, 128.06, 128.51, 131.86, 131.91, 138.18, 140.00, 140.14, 140.28, 142.17, 142.65.

Compound 33 was prepared from 32 and 14 in 51% yield as described above for 22. $^1$H-NMR (CDCl$_3$): δ 0.99 (5, J=7.19 Hz, 6H, CH$_3$), 1.33 (m, 8H, CH$_2$), 2.29 (s, 15H, CH$_3$), 2.55 (s), 2.57 (s), 3.10 (m, 12H, NCH$_2$), 3.70 (m, 4H, NCH$_2$), 3.77 (m, 4H, NCH$_2$), 5.42 (m, 4H, CH═CH), 6.93 (s, 10H, Ph); $^{13}$C-NMR (CDCl$_3$): δ 12.70, 12.71, 20.89, 22.66, 22.72, 22.78, 22.81, 24.60, 26.53, 40.39, 41.37, 41.87, 42.20, 45.47, 128.26, 128.62, 131.78, 131.84, 131.86, 131.92, 132.77, 138.92, 139.96, 140.09, 140.17, 142.57, 142.63.

Compound 34 was prepared from 33 as described above for 21 in 40% yield.

Compound 35 was prepared from 15 in 94% yield as described above for 32.

Compound 36 was prepared from 35 and 14 in 82% yield as described above for 33. $^1$H-NMR (CDCl$_3$): δ 0.99 (t, J=7.11 Hz, 6H, CH$_3$), 1.33 (m, 4H, CH$_2$), 2.29 (s, 15H, CH$_3$), 2.55 (s), 2.57 (s), 3.07 (m, 8H, NCH$_2$), 3.70 (m, 12H, NCH$_2$), 5.46 (m, 6H, CH═CH), 6.92 (s, 10H, Ph); $^{13}$C-NMR (CDCl$_3$): δ 12.69, 12.80, 20.84, 22.62, 22.68, 22.73, 22.77, 24.58, 26.55, 40.44, 41.51, 41.86, 42.04, 42.24, 45.49, 128.10, 128.25, 128.52, 128.62, 128.82, 131.89, 131.95, 132.79, 138.89, 140.07, 140.14, 140.23, 141.94, 142.44, 142.53, 142.82. MS-FAB (m/z) 1262.8 (M$^+$, 75%), 1080.01, 896, 119 (100%).

Compound 37 was prepared from 36 in 65% yield as described above for 21. $^1$H-NMR (D$_2$O): δ 1.31 (t, J=6.97 Hz, 6H, CH$_3$), 1.79 (m, 4H, CH$_2$), 3.12 (m, 8H, NCH$_2$), 3.83 (m, 12H, NCH$_2$), 5.96 (m, 6H, CH═CH); $^{13}$C-NMR (D$_2$O): δ 13.48, 25.69, 26.76, 41.67, 45.44, 46.24, 46.45, 46.80, 49.41, 129.00, 129.12, 129.45, 129.71. MS-MALDI (m/z) 352.3 (MH$^+$).

Compound 38 was prepared from 35 and 19 in 89% yield as described. $^1$H-NMR (CDCl$_3$): δ 0.95 (m, 6H, CH$_3$), 1.33 (m, 4H, CH$_2$), 2.29 (s, 15H, CH$_3$), 2.54 (s), 2.55 (s), 2.57 (s), 3.09 (m, 8H, NCH$_2$), 3.66 (m, 12H, NCH$_2$), 5.48 (m, 6H, CH═CH), 6.93 (s, 10H, Ph); $^{13}$C-NMR (CDCl$_3$): δ 12.51, 12.63, 20.84, 20.86, 22.63, 22.65, 22.84, 24.61, 38.92, 40.40, 41.40, 42.11, 42.18, 44.44, 45.48, 127.95, 128.07, 128.49, 128.62, 128.80, 131.76, 131.83, 131.85, 131.88, 132.01, 138.05, 139.01, 140.07, 140.13, 140.24, 142.15, 142.21, 142.87. MS-FAB (m/z) 1263.1 (M$^+$, 90%), 1080.1, 896.01, 119 (100%).

Compound 39 was prepared from 38 in 54% yield as described above for 21; mp 270° C. (dec.). $^1$H-NMR (D$_2$O): δ 1.31 (m, 6H, CH$_3$), 1.80 (m, 4H, CH$_2$), 3.10 (m, 8H, NCH$_2$), 3.86 (m, 12H, NCH$_2$), 5.98 (m, 6H, CH═CH);

$^{13}$C-NMR (D$_2$O): δ 13.30, 13.42, 25.58, 25.70, 45.69, 46.21, 46.43, 46.81, 49.02, 49.37, 129.00, 129.15, 129.37, 129.59. MS-MALDI (m/z): 352.343 (MH$^+$).

Compound 42: NaH (80%, 132 mg, 4.4 mmol) was added to a solution of diamide 41 (1.98 g, 4.4 mmol) in DMF (10 ml). The mixture was stirred at 20° C. for 30 minutes and a solution of the diester 40 (Reddy et al. (1998) J. Med Chem., 41:4723) (960 mg, 2 mmol) in DMF (10 ml) was added dropwise. The mixture was stirred at 75° C. for 2 h, the solvent was distilled off, the residue was taken in chloroform, washed with a saturated solution of ammonium chloride, dried (Na$_2$SO$_4$) and evaporated to dryness. The crude oil was purified by column chromatography using hexane-ethyl acetate (8:2) as running solvent. 1.4 g (70%) was obtained as a glassy oil. $^{13}$C-NMR (CDCl$_3$): δ 20.58, 22.63, 22.80, 32.42, 33.86, 43.16, 45.42, 46.26, 132.75, 133.21, 139.82, 142.40. MS-FAB 984 (M$^+$), Compound 43: Phenol (1.86 g, 19.7 mmol) and 30% HBr in glacial acetic acid (35 ml) were added in that order to a solution of 42 (600 mg, 0.6 mmol) in CH$_2$Cl$_2$ (35 ml) at room temperature. The solution was stirred for 24 h, water (30 ml) was added, followed by extraction with methylene chloride (3×20 ml). The aqueous layer was evaporated under reduced pressure and the residue was taken up in 2N NaOH (2 ml) and then 50% KOH (2 ml) followed by extraction with chloroform (6×10 ml). After removal of chloroform, the residue was taken up in ethanol (15 ml) and acidified with concentrated hydrochloric acid (0.4 ml). The product 43 (230 mg, 93%) was recrystallized from aqueous ethanol; mp>270° C. (decomp). $^1$H-NMR (D$_2$O): δ 1.95 (m, 2H), 2.05-2.25 (m, 6H), 2.75 (s, 6H), 2.90 (b, 2H), 3.103.35 (m, 12H); $^{13}$C-NMR (D$_2$O): δ 25.21, 25.24, 35.60, 35.64, 47.41, 48.58, 50.87. MS-MALDI (m/z) 240 (M$^+$+1).

Compound 47: NaH (80%, 132 mg, 4.4 mmol) was added to a solution of diamide 46 (1.98 g, 4.4 mmol) in DMF (10 ml). The mixture was stirred at 20° C. for 30 min and a solution of the diester 8 (900 mg, 2 mmol) in DMF (10 ml) was added dropwise. The mixture was stirred at 75° C. for 2 h. The solvent was distilled off, the residue was taken up in chloroform, washed with a saturated solution of ammonium chloride, dried (NaSO$_4$) and evaporated to dryness. The oily residue was crystallized from ethyl acetate/hexane 1.2 g (61%); mp 165-166° C. $^1$H-NMR (CDCl$_3$): δ 1.08 (t, 3H), 1.75 (m 4H), 2.28 (s, 12H), 2.55 (bs, 24H), 3.10 (m, 12H), 3.98 (s, 4H), 6.95 (m, 8H); $^{13}$C-NMR (CDCl$_3$): δ 12.70, 20.86, 22.64, 25.14, 34.85, 40.22, 42.62, 43.37, 78.80, 131.99, 132.26, 133.21, 140.26, 142.28, 142.71. MS-FAB (m/z) 982 (M$^+$).

Compound 48 was obtained as described for 47. From 1.2 g (1.22 mmol) of tetramide 47, 420 mg (86%) of the tetrahydrochloride 48 was obtained; mp>270° C. (decomp). $^1$H-NMR (D$_2$O): δ 1.29 (t, 6H), 2.13 (m, 4H), 3.14 (m, 12H), 4.06 (s, 4H); $^{13}$C-NMR (D$_2$O): δ 13.34, 25.52, 39.45, 45.90, 45.64, 46.71, 81.32. MS-MALDI (m/z) 255 (M$^+$+1).

Compound 44 was obtained as described for 47. From 450 mg (1 mmol) of diester 8 and 994 mg (2.2 mmol) of diamide 41, 500 mg (52%) of the tetramide 44 was obtained and crystallized from ethyl acetate-hexane; mp 155-156° C.

Compound 45 was obtained as described for 43. From 500 mg (0.52 mmol) of tetramide 44, 160 mg (82%) of the tetrahydrochloride 45 was obtained; mp>270° C. (decomp). $^1$H-NMR (D$_2$O): δ 2.15 (m, 4H), 2.73 (s, 3H), 3.05-3.40 (m, 8H), 4.10 (s, 4H); $^{13}$C-NMR (D$_2$O): δ 25.59, 35.66, 45.90, 46.57, 48.61.

Compound 51 is a mixture of cis/trans-isomers. $^1$H-NMR (D$_2$O): δ 1.15-2.10 (m, 7H), 2.90 (q, 1H), 3.30-3.80 (b, 2H); $^{13}$C-NMR (D$_2$O): δ 24.16, 24.97, 28.44, 30.42, 36.58, 37.14, 48.24, 52.27, 55.19, 57.45, 64.55, 67.26.

Compound 52: Mesitylenesulfonylchloride (6.5 g, 30 mmol) in dioxane (10 ml) was added dropwise to a stirred and cooled mixture of amine alcohol 51 (1.15 g, 10 mmol), triethylbenzyl ammonium bromide (135 mg, 0.5 mmol), 50% KOH (10 ml) and dioxane (10 ml). The reaction mixture was left over night at 20 ° C. with magnetic stirring. An excess of water was added, the solution was extracted with chloroform (3×30 ml), dried (Na$_2$SO$_4$) and evaporated to dryness. The oily residue was chromatographed on a silica-gel column using hexane:ethyl acetate (8:2) as eluants. Crystallization from ethyl acetate-hexane afforded 1.2 g (25%) of pure 52; mp 167-168° C. $^1$H-NMR (CDCl$_3$): δ 1.35-1.90 (6H), 1.90-2.15 (m, 1H), 2.30, 2.35 (s, 6H), 2.65 (s, 12H), 3.20 (m, 1H), 3.70 (m, 1H), 3.90 (m, 1H), 5.15 (d, 1H), 6.90, 7.00 (s, 4H); $^{13}$C-NMR (CDCl$_3$): δ 20.73, 20.85, 22.15, 22.37, 22.70, 26.94, 32.75, 45.34, 56.09, 70.38, 130.22, 131.57, 133.98, 138.68, 139.64, 142.02, 143.10. MS-EI (m/z) 479 (M$^+$), 280 (M$^⊕$−199).

Compound 54: NaH (105 mg, 3.5 mmol) was added to a solution of compound 52 (1.7 g, 3.5 mmol) in DMF (10 ml). The mixture was stirred at 20° C. for 30 min and a solution of compound 53 (1.34 g, 3.85 mmol) in DMF (5 ml) was added in small portions. The mixture was stirred at 75° C. for 2 h. The solvent was distilled off, the residue was taken up in chloroform, washed with a saturated solution of ammonium chloride, dried (Na$_2$SO$_4$) and evaporated. The oily residue was purified by column chromatography (hexane-ethyl acetate 8:2) which gave compound 54 (1.22 g, 47%). $^1$H-NMR (CDCl$_3$): δ 1.98 (t, 3H), 1.20-2.05 (9H), 2.20 (s, 6H), 2.55, 2.65 (s, 12H), 2.70-3.55 (9H), 6.85 (s, 4H); $^{13}$C-NMR (CDCl$_3$): δ 12.49, 20.80, 21.64, 21.87, 22.88, 28.72, 33.16, 36.13, 39.96, 43.80, 47.95, 57.77, 61.26, 131.83, 132.94, 133.14, 138.82, 139.90, 142.07, 142.63. MS-FAB (m/z) 628 (M$^+$+1), 546 (M$^+$−81).

Compound 55 was obtained following the procedure described for compound 42. From 1.22 g (1.6 mmol) of bromoderivative 54 and 820 mg (1.76 mmol) of diamide 46, 1.26 g (77%) of tetramide 55 was obtained as a glassy oil. $^1$H-NMR (CDCl$_3$): δ 0.80 (t, 6H), 1.20-1.75 (6H), 1.90 (m, 1H), 2.15 (s, 12H), 2.35-2.60 (s, 24H), 2.65-3.40 (15H), 6.85 (b, 8H); $^{13}$C-NMR (CDCl$_3$): δ 12.38, 20.71, 22.52, 22.66, 24.72, 27.55, 28.04, 39.19, 39.71, 41.02, 42.33, 42.62, 43.37, 48.81, 61.44, 131.76, 131.88, 133.10, 133.89, 138.66, 139.93, 142.17, 142.33, 142.57. MS-FAB (m/z) 1012 (M$^+$), 828 (M$^+$−184).

Compound 56 was obtained following the procedure described for compound 43. From 1.26 g (1.24 mmol) of tetramide 55, 300 mg (56%) of the tetrahydrochloride 56 was obtained; mp>270° C. (decomp). $^1$H-NMR (D$_2$O): δ 1.35 (t, 6H), 1.60 (m, 1H), 1.80 (b, 3H), 2.15 (b, 6H), 2.50 (b, 1H), 3.20 (m, 13H), 3.45 (m, 2H); $^{13}$C-NMR (D$_2$O): δ 13.23, 25.48, 25.73, 25.79, 31.69, 31.99, 43.40, 45.91, 46.43, 46.71, 48.07, 53.20, 75.28. MS-MALDI (m/z) 285 (M$^+$+1).

Compound 57: NaH (80%, 150 mg, 5 mmol) and NaBr (2.5 g, 25 mmol) were added to a solution of compound 52 (2.35 g, 4.9 mmol) in DMF (15 ml). The mixture was stirred at 20° C. for 30 min and a solution of 1-bromoethane (2.2 g, 25 mmol) in DMF (10 ml) was added in small portions. The mixture was stirred at 90° C. for 3 h. The solvent was distilled off, the residue taken up in chloroform, washed with a saturated solution of ammonium chloride, dried (Na$_2$SO$_4$) and evaporated. The product was purified by silica gel chromatography (hexane/ethyl acetate 9:1). The oily residue (1.5 g, 79%) crystallized on standing; mp 68-69° C.

¹H-NMR (CDCl₃): δ 1.10 (t, 3H), 1.30-2.10 (6H), 2.25 (b, 4H), 2.60 (s, 6H), 3.20 (m, 2H), 3.35 (m, 2H), 3.60 (m, 2H), 6.95 (s, 2H); ¹³C-NMR (CDCl₃): δ 16.35, 20.93, 21.79, 22.89, 29.32, 29.37, 36.54, 38.12, 44.13, 61.40, 131.99, 132.80, 140.20, 142.52. MS-FAB 389 (M⁺+1), 308 (M⁺−80).

Compound 59 was obtained following the procedure described for compound 42. From 700 mg (1.80 mmol) of compound 57 and 394 mg (0.9 mmol) of diamide 58, 400 mg (37%) of tetramide 59 were obtained. ¹H-NMR (CDCl₃): δ 0.90 (t, 6H), 1.25-1.80 (m, 8H), 1.80-2.10 (m, 8H), 2.15 (s, 12H), 2.40, 2.50 (s, 24H), 2.60-3.35 (m, 6H), 2.85, 2.90 (s, 8H); ¹³C-NMR (CDCl₃): δ 16.14, 20.85, 21.95, 21.99, 22.55, 25.49, 28.78, 28.88, 31.49, 37.87, 40.50, 40.83, 43.85, 44.06, 49.30, 61.42, 131.86, 131.96, 133.09, 133.40, 139.93, 139.98, 142.27, 142.40. MS-FAB (m/z) 1052 (M⊕), 891 (M⁺−184).

Compound 60 was obtained following the procedure described for compound 43. From 400 mg (0.38 mmol) of tetramide 59, 95 mg (53%) of the tetrahydrochloride derivative were obtained; mp>270° C. (decomp.) ¹H-NMR (D₂O): δ 1.30 (t, 6H), 1.60 (m, 2H), 1.80 (m, 6H), 1.95-2.35 (6H), 2.45 (m, 2H), 3.20 (m, 10H), 3.40 (m, 4H); ¹³C-NMR (D₂O): δ 13.59, 25.34, 25.71, 31.75, 32.00, 43.34, 44.83, 48.02, 53.24, 64.52. MS-MALDI (m/z) 325 (M⁺+1).

Compound 62: Mesitylenesulfonylchloride (3.27 g, 15 mmol) in dioxane (20 ml) was added dropwise to a stirred solution of 61 (1.3 g, 10 mmol) in dioxane (20 ml) and 50% KOH (15 ml) at 0° C. When addition was completed, the mixture was left over night at 20° C. Excess water was added, the solution cooled and the precipitate filtered off. Crystallization from ethylacetate-hexane gave compound 62 (2 g, 80%); mp 115-116° C. ¹H-NMR (CDCl₃): δ 2.35 (s, 3H), 2.55 (t, 2H), 2.65 (s, 6H), 3.25 (q, 2H), 5.15 (t, 1H), 7.0 (s, 2H); ¹³C-NMR (CDCl₃): δ 19.07, 20.82, 22.78, 38.37, 117.56, 132.07, 133.0, 138.99, 142.67. MS-EI (m/z) 252 (M⁺).

Compound 63: NaH (80%, 330 mg, 11 mmol) was added to a solution of compound 62 (2.52 g, 10 mmol) in DMF (20 ml) under N₂. The mixture was stirred for 30 min and a solution of compound 53 (3.82 g, 11 mmol) in DMF (10 ml) was added in small portions. The mixture was stirred at 70° C. for 2 h. The solvent was distilled off, the residue taken up in chloroform, washed with a saturated solution of ammonium chloride, dried (Na₂SO₄) and evaporated to dryness. The product was purified by silica-gel chromatography (hexane-ethyl acetate 8:2). The oily residue (3.0 g, 57%) crystallized on standing; mp 105-106° C. ¹H-NMR (CDCl₃): δ 1.00 (t, 3H), 1.75 (m, 2H), 2.35 (s, 6H), 2.60 (14H), 3.10 (m, 6H), 3.45 (t, 3H), 6.90, 6.95 (s, 4H); ¹³C-NMR (CDCl₃): δ 12.63, 16.94, 20.89, 22.67, 25.73, 40.27, 42.19, 42.51, 44.72, 117.36, 131.95, 132.22, 140.06, 140.34, 142.52, 143.33. MS-EI (m/z) 519 (M⁺), 429 (M⁺−HCN).

Compound 65: The nitrile 63 (3.0 g, 5.7 mmol) was dissolved in a mixture of ethanol (150 ml) and concentrated hydrochloric acid (1.5 ml). PtO₂ was added (300 mg), the mixture was hydrogenated at 50 psi over night, the catalyst was filtered off and the solvent evaporated to afford an oily residue of compound 64, which was used in the next step without further purification. Free base ¹H-NMR (CDCl₃): δ 1.00 (t, 3H), 1.55 (m, 2H), 1.75 (m, 2H), 2.30 (s, 6H), 2.55 (14 H), 2.90-3.30 (8H), 6.95 (s, 4H); ¹³C-NMR (CDCl₃): δ 12.64, 20.87, 22.69, 25.35, 30.93, 39.04, 40.12, 42.65, 43.11, 131.86, 133.10, 140.04, 142.43. MS-FAB (m/z) 524 (M⁺+1).

Mesitylenesulfonylchloride (1.86 g, 8.55 mmol) in dioxane (15 ml) was added dropwise to a stirred mixture of 64 (3.0 g, 5.7 mmol) dissolved in dioxane (30 ml) and 50% KOH (15 ml) at 0° C. The reaction mixture was allowed to reach room temperature and was kept for further 2 h. An excess of water was added and the mixture was extracted with chloroform, dried (Na₂SO₄) and evaporated to dryness. Purification was achieved by silica gel column chromatography using hexane-ethyl acetate (8:2) as eluant; 2.79 g (69%) of 65 were obtained. ¹H-NMR (CDCl₃): δ 0.95 (t, 3H), 1.60 (m, 4H), 2.30 (s, 9H), 2.50 (s, 12H), 2.65 (s, 6H), 2.85 (m, 2H), 3.05 (6H), 3.20 (t, 2H), 5.00 (t, 1H), 6.95 (6H); ¹³C-NMR (CDCl₃): δ 12.45, 20.81, 22.73, 25.23, 27.46, 39.19, 33.99, 42.49, 42.92, 43.17, 131.84, 133.05, 133.82, 138.80, 139.90, 141.92, 142.36, 142.64. MS-FAB (m/z) 705 (M⊕).

Compound 66 was obtained following the procedure described for compound 42. From 705 mg (1 mmol) of 65 and 426 mg (1.1 mmol) of 57, 470 mg (46%) of tetramide 66 was obtained as a glassy product. ¹H-NMR (CDCl₃): δ 0.85-1.10 (t, 6H), 1.35-2.10 (m, 11H), 2.30 (s, 12H), 2.40-2.65 (m, 24H), 2.75-3.55 (m, 13H), 6.95 (m, 8H); ¹³C-NMR (CDCl₃): δ 12.64, 16.11, 20.91, 22.08, 22.75, 24.81, 25.09, 28.83, 29.07, 37.93, 40.08, 40.84, 42.50, 42.81, 43.11, 43.42, 49.11, 61.43. MS-FAB (m/z) 1013 (M⁺+1).

Compound 67 was obtained following the procedure described for compound 43. From 470 mg (0.46 mmol) of tetramide 66, 142 mg (71%) of the tetrahydrochloride derivative was obtained; mp>250° C. (decomp). ¹H-NMR (D₂O): δ 1.30 (t, 6H), 1.60 (m, 1H), 1.85 (b, s, 3H), 2.15 (m, 6H), 2.45 (m, 1H), 3.15 (m, 13H), 3.45 (m, 2H); ¹³C-NMR (D₂O): δ 13.29, 13.57, 25.34, 25.44, 25.64, 31.68, 31.94, 43.27, 44.80, 45.86, 46.62, 47.42, 47.97, 53.19, 64.50. MS-MALDI 285 (M⁺+1), 286 (M⁺+2).

Compound 68a: 4-Cyanobenzaldehyde (Aldrich, 1.31 g, 10 mmol) was dissolved in 30 ml anhydrous MeOH followed by the addition of MgSO₄ (anhydrous, 1.5 g) and 1,4-diaminobutane (Aldrich, 0.44 g, 5 mmol) and the mixture was stirred under argon over night. The suspension was cooled in an ice bath and NaBH₄ (2.0 g) was added in portions and stirring continued for 2 h at 0° C. The methanol was evaporated under vacuum and the resulting solid was partitioned between 35 ml H₂O and 50 ml CHCl₃. Some of the solid was not soluble in either the H₂O or the CHCl₃ and was filtered off and the aqueous layer was extracted with CHCl₃ (2×25 ml). The pooled organic layers were dried (MgSO₄), evaporated and the solid was recrystallized from ethyl acetate-hexane, yield 1.1 g (35%); mp 90.6-90.8° C. ¹H-NMR (CDCl₃): δ 1.43 (broad, 2H, NH), 1.55 (m, 4H, CH₂), 2.63 (m, 4H, NCH₂), 3.85 (s, 4H, benzylic CH₂), 7.44 (m, 4H, Ph), 7.60 (m, 4H, Ph); ¹³C-NMR (CDCl₃): δ 27.78, 49.28, 53.44, 110.65, 118.88, 128.52, 132.12, 146.21. MS (m/z) 318 (M⁺), 185, 145, 131, 116 (100%), 70.

Compound 68b was prepared from 4-cyano-benzaldehyde and 1,5-diaminopentane as described above for 68a; 42% yield; mp 92.9-93.0° C. ¹H-NMR (CDCl₃): δ 1.40 (m, 4H, NH, CH₂), 1.50 (m, 4H, CH₂), 2.59 (m, 4H, NCH₂), 3.83 (s, 4H, benzylic CH₂), 7.45 (m, 4H, Ph), 7.59 (m, 4H, Ph); ¹³C-NMR (CDCl₃): δ 24.86, 29.87, 49.29, 53.40, 110.50, 118.85, 128.48, 132.04, 146.19. MS (m/z) 332 (M⁺), 216, 199, 145, 116 (100%), 84.

Compound 68c was prepared from 4-cyanobenzyldehyde and 1,6-diaminohexane as described above for 68a; 45% yield; mp 95.6-95.8° C. ¹H-NMR (CDCl₃): δ 1.35 (m, 4H, CH₂), 1.50 (m, 6H, NH, CH₂), 2.60 (t, J=6.92 Hz, 4H, NCH₂), 3.84 (s, 4H, benzylic CH₂), 7.44 (m, 4H, Ph), 7.60 (m, 4H, Ph); ¹³C-NMR (CDCl₃): δ 27.17, 30.02, 49.42, 53.50, 110.65, 118.92, 128.55, 132.14, 146.27. MS (m/z) 346 (M⁺), 230, 213, 145, 116 (100%) 98.

Compound 69a: Dinitrile 68a (0.75 g, 2.36 mmol) was dissolved in anhydrous THF, lithium bis(trimethylsilyl)amide (9.43 ml of a 1 m solution in THF) was added slowly under argon atmosphere. The mixture was stirred at room temperature for 2 h; then cooled in an ice bath, followed by the addition of 4 equivalents of 6N HCl in ether. A white solid precipitated immediately and was filtered after 12 h. The solid was recrystallized from ethanol-ether to afford 1.19 g of compound 69a (93%). $^1$H-NMR (D$_2$O): δ 1.87 (m, 4H, CH$_2$), 3.22 (m, 4H, CH$_2$N), 4.40 (s, 4H, benzylic CH$_2$), 7.74 (m, 4H, Ph), 7.91 (m, 4H, Ph); $^{13}$C-NMR (DMSO-d$_6$): δ 22.68, 46.09, 49.28, 128.10, 128.47, 130.69, 138.15, 165.44. MS-ESI (m/z) 353.2 (M$^+$), 177.2 (100%).

Compound 69b was prepared from 68b in 92% yield as described above for 69a. $^1$H-NMR (D$_2$O): δ 1.52 (m, 2H, CH$_2$), 1.80 (m, 4H, CH$_2$), 3.19 (m, 4H, NCH$_2$), 4.40 (s, 4H, benzylic CH$_2$), 7.75 (m, 4H, Ph), 7.91 (m, 4H, Ph); $^{13}$C-NMR (DMSO-d$_6$): δ 24.90, 26.91, 48.96, 51.88, 130.29, 130.46, 132.43, 139.51, 167.52. MS-ESI (m/z) 367.2 (M$^+$), 350.2 (100%), 301.2.

Compound 69c was prepared from 68c as described above for 69a in 96% yield. $^1$H-NMR (D$_2$O): δ 1.46 (m, 4H, CH$_2$), 1.78 (m, 4H, CH$_2$), 3.16 (m, 4H, NCH$_2$), 4.39 (s, 4H, benzylic CH$_2$), 7.74 (m, 4H, Ph), 7.91 (m, 4H, Ph); $^{13}$C-NMR (DMSO-d$_6$): δ 25.24, 25.82, 46.73, 49.44, 128.35, 128.56, 130.81, 138.38, 165.58. MS-ESI (m/z) 381.2 (M$^+$), 191.2 (100%), 150, 116.

Compound 70: Triamide 18 (4.3 g, 5.8 mmol) was dissolved in 30 ml of DMF and 80% NaH (208 mg, 6.9 mmol) was added. The mixture was stirred under a N$_2$ atmosphere for 1 h and 1.12 g (7.5 mmol) of bromobutyronitrile dissolved in 3 ml of DMF were added all at once. The reaction mixture was heated for 3 h at 90° C. The solvent was distilled-off and the residue was dissolved in chloroform and washed twice with a saturated solution of amonium chloride; dried (NaSO$_4$) and evaporated to dryness. Flash chromatography of the residue using hexane-ethyl acetate (6:4) as eluant gave the yellow oil 70 (3.7 g, 77%). $^1$H-NMR (CDCl$_3$): δ 0.95 (t, 3H), 1.35 (m, 8H), 1.85 (m, 2H), 2.20 (t, 2H), 2.30 (s, 9H), 2.55 (s, 18H), 3.10 (m, 10H), 3.25 (t, 2H), 6.95 (s, 6H), MS-FAB (m/z) 823 (M$^+$+Na), 639, 457.

Compound 71: Nitrile 70 (3.7 g, 4.6 mmol) was dissolved in 20 ml of chloroform and 150 ml of ethanol were added. The mixture was reduced over 0.35 g of PtO$_2$ at 50 psi overnight. The catalyst was filtered-off and the solvent evaporated to dryness. The oily residue was dried in vacuo for 2 h and dissolved in 50 ml of Cl$_3$CH and 12 ml 2N NaOH. The mixture was cooled in an icewater bath with efficient magnetic stirring and 1.50 g (6.9 mmol) of mesitylene chloride dissolved in 10 ml of chloroform were added all at once. After 2 h the organic layer was separated, washed twice with a saturated solution of amonium chloride, dried (NaSO$_4$) and evaporated to dryness. Flash chromatography of the residue using hexane-ethyl acetate (7:3) as eluant provided the tetramide 71 as a colorless oil (3.3 g, 73% over two steps). $^1$H-NMR (CDCl$_3$): δ 0.95 (t, 3H), 1.40 (m, 12H), 2.30 (s, 12H), 2.60 (s, 24H), 2.80 (b, 2H), 3.10 (m, 12H), 4.70 (b, 1H), 6.90 (s, 8H). MS-FAB (m/z) 1010 (M$^+$+1+Na), 826, 643.

Compound 72: The tetramide 71 (6.28 g, 6.3 mmol) was dissolved in 40 ml of DMF and 80% NaH (230 mg, 7.6 mmol) was added. The mixture was stirred under a N$_2$ atmosphere for 1 h and 1.30 g (8.8 mmol) of bromobutyronitrile dissolved in 3 ml of DMF were added all at once. The reaction mixture was heated for 3 h at 90° C., the solvent was distilled-off and the residue was extracted into chloroform and washed twice with a saturated solution of amonium chloride; dried (NaSO$_4$) and evaporated to dryness. Flash chromatography of the residue with hexane-ethyl acetate (7:3) as eluant provided the nitrile 72 (5.0 g, 74%). $^1$H-NMR (CDCl$_3$): δ 0.95 (t, 3H), 1.35 (m, 12H), 1.80 (m, 2H), 2.25 (t, 2H), 2.35 (s, 12H), 2.70 (s, 24H), 3.10 (m, 14H), 3.25 (t, 2H), 7.0 (s, 8H). MS-FAB (m/z) 1077 (M$^+$+1+Na), 893, 711, 586.

Compound 73: Nitrile 72 (6.0 g, 5.6 mmol) was dissolved in 20 ml of chloroform and 150 ml of ethanol were added. The mixture was reduced over 600 mg of PtO$_2$ at 50 psi overnight. The catalyst was filtered-off and the solvent evaporated to dryness. The oily residue was dried in vacuo for 2 h and dissolved in 100 ml of chloroform and 15 ml 2N NaOH. The mixture was cooled in an icewater bath with efficient magnetic stirring, and 1.80 g (8.4 mmol) of mesitylene chloride dissolved in 10 ml of Cl$_3$CH was added all at once. After 2 h the organic layer was separated, washed twice with a saturated solution of amonium chloride, dried (Na$_2$SO$_4$) and evaporated to dryness. Flash chromatography of the residue using hexane-ethyl acetate (7:3) as eluant gave the pentamide 73 as a colorless oil (5.0 g, 71% over two steps). $^1$H-NMR (CDCl$_3$): δ 0.95 (t, 3H), 1.35 (m, 16H), 2.30 (s, 15H), 2.55 (s, 30H), 2.75 (bs, 2H), 3.05 (m, 16H), 4.70 (b, 1H), 6.90 (s, 10H). MS-FAB (m/z) 1261 (M$^+$–1+Na), 1077, 895.

Compound 74: Pentamide 73 (3.4 g, 2.7 mmol) was dissolved in 30 ml of DMF and 60% NaH (162 mg, 4.05 mmol) was added. The mixture was stirred under a N$_2$ atmosphere for 0.5 h and 2.3 g (10.8 mmol) of 2-bromoethanol benzylether dissolved in 3 ml of DMF were added all at once. The reaction mixture was heated for 2 h at 80° C., the solvent was distilled-off and the residue was dissolved in chloroform and washed twice with a saturated solution of amonium chloride, dried (NaSO$_4$) and evaporated to dryness. Flash chromatography of the residue using hexane-ethyl acetate (7:3) as eluant provided the product 74 (2.6 g, 70%). $^1$H-NMR (CDCl$_3$): δ 0.95 (t, 3H), 1.30 (m, 16H), 2.30 (s, 15H), 2.50 (s, 30H), 2.90-3.20 (m, 18H), 3.25 (t, 2H), 2.35 (t, 2H), 4.35 (s, 2H), 6.95 (s, 10H), 7.20-7.35 (m, 5H). $^{13}$C NMR (CDCl$_3$): δ 12.65, 20.84, 22.67, 22.71, 24.41, 24.66, 39.97, 44.48, 44.88, 46.59, 68.01, 72.95, 127.46, 127.57, 128.25, 131.83, 131.89, 133.28, 139.88, 139.95, 140.04, 142.16, 142.23. MS-FAB (m/z) 1394 (M$^+$–2+Na) 1030.

Compound 75: Pentamide 74 (1.2 g, 0.87 mmol) was dissolved in 12 ml of methylene chloride followed by the addition of 30% HBr/acetic acid (16 ml) and phenol (3.0 g, 32 mmol). The mixture was stirred at room temperature overnight, water (16 ml) was added, followed by extraction with methylene chloride (3×10 ml). The aqueous layer was evaporated in vacuo. The residue was dissolved in 2N NaOH (4 ml) and 50% KOH (4 ml) followed by extraction with chloroform (4×10 ml). After removal of the solvent the residue was dissolved in ethanol (20 ml) and acidified with concentrated hydrochloric acid (0.5 ml). The white precipitate (75) was recrystallized from aqueous ethanol (440 mg, 90%); mp above 270° C. (decomp). $^1$H-NMR (D$_2$O): δ 1.30 (t, 3H), 1.75 (b, 16H), 2.90-3.30 (m, 20H), 2.85 (t, 2H). $^{13}$C NMR (D$_2$O): δ 13.29, 25.48, 25.59, 45.70, 49.04, 49.49, 49.67, 51.88, 59.39. MS-MALDI (m/z) 374 (M$^+$+1).

Compound 76: Pentamide 73 (850 mg, 0.68 mmol) was dissovled in DMF (15 ml) and 80% NaH (30 mg, 1 mmol) was added. The mixture was stirred under a N$_2$ atmosphere at room temperature for 0.5 h and 137 mg (0.30 mmol) of 73 dissolved in 5 ml of DMF were slowly added. The reaction mixture was heated for 2 h at 80° C., the solvent was distilled-off and the residue was dissolved in chloroform and washed twice with a saturated solution of amonium chloride, dried (NaSO$_4$) and evaporated to dryness. Flash chromatography of the residue using hexane-ethyl acetate-methanol (6:4:0.1) as eluant afforded the product 76 (590 mg, 77%). $^1$H-NMR (CDCl$_3$): δ 0.95 (t, 6H), 1.15-1.40 (m, 32H), 2.30 (s, 30H), 2.55 (s, 60H), 2.90-3.25 (m, 36H), 3.60 (d, 4H), 5.40 (t, 2H), 6.95 (s, 20H). MS-FAB 2553 (M$^+$+Na).

Compound 77 was obtained following the procedure described for compound 75. From 650 mg (0.25 mmol) of decamide 76, 225 mg (81%) of decahydrochloride 77 was obtained; mp>270° C. (decomp). $^1$H-NMR (D$_2$O): δ 1.30 (t, 6H), 1.75 (b, 32H), 3.10 (b, 36H), 3.75 (b, 4H), 6.05 (b, 2H); $^{13}$C NMR (D$_2$O): δ 13.28, 25.57, 45.66, 49.00, 49.13, 49.64, 50.86, 131.15. MS-ESI 711 (M$^+$+1).

Compound 78 was obtained following the procedure described for compound 76. From 850 mg of 73, 360 mg (47%) of decamide 78 were obtained. $^1$H-NMR (CDCl$_3$): δ 0.95 (t, 6H), 1.15-1.45 (m, 32H), 2.30 (s, 30H), 2.55 (s, 60H), 2.90-3.20 (b, 36H), 3.65 (d, 4H), 5.40 (t, 2H), 6.90 (s, 20H). MS-FAB (m/z) 2553 (M$^+$+Na).

Compound 79 was obtained following the procedure described for compound 75. From 330 mg (0.13 mmol) of decamide 78, 127 mg (90%) of decahydrochloride 79 was obtained; mp>270° C. (decomp). $^1$H-NMR (D$_2$O): δ 1.30 (t, 6H), 1.80 (b, s, 32H), 3.10 (b, 36H), 3.85 (d, 4H), 6.0 (t, 2H). $^{13}$C NMR (D2O): δ 13.31, 25.59, 45.71, 46.83, 49.05, 49.39, 49.69, 129.21. MS-ESI (m/z) 512 (M$^+$+2).

Compound 96.

Pentamide 74 (1.4 g, 1.01 mmol) was dissolved in 100 ml of ethanol and 200 mg of 10% Pd/C was added. The mixture was hydrogenated for 4 h at 50 psi. The catalyst was filtered off and and solvent evaporated to dryness. Silica-gel column chromatography using ethyl acetate/hexane 6:4 as running solvent afforded 1.0 g (80%) of desired product, as an oil. $^1$H NMR (CDCl$_3$) δ: 0.95 (t, 3H), 1.30 (m, 16H), 2.30 (s, 15H); 2.55 (s, 30H), 3.10 (m, 18H), 3.25 (t, 2H), 3.60 (t, 2H), 6.95, (s, 10H), $^{13}$C NMR δ: 12.67, 20.89, 22.75, 24.52, 40.02, 44.54, 44.97, 46.83, 48.22, 60.29, 131.88, 132.78, 133.28, 139.95, 140.11, 142.33

Compound 97

Alcohol 96 (470 mg, 0.36 mmole) was dissolved in tetrahydrofuran (5 ml), Boc-Gln (97 mg, 0.39 mmole), dicyclohexylcarbodiimide (89 mg, 0.43 mmole), and dimethylaminopyridine (5 mg, 0.039 mmole) were added. The reaction mixture was stirred overnight at room temperature. The cyclohexylurea was filtered off and the filtrate evaporated to dryness. The residue was dissolved in chloroform, washed twice with 2N HCl, once with water, and twice with a saturated solution of NaHCO$_3$, then dried and evaporated. The product was purified by silica-gel column chromatography using methanolchloroform 2% as running solvent. The amino acid-polyamine conjugate weighed 250 mg (45%). $^1$H NMR (CDCl$_3$) δ: 0.95 (t, 3H), 1.30 (m, 18H), 1.45 (s, 9H), 1.90-2.20 (m, 2H), 2.35 (s, 15H), 2.60 (s, 30H) 2.90-3.25 (m, 18H), 3.45 (m, 2H), 4.10-4.35 (m, 3H), 6.95 (s, 10H); $^{13}$C NMR (CDCl$_3$) δ: 12.57, 20.78, 22.63, 24.63, 28.19, 31.48, 39.92, 44.04, 44.43, 44.82, 45.92, 53.06, 61.96, 79.80, 131.99, 133.33, 139.80, 142.12, 156.40, 171.70, 174.25.

Compound 98

Amino acid-polyamine conjugate 97 (170 mg, 0.11 mmole) was treated with trifluoroacetic acid (1.25 ml) in methylene chloride (5 ml) for 30 minutes. The solvent was evaporated at room temperature, the residue was dissolved in chloroform and washed with a saturated solution of NaHCO$_3$, then dried and evaporated to dryness. After drying in vacuo, the residue weighted 158 mg (100%) and was used in the next step without further purification.

The deprotected amino acid-polyamine conjugate (158 mg, 0.11 mmole) was dissolved in tetrahydrofuran (5 ml), Boc-Leu (30 mg, 0.13 mmole), dicyclohexylcarbodiimide (27 mg, 0.14 mmole) and dimethylaminopyridine (16 mg, 0.13 mmole) were added. The reaction mixture was stirred overnight at room temperature. The cyclohexylurea was filtered off and the filtrate evaporated to dryness. The residue was dissolved in chloroform, washed twice with 2N HCl, once with water, and twice with a saturated solution of NaHCO$_3$, dried and evaporated. The dipeptide-polyamine conjugate was purified by silica-gel column chromatography using methanol/chlorofom 4% as running solvent to yield 130 mg (70%). $^1$H NMR (CDCl$_3$) δ: 0.95 (m, 9H), 1.30 (m, 16H), 1.45 (s, 9H), 1.50-2.05 (m, 3H), 2.30 (s, 19H), 2.60 (s, 30H), 3.50 (m, 2H) 3.90-4.30 (m, 3H), 4.50 (m, 1H), 6.95 (s, 10H).

Compound 99 was obtained following the procedure described for compound 21. From 100 mg (0.061 mmol) of dipeptide-polyamine conjugate 98, 26 mg (50%) of the hexachloride 99 was obtained; mp>270° C. (decomp). $^1$H NMR (CDCl$_3$) δ: 0.95 (m, 6H), 1.30 (t, 3H), 1.40-1.90 (m, 20H), 1.90-2.50 (m, 3H), 3.0-3.30 (m, 20H), 3.40-4.20 (m, 4H). ESI-MS (m/z) 615 (M$^+$+1), 651 (M$^+$+1+HCl), 687 (M$^+$+1+2HCl)

Example 2

Synthesis of Novel Quinone Derivatives

Synthetic Preparation of Quinone Compounds

Preparation of quinones of the invention is described below and depicted in the Figures. New chemistry was developed in order to construct drugs where the 1,2-naphthoquinone moiety is bound to a DNA minor groove binder unit or a DNA intercalator. While not wishing to limit the invention to any particular theory of operation, it is believed that the 1,2-naphthoquinone derivatives "poison" topoisomerase II and transform this essential DNA replication enzyme into a nuclease-type enzyme that cleaves DNA. It is postulated that this modification of topoisomerase II by the 1,2-naphthoquinones is very likely due to the alkylation of the thiol residues of the enzyme by the quinones (Michael additions). Scheme 501 outlines derivatization reactions leading to 1,2-naphthoquinone intermediates. The silver salt of 2-hydroxy-1,4-naphthoquinone was alkylated with the tert-butyl or benzyl esters of 5-bromo-pentanoic acid to give either 501 or 502. The benzyl ester 502 was transformed into the acid 503 by hydrogenolysis. The silver salt was also alkylated with 6-bromohexanol to give 504, or with 1,6-diiodohexane to give 505. The alcohol 504 treated with triphosgene gives 506 (Scheme 502). The acid 503 can be derivatized by reaction with 3-amino-1-methyl-5-methyloxycarbonylpyrrole (Baird and Dervan (1996) *J. Am. Chem. Soc.* 118:6141) in the presence of o-benzotriazol-1-yl-N,N,N',N'-tetramethyluronium hexafluorophosphate (HBTU) and diisopropylethyl amine (DIEA) to give the amide 507. The silver salt of 2-hydroxy-1,4-naphthoquinone reacted with pivalyl chloride to give 508 (Scheme 502). Acid 503 was condensed with the polypyrrole amide 509 (Baird and Dervan (1996) *J. Am. Chem. Soc.* 118:6141) after cleavage of the protecting t-butyl group with TFA. The resulting product 510 is a molecule where the 1,2-naphthoquinone moiety is covalently bound to a DNA minor groove binder (Scheme 503). Alcohol 504 was condensed using the Mitsonobu reaction (triphenylphosphine, diethyl acetylenedicarboxylate) with 4-hydroxy-benzonitrile to give 511. Iodide 505 was reacted with the tetrabutyl ammonium salt of phenol to give 512. The acid 503 was esterified with 3-dimethylaminophenol using dicyclohexylcarbodiimide (DCC) and 4-dimethylamino pyridine (DMAP) and gave 513. By reaction of 505 and the tetrabutylammonium salt of Hoechst 33528 it was possible to obtain 514, where the quinone is covalently bound to the DNA minor groove binder. By esterification of 504 with 6-aminohexanoic acid (used as its BOC derivative and deprotected with TFA) in the presence of DCC and DMAP, it was possible to obtain 515 as its trifluoroacetate (Scheme 504). By condensation of the acid 503 with the N-ethyl diamide 516, the polyamide quinone 517 was prepared (Scheme 504).

A new class of 4-aminoalkyl substituted 1,2-naphthoquinones was obtained following the outline depicted in Scheme 505. A Vilsmeier reaction on 1,2-dimethoxynaphthalene gave the formyl derivative 518. It was converted by reductive amination with n-butylamine into 519. Treatment of 519 with acetyl chloride gave 520, while treatment with trifluoroacetic anhydride gave 521 (Scheme 505). Acylation of 519 with morpholino succinyl chloride gave 522. Cleavage of the 1,2-dimethoxy groups of 519 with boron tribromide gave the quinone 523 which was found to exist in the p-quinonemethine form. Cleavage of the dimethoxy residues of 520 and 521 led to the expected quinones 524 and 525. Cleavage of the methoxy residues of 522 gave the quinone 526 (Scheme 505).

The 1,2-naphthoquinone residue was also covalently bound to a porphyrin backbone, since porphyrins are known to concentrate in cancer tissues. By reaction of the iodide 505 with the tetrabutylammonium salt of meso-p-hydroxyphenylporphyrin, the porphyrin quinone 527 was obtained (Scheme 506).

By esterification of 4,4',4'',4'''-(21H, 23H-porphine-5,10,15,20-tetrayl)tetrakis(benzoic acid) with the quinone alcohol 504 in the presence of EDCI (1,(3-dimethyl aminopropyl)-3-ethylcarbodiimide) and DMAP it was possible to prepare the quinone-porphyrin 528 (Scheme 507).

Synthesis of 1,2-naphthoguinones bound to DNA intercalators

It is known that 4-aminoacridine derivatives intercalate in the DNA helix. Therefore syntheses of 1,2-naphthoquinone residues bound to 4-aminoacridine derivatives were designed (Scheme 508). The salt (6-hydroxyhexyl)triphenylphosphonium bromide was prepared by the reaction of 6-bromohexanol with triphenylphosphine in refluxing acetonitrile. Wittig reaction of (6-hydroxyhexyl)triphenylphosphonium bromide with 4-acetamidobenzaldehyde produced alkene 529 as a mixture of E and Z isomers. Reduction of the double bond ($H_2$, Pd/C) and acidic hydrolysis (2N HCl, MeOH) afforded 4-(7-hydroxyheptyl)-aniline 530. Aniline 530 was reacted with 9-chloroacridine in MeOH in the presence of triethylamine to give alcohol 531. Alcohol 531 was converted to iodide 532 by reaction with methanesulfonyl chloride in pyridine, followed by reaction with sodium iodide in acetone. Reaction of iodide 532 with the silver salt of 2-hydroxy-1,4-naphthoquinone afforded quinone 533 as a mixture of ortho- and para-quinone isomers. The ortho- and para-quinone isomers could be separated and purified by column chromatography.

A second approach to these types of compounds is shown in Scheme 509. The isomer mixture 534 was converted to the iodide 535 by reaction with methanesulfonyl chloride in $CH_2Cl_2$ in the presence of pyridine, followed by a displacement with sodium iodide in acetone. Reaction of 535 with triphenylphosphine in refluxing acetonitrile afforded the phosphonium salt. A Wittig reaction between the phosphonium salt and naphthaldehyde 518 produced diene 536 (as a mixture of double bond isomers). Reduction with $H_2$ over Pd/C followed by hydrolysis (2N HCl, MeOH) gave aniline 537. Aniline 537 was reacted with 9-chloroacridine in MeOH in the presence of triethylamine to give 538. Cleavage of the methyl ethers with boron tribromide gave quinone 539.

A third synthetic approach to a 1,2-naphthoquinone moiety bound to an aminoacridine intercalator is depicted in Scheme 510. Aminoacridine was protected with mesitylenesulfonyl chloride to give 541, which was then alkylated with 1,5-dibromopentane to 542. The latter is brought into reaction with the silver salt of 2-hydroxy-1,4-naphthoquinone and the quinone-acridine 543 was thus obtained. Cleavage of the amide group using samarium iodide gave 544, the expected compound.

Synthesis of 1,2-naphthoquinol phosphates

In order to obtain 1,2-naphthoquinone derivatives that behave as "pro-drugs" the synthesis of quinol phosphates that can be hydrolyzed by cell phosphatases to liberate the parent quinones was carried out. Scheme 511 outlines the synthesis of the quinol phosphates. The parent 1,2-naphthoquinone 546 was brought into reaction with dibenzylphosphite to give a mixture of the two possible regioisomers 547. By cleavage of the benzyl residues with hydrogen in the presence of 10% Pd on charcoal the mixture of the two possible quinol phosphates 548 was obtained. They were used as such in the biological studies.

Synthesis of 8-hydroxy-β-lapachone 555

Scheme 512 outlines the synthesis of 555, a phenol derivative of β-lapachone that could be used as a building block for the construction of peptide derivatives of β-lapachone. The synthesis starts with the commercially available ester 549, that is acetylated using a Friedel-Crafts reaction to give 550. Cyclization of 550 in the presence of base and air gave the p-quinone 551. Alkylation of 551 with dimethyl allyl bromide gave a mixture of the C-alkyl derivative 552 and the O-alkyl derivative 553. They were separated and on treatment of 552 with concentrated sulfuric acid, the 8-methoxy-β-lapachone 554 was obtained. Cleavage of the methoxy group with boron tribromide gave the expected σ-naphthoquinone 555.

Synthesis of 1,2-naphthoguinone bisulfite adducts

Bisulfite adducts of 1,2-naphthoquinones were prepared as "pro-drugs." They are stable in aqueous solutions at pH below 7 but liberate the quinone core at pH above 7. Since biological media are usually above pH 7, the bisulfite adducts led to a slow release of the quinones after administration in an aqueous medium. General preparation procedures are given in the Experimental section.

Synthesis of 1,2-naphthocluinone peptides 1,2-Naphthoquinone conjugates of tetra and hexapeptides were prepared to obtain "prodrug" derivatives that can be cleaved by prostatic PSA. The guidelines followed for the synthesis of the peptides were based on the published results of Isaacs and coworkers (Denmeade et al. Cancer Res. 1997, 57, 4924), where they define the substrate specificity of PSA (prostate specific antigen). The synthesis of a quinone tetrapeptide is outlined in Scheme 513 for the 3-β-alanyloxy-β-lapachone (SL-11006) conjugate. SL-11006 (Quin) was coupled to Boc-Gln with DCC in the presence of 1-hydroxybenzotriazole to give Boc-Gln-Quin. Removal of the Boc group from Boc-Gln-Quin with TFA in $CH_2Cl_2$ gave TFA·Gln-Quin. Boc-Leu was coupled to TFA.Gln-Quin with DCC in the presence of 1-hydroxybenzotriazole to give Boc-Leu-Gln-Quin. Removal of the Boc group from Boc-Leu-Gln-Quin with TFA in $CH_2Cl_2$ gave TFA.Leu-Gln-Quin. Boc-Lys(Nε-Cbz) was coupled to TFA.Leu-Gln-Quin with DCC in the presence of 1-hydroxybenzotriazole to give Boc-Lys(Nε-Cl-Cbz)-Leu-Gln-Quin. Removal of the Boc group from Boc-Lys(Nε-Cbz)-Leu-Gln-Quin with TFA in $CHCl_3$ gave TFA. Lys(Nε-Cbz)-Leu-Gln-Quin. Morpholino-Ser(OBn) was coupled to TFA-Lys(Nε-Cbz)-Leu-Gln-Quin with DCC in the presence of 1-hydroxybenzotriazole to give morpholino-Ser(OBn)-Lys(Nε-Cbz)-Leu-Gln-Quin. The side chain protecting groups were removed by hydrogenolysis to yield morpholino-Ser-Lys-Leu-Gln-Quin (SEQ ID NO:14). During the hydrogenolysis, the quinone was reduced to the hydroquinone, which reoxidized to the quinone on exposure to air.

Morpholino-Ser(OBn) was prepared from N-Fmoc-Ser(OBn). Esterification of N-Fmoc-Ser(OBn) with isobutylene in the presence of a catalytic amount of $H_2SO_4$ afforded N-Fmoc-Ser(OBn)-OtBu. The Fmoc group was removed with piperidine in $CH_2Cl_2$ to produce Ser(OBn)-OtBu. Reaction of Ser(OBn)-OtBu with 4-morpholinecarbonyl chloride in pyridine yielded morpholino-Ser(OBn)-OtBu. Morpholino-Ser(OBn)-OtBu was hydrolyzed with TFA in $CH_2Cl_2$ to yield morpholine-Ser(OBn).

The synthesis of a tetrapeptide conjugate of 3-leucyloxy-β-lapachone is outlined in Scheme 514.

EXPERIMENTAL tert-Butyl δ-[(1,2-dihydro-1,2-dioxonaphth-4-yl)oxy]valerate (501). A mixture of tert-butyl 5-bromovalerate (1 g, 4.2 mmol) and the silver salt of 2-hydroxy-1,4-naphthoquinone (0.8 g, 3.84 mmol) in benzene (10 mL), was stirred for 24 h at 50° C. The reaction mixture was filtered through celite and the solvent was removed in vacuo. The residue was purified by flash chromatography (5% methanol in chloroform) to give a yellow solid (384 mg, 30%). $^1$H NMR ($CDCl_3$) 8.12 (d, J=7.7 Hz, 1H), 7.89 (d, J=7.7 Hz, 1H), 7.70 (t, J=6.1 Hz, 1H), 7.59 (t, J=6.4 Hz, 1H), 5.95 (s, 1H), 4.17 (t, J=5.9 Hz, 2H), 2.35 (t, J=7.2 Hz, 2H), 1.90-2.05 (m, 2H), 1.78-1.90 (m, 2H), 1.47 (s, 9H).

Benzyl 5-[(1,2-dihydro-1,2-dioxonaphth-4-yl)oxy]valerate (502). A mixture of benzyl 5-bromovalerate (2.27 g, 8.4 mmol) and the silver salt of 2-hydroxy-1,4-naphthoquinone (1.63 g, 5.81 mmol) in benzene (8 mL) was stirred for 48 h at 55° C. and filtered through celite. The filtrate was diluted with diethyl ether, extracted with a 20% aqueous solution of $NaHSO_3$ then basified to pH 10-11 with $Na_2CO_3$, and extracted with $CH_2Cl_2$. Yellow solid (1.334 g, 63%). $^1$H NMR ($CDCl_3$) 8.12 (d, J=7.5 Hz, 1H), 7.85 (d, J=7.7 Hz, 1H), 7.68 (t, J=7.5, 1H), 7.58 (t, J=7.7 Hz, 1H), 7.25-7.50 (m, 5H), 5.93 (s, 1H), 5.14 (s, 2H), 4.15 (t, J=5.7 Hz, 2H), 2.50 (t, J=7.0 Hz, 2H), 1.8-2.2 (m, 4H).

5-[(1,2-Dioxo-1,2-dihydronaphth-4-yl)oxy]valeric Acid (503). Benzyl ester 502 (1.90 g, 5.22 mmol) was hydrogenated at 30 psi with Pd (400 mg) in ethyl acetate (120 mL) for 6 h. The catalyst was removed by filtration through celite, the solvent was evaporated in vacuo and the residue was oxidized with $Ag_2O$ (1.45 g, 6.25 mmol) in $Et_2O$ by stirring for 10 h. Following filtration and evaporation of the solvent the product was crystallized from benzene to afford 0.53 g of pure material. The mother liquor was purified by flash chromatography ($CH_2Cl_2$/MeOH 15:1), the product dissolved in $CH_2Cl_2$, extracted with aqueous $NaHCO_3$ solution, acidified to pH 1 with 3% HCl and extracted back with $CH_2Cl_2$ to give additional 0.25 g of pure material (total yield 55%), mp 134-136° C.; $^1$H NMR ($CDCl_3$) 8.12 (d, J=7.0 Hz, 1H), 7.87 (d, J=7.6 Hz, 1H), 7.70 (t, J=7.5 H), 7.59 (t, J=7.4 Hz, 1H), 7.27 (s, 1H), 4.18 (t, J=5.9 Hz, 2H), 2.51 (t, J=7.0 Hz, 2H), 1.75-2.15 (m, 4H).

1,2-Dihydro-4-(6-hydroxyhexyloxy)-1,2-dioxo-naphthalene (504). A mixture of 6-bromohexanol-1 (4.5 g, 24.85 mmol) and the silver salt of 2-hydroxy-1,4-naphthoquinone (6.46 g, 23.01 mmol) in benzene (24 mL) was stirred for 48 h at 60° C. The reaction mixture was worked up as described for 502 and crystallized from hexane to afford a yellow solid (3.18 g, 50%). mp 96-98° C., $^1$H NMR ($CDCl_3$) 8.12 (d, J=7.5 Hz, 1H), 7.87 (d, J=7.7 Hz, 1H), 7.70 (t, J=7.5 Hz, 1H), 7.58 (t, J=7.5 Hz, 1H), 5.95 (s, 1H), 4.15 (t, J=6.3 Hz, 2H), 3.69 (t, J=6.2 Hz, 2H), 1.92-1.97 (m, 2H), 1.3-1.8 (m, 7H)

1,2-Dihydro-4-(6-iodohexyloxy)-1,2-dioxonaphthalene (505). A mixture of 1,6-diiodohexane (10.14 g, 30 mmol) and the silver salt of 2-hydroxy-1,4-naphthoquinone (2.81 g, 10 mmol) in benzene (60 mL) was stirred for 12 h at room temperature. The reacton mixture was filtered through Celite, concentrated in vacuo, and purified by flash chromatography (hexane/EtOAc 4:1) to give a yellow solid (2.19 g, 57%); mp 85-87° C.; $^1$H NMR ($CDCl_3$) 8.12 (dd, J=6.5, 1.0 Hz, 1H), 7.86 (dd, J=6.9, 0.9 Hz, 1H), 7.70 (dt, J=7.6, 1.5 Hz, 1H), 7.58 (dt, J=7.5, 1.3 Hz, 1H), 5.95 (s, 1H), 4.15 (t, J=6.3, 2H), 3.22 (t, J=6.9 Hz, 2H), 1.80-2.05 (m, 4H), 1.45-2.10 (m, 4H).

bis [6-[(1,2-Dihydro-1,2-dioxonaphth-4-yl)oxy]hexyl] carbonate (506). Pyridine (0.12 ml, 1.5 mmol) was added to a stirred solution of the alcohol 504 (200 mg, 0.73 mmol) and bis(trichloromethyl)carbonate (40 mg, 0.134 mmol) in $CH_2Cl_2$ (5 mL) at 0° C. The cooling bath was removed, the reaction mixture was diluted with $CH_2Cl_2$, washed with 3% HCl, brine, dried ($Na_2SO_4$) and purified by column chromatography (benzene/EtOAc 4:1, 2:1). The product was triturated with $Et_2O$ to afford a yellow solid (127 mg, 30%), mp 78-82° C. (decomp.). MS (LSIMS, 3-NBA) 576 ($M^+$+2), 401, 175; $^1$H NMR ($CDCl_3$) 8.09 (dd, J=6.0, 1.6 Hz, 1H), 7.85 (dd, J=7.8, 1.2 Hz, 1H), 7.71 (t, J=6.9 Hz, 1H), 7.58 (t, J=6.2 Hz, 1H), 5.94 (s, 1H), 4.17 (t, J=6.0 Hz, 2H), 4.15 (t, J=5.6 Hz, 2H), 1.85-2.10 (m, 2H), 1.65-1.85 (m, 2H), 1.40-1.65 (m, 4H).

N-(1-Methyl-5-methyloxycarbonylpyrrol-3-yl)-5-[(1,2-dihydro-1,2-dioxonaphth-4-yl)oxy]valeramide (507). A solution of an acid 503 (334 mg, 1.22 mmol) in DMF (1.67 mL) was treated with HBTU (462 mg, 1.22 mmol) followed by DIEA (452 mg, 3.5 mmol) and stirred for 5 min. 3-Amino-1-methyl-5-methyloxycarbonylpyrrol hydrochloride (232 mg, 1.22 mmol) and DIEA (378 mg, 3 mmol) were added to the reaction mixture. The latter was stirred for 2 h, diluted with $Et_2O$, the precipitate was removed, dissolved in $CHCl_3$, washed with 3% HCl, $H_2O$, aqueous $NaHCO_3$, $H_2O$ again, dried ($MgSO_4$) and purified by chromatography on alumina column ($CHCl_3$/MeOH 80:1, 50:1). The product was triturated with $Et_2O$/$CHCl_3$ to obtain a yellow-red solid (200 mg, 40%); mp 122-123° C. (decomp.): MS (LSIMS, 3-NBA) 410 ($M^+$), 237 ($M^+$−173). $^1$H NMR ($CDCl_3$) 8.08 (d, J=7.5 Hz, 1H), 7.86 (d, J=7.3 Hz, 1H), 7.68 (t, J=7.5 Hz, 1H), 7.57 (t, J=7.5 Hz, 1H), 7.38 (d, J=1.8 Hz, 1H), 7.34 (s, 1H), 6.65 (d, J=2 Hz, 1H), 5.95 (s, 1H), 4.19 (t, J=5.53 Hz, 2H), 3.88 (s, 3H), 3.80 (s, 3H), 2.46 (t, J=6.6 Hz, 2H), 1.90-2.15 (m, 4H).

4-(tert-Butylcarbonyloxy)-1,2-dihydro-1,2-dioxonaphthalene (508). A mixture of the silver salt of 2-hydroxy-1,4-naphthoquinone (842 mg, 3 mmol), and pivaloyl chloride (434 mg, 3.6 mmol) in benzene (5 mL) was stirred for 8 h at room temperature. The reaction mixture was filtered through Celite, the precipitate washed with EtOAc, and the combined organic solutions were concentrated in vacuo and purified by flash chromatography (EtOAc/hexane 1:10, 1:5). The product was recrystallized from hexane to afford a yellow solid (190 mg, 25%); mp 125-126° C.; $^1$H NMR (CDCl$_3$) 8.15(dd, J=7.7, 1.1 Hz, 1H), 7.71(dt, J=7.7, 1.5 Hz, 1H), 7.59 (dt, J=7.5, 1.2 Hz, 1H), 7.57 (dd, J=7.6, 1.1 Hz, 1H), 6.48 (s, 1H), 1.44 (s, 9H).

N-[3-(Dimethylamino)propyl][3-[[3-[[3-[4-[(1,2-dihydro-1,2-dioxonaphth-4-yl)oxy]butylcarbonylamino]-1-methylpyrrol-5-yl]carbonylamino]-1-methylpyrrol-5-yl]carbonylamino]-1-methylpyrrol-5-yl]carboxamide (510) was prepared from acid 503 (61 mg, 0.222 mmol) and Boc-protected pyrrolylamine 509 (84 mg, 0.148 mmol) using the procedure described for 507. After the reaction was completed, the reaction mixture was diluted with Et$_2$O, the precipitate was removed, triturated with hot EtOAc and crystallized from a CHCl$_3$/Et$_2$O mixture. The product was a yellow solid (30 mg, 28%); mp 159-162° C. (decomp.); $^1$H NMR (DMSO-d$_6$) 9.90 (s, 1H), 9.89 (s, 1H), 9.86 (s, 1H), 8.08 (bs, 1H), 7.97 (d, J=7.7 Hz, 1H), 7.87 (d, J=7.2 Hz, 1H), 7.81 (t, J=7.9 Hz, 1H), 7.68 (t, J=7.2, 1H), 7.24 (s, 1H), 7.19 (s, 1H), 7.04 (s, 1H), 6.89 (s, 1H), 6.84 (s, 1H), 6.06 (s, 1H), 4.25 (t, J=5.8 Hz, 1H), 3.85 (s, 3H), 3.84 (s, 3H), 3.80 (s, 3H), 3.12-3.30 (m, 2H), 2.25-2.45 (m, 4H), 2.19 (s, 6H), 1.72-2.00 (m, 4H), 1.60-1.70 (m, 2H).). MS (LSIMS, 3-NBA) 725.2 (M$^+$+1).

1,2-Dihydro-4-[6-[(4-cyanophenyl)oxy]hexyloxy]-1,2-dioxonaphthalene (511). A mixture of 4-hydroxybenzonitrile (87 mg, 0.73 mmol), naphthoquinone 504 (200 mg, 0.73 mmol), PPh$_3$ (191 mg, 0.73 mmol) in dioxane (10 mL) was cooled to 10° C. and treated with DEAD (140 mg, 0.80 mmol). The reaction mixture was stirred for 10 h, concentrated in vacuo and purified by chromatography (5% EtOAc in benzene) to afford 511 as a yellow solid (171 mg, 53%), $^1$H NMR (CDCl$_3$) 8.13 (dd, J=7.3, 1.4 Hz, 1H), 8.86 (dd, J=7.7, 1.1 Hz, 1H), 7.67 (dt, J=7.5, 1.5 Hz 1H), 7.60 (dt, J=7.5, 1.5 Hz, 1H), 7.57 (d, J=8.8 Hz, 2H), 6.93 (d, J=8.9 Hz, 2H),5.96 (s, 1H), 4.17 (t, J=6.4 Hz, 2H), 4.03 (t, J=6.3 Hz, 2H), 1.80-2.05 (m, 4H), 1.58-1.68 (m, 4H).

1,2-Dihydro-4-[6-(phenyloxy)hexyloxy]-1,2-dioxonaphthalene (512). Phenol (28 mg, 0.3 mmol) was treated with tetrabutylammonium hydroxide (0.3 mL of 1.0 M solution in methanol) and the reaction mixture was concentrated to dryness in vacuo. Iodonaphtoquinone 505 (115 mg, 0.3 mmol) in DMF (3 mL) was added to the tetrabutylammonium salt, stirred for 48 h and quenched with H$_2$O (10 mL). The product was extracted with CHCl$_3$, the extract was washed with H$_2$O, then brine, dried (Na$_2$SO$_4$), and purified by chromatography (5% EtOAc in benzene) to give 512 as a yellow solid (45 mg, 43%) $^1$H NMR (CDCl$_3$) 8.13 (d, J=7.4 Hz, 1H), 7.86 (d, J=7.4 Hz, 1H), 7.67 (t, J=7.6 Hz, 1H), 7.61 (t, J=7.5 Hz, 1H), 7.15-7.40 (m, 2H), 6.85-7.10 (m, 3H), 5.96 (s, 1H), 4.17 (t, J=6.5 Hz, 2H), 3.99 (t, J=6.2 Hz), 1.70-2.10 (m, 4H), 1.35-1.70 (m, 4H).

3-Dimethylaminophenyl 5-[(1,2-dihydro-1,2-dioxonaphth-4-yl)oxy]valerate (513). A mixture of acid 503 (137 mg, 0.5 mmol), 3-dimethylaminophenol (82 mg, 0.6 mmol), DCC (103 mg, 0.5 mmol), and DMAP (12 mg, 0.01 mmol) in THF (2 mL) was stirred for 2 h. The reaction mixture was concentrated in vacuo, the residue dissolved in benzene, washed with H$_2$O and dried (Na$_2$SO$_4$). Column chromatography (10% EtOAc) in benzene gave 513 as a yellow solid (70 mg, 36%), $^1$H NMR (CDCl$_3$) 8.13, (d, J=7.3 Hz, 1H), 7.90 (d, J=7.4 Hz, 1H), 7.69 (t, J=6.1 Hz, 1H), 7.58 (t, J=7.6 Hz, 1H), 7.22 (dd, J=8.1, 8.1 Hz, 1H), 6.30-6.70 (m, 2H), 5.96 (s, 1H), 4.21 (t, J=5.6 Hz, 2H), 2.69 (t, J=6.5 H, 2H), 1.90-2.15 (m, 4H).

2'-[4-[6-(1,2-Dihydro-1,2-dioxo-naphth-4-yl)oxyhexyl]oxyphenyl]-5-(4-methylpiperazin-1-yl)-2,5'-bi-1H-benzimidazole (514). Hoechst 33258 (3.0 g, 5 mmol) was dissolved in a hot mixture of isopropanol-water (24 mL/12 mL) and neutralized with ammonium hydroxide (3 mL). The precipitate was filtered, triturated with Et$_2$O and dried in vacuo to obtain the free base of bisbenzimidazole. A 1.0 M solution of Bu$_4$NOH in MeOH (0.6 mL, 0.6 mmol) was added to the solution of bisbenzimidazole (1.635 g, 3.85 mmol) in MeOH (30 mL), stirred for 15 min and concentrated to dryness in vacuo. Iodonaphthoquinone 505 (1.485 g, 3.87 mmol) in DMF (30 mL) was added to the tetrabutyl ammonium salt and the mixture was stirred for 48 h. The reaction mixture was suspended in H$_2$O, the crude product was filtered, washed with H$_2$O, dried and purified by flash chromatography (MeOH/CHCl$_3$ 1:9, 1:5) to afford 514 as a yellow solid (790 mg, 30%). $^1$H NMR (CDCl$_3$/MeOH-d$_4$) 8.21 (s, 1H), 8.09 (d, J=7.6 Hz, 1H), 8.05 (d, J=8.7 Hz, 2H), 7.85-7.95 (m, 2H), 7.48-7.75 (m, 4H), 7.14 (bs, 1H), 7.10-6.98 (m 3H), 4.21 (t, J=6.3 Hz, 2H), 4.08 (t, J=6.2 Hz, 2H), 2.65-2.75 (m, 4H), 2.40 (s, 3H), 1.80-2.15 (m, 4H), 1.60-1.75 (m, 4H). MS (LSIMS, 3-NBA) 725.2 (M$^+$+1).

Trifluoroacetate of 6-[1(1,2-dihydro-1,2-dioxonaphth-4-yl)oxy]hexyl 6-aminohexanoate (515). [6-(tert-Butyloxycarbonyl)amino]hexanoic acid (139 mg, 0.6 mmol) was added into solution of DCC (113 mg, 0.55 mmol) and DMAP (64 mg, 0.52 mmol) in CH$_2$Cl$_2$ (10 mL) at 0° C. and stirred for 15 min, when naphthoquinone 504 (137 mg, 0.5 mmol) was added. The reaction mixture was stirred for 12 h at room temperature, diluted with CH$_2$Cl$_2$, extracted 3 times with an aqueous solution of KHSO$_4$, then with a NaHCO$_3$ solution followed by brine, dried (MgSO$_4$), and finally it was concentrated to dryness in vacuo and triturated with Et$_2$O. The residue was dissolved in CH$_2$Cl$_2$ (3 mL), TFA (0.5 mL) was added to the solution and the mixture stirred at 0° C. for 1 h. All volatiles were removed in vacuo and the residue was triturated in Et$_2$O to give 515 (100 mg, 40%). as a dark yellow oil. $^1$H NMR (CDCl$_3$) 8.90 (d, J=7.6 Hz, 1H), 7.99 (bs, 3H), 7.87 (d, J=7.8 Hz, 1H), 7.71 (t, J=7.6 Hz, 1H), 7.59 (t, J=7.5 Hz, 1H), 5.96 (s, 1H), 4.17 (t, J=6.3 Hz, 2H), 4.09 (t, J=6.2 Hz, 2H), 2.90-3.15 (m, 2H), 2.29 (t, J=7.1 Hz, 2H), 1.90-2.10 (m, 2H), 1.30-1.85 (m, 12H).

1,2-Dihydro-1,2-dioxo-4-[4-[2-[3-[2-(Ethylaminocarbonyl)ethylaminocarbonyl]propyl=aminocarbonyl]ethylaminocarbonyl]butyloxy]naphthalene (517). Acid 503 (137 mg, 0.5 mmol) was dissolved in DMF (1 mL), treated with HBTU (190 mg, 0.5 mmol) followed by DIEA (260 μL, 1.5 mmol) and stirred for 10 min. N-Ethyl[2-[3-(2-aminoethylcarbonylamino)propylcarbonylamino]ethyl]carboxamide hydrochloride 516 (154 mg, 0.5 mmol) and DIEA (260 μL, 1.5 mmol) were added to the reaction mixture, the latter was stirred for 2 h, and the reaction mixture was diluted with Et$_2$O. The product was filtered and triturated with CHCl$_3$ to afford a yellow solid (100 mg, 38%), mp 145-170° C. (decomp.) $^1$H NMR (CDCl$_3$, MeOH-d$_4$) 8.10 (dd, J=7.6, 1.4 Hz, 1H), 7.92 (dd, J=7.8, 1.2 Hz, 1H), 7.72 (dt, J=7.7, 1.2 Hz, 1H), 7.62 (dt, J=7.6, 1.3 Hz, 1H), 7.30-7.50 (m, 2H), 7.15

(bs, 1H), 5.97 (s, 1H), 4.20 (t, J=5.8 Hz, 2H), 3.35-3.50 (m, 4H), 3.10-3.30 (m, 4H), 3.32-3.42 (m, 4H), 2.30 (t, J=6.9 Hz, 2H), 2.19 (t, J=7.4 Hz, 2H), 1.75-2.05 (m, 4H), 1.78 (t, J=7.2, 2H), 1.13 (t, J=7.3, 3H). MS (FAB, NaI) 551.2 (M+Na), 529 (M$^+$+1).

3,4-Dimethoxy-1-naphthaldehyde (518). A mixture of 1,2-dimethoxynaphthalene (0.74 g, 4 mmol) and DMF (0.8 mL, 10 mmol) in dichlorobenzene (0.8 mL) was stirred with $POCl_3$ at 100° C. for 2 h. The reaction mixture was cooled to 0° C., quenched with a cold aqueous solution of NaOAc, diluted with $H_2O$ and extracted with benzene. The extracts were dried ($MgSO_4$), concentrated and in vacuo and dichlorobenzene was removed by kugelrohr distillation at 110° C./0.5 mm Hg. Column chromatography (20% EtOAc in hexane) gave the product 518 (596 mg, 68%), which was used in the following step without further purification. $^1$H NMR ($CDCl_3$) 10.42 (s, 1H), 9.00-9.15 (m, 1H), 8.15-8.30 (m, 1H), 7.61 (s, 1H), 7.50-7.65 (m, 2H), 4.12 (s, 3H), 4.07 (s, 3H).

4-Butylaminomethyl-1,2-dimethoxy-naphthalene (519). A suspension of $PtO_2$ (40 mg) in EtOH (2 mL) was stirred with $H_2$ at 25 psi for 30 min. Naphthaldehyde 518 (596 mg, 2.8 mmol) was dissolved in EtOH and added into the suspension followed by the addition of butylamine (219 mg, 3 mmol). The reaction mixture was hydrogenated for 6 h at 50 psi. The catalyst was filtered through Celite, washed with acetone and the filtrate was concentrated to dryness to give 519 as an oil (665 mg, 87%). The product was utilized in the following step without further purification. $^1$H NMR ($CDCl_3$) 8.16 (d, J=7.5 Hz, 1H), 7.99 (d, J=7.6 Hz, 2H), 7.40-7.60 (m, 2H), 7.35 (s, 1H), 4.19 (s, 2H), 4.00 (s, 3H), 3.98 (s, 3H), 2.76 (t, J=7.0 Hz, 2H), 1.64 (bs, 1H), 1.45-1.60 (m, 2H), 1.30-1.45 (m, 2H), 0.93 (t, J=7.2 Hz, 3H).

4-(N-Acetyl-N-butylaminomethyl)-1,2-dimethoxy-naphthalene (520). Triethylamine (350 μL, 2.5 mmol) was added to a solution of aminonaphthalene 519 (250 mg, 0.9 mmol) and AcCl (90 μL, 1.27 mmol) in $CH_2Cl_2$ (5 mL) at 0° C. The cooling bath was removed after 10 min, the reaction mixture was stirred for 1 h at room temperature, diluted fivefold with $CH_2Cl_2$, washed with an aqueous solution of $NaHCO_3$ followed by 3% HCl, brine and dried ($MgSO_4$). The crude product (315 mg, 100%) obtained after evaporation of the solvent was used in the following step without further purification. $^1$H NMR ($CDCl_3$) 8.19, 8.15 (2d, J=7.6, 8.4 Hz, 1H), 8.97, 7.80 (2d, J=7.9, 8.2 Hz, 1H), 7.35-7.58 (m, 2H), 7.16, 7.04 (2s, 1H), 5.05, 4.95 (2s, 2H), 4.01, 3.99 (2s, 3H), 3.99, 3.96 (2s, 3H), 3.47, 3.13 (2t, J=7.4, 7.8 Hz, 2H), 2.20, 2.09 (2s, 3H), 1.15-1.70 (m, 4H), 0.91, 0.87 (2t, J=7.2, 7.3 Hz, 3H).

4-(N-Butyl-N-trifluoroacetylaminomethyl)-1,2-dimethoxy-naphthalene (521). Naphthalene 519 (200 mg, 0.73 mmol) was acylated with trifluoroacetyl anhydride (210 mg, 1 mmol) in the presence of TEA (0.2 mL, 1.5 mmol) by raising the temperature during 3 h from −40° to 0° C. The reaction mixture was diluted with $CH_2Cl_2$, washed with aqueous $NaHCO_3$, 3% HCl, brine and finally dried ($MgSO_4$). The crude product (266 mg, 99%) was used in the following step without further purification. $^1$H NMR ($CDCl_3$) 8.17-8.25 (m, 1H), 7.82 (t, J=7.7 Hz, 1H), 7.40-7.55 (m, 2H), 7.16, 7.03 (2s, 1H), 5.11, 5.08 (2s, 2H), 4.01, 4.03 (2s, 3H), 3.98, 3.96 (2s, 3H), 3.40, 3.25 (2t, J=7.5, 7.4 Hz, 2H), 1.45-2.75 (m, 2H), 1.10-1.45 (m, 2H), 0.89 (t, J=7.4, 3H).

4-[N-Butyl-N-[3-(4-morpholinocarbonyl)ethylcarbonyl]aminomethyl]-1,2-dimethoxynaphthalene (522). 3-(N-Morpholinocarbonyl)propionic acid (139 mg, 0.74 mmol) in $CH_2Cl_2$ (5 mL) was heated to reflux with thionyl chloride (440 mg, 3.7 mmol) for 1 h and all volatiles were evaporated in vacuo. The residue was dissolved in anhydrous $CH_2Cl_2$ (3 mL), cooled to 0° C. and naphthalene 519 (100 mg, 0.37 mmol), followed by DMAP (45 mg, 0.37 mmol) and TEA (140 μL, 1 mmol) were added into the reaction mixture. After stirring for 1 h at room temperature the reaction was quenched with wet EtOAc (10 mL), washed with 3% HCl, aqueous $NaHCO_3$, brine, and dried ($Na_2SO_4$). Purification by chromatography (15% EtOAc in hexane) gave 522 (160 mg, 98%). The product was used directly in the next step. $^1$H NMR ($CDCl_3$) 8.19, 8.17 (2d, J=7.7, 7.8 Hz, 1H), 7.92, 7.85 (2d, J=8.2, 8.05 Hz, 1H), 7.38-7.56 (m, 4H), 7.25, 7.17 (2s, 1H), 5.05, 5.03 (2s, 2H), 4.03, 4.00 (2s, 3H), 3.99, 3.98 (2s, 3H), 3.25-3.82 (m, 14H), 1.15-1.82 (m, 4H), 0.88, 0.85 (2t, J=7.1, 6.7 Hz, 3H).

Demethylation of dimethoxynaphthalenes with boron tribromide. 4-(Butylamino=methylene)-1,4-dihydro-2-hydroxy-1-oxo-naphthalene (523). A solution of dimethoxynaphthalene 519 (30 mg, 0.11 mmol) in $CH_2Cl_2$ (2 mL) was treated with a 1M solution of $BBr_3$ in $CH_2Cl_2$ (1.1 mL) at −78° C. and stirred at this temperature for 2 h. The reaction mixture was placed in a freezer at −10° C. for 3 h, quenched with $Et_2O$ (1 mL) by stirring for 15 min at room temperature and neutralized with aqueous solution of $NaHCO_3$. The product was extracted with EtOAc, dried ($MgSO_4$), and the solvent was removed in vacuo. The residue was dissolved in $Et_2O$, stirred for 10 h in an open flask and purified by chromatography (5% MeOH in $CHCl_3$). Trituration with $Et_2O$ yielded the product 523 (8 mg, 30%). $^1$H NMR ($CDCl_3$) 9.05 (bs, 1H), 8.31 (d, J=8.1 Hz, 1H), 7.65-7.85 (m, 1H), 7.05-7.65 (m, 3H), 3.20-3.60 (m, 2H), 1.50-1.85 (m, 2H), 2.25-1.50 (m, 2H), 0.80-1.10 (m, 3H). HRMS (EI) 243.1250. Calcd for $C_{15}H_{17}NO_2$ 243.1259.

4-(N-Acetyl-N-butylaminomethyl)-1,2-dihydro-1,2-dioxonaphthalene (524) was prepared from dimethoxynaphthalene 520 using the procedure described for 523. The product (60%) was purified by chromatography (1.5% MeOH in $CHCl_3$) followed by trituration with $Et_2O$. $^1$H NMR ($CDCl_3$) 8.1 (dd, J=7.53, 1.2 Hz, 1H), 7.67 (dd, J=7.7, 1.1 Hz, 1H), 7.50-7.62 (m, 2H), 6.21 (s, 1H), 4.68 (s, 2H), 3.35 (t, J=8.0 Hz, 2H), 2.25 (s, 3H), 1.50-1.75 (m, 2H), 1.15-1.50 (m, 2H), 0.96 (t, J=5.8, 3H). HRMS (EI) 285.1383. Calcd for $C_{17}H_{19}NO_3$ 285.1365.

4-(N-Butylaminomethyl-N-trifluorocetyl)-1,2-dihydro-1,2-dioxonaphthalene (525) was obtained from dimethoxynaphthalene 521 using the procedure described for 523. The product (37%) was purified by chromatography (3% MeOH in $CHCl_3$) followed by trituration in $Et_2O$. $^1$H NMR ($CDCl_3$) 8.29 (d, J=7.13 Hz, 1H), 7.40-7.85 (m, 3H), 6.19 (s, 1H), 4.73 (s, 2H), 3.35-3.70 (m, 2H), 1.50-1.80 (m, 2H), 1.35-1.80 (m, 2H), 0.96 (t, J=7.2 Hz, 3H). HRMS (EI) 339.1106. Calcd for $C_{17}H_{16}F_3NO_3$ 339.1082.

4-[[N-Butyl-N-(4-morpholino-4-oxobutyryl)amino]methyl]-1,2-dihydro-1,2-dioxonaphthalene (526) was obtained from dimethoxynaphthalene 522 using the procedure described for 523. The product (10%) was purified by chromatography (25%-40% EtOAc in hexane) followed by trituration in $Et_2O$. $^1$H NMR ($CDCl_3$) 8.19 (d, J=7.4 Hz, 1H), 7.70 (t, J=6.4 Hz, 1H), 7.59 (d, J=6.5 Hz, 1H), 7.50 (t, J=7.9 Hz, 1H), 6.33 (s, 1H), 4.65 (s, 2H), 3.35-3.80 (m, 14H), 1.65-1.85 (m, 2H), 1.25-1.50 (m, 2H), 0.96 (t, J=7.2 Hz, 3H).

meso-Tetra[4-[6-[(1,2-dihydro-1,2-dioxonaphth-4-yl) oxy]hexyloxy]phenyl]porphine (527). A 1 M solution of $Bu_4NOH$ in MeOH (0.212 mL,) was added to a stirred solution of meso-tetra(4-hydroxyphenyl)porphine (36 mg, 0.53 mmol) in MeOH (5 mL), stirring was kept for 10 min and the mixture concentrated to dryness in vacuo. Naphthoquinone 505 (81 mg, 0.21 mmol) in DMF (2 mL) was added to the porphyrin, the solution stirred for 48 h and diluted with $H_2O$ (20 mL). The product was extracted with $CHCl_3$, washed with brine, the solvent was evaporated and the residue was triturated with $Et_2O$. Purification by flash chromatography (2-3% MeOH in $CHCl_3$) followed by recrystallization from $CHCl_3/Et_2O$ (1:3) afforded the product as a dark red solid (19.6 mg, 21%). $^1$H NMR ($CDCl_3$) 8.86 (s, 8H), 8.01-8.15 (m, 12H), 7.9 (d, J=7.8 Hz, 4H), 7.68 (t, J=6.3 Hz, 4H), 7.55 (t, J=7.5 Hz, 4H), 7.27 (d, J=7.8 Hz, 8H), 5.98 (s, 4H), 4.15-4.30 (m, 16 H), 1.80-2.10 (m, 16H), 1.65-1.80 (m, 16H). Anal. Calcd for $C_{108}H_{94}N_4O_{16} \times 1.5$ $H_2O$: C, 74.87; H, 5.43; N, 3.23. Found: C, 74.62; H, 5.57; N, 3.11.

meso-Tetra[4-[6-[(1,2-dihydro-1,2-dioxanaphth-4-yl)oxyhexyl]oxycarbonyl]phenyl]porphyrin (528). EDCI (518 mg, 2.7 mmol) was added at 0° C. to a mixture of meso-tetra(4-carboxyphenyl)porphyrin (500 mg, 0.63 mmol), alcohol 4 (831 mg, 3 mmol), and DMAP (159 mg, 1.3 mmol) in $CH_2Cl_2$ (10 mL). The solution was stirred for 2 h, the cooling bath was removed and the reaction mixture was left at room temperature overnight. It was diluted with $CH_2Cl_2$, washed with 2% HCl, $H_2O$, aqueous solution of $NaHCO_3$, $H_2O$, 5% aqueous solution of $NaHSO_3$, $H_2O$, dried ($Na_2SO_4$) and concentrated in vacuo. The analytical sample was prepared by column chromatography on silica (2% MeOH in $CHCl_3$). Mp 98-110° C. (decomp.) Yield 572 mg, 50%. $^1$H NMR ($CDCl_3$) 8.81 (s, 8H,), 8.45 (d, J=8.2 Hz, 8H), 8.30 (d, J=8.0 Hz, 8H), 8.09 (d, J=6.9 Hz, 4H), 7.89 (d, J=7.3 Hz, 4H), 7.70 (t, J=7.1 Hz, 4H), 7.56 (t, J=7.1 Hz, 4H), 5.98 (s, 4H), 4.56 (t, J=6.5 Hz, 8H), 4.21 (t, J=6.1 Hz, 8H), 1.85-2.20 (m, 16H), 1.60-1.80 (m, 16H). MS (MALDI) 1838 ($M^+$+23), 1817 ($M^+$+1). Anal. Calcd for $C_{112}H_{94}N_4O_{20} \times 4$ $H_2O$: C, 71.18; H, 5.40; N, 2.97. Found: C, 71.27; H, 5.24; N, 3.03.

N-Acetyl-4-(7-hydroxy-1-heptenyl)-aniline (529). A solution of 5.213 g (28.8 mmol) of 6-bromohexanol and 7.55 g (28.8 mmol) of triphenylphosphine in 50 mL of $CH_3CN$ was refluxed for 24 hr. Evaporation of solvent yielded the crude phosphonium salt, which was used directly in the next reaction. The crude phosphonium salt and 4.690 g (28.7 mmol) of 4-acetamidobenzaldehyde were dissolved in a mixture of 150 mL of $CH_2Cl_2$ and 150 mL of THF. To the cooled solution was added 1.529 g (60.5 mmol) of 95% NaH as a slurry in $CH_2Cl_2$ (10 mL). The reaction mixture was stirred in an ice bath for 1 hr, then at room temperature for 19 hr. The mixture was partitioned between 350 mL $CH_2Cl_2$ and 500 mL 1N HCl. The aqueous phase was extracted with $CH_2Cl_2$ (4×100 mL). The $CH_2Cl_2$ extracts were combined, dried with $MgSO_4$, and evaporated to dryness. Column chromatography on silica gel eluting first with 1% MeOH in $CH_2Cl_2$ and then with 2% MeOH in $CH_2Cl_2$ afforded 4.913 g (69% from 6-bromohexanol) of alkene 529 as a mixture of E and Z isomers: $^1$H NMR (250 MHz, $CDCl_3$, TMS) δ 7.5-7.4 (m, 4H), 7.3-7.1 (m, 4H), 6.4-6.3 (m, 2H), 6.2-6.1 (m, 1H), 5.7-5.6 (m, 2H), 3.65 (t, J=6.5 Hz, 2H), 3.63 (t, J=6.5 Hz, 2H), 2.4-2.1 (m, 4H), 2.18 (s, 3H), 2.17 (s, 3H), 1.7-1.3 (m, 12H).

4-(7-Hydroxyheptyl)-aniline (530). To a solution of 4.913 g (19.9 mmol) of N-acetyl-4-(7-hydroxy-1-heptenyl)-aniline 529 in 100 mL of 10% MeOH in $CH_2Cl_2$ in a Parr bottle were added 490 mg of 10% Pd/C. The bottle was placed on a hydrogenation apparatus and shaken for 4 hr at 25 psi of hydrogen. Removal of catalyst by filtration through a celite pad and evaporation of solvent afforded 5.294 g of alkane: $^1$H NMR (300 MHz, $CDCl_3$, TMS) δ 7.80 (s, NH), 7.38 (d, J=8 Hz, 2H), 7.09 (d, J=8 Hz, 2H), 3.61 (t, J=6.6 Hz, 2H), 2.54 (t, J=7.6 Hz, 2H), 2.12 (s, 3H), 1.6-1.5 (m, 4H), 1.4-1.3 (m, 6H). A solution of the alkane in 40 mL of MeOH was mixed with 190 mL of 2N HCl. The reaction mixture was refluxed for 23 hr. Then the reaction mixture was added to a cooled mixture of 190 mL 2N NaOH and 200 mL $CH_2Cl_2$. The aqueous phase was extracted with $CH_2Cl_2$ (4×100 mL). The $CH_2Cl_2$ extracts were combined, dried with $MgSO_4$, and evaporated to dryness, to afford 3.579 g of aniline 530 (87% from alkene): $^1$H NMR (300 MHz, $CDCl_3$, TMS) δ 6.95 (d, J=8.3 Hz, 2H), 6.61 (d, J=8.3 Hz, 2H), 3.60 (t, J=6.6 Hz, 2H), 2.48 (t, J=7.6 Hz, 2H), 1.6-1.5 (m, 4H), 1.4-1.3 (m, 6H).

N-(9-Acridinyl)-4-(7-hydroxyheptyl)-aniline (531). To a solution of 636.9 mg (3.07 mmol) of 4-(7-hydroxyheptyl)-aniline 530 and 428 μL (3.07 mmol) of $Et_3N$ in 20 mL of MeOH were added 656.4 mg (3.07 mmol) of 9-chloroacridine. After stirring for 7 hr at room temperature, the solvent was evaporated. Purification by column chromatography on silica gel with 5% MeOH in $CH_2Cl_2$ gave 1.079 g (91%) of N-(9-acridinyl)-4-(7-hydroxyheptyl)-aniline 531: $^1$H NMR (300 MHz, $CDCl_3$, TMS) δ 8.0-7.9 (m, 4H), 7.63 (t, J=7 Hz, 2H), 7.3-7.2 (m, 2H), 7.07 (d, J=8.3 Hz, 2H), 6.85 (d, J=8.3 Hz, 2H), 3.64 (t, J=6.6 Hz, 2H), 2.57 (t, J=7.6 Hz, 2H), 1.7-1.5 (m, 4H), 1.4-1.3 (m, 6H).

N-(9-acridinyl)-4-(7-iodoheptyl)-aniline (532). To a solution of 604.1 mg (1.57 mmol) of N-(9-acridinyl)-4-(7-hydroxyheptyl)-aniline 531 in 20 mL of pyridine cooled to 0° C. was added 200 μL (2.58 mmol) of methanesulfonyl chloride. The reaction mixture was stirred at 0° C. for 1 hr 20 min, then partitioned between 180 mL of $CH_2Cl_2$ and 75 mL of water. The aqueous phase was extracted with $CH_2Cl_2$ (3×30 mL). The $CH_2Cl_2$ extracts were combined, washed with 40 mL of saturated NaCl solution, dried with $MgSO_4$, and evaporated to dryness.

The sulfonate was dissolved in 20 mL of acetone. To the solution was added 355.0 mg (2.37 mmol) of NaI, and the mixture was refluxed for 8 hr, then stirred at room temperature for 16 hr. The reaction mixture was partitioned between 200 mL of ethyl acetate and 100 mL of water. The organic phase was washed with 5% sodium thiosulfate (3×30 mL). All aqueous phases were combined and backextracted with 75 mL of ethyl acetate. Both ethyl acetate phases were combined, dried with $MgSO_4$, and evaporated to dryness, to afford 600.2 mg (77%) of N-(9-acridinyl)-4-(7-iodoheptyl)-aniline 532: $^1$H NMR (300 MHz, $CDCl_3$, TMS) δ 8.0-7.9 (m, 4H), 7.66 (t, J=7 Hz, 2H), 7.3-7.2 (m, 2H), 7.06 (d, J=8 Hz, 2H), 6.81 (d, J=8 Hz, 2H), 3.18 (t, J=7 Hz, 2H), 2.57 (t, J=7.6 Hz, 2H), 1.9-1.8 (m, 2H), 1.7-1.7 (m, 2H), 1.4-1.3 (m, 6H).

Quinone-anilinoacridine (533) (SL-11064). To a solution of 1.554 g (3.14 mmol) of N-(9-acridinyl)-4-(7-iodoheptyl)-aniline 532 in a mixture of 40 mL of $CHCl_3$ and 2 mL of MeOH was added 1.765 g (6.28 mmol) of silver salt. The reaction mixture was refluxed for 23 hr. The reaction mixture was diluted with $CH_2Cl_2$, filtered, and evaporated to dryness. Purification and separation of the para- and ortho-quinone isomers were accomplished using a series of columns on silica gel using 5% MeOH in $CH_2Cl_2$, $Et_2O$, and 10% MeOH in $CH_2Cl_2$. Isolated 108.9 mg of 533 as a dark orange solid.

N-Acetyl-4-(7-methanesulfonyl-1-heptenyl)-aniline. To a cooled solution of 500 mg (2.02 mmol) of N-acetyl-4-(7-hydroxy-1-heptenyl)-aniline 529 and 0.5 mL (6.18 mmol) of pyridine in 10 mL of $CH_2Cl_2$ was added 240 μL (3.10 mmol) of methane-sulfonyl chloride. The reaction mixture was stirred at room temperature for 22 hr. The reaction mixture was diluted with $CH_2Cl_2$, washed with 1N HCl (4×50 mL), washed with saturated NaCl solution (50 mL), dried with $MgSO_4$, and evaporated to dryness. Column chromatography on silica gel with 5% MeOH in $CH_2Cl_2$ afforded 416.1 mg (63%) of mesylate (mixture of E and Z isomers): $^1H$ NMR (250 MHz, $CDCl_3$, TMS) δ 7.47 (d, J=8 Hz), 7.43 (d, J=8 Hz), 7.29 (d, J=8 Hz), 7.22 (d, J=8 Hz), 6.4-6.3 (m), 6.2-6.0 (m), 5.7-5.6 (m), 4.23 (t, J=6.6 Hz), 4.22 (t, J=6.6 Hz), 2.4-2.3 (m), 2.3-2.1 (m), 2.18 (s), 2.17 (s), 1.9-1.7 (m), 1.6-1.4 (m).

N-Acetyl-4-(7-iodo-1-heptenyl)-aniline (534). To a solution of 2.641 g (8.11 mmol) of N-acetyl-4-(7-methanesulfonyl-1-heptenyl)-aniline in 60 mL of acetone was added 1.832 g (12.2 mmol) of NaI. The reaction mixture was refluxed for 19 hr. Then, filtration and evaporation of solvent gave 3.410 g (quant) of iodide 534, which was used as is in the next reaction.

Phosphonium iodide (535). A solution of 3.410 g of N-acetyl-4-(7-iodo-1-heptenyl)-aniline 534 and 2.143 g (8.17 mmol) of triphenylphosphine in 70 mL of $CH_3CN$ was refluxed for 43 hr. Evaporation of solvent and column chromatography on silica gel with 5% MeOH in $CH_2Cl_2$ yielded 4.781 g (95% from mesylate) of phosphonium iodide.

1-(3,4-Dimethoxy-1-naphthyl)-8-(4-acetamidophenyl)-1,7-octadiene (536). To a cooled solution of 3.17 g (5.12 mmol) of phosphonium iodide 535 and 1.093 g (5.05 mmol) of 3,4-dimethoxy-1-naphthaldehyde 518 in 20 mL of THF and 25 mL of $CH_2Cl_2$ was added 130 mg (5.14 mmol) of 95% NaH. The reaction mixture was stirred at room temperature for 21 hr. The mixture was partitioned between 200 mL 1N HCl and 350 mL $CH_2Cl_2$. The aqueous phase was extracted with $CH_2Cl_2$ (6×75 mL). The $CH_2Cl_2$ extracts were combined, dried with $MgSO_4$, and evaporated to dryness. Column chromatography on silica gel with 1% MeOH in $CH_2Cl_2$ afforded 1.073 g (49%) of diene 536.

1-(3,4-Dimethoxy-1-naphthyl)-8-(4-acetamidophenyl)-octane. To a solution of 556.3 mg (1.29 mmol) of 1-(3,4-dimethoxy-1-naphthyl)-8-(4-acetamidophenyl)-1,7-octadiene 536 in 20 mL of $CH_2Cl_2$ in a Parr bottle were added 55.4 mg of 10% Pd/C. The bottle was placed on a hydrogenation apparatus and shaken for 2.5 hr at 32 psi of hydrogen. Removal of catalyst by filtration through a celite pad and evaporation of solvent afforded 554.6 mg (99%) of octane: $^1H$ NMR (250 MHz, $CDCl_3$, TMS) δ 8.14 (d, J=8 Hz, 1H), 7.94 (d, J=8 Hz, 1H), 7.5-7.4 (m, 1H), 7.4-7.3 (m, 3H), 7.12 (s 1H), 7.11 (d, J=8.2 Hz, 2H), 3.99 (s, 3H), 3.98 (s, 3H), 3.0-2.9 (m, 2H), 2.6-2.5 (m, 2H), 2.16 (s, 3H), 1.8-1.3 (m 12H).

1-(3,4-Dimethoxy-1-naphthyl)-8-(4-aminophenyl)-octane (537). A solution of 554.6 mg (1.28 mmol) of 1-(3,4-dimethoxy-1-naphthyl)-8-(4-acetamidophenyl)-octane in 20 mL of MeOH was mixed with 21 mL of 2N HCl. The reaction mixture was refluxed for 23 hr. Then the reaction mixture was partitioned between 75 mL of $CH_2Cl_2$ and 21 mL of 2N NaOH. The aqueous phase was extracted with $CH_2Cl_2$ (5×40 mL). The $CH_2Cl_2$ extracts were combined, dried with $MgSO_4$, and evaporated to dryness. Column chromatography on silica gel with 1% MeOH in $CH_2Cl_2$ gave 374.6 mg (75%) of aniline 537: $^1H$ NMR (250 MHz, $CDCl_3$, TMS) δ 8.14 (d, J=8 Hz, 1H), 7.94 (d, J=8 Hz, 1H), 7.47 (t, J=8 Hz, 1H), 7.37 (t, J=8 Hz, 1H), 7.12 (s, 1H), 6.96 (d, J=8 Hz, 2H), 6.62 (d, J=8 Hz, 2H), 3.99 (s, 3H), 3.97 (s, 3H), 3.1-3.0 (m, 2H), 2.5-2.4 (m, 2H), 1.8-1.3 (m 12H).

Naphthylacridine (538). To a solution of 99 mg (2.53× $10^{-4}$ mol) of 1-(3,4-dimethoxy-1-naphthyl)-8-(4-aminophenyl)-octane 537 and 35 mL (2.51×$10^{-4}$ mol) of $Et_3N$ in 4 mL of MeOH were added 54 mg (2.53×$10^{-4}$ mol) of 9-chloro-acridine. The reaction mixture was stirred at room temperature for 20 hr. Evaporation of solvent and column chromatography on silica gel with first 1% MeOH in $CH_2Cl_2$ and then 3% MeOH in $CH_2Cl_2$ afforded 118.2 mg (82%) of acridine 538: $^1H$ NMR (250 MHz, $CDCl_3$, TMS) δ 8.14 (d, J=8 Hz, 1H), 8.0-7.9 (m, 5H), 7.66 (br t, 2H), 7.46 (t, J=8 Hz, 1H), 7.37 (t, J=8 Hz, 1H), 7.3-7.2 (m, 2H), 7.12 (s, 1H), 7.06 (d, J=8.4 Hz, 2H), 6.82 (d, J=8.4 Hz, 2H), 3.1-3.0 (m, 2H), 2.6-2.5 (m, 2H), 1.8-1.3 (m, 12H).

Quinone-acridine (539) (SL-11125). To a solution of 546 mg (9.60×$10^{-4}$ mol) of acridine 538 in 15 mL of $CH_2Cl_2$ cooled to −68° C. was added 9.6 mL of 1M $BBr_3$ in $CH_2Cl_2$. After 18.5 hr at −10° C., the reaction mixture was cooled to −68° C. and 10 mL of $Et_2O$ were added. After stirring at room temperature for 30 min, 20 mL of saturated $NaHCO_3$ solution were added. The resulting precipitate was collected by filtration and triturated twice with 50 mL of $CH_2Cl_2$ to give 555.9 mg of quinone 539: $^1H$ NMR (250 MHz, DMSO-$d_6$, TMS) δ 9.11 (s), 8.59 (s), 8.14 (d, J=9 Hz), 8.0-7.9 (m), 7.82 (d, J=8 Hz), 7.4-7.2 (m), 6.98 (s), 2.87 (t, J=7 Hz), 2.65 (t, J=7 Hz), 1.7-1.5 (m), 1.4-1.3 (m).

N-(9-acridyl)-mesitylenesulfonamide (541). To a suspension of 4.00 g (20.6 mmol) of 9-aminoacridine 540 in 350 mL of $CHCl_3$ was added 2.9 mL (20.8 mmol) of $Et_3N$ and 4.50 g (20.6 mmol) of mesitylenesulfonyl chloride. The reaction mixture was refluxed for 72 hr. Then the reaction mixture was filtered and the solvent was evaporated. The material was purified by column chromatography on silica gel by eluting first with 1% MeOH in $CH_2Cl_2$ and then with 5% MeOH in $CH_2Cl_2$ to yield 458.4 mg (6%) of sulfonamide 541 as an orange solid: $^1H$ NMR (300 MHz, $CDCl_3$, TMS) δ 9.25 (s, 1H), 8.77 (d, J=8 Hz, 2H), 7.46 (t, J=8 Hz, 2H), 7.21 (d, J=8 Hz, 2H), 7.15 (t, J=8 Hz, 2H), 7.02 (s, 2H), 2.78 (s, 6H), 2.36 (s, 3H).

N-(9-acridyl)-N-(5-bromopentyl)-mesitylenesulfonamide (542). A solution of 450 mg (1.20 mmol) of N-(9-acridyl)-mesitylenesulfonamide in 20 mL of DMF was placed under an atmosphere of argon and cooled to 0° C. To the cooled solution was added 36 mg (1.42 mmol) of NaH (95%). The reaction mixture was stirred at 0° C for 5 min and at room temperature for 1 hr. Then the reaction mixture was cooled to 0° C., and 1.65 mL (12.1 mmol) of 1,5-dibromopentane were added. The reaction mixture was stirred at 70-80° C. for 23 hr. The reaction mixture was cooled, and quenched with 20 mL of water. The mixture was partitioned between $CH_2Cl_2$ and water. The aqueous phase was washed with $CH_2Cl_2$ (2×20 mL). The $CH_2Cl_2$ washes were combined with the organic phase, dried with $MgSO_4$, and evaporated to dryness. The material was purified by column chromatography on silica gel with $CH_2Cl_2$ to afford 382.2 mg (60%) of bromide 542 as an orange oil: $^1H$ NMR (300 MHz, $CDCl_3$, TMS) δ 8.25 (d, J=9 Hz, 2H), 7.94 (d, J=9 Hz, 2H), 7.76 (t, J=8 Hz, 2H), 7.45 (t, J=8 Hz, 2H), 6.87 (s, 2H), 4.0-3.9 (m, 2H), 3.27 (t, J=6.5 Hz, 2H), 2.30 (s, 3H), 2.22 (s, 6H), 1.8-1.6 (m, 4H), 1.4-1.3 (m, 2H).

Mesityl-acridine-quinone (543). To a solution of 632.6 mg (1.20 mmol) of N-(9-acridyl)-N-(5-bromopentyl)-mesitylenesulfonamide 542 in 15 mL of benzene was added 338.4 mg (1.20 mmol) of silver salt. The reaction mixture was refluxed for 24 hr. The reaction mixture was diluted with $CH_2Cl_2$ and filtered to remove insoluble salts. The solvent was removed and the material was purified by column chromatography on silica gel with $Et_2O$ to afford 333.1 mg (45%) of ortho-quinone 543 as an orange glassy solid: $^1H$ NMR (300 MHz, $CDCl_3$, TMS) δ 8.24 (d, J=9 Hz, 2H), 8.11

(d, J=8 Hz, 1H), 7.95 (d, J=9 Hz, 2H), 7.8-7.7 (m, 3H), 7.7-7.5 (m, 2H), 7.5-7.4 (m, 2H), 6.86 (s, 2H), 5.85 (s, 1H), 4.1-4.0 (m, 4H), 2.29 (s, 3H), 2.21 (s, 6H), 1.9-1.5 (m, 4H), 1.5-1.4 (m, 2H).

Acridine-quinone (544) (SL-11059). Under an atmosphere of argon, 151.4 mg ($2.45 \times 10^{-4}$ mol) of mesityl-acridine-quinone 543 was dissolved in 30 mL of 0.1M $SmI_2$ in THF. Then, 2.2 mL (18.2 mmol) of DMPU were added dropwise. The reaction mixture was refluxed for 24 hr. Filtration to remove a precipitate and evaporation of solvent yielded an orange oil, which was purified by column chromatography on silica gel with 5% MeOH in $CH_2Cl_2$ to afford 48.7 mg (45%) of acridine-quinone 544 as an orange glassy solid: $^1$H NMR (300 MHz, DMSO-$d_6$, TMS) δ 8.54 (d, J=8 Hz, 2H), 7.96 (t, J=7 Hz, 2H), 7.92 (d, J=7 Hz, 1H), 7.79 (d, J=8 Hz, 2H), 7.7-7.6 (m, 3H), 7.51 (t, J=8 Hz, 2H), 6.01 (s, 1H), 4.20 (t, J=6 Hz, 2H), 4.13 (t, J=7 Hz, 2H), 2.1-1.9 (m, 4H), 1.7-1.6 (m, 2H).

Synthesis of Quinol Phosphates: General Procedure

To a solution of 500 mg (2.05 mmol) of 4-pentyloxy-1,2-naphthoquinone 546 in 10 mL of benzene was added 2.3 mL (25.1 mmol) of dibenzylphosphite. The reaction mixture was refluxed under nitrogen for 2.5 hr, after which the benzene was removed. Column chromatography of the residue on silica gel with 1% MeOH in $CH_2Cl_2$ afforded 729.3 mg (70%) of aryldibenzylphosphate 547 (mixture of two regioisomers) as an orange oil: $R_f$=0.51, 0.66 (1% MeOH in $CH_2Cl_2$); $^1$H NMR (250 MHz, $CDCl_3$, TMS) major regioisomer δ 8.1 (d), 8.0 (br, s), 7.8 (d), 7.4 (t), 7.3-7.1 (m), 6.50 (s), 5.3-5.0 (AB of ABX, $δ_A$=5.16, $δ_B$=5.08, $J_{AB}$=11.5 Hz, $J_{AX}$=8.3 Hz, $J_{BX}$=8.8 Hz), 4.01 (t, J=6 Hz), 2.0-1.8 (m), 1.6-1.3 (m), 0.96 (t, J=7 Hz); $^{13}$C NMR (52 MHz, $CDCl_3$, TMS) both regioisomers δ 153.4, 144.7, 135.6 (d, J=6.1 Hz, minor regioisomer), 134.8 (d, J=5.5 Hz, major regioisomer), 128.7-127.7 (m), 127.2, 123.0, 122.2, 121.4, 119.8, 99.5, 71.0 (q, J=4.8 Hz), 68.3, 28.8, 22.5.

To a solution of 1.637 g (3.23 mmol) of aryldibenzylphosphate 547 in 40 mL of MeOH was added 150 mg of 10% Pd/C. The reaction mixture was placed under an atmosphere of hydrogen (balloon) and stirred at room temperature for 1 hr. Removal of catalyst by filtration and evaporation of solvent afforded phosphate as a brown oil. The phosphate was dissolved in 6 mL of benzene. Addition of 9 mL of hexane and cooling gave a precipitate. The precipitate was collected by filtration, washed with benzene/hexane=2:3, and dried, affording 797.3 mg (76%) of arylphosphate 548 as a gray solid; $R_f$=0.77 (MeOH); $^1$H NMR (250 MHz, acetone-$d_6$, TMS) δ 8.13 (d, J=8 Hz, 1H), 7.96 (d, J=8 Hz, 1H), 7.49 (t, J=7 Hz, 1H), 7.32 (t, J=7 Hz, 1H), 6.59 (s, 1H), 4.13 (t, J=6 Hz, 1H), 2.0-1.8 (m, 2H), 1.6-1.3 (m, 4H), 0.96 (t, J=7 Hz, 3H); $^{13}$C NMR (52 MHz, acetone-$d_6$, TMS) δ 153.3 (d, J=1.3 Hz), 145.8 (narrow t), 129.3 (d, J=3.3 Hz), 127.4, 123.2, 122.2, 121.6, 120.9, 100.0, 68.7, 29.2, 28.7, 22.7, 13.9.

Ethyl 2'-acetyl-5'-methoxyphenylacetate (550) Acetyl chloride (21.3 mL, 300 mmol) was added to a mixture of $AlCl_3$ (26.7 g, 200 mmol) and ethyl 3'-methoxyphenylacetate (549, 28.66 g, 147.6 mmol) in $CS_2$ (200 mL) at 0° C. The ice bath was removed and the mixture was allowed to warm to 20° C. with HCl gas bubbling out. After stirring at 20° C. for 30 min, the mixture was refluxed for 30 min. Upon cooling down, the mixture was added ice (200 g) and aqueous 2 N HCl (400 mL). The resulting mixture was extracted with ethyl acetate (2×200 mL). The extracts were washed with water (2×100 mL), dried over $MgSO_4$ and concentrated in vacuo. The residue was crystallized from a mixture of ethyl acetate (20 mL) and hexanes (60 mL) to afford 550 (30.60 g, 88%): $^1$H NMR ($CDCl_3$) δ 7.84 (1H, d, J=8.6 Hz), 6.86 (1H, dd, J=8.6, 2.6 Hz), 6.75 (1H, d, J=2.6 Hz), 4.17 (2H, q, J=7.1 Hz), 3.92 (2H, s), 3.86 (3H, s), 2.55 (3H, s), 1.28 (3H, t, J=7.1 Hz); $^{13}$C NMR ($CDCl_3$) δ 199.04 (s), 171.44 (s), 162.22 (s), 137.70 (s), 132.97 (d), 129.48 (s), 118.68 (d), 111.84(d), 60.60(t), 55.39 (q), 41.17 (t), 28.39 (q), 14.24 (q).

2-Hydroxy-7-methoxy-1,4-naphthoquinone(551).

Sodium ethoxide (10.40 g, 150 mmol) was added to a suspension of 550 (30.45 g, 128.90 mmol) in absolute alcohol (200 mL) at 20° C. After stirring the mixture for 1 h, air was bubbled in for 20 h. The mixture was concentrated in vacuo. The residue was dissolved in water (500 mL), and extracted with diethyl ether (200 mL). The ether layer was counter-extracted with water (50 mL). The combined aqueous phase was acidified with concentrated HCl (30 mL). The mixture was filtered to afford 551 (14.42 g, 55%): $^1$H NMR (DMSO-d6) δ 11.56 (1H, s, br), 7.89 (1H, d, J=8.5 Hz), 7.42 (1H, d, J=2.8 Hz), 7.36 (1H, dd, J=8.5, 2.8 Hz), 6.10 (1H, s), 3.92 (3H, s); $^{13}$C NMR (DMSO-d6) δ.184.07 (s), 181.20 (s), 162.92 (s), 159.16 (s), 132.35 (s), 127.82 (d), 125.16(s), 120.02 (d), 110.85 (s), 109.94(d), 55.90 (q).

7-Methoxy-lapachol (552). A mixture of $K_2CO_3$ (30 mmol) and 551 (10.21 g, 50 mmol) in HMPA (100 mL) was stirred for 30 min, when it became a suspension. Dimethylallyl bromide (8.7 mL, 75 mmol) and KI (4.15 g, 25 mmol) were added, and stirring was continued for 20 h at 20° C. The mixture was diluted with ice water (600 mL) and concentrated HCl (30 mL), and extracted with ethyl acetate (2×200 mL). Some solid was collected by filtration to afford the first portion of 553 (0.628 g): $^1$H NMR ($CDCl_3$) δ 8.01 (1H, d, J=8.6 Hz), 7.56 (1H, d, J=2.7 Hz), 7.20 (1H, dd, J=8.6, 2.7 Hz), 6.09 (1H, s), 5.49 (1H, t, J=6.8 Hz), 4.57 (2H, d, J=6.8 Hz), 3.94 (3H), s), 1.81 (3H, s), 1.76 (3H, S). The ethyl acetate extracts were pooled, extracted with saturated $NaHCO_3$ (2×150 mL), and the resultant aqueous extracts were acidified with concentrated HCl and filtered to recover 551 (2.10 g, 21%).

The main ethyl acetate extract was concentrated in vacuo. The residue was dissolved in a mixture of 1 N NaOH (500 mL) and diethyl ether (300 mL). After separation, the organic layer was extracted with 1 N NaOH (100 mL) and concentrated in vacuo. The residue was chromatographed on silica gel (10% ethyl acetate in hexanes) to afford a second portion of 553 (3.43 g, 30% total).

The NaOH extracts were acidified by concentrated HCl (50 mL), and extracted with ethyl acetate (2×200 mL). The pooled extracts were dried ($MgSO_4$), concentrated in vacuo, and the residue was purified by chromatography on silica gel (10% ethyl acetate in hexanes) to afford 552 (4.39 g, 32%): $^1$H NMR ($CDCl_3$) δ 8.05 (1H, d, J=8.6 Hz), 7.51 (1H, d, J=2.7 Hz), 7.20 (1H, dd, J=8.6, 2.7 Hz), 7.18 (OH, s), 5.20 (1H, tt, J=6.7, 1.5 Hz), 3.93 (3H, s), 3.29 (2H, d, J=7.2 Hz), 1.79 (3H, s), 1.68 (3H, s); $^{13}$C NMR ($CDCl_3$) δ 183.99 (s), 181.85 (s), 163.28 (s), 152.51 (s), 133.71 (s), 131.18 (s), 129.04 (d), 126.23 (d), 123.28 (s), 120.69 (d), 119.82 (d), 109.82 (d), 55.89 (q), 25.77 (q), 22.60 (t), 17.90 (q).

8-Methoxy-β-lapachone (554) Concentrated $H_2SO_4$ (25 mL) was added to compound 552 (2.454 g) at 20° C. After stirring for 20 min, the mixture was diluted with ice water (500 mL). The resulting red precipitate 554 was collected by filtration, washed with water, and dried in vacuo. It was obtained as a red powder (2.36 g, 96%): $^1$H NMR ($CDCl_3$) δ 7.72 (1H, d, J=8.6 Hz), 7.56 (1H, d, J=2.7 Hz), 7.12 (1H, dd, J=8.6, 2.7 Hz), 3.90 (3H, S), 2.55 (2H, t, J=6.7 Hz), 1.84 (2H, t, J=6.7 Hz), 1.46 (6H, S).

8-Hydroxy-β-lapachone (555) Boron tribromide (15.0 mL, 1.0 M in CH$_2$Cl$_2$) was added to a solution of 554 (1.05 g, mmol) in anhydrous CH$_2$Cl$_2$ (40 mL) at 0° C. After stirring for 15 min, the mixture was allowed to warm to 20° C. and kept stirring for 2 h. Ice water (500 mL) was added, the mixture was extracted with CHCl$_3$ (3×100 mL), the combined extracts were dried, and concentrated in vacuo. The residue was treated with concentrated H$_2$SO$_4$ (20 mL) at 20° C. The mixture was diluted with ice water (500 mL) and extracted with CHCl$_3$ (3×100 mL). The combined extracts were reextracted with aqueous 5% NaHSO$_3$ (3×150 mL). The aqueous extracts were acidified with concentrated HCl (100 mL), and extracted with CHCl$_3$ (3×150 mL). The extracts were dried and concentrated to afford 555 (270 mg, 27%): $^1$H NMR (CDCl$_3$) δ 9.81 (OH, s), 7.64 (1H, d, J=8.5 Hz), 7.49 (1H, d, J=2.6 Hz), 7.06 (1H, dd, J=8.5, 2.6 Hz), 2.51 (2H, t, J=6.6 Hz), 1.84 (2H, t, J=6.6 Hz), 1.45 (6H, s); HRMS (m/z) calcd for C$_{15}$H$_{14}$O$_4$ 258.0892, found 258.0885.

Preparation of 1,2-Naphthoquinone bisulfite adducts

General Procedure I. The quinone was dissolved in 10% NaHSO$_3$. After standing for several hours at room temperature or with cooling, the quinone-bisulfite adduct precipitated. The quinone-bisulfite was collected by filtration and dried. The quinone-bisulfite was stablized with addition of 300% its weight of sodium bisulfite.

General Procedure II. The quinone is dissolved in 10% NaHSO$_3$ in a volume of solution such that there is no more than 300% weight excess of NaHSO$_3$ (relative to quinone-bisulfite). When the quinone-bisulfite did not precipitate, it was recovered from the solution by evaporation of the water in vacuo. This procedure gives a quinone-bisulfite adduct with a 300% weight excess NaHSO$_3$.

Synthesis of morpholino-Ser-Lys-Leu-Gln-β-Ala-β-Lapachone (SEQ ID NO:8) (Scheme 513) Boc-Gln-β-Ala-β-Lapachone To a solution of 1.000 g (2.437 mmol) of β-Ala-β-Lapachone-TFA salt (SL-11006) and 600.3 mg (2.437 mmol) of Boc-Gln in 10 mL of DMF was added 395.3 mg (2.925 mmol) of 1-hydroxybenzotriazole. The mixture was cooled in an ice bath. Then 270 μL (2.456 mmol) of N-methylmorpholine were added, followed by 553.0 mg (2.680 mmol) of DCC. The reaction mixture was stirred in the ice bath for 30 min and at room temperature for 6.5 hr. The reaction mixture was then diluted with CH$_2$Cl$_2$ and filtered. The filtrate was washed with saturated NaHCO$_3$ (50 mL), with 5% citric acid (3×50 mL), with saturated NaHCO$_3$ (2×50 mL), with saturated NaCl (50 mL), dried with MgSO$_4$, and evaporated to dryness. Purification by column chromatography on silica gel with 5% MeOH in CH$_2$Cl$_2$ afforded 692.7 mg (51%) of peptide as an orange glassy solid: R$_f$=0.11 (5% MeOH in CH$_2$Cl$_2$); $^1$H NMR (250 MHz, acetone-d$_6$, TMS) δ 8.00 (dd, J=7.6, 1.3 Hz, 1H), 7.9-7.7 (m, 2H), 7.64 (td, J=7.6, 1.3 Hz, 1H), 7.5-7.4 (br d, NH), 6.9 (br s, NH), 6.2 (br s, NH), 5.2-5.1 (m, 1H), 4.1-4.0 (m, 1H), 3.5-3.4 (m, 2H), 2.7-2.5, (m, 4H), 2.3-2.2 (m, 2H), 2.0-1.8 (m, 2H), 1.53 (s, 3H), 1.51 (s, 3H), 1.39 (s, 9H); $^{13}$C NMR (52 MHz, acetone-d$_6$, TMS) δ 179.8, 178.8, 175.0, 172.5, 171.6, 160.8, 156.2, 111.1, 135.6, 133.0, 131.6, 131.2, 128.7, 124.8, 80.8, 80.3, 79.2, 70.2, 54.8, 35.6, 34.7, 32.1, 28.4, 24.8, 23.2, 23.1.

Gln-β-Ala-β-Lapachone

To a solution of 681.9 mg (1.223 mmol) of Boc-Gln-β-Ala-β-Lapachone in 10 mL of CH$_2$Cl$_2$ was added 10 mL of TFA. The reaction mixture was stirred at room temperature for 25-30 min. The solvent was removed in vacuo. Column chromatography on silica gel with 10-20% MeOH in CH$_2$Cl$_2$ afforded 578.5 mg (83%) of the TFA salt as an orange glassy solid: R$_f$=0.55 (BuOH/H$_2$O/AcOH=5:3:2), 0.05 (10% MeOH in CH$_2$Cl$_2$), 0.24 (5% MeOH in CH$_2$Cl$_2$).

Boc-Leu-Gln-β-Ala-β-Lapachone

To a solution of 650.2 mg (1.138 mmol) of Gln-β-Ala-β-Lapachone-TFA salt and 263.0 mg (1.138 mmol) of Boc-Leu in 4.6 mL of DMF was added 184.5 mg (1.365 mmol) of 1-hydroxybenzotriazole. The mixture was cooled in an ice bath. Then 130 μL (1.182 mmol) of N-methylmorpholine were added, followed by 258.4 mg (1.252 mmol) of DCC. The reaction mixture was stirred in the ice bath for 30 min and at room temperature for 6.5 hr. The reaction mixture was then diluted with CH$_2$Cl$_2$ and filtered. The filtrate was washed with saturated NaHCO$_3$ (30 mL), with 5% citric acid (4×30 mL), with saturated NaHCO$_3$ (3×30 mL), with saturated NaCl (30 mL), dried with MgSO$_4$, and evaporated to dryness. Purification by column chromatography on silica gel with 5% MeOH in CH$_2$Cl$_2$ afforded 396.9 mg (51%) of peptide as a yellow-orange glassy solid: R$_f$=0.11 (5% MeOH in CH$_2$Cl$_2$), 0.45 (10% MeOH in CH$_2$Cl$_2$), 0.81 (20% MeOH in CH$_2$Cl$_2$), 0.78 (BuOH/H$_2$O/AcOH=5:3:2); $^1$H NMR (250 MHz, acetone-d$_6$, TMS) δ 8.00 (d, J=7.5 Hz, 1H), 7.9-7.7 (m, 2H), 7.64 (t, J=7.5 Hz, 1H), 7.5 (br d, NH), 6.9 (br s, NH), 6.3 (br s, NH), 5.2-5.1 (m, 1H), 4.4-4.2 (m, 1H), 4.1-4.0 (m, 1H), 3.6-3.3 (m, 2H), 2.7-2.5 (m, 4H), 2.3-2.2 (m, 2H), 2.0-1.8 (m, 2H), 1.8-1.7 (m, 1H), 1.6-1.5 (m, 2H), 1.53 (s, 3H), 1.51 (s, 3H), 1.39 (s, 9H), 1.0-0.9 (m, 6H); $^{13}$C NMR (52 MHz, acetone-d$_6$, TMS) δ 179.9, 179.0, 175.2, 173.4, 172.0, 171.5, 160.9, 156.8, 135.7, 133.1, 131.6, 131.2, 128.8, 124.9, 111.2, 80.9, 80.4, 79.5, 70.3, 54.5, 53.5, 41.7, 35.8, 34.8, 32.1, 28.5, 27.8, 25.4, 24.9, 23.4, 23.2, 21.9.

Leu-Gln-β-Ala-β-Lapachone

To a solution of 317.0 mg (4.725×10$^{-4}$ mol) of Boc-Leu-Gln-β-Ala-β-Lapachone in 4 mL of CH$_2$Cl$_2$ was added 4 mL of TFA. The reaction mixture was stirred at room temperature for 25-30 min. The solvent was removed in vacuo. Column chromatography on silica gel with 20% MeOH in CH$_2$Cl$_2$ afforded 277.3 mg (86%) of the TFA salt as an orange glassy solid: R$_f$=0.17 (10% MeOH in CH$_2$Cl$_2$), 0.39 (20% MeOH in CH$_2$Cl$_2$), 0.74 (BuOH/H$_2$O/AcOH=5:3:2).

Nα-Boc-Lys(Nε-Cbz)-Leu-Gln-β-Ala-β-Lapachone (SEQ ID NO:5)

To a solution of 277.3 mg (4.050×10$^{-4}$ mol) of Leu-Gln-β-Ala-β-Lapachone-TFA salt and 168.0 mg (4.049×10$^{-4}$ mol) of Nα-Boc-Lys(Nε-Cbz) in 1.6 mL of DMF was added 65.7 mg (4.862×10$^{-4}$ mol) of 1-hydroxybenzotriazole. The mixture was cooled in an ice bath. Then 50 μL (4.548×10$^{-4}$ mol) of N-methylmorpholine were added, followed by 91.9 mg (4.454×10$^{-4}$ mol) of DCC. The reaction mixture was stirred in the ice bath for 30 min and at room temperature for 6.5 hr. The reaction mixture was then diluted with 2 mL of CHCl$_3$ and filtered. The filtrate was washed with saturated NaHCO$_3$ (20 mL), with 5% citric acid (4×20 mL), with saturated NaHCO$_3$ (3×20 mL), with saturated NaCl (2×20 mL), dried with MgSO$_4$, and evaporated to dryness. Purification by column chromatography on silica gel with 10% MeOH in CH$_2$Cl$_2$ afforded 167.5 mg (42%) of peptide as an orange glassy solid: R$_f$=0.08 (5% MeOH in CH$_2$Cl$_2$), 0.44 (10% MeOH in CH$_2$Cl$_2$); $^1$H NMR (250 MHz, DMSO-d$_6$, TMS) δ 8.0-7.7 (m, 6H, quinone-H5, H6, H7, H8, & NH's), 7.7-7.6 (m, NH), 7.5-7.4 (m, 2H, Cl-Cbz), 7.4-7.3 (m, 2H, Cl-Cbz), 7.20 (br s, NH), 6.73 (br s, NH), 6.90 (br d, J=7.9 Hz, NH), 5.07 (s, 3H), 4.3-4.2 (m, 1H), 4.2-4.1 (m, 1H), 3.9-3.8 (m, 1H), 3.3-3.2 (m, 2H), 3.0-2.9 (m, 2H), 2.8-2.7 (m, 2H), 2.6-2.4 (m, 2H), 2.1-2.0 (m, 2H), 1.8-1.3 (m, 11H), 1.43 (s, 3H), 1.39 (s, 3H), 0.85 (d, J=6.5 Hz, 3H), 0.81 (d, J=6.6 Hz, 3H); $^{13}$C NMR (52 MHz, DMSO-d$_6$, TMS) δ 178.6, 177.8, 173.5, 173.4, 172.0, 171.7, 171.0, 170.5, 162.2, 155.7, 134.9, 134.5, 132.2, 131.4, 130.9, 129.9, 129.5, 129.2, 127.9, 127.2, 123.7, 79.7, 79.3, 78.0, 68.9, 62.4, 54.2, 52.0, 50.8, 40.7, 35.7, 33.5, 31.2, 30.7, 29.0, 28.1, 27.8, 24.1, 23.9, 23.0, 22.8, 22.7, 22.1, 21.4.

Lys(Nε-Cbz)-Leu-Gln-β-Ala-β-Lapachone (SEQ ID NO:6)

To a suspension of 203.1 mg (2.099×10$^{-4}$ mol) of Boc-Lys(Nε-Cbz)-Leu-Gln-β-Ala-β-Lapachone (SEQ ID NO:5) in 2 mL of CHCl$_3$ was added 1.7 mL of TFA (material dissolved). The reaction mixture was stirred at room temperature for 20-25 min. The solvent was removed in vacuo. Column chromatography on silica gel with 20% MeOH in CH$_2$Cl$_2$ afforded 202.0 mg (98%) of the TFA salt as an orange glassy solid: R$_f$=0.10 (10% MeOH in CH$_2$Cl$_2$), 0.40 (20% MeOH in CH$_2$Cl$_2$).

Morpholino-Ser(OBn)-Lys(Nε-Cbz)-Leu-Gln-β-Ala-β-Lapachone (SEQ ID NO:7)

To a solution of 194.8 mg (1.985×10$^{-4}$ mol) of Lys(Nε-Cbz)-Leu-Gln-β-Ala-β-Lapachone-TFA (SEQ ID NO:6) salt and 61.2 mg (1.985×10$^{-4}$ mol) of morpholino-Ser(OBn) in 1.0 mL of DMF was added 32.2 mg (2.383×10$^{-4}$ mol) of 1-hydroxybenzotriazole. The mixture was cooled in an ice bath. Then 23 μL (2.092×10$^{-4}$ mol) of N-methylmorpholine were added, followed by 45.1 mg (2.186×10$^{-4}$ mol) of DCC. The reaction mixture was stirred in the ice bath for 35 min and at room temperature for 6 hr. The reaction mixture was then diluted with 2 mL of CH$_2$Cl$_2$ and filtered. The filtrate was washed with 5% citric acid (3×20 mL), with saturated NaHCO$_3$ (3×20 mL), with saturated NaCl (20 mL), dried with MgSO$_4$, and evaporated to dryness. Purification by column chromatography on silica gel with 10% MeOH in CH$_2$Cl$_2$ afforded 83.3 mg (36%) of peptide as an orange glassy solid: R$_f$=0.05 (5% MeOH in CH$_2$Cl$_2$), 0.41 (10% MeOH in CH$_2$Cl$_2$); $^1$H NMR (250 MHz, acetone-d$_6$, TMS) δ 8.0-7.7 (m, 7H, quinone-H5, H6, H7, H8, NH's), 7.7-7.6 (m, NH), 7.5-7.2 (m, 10H, Cl-Cbz, OBn, NH), 6.75 (br s, NH), 6.60 (br d, J=7.1 Hz, NH), 5.07 (s, 3H), 4.49 (s, 2H), 4.4-4.3 (m, 1H), 4.3-4.0 (m, 3H), 3.7-3.6 (m, 2H), 3.6-3.5 (m, 4H), 3.3-3.2 (m, 6H), 3.0-2.9 (m, 2H), 2.8-2.7 (m, 2H), 2.5-2.4 (m, 2H), 2.1-2.0 (m, 2H), 1.8-1.3 (m, 11H), 1.43 (s, 3H), 1.38 (s, 3H), 0.82 (d, J=6.0 Hz, 3H), 0.78 (d, J=6.1 Hz, 3H).

Morpholino-Ser-Lys-Leu-Gln-β-Ala-β-Lapachone (SEQ ID NO:8) (SL-11147)

To a solution of 78.3 mg (6.763×10$^{-5}$ mol) of morpholino-Ser(OBn)-Lys(Nε-Cbz)-Leu-Gln-β-Ala-β-Lapachone (SEQ ID NO:7) in 1.5 mL of MeOH/CH$_2$Cl$_2$=1:9 was added 30.6 mg 10% Pd/C. Then 0.5 mL of MeOH and one drop of HCl were added. The reaction mixture was placed under an atmosphere of H$_2$ (balloon) and stirred at room temperature for 16 hr. Removal of catalyst by filtration and evaporation of solvent afforded 64.5 mg of crude quinone-tetrapeptide. The material was purified by prep HPLC to yield 14.4 mg (24%): R$_f$=0.04 (20% MeOH in CH$_2$Cl$_2$).

N-Fmoc-Ser(OBn) t-butyl Ester

Isobutylene was condensed into a 500 mL pressure bottle until the volume was between 30 and 40 mL. A solution of 3.02 g (7.23 mmol) of N-Fmoc-Ser(OBn) in 20 mL of THF was added, followed by 2 mL of concentrated H$_2$SO$_4$. The bottle was securely stoppered and shaken at room temperature for 24 hr. The reaction mixture was poured into an ice-cold mixture of 150 mL of ethyl acetate and 150 mL of saturated NaHCO$_3$. The organic phase was washed with water (3×50 mL) and dried with MgSO$_4$. The solvent was removed, and column chromatography on silica gel with CH$_2$Cl$_2$ afforded 2.453 g (72%) of t-butyl ester as a colorless oil: $^1$H NMR (250 MHz, acetone-d$_6$, TMS) δ 7.85 (d, J=7.5 Hz, 2H), 7.74 (d, J=7.3 Hz, 2H), 7.5-7.3 (m, 9H), 6.71 (br d, J=8.6 Hz, NH), 4.55 (ABq, δ$_A$=4.57, δ$_B$=4.52, J$_{AB}$=12 Hz, 2H), 4.4-4.2 (m, 4H), 3.9-3.7 (AB of ABX, δ$_A$=3.89, δ$_B$=3.75, J$_{AB}$=9.5 Hz, J$_{AX}$=4.6 Hz, J$_{BX}$=3.6 Hz, 2H); $^{13}$C NMR (52 MHz, acetone-d$_6$, TMS) δ 170.0, 156.8, 145.0, 144.9, 142.0, 129.0, 128.4, 128.3, 128.2, 127.8, 126.1, 120.7, 81.9, 73.6, 70.9, 67.3, 55.9, 47.9, 28.1.

Ser(OBn) t-butyl Ester

To a solution of 3.049 g (6.44 mmol) of N-Fmoc-Ser(OBn) t-butyl ester in 50 mL of CH$_2$CL$_2$ was added 3 mL of piperidine. The reaction mixture was stirred at room temperature for 2.3 hr. Removal of solvent and column chromatography on silica gel with 5% MeOH in CH$_2$Cl$_2$ yielded 1.306 g (81%) of Ser(OBn) t-butyl ester as a colorless oil: R$_f$=0.12 (2% MeOH in CH$_2$Cl$_2$); $^1$H NMR (250 MHz, acetone-d$_6$, TMS) δ 7.4-7.2 (m, 5H), 4.53 (Abq, δ$_A$=4.55, δ$_B$=4.52, J$_{AB}$=12 Hz, 2H), 3.7-3.6 (m, AB of ABX, δ$_A$=3.68, δ$_B$=3.61, J$_{AB}$=12 Hz, J$_{AX}$=4.9 Hz, J$_{BX}$=4.4 Hz, 2H), 3.5-3.4 (m, X of ABX, δ$_X$=3.45, 1H), 1.43 (s, 9H); $^{13}$C NMR (52 MHz, acetone-d$_6$, TMS) δ 173.9, 139.5, 128.9, 128.2, 128.1, 80.7, 73.8, 73.5, 56.2, 28.1.

Morpholino-Ser(OBn) t-butyl Ester

To a solution of 140.6 mg (5.59×10$^{-4}$ mol) of Ser(OBn) t-butyl ester in 4 mL of pyridine was added 66 μL (5.66×10$^{-4}$ mol) of 4-morpholinecarbonyl chloride. After stirring for 1 hr, the reaction mixture was partitioned between 75 mL of CH$_2$Cl$_2$ and 60 mL of water. The organic phase was washed with saturated NaHCO$_3$ (50 mL), with 1N HCl (2×50 mL), with saturated NaCl (50 mL), dried with MgSO$_4$, and evaporated to dryness. The crude amide was purified by column chromatography on silica gel with ethyl acetate to yield 80.9 mg (40%) of amide as a light orange oil: R$_f$=0.58 (ethyl acetate), 0.60 (5% MeOH in CH$_2$Cl$_2$); $^1$H NMR (250 MHz, acetone-d$_6$, TMS) δ 7.4-7.2 (m, 5H), 5.8 (br d, NH), 4.53 (Abq, δ$_A$=4.55, δ$_B$=4.52, J$_{AB}$=12 Hz, 2H), 4.5-4.4 (m, X of ABX, δ$_X$=4.47, 1H), 3.9-3.6 (m, AB of ABX, δ$_A$=3.86, δ$_B$=3.69, J$_{AB}$=9.4 Hz, J$_{AX}$=4.4 Hz, J$_{BX}$=3.7 Hz, 2H), 3.63-3.58 (m, 4H), 3.4-3.3 (m, 4H), 1.44 (s, 9H); $^{13}$C NMR (52 MHz, acetone-d$_6$, TMS) δ 170.9, 157.9, 139.2, 129.0, 128.3, 128.2, 81.5, 73.5, 71.3, 67.0, 55.5, 44.9, 28.1.

Morpholino-Ser(OBn)

A solution of 80 mg (2.195×10$^{-4}$ mol) of morpholino-Ser(OBn) t-butyl ester in a mixture of 1.5 mL of CH$_2$Cl$_2$ and 1.5 mL of TFA was stirred at room temperature for 30 min. The solvent was removed in vacuo and the remaining TFA was removed by repeated evaporation with acetone. The residue was triturated with Et$_2$O. The material was then filtered, washed with Et$_2$O, washed with 0.5 mL acetone, washed again with Et$_2$O, and dried to yield 41.8 mg (62%) of amino acid as an off-white solid: R$_f$=0.72 (BuOH/H$_2$O/AcOH=5:3:2); $^1$H NMR (250 MHz, acetone-d$_6$, TMS) δ 7.4-7.3 (m, 5H), 6.0-5.9 (br d, NH), 4.6-4.5 (m, 3H, OCH$_2$Ph & X of ABX), 3.95-3.75 (m, AB of ABX, δ$_A$=3.90, δ$_B$=3.73, J$_{AB}$=9.6 Hz, J$_{AX}$=4.9 Hz, J$_{BX}$=3.9 Hz, 2H), 3.6-3.5 (m, 4H), 3.4-3.3 (m, 4H); $^{13}$C NMR (52 MHz, DMSO-d$_6$, TMS) d 172.4, 157.2, 138.2, 128.2, 127.4, 127.4, 72.0, 69.5, 65.9, 53.8, 43.9.

Synthesis of Morpholino-Ser-Lys-Leu-Gln-Leu-β-Lapachone (SEQ ID NO:12) (Scheme 514)

Boc-Leu-β-Lapachone

A solution of 2.820 g (12.20 mmol) of Boc-Leu and 1.976 g (12.19 mmol) of 1,1-carbonyldiimidazole in 33 mL of DMF was stirred at room temperature for 20 min. To the solution was added 2.100 g (8.130 mmol) of 3-hydroxy-p- lapachone followed by 1.6 mL (10.70 mmol) of DBU. After stirring at room temperature for 5 hr, the reaction mixture was partitioned between 200 mL of water and 200 mL of CHCl$_3$. The aqueous phase was washed with CHCl$_3$ (4×50 mL). The CHCl$_3$ extracts were combined, dried with MgSO$_4$, and evaporated to dryness. Column chromatography on silica gel with 2% MeOH in CH$_2$Cl$_2$ afforded 2.038 g (53%) of quinone as an orange glassy solid (and mixture of two diastereomers): R$_f$=0.45 (5% MeOH in CH$_2$Cl$_2$); $^1$H NMR (250 MHz, acetone-d$_6$, TMS) δ 8.1-8.0 (m, 1H), 8.0-7.9 (m, 1H), 7.9-7.8 (m, 1H), 7.7-7.6 (m, 1H), 6.34 (br d, NH), 5.2-5.1 (m, 1H), 4.2-4.1 (m, 1H), 2.9-2.8 (m, 1H), 2.7-2.5 (m, 1H), 1.8-1.6 (m, 3H), 1.56 (s, 1.5H), 1.53 (s, 3H), 1.52 (s, 1.5H), 1.34 (s, 4.5H), 1.33 (s, 4.5H), 0.91 (d, J=7.0 Hz, 1.5H), 0.88 (d, J=6.7 Hz, 1.5H), 0.84 (d, J=6.3 Hz, 1.5H), 0.82 (d, J=6.1 Hz, 1.5H).

Leu-β-Lapachone

To a solution of 2.017 mg (4.277 mmol) of Boc-Leu-β-Lapachone in 20 mL of CH$_2$Cl$_2$ was added 20 mL of TFA. The reaction mixture was stirred at room temperature for 30 min. The solvent was removed in vacuo. Column chromatography on silica gel with 20% MeOH in CH$_2$Cl$_2$ afforded 2.507 g (quant.) of the TFA salt as an orange glassy solid: R$_f$=0.52 (10% MeOH in CH$_2$Cl$_2$), 0.82 (20% MeOH in CH$_2$Cl$_2$); $^1$H NMR (250 MHz, DMSO-d$_6$, TMS) δ 8.6-8.5 (br s, NH), 8.0-7.9 (m, 1H), 7.9-7.8 (m, 2H), 7.7-7.6 (m, 1H), 5.3-5.2 (m, 1H), 4.1-4.0 (m, 1H), 2.8-2.5 (m, 2H), 1.8-1.5 (m, 3H), 1.52 (s, 1.5H), 1.49 (s, 1.5H), 1.43 (s, 3H), 0.83 (d, J=6.0 Hz, 3H), 0.66 (br t, 3H); $^{13}$C NMR (52 MHz, DMSO-d$_6$, TMS) δ 178.7, 177.8, 169.2, 169.1, 160.0, 159.7, 135.1, 135.1, 131.5, 131.4, 131.1, 131.0, 129.8, 129.8, 127.9, 123.9, 123.8, 109.6, 109.3, 79.4, 79.1, 71.1, 70.9, 50.6, 50.4, 39.0, 24.0, 23.9, 22.9, 22.3, 22.1, 22.0, 21.8, 21.7, 21.1.

Boc-Gln-Leu-β-Lapachone

To a solution of 2.235 g (3.895 mmol) of Leu-β-Lapachone-TFA salt and 959.1 mg (3.894 mmol) of Boc-Gln in 15.6 mL of DMF was added 631.4 mg (4.673 mmol) of 1-hydroxybenzotriazole. The mixture was cooled in an ice bath. Then 760 μL (6.912 mmol) of N-methylmorpholine were added, followed by 883.9 mg (4.284 mmol) of DCC. The reaction mixture was stirred in the ice bath for 30 min and at room temperature for 5.8 hr. The reaction mixture was then diluted with 8 mL of CH$_2$Cl$_2$ and filtered. The filtrate was washed with 5% citric acid (3×50 mL), with saturated NaHCO$_3$ (3×50 mL), with saturated NaCl (50 mL), dried with MgSO$_4$, and evaporated to dryness. Purification by column chromatography on silica gel with 5% MeOH in CH$_2$Cl$_2$ afforded 1.555 g (66%) of peptide as an orange glassy solid: R$_f$=0.19 (5% MeOH in CH$_2$Cl$_2$), 0.09 (5% MeOH in CHCl$_3$), 0.37 (10% MeOH in CHCl$_3$); $^1$H NMR (250 MHz, DMSO-d$_6$, TMS) δ 8.24 (br d, J=7 Hz, NH), 8.17 (br d, J=7 Hz, NH), 8.0-7.9 (m, 1H), 7.8-7.7 (m, 2H), 7.7-7.6 (m, 1H), 7.22 (br s, NH), 6.83 (br d, J=8 Hz, NH), 6.76 (br s, NH), 5.1-5.0 (m, 1H), 4.3-4.1 (m, 1H), 3.9-3.8 (m, 1H), 2.8-2.6 (m, 1H), 2.6-2.4 (m, 1H), 2.1-2.0 (m, 2H), 1.8-1.4 (m, 5H), 1.47 (s, 1.5H), 1.43 (s, 1.5H), 1.42 (s, 1.5H), 1.40 (s, 1.5H), 1.36 (s, 9H), 0.86 (d, J=6.3 Hz, 1.5H), 0.79 (d, J=6.2 Hz, 1.5H), 0.73 (br t, 3H); $^{13}$C NMR (52 MHz, DMSO-d$_6$, TMS) δ 178.7, 177.8, 177.7, 173.7, 172.0, 171.7, 171.5, 159.9, 159.7, 155.1, 135.1, 135.0, 131.5, 131.4, 131.0, 130.9, 129.8, 129.7, 127.9, 127.8, 123.8, 109.8, 109.6, 79.5, 79.3, 77.9, 69.6, 69.4, 53.7, 53.6, 50.5, 50.4, 31.4, 28.1, 27.6, 27.4, 24.2, 24.1, 24.0, 22.6, 22.5, 22.1, 21.9, 21.6, 21.2.

Gln-Leu-β-Lapachone

To a solution of 1.519 g (2.533 mmol) of Boc-Gln-Leu-β-Lapachone in 12 mL of CH$_2$Cl$_2$ was added 11 mL of TFA. The reaction mixture was stirred at room temperature for 30 min. The solvent was removed in vacuo. Column chromatography on silica gel with 20% MeOH in CH$_2$Cl$_2$ afforded 1.976 mg (quant) of the TFA salt as an orange glassy solid; $^1$H NMR (250 MHz, DMSO-d$_6$, TMS) δ 8.97 (br d, J=6.5 Hz, NH), 8.90 (br d, J=7.0 Hz, NH), 8.30 (br s, NH), 8.0-7.9 (m, 1H), 7.9-7.8 (m, 2H), 7.7-7.6 (m, 1H), 7.45 (br s, NH), 6.98 (br s, NH), 5.2-5.1 (m, 1H), 4.3-4.2 (m, 1H), 3.9-3.8 (m, 1H), 2.8-2.7 (m, 1H), 2.5-2.4 (m, 1H), 2.2-2.1 (m, 2H), 2.0-1.8 (m, 2H), 1.7-1.5 (m, 3H), 1.49 (s, 1.5H), 1.44 (s, 1.5H), 1.42 (s, 1.5H), 1.41 (s, 1.5H), 0.87 (d, J=6.3 Hz, 1.5H), 0.81 (d, J=6.3 Hz, 1.5H), 0.75 (d, J=5.8 Hz, 1.5H), 0.73 (d, J=5.8 Hz, 1.5H); $^{13}$C NMR (52 MHz, DMSO-d$_6$, TMS) δ 178.7, 177.8, 177.8, 173.5, 171.3, 171.1, 168.7, 168.7, 159.9, 159.8, 135.1, 131.5, 131.4, 131.1, 131.0, 129.9, 129.8, 128.0, 123.8, 109.7, 109.5, 79.5, 79.3, 69.9, 69.8, 51.7, 51.6, 50.8, 50.8, 30.3, 26.8, 24.2, 24.1, 22.7, 22.5, 22.2, 22.0, 21.9, 21.6, 21.2.

Boc-Leu-Gln-Leu-β-Lapachone

To a solution of 1.949 g (max 2.533 mmol) of Gln-Leu-β-Lapachone-TFA salt and 585.7 mg (2.533 mmol) of Boc-Leu in 10 mL of DMF was added 410.6 mg (3.038 mmol) of 1-hydroxybenzotriazole. The mixture was cooled in an ice bath. Then 685 μL (6.230 mmol) of N-methylmorpholine were added, followed by 574.7 mg (2.785 mmol) of DCC. The reaction mixture was stirred in the ice bath for 30 min and at room temperature for 5.5 hr. The reaction mixture was then diluted with CHCl$_3$ and filtered. The filtrate was washed with 5% citric acid (5×50 mL), with saturated NaHCO$_3$ (4×70 mL), with saturated NaCl (70 mL), dried with MgSO$_4$, and evaporated to dryness. Purification by column chromatography on silica gel with 5% MeOH in CHCl$_3$ afforded 1.221 g (68%, from Boc-Gln-Leu-β-Lapachone) of peptide as an orange glassy solid: R$_f$=0.09 (5% MeOH in CHCl$_3$), 0.29 (7% MeOH in CHCl$_3$); $^1$H NMR (250 MHz, DMSO-d$_6$, TMS) δ 8.36 (br d, NH), 8.30 (br d, NH), 8.0-7.9 (m, 1H), 7.9-7.7 (m, 2H), 7.7-7.6 (m, 1H), 7.19 (br s, NH), 6.90 (br s, NH), 6.75 (br d, NH), 5.1-5.0 (m, 1H), 4.3-4.1 (m, 2H), 4.0-3.9 (m, 1H), 2.8-2.7 (m, 1H), 2.5-2.4 (m, 1H), 2.1-2.0 (m, 2H), 1.8-1.4 (m, 8H), 1.47 (s, 1.5H), 1.43 (s, 1.5H), 1.41 (s, 1.5H), 1.40 (s, 1.5H), 1.37 (s, 4.5H) 1.35 (s, 4.5H), 0.9-0.8 (m, 7.5H), 0.78 (d, J=6.2 Hz, 1.5H), 0.73 (d, J=5.5 Hz, 1.5H), 0.71 (d, J=5.3 Hz, 1.5H); $^{13}$C NMR (52 MHz, DMSO-d$_6$, TMS) δ 178.7, 177.8, 177.7, 173.6, 173.6, 172.3, 171.5, 171.4, 171.3, 159.9, 159.7, 155.2, 135.0, 131.5, 131.4, 131.0, 130.9, 129.8, 129.8, 127.9, 127.9, 123.8, 109.7, 109.6, 79.5, 79.3, 78.0, 69.6, 69.5, 52.8, 51.4, 50.5, 50.5, 40.7, 31.2, 28.1, 24.2, 24.1, 22.9, 22.6, 22.5, 22.1, 22.0, 21.9, 21.6, 21.4, 21.2.

Leu-Gln-Leu-β-Lapachone

To a solution of 1.196 g (1.678 mmol) of Boc-Leu-Gln-Leu-β-Lapachone in 8 mL of CH$_2$Cl$_2$ was added 8 mL of TFA. The reaction mixture was stirred at room temperature for 30 min. The solvent was removed in vacuo. Column chromatography on silica gel with 20% MeOH in CHCl$_3$ afforded 1.430 g (quant) of the TFA salt as an orange glassy solid: R$_f$=0.04 (10% MeOH in CHCl$_3$), 0.10 (15% MeOH in CHCl$_3$), 0.19 (20% MeOH in CHCl$_3$); $^1$H NMR (250 MHz, DMSO-d$_6$, TMS) δ 8.46 (br d, J=6.6 Hz, NH), 8.41 (br d, J=7.2 Hz, NH), 8.0-7.9 (m, 1H), 7.9-7.8 (m, 2H), 7.7-7.6 (m, 1H), 7.26 (br s, NH), 6.77 (br s, NH), 5.1-5.0 (m, 1H), 4.3-4.1 (m, 2H), 3.5-3.4 (m, 1H), 2.8-2.7 (m, 1H), 2.5-2.4 (m, 1H), 2.1-2.0 (m, 2H), 1.9-1.4 (m, 8H), 1.47 (s, 1.5H), 1.43 (s, 1.5H), 1.41 (s, 1.5H), 1.40 (s, 1.5H), 0.9-0.8 (m, 7.5H), 0.78 (d, J=6.1 Hz, 1.5H), 0.74 (d, J=5.9 Hz, 1.5H), 0.72 (d, J=5.5 Hz, 1.5H); $^{13}$C NMR (52 MHz, DMSO-d$_6$, TMS) δ 178.7, 177.8, 177.8, 173.6, 171.6, 171.4, 171.2, 159.9, 159.8, 135.1, 131.5, 131.4, 131.1, 131.0, 129.9, 129.8, 127.9, 123.9, 109.8, 109.6, 79.6, 79.3, 69.6, 69.5, 51.9-51.6, 51.6, 50.5, 42.3-41.8, 31.2, 28.2, 28.0, 24.2, 24.1, 23.7, 22.8, 22.7, 22.6, 22.1, 21.9, 21.8, 21.6, 21.3, 21.2.

Nα-Boc-Lys(Nε-Cl-Cbz)-Leu-Gln-Leu-β-Lapachone (SEQ ID NO:10)

To absolution of 1.400 g (max 1.643 mmol) of Leu-Gln-Leu-β-Lapachone-TFA salt and 681.6 mg (1.643 mmol) of Nα-Boc-Lys(Nε-Cl-Cbz) in 6.6 mL of DMF was added 266.3 mg (1.971 mmol) of 1-hydroxybenzotriazole. The mixture was cooled in an ice bath. Then 380 μL (3.456 mmol) of N-methylmorpholine were added, followed by 372.9 mg (1.807 mmol) of DCC. The reaction mixture was stirred in the ice bath for 30 min and at room temperature for 5.5 hr. The reaction mixture was then diluted with CHCl$_3$ and filtered. The filtrate was washed with 5% citric acid (4×50 mL), with saturated NaHCO$_3$ (4×50 mL), with saturated NaCl (65 mL), dried with MgSO$_4$, and evaporated to dryness. Purification by column chromatography on silica gel with 5% MeOH in CHCl$_3$ afforded 897.4 mg (54%) of peptide as an orange glassy solid: R$_f$=0.10 (5% MeOH in CHCl$_3$); $^1$H NMR (250 MHz, DMSO-d$_6$, TMS) δ 8.31 (br d, J=7 Hz, NH), 8.25 (br d, J=7 Hz, NH), 8.0-7.9 (m, 2H (1 quinone-H+1 NH)), 7.8-7.7 (m, 3H (2 quinone-H+1 NH)), 7.7-7.6 (m, 1H (quinone-H)), 7.5-7.4 (m, 2H), 7.4-7.3 (m, 3H (2 Cl—Ph—H+1 NH)), 7.19 (br s, NH), 6.90 (br d, J=8 Hz, NH), 6.77 (br s, NH), 5.1-5.0 (m, 4H), 4.3-4.1 (m, 3H), 3.9-3.8 (m, 1H), 3.0-2.9 (m, 2H), 2.8-2.7 (m, 1H), 2.5-2.4 (m, 1H), 2.1-2.0 (m, 2H), 1.9-1.4 (m, 14H), 1.47 (s, 1.5H), 1.42 (s, 1.5H), 1.41 (s, 1.5H), 1.40 (s, 1.5H), 1.37 (s, 9H), 0.9-0.8 (m, 7.5H), 0.77 (d, J=6.2 Hz, 1.5H), 0.73 (d, J=5.7 Hz, 1.5H), 0.70 (d, J=5.6 Hz, 1.5H); $^{13}$C NMR (52 MHz, DMSO-d$_6$, TMS) δ 178.7, 177.8, 177.7, 173.6, 171.8, 171.6, 171.4, 171.3, 159.9, 159.7, 155.7, 155.3, 135.0, 134.5, 132.2, 131.5, 131.4, 131.0, 130.9, 129.8, 129.8, 129.5, 129.1, 127.9, 127.8, 127.2, 123.8, 109.7, 109.6, 79.5, 79.3, 78.0, 69.6, 69.5, 62.4, 54.3, 51.6, 50.7, 50.5, 50.4, 41.0, 40.1, 31.3, 29.0, 28.1, 27.9, 27.7, 24.2, 24.1, 24.0, 23.9, 23.0, 22.7, 22.6, 22.5, 22.1, 22.0, 21.9, 21.6, 21.5, 21.2.

Lys(Nε-Cl-Cbz)-Leu-Gln-Leu-β-Lapachone (SEQ ID NO:10)

To a solution of 1.196 g (1.678 mmol) of Boc-Lys(Nε-Cl-Cbz)-Leu-Gln-Leu-β-Lapachone (SEQ ID NO:9) in 6 mL of CH$_2$Cl$_2$ was added 5 mL of TFA. The reaction mixture was stirred at room temperature for 30 min. The solvent was removed in vacuo. Column chromatography on silica gel with 15% MeOH in CHCl$_3$ afforded 568.9 mg (65%) of the TFA salt as an orange glassy solid: R$_f$=0.09 (10% MeOH in CHCl$_3$), 0.23 (15% MeOH in CHCl$_3$), 0.38 (20% MeOH in CHCl$_3$); $^1$H NMR (250 MHz, DMSO-d$_6$, TMS) δ 8.28 (br d, J=7 Hz, NH), 8.23 (br d, J=7 Hz, NH), 8.1-8.0 (m, NH), 8.0-7.9 (m, 2H (1 quinone-H+1 NH)), 7.8-7.7 (m, 2H), 7.7-7.6 (m, 1H), 7.5-7.4 (m, 2H), 7.4-7.3 (m, 3H (2 Cl—Ph—H+1NH)), 7.23 (br s, NH), 6.78 (br s, NH), 5.1-5.0 (m, 4H), 4.3-4.1 (m, 4H), 3.0-2.9 (m, 2H), 2.8-2.7 (m, 1H), 2.5-2.4 (m, 1H), 2.1-2.0 (m, 2H), 1.9-1.4 (m, 14H), 1.47 (s, 1.5H), 1.42 (s, 1.5H), 1.41 (s, 1.5H), 1.39 (s, 1.5H), 0.9-0.8 (m, 7.5H), 0.77 (d, J=6.2 Hz, 1.5H), 0.73 (d, J=5.8 Hz, 1.5H), 0.71 (d, J=5.6 Hz, 1.5H); $^{13}$C NMR (52 MHz, DMSO-d$_6$, TMS) δ 178.7, 177.8, 177.7, 173.7, 171.8, 171.6, 171.4, 171.3, 159.9, 159.7, 155.7, 135.0, 134.6, 132.2, 131.5, 131.4, 131.0, 130.9, 129.9, 129.8, 129.5, 129.2, 127.9, 127.8, 127.2, 123.8, 109.7, 109.6, 79.5, 79.3, 69.6, 69.4, 62.4, 54.4, 51.7, 50.6, 50.5, 50.4, 41.1, 31.2, 29.2, 27.6, 27.5, 24.2, 24.2, 24.1, 23.0, 22.6, 22.5, 22.4, 22.0, 21.9, 21.6, 21.2.

Morpholino-Ser(OBn)-Lys(Nε-Cl-Cbz)-Leu-Gln-Leu-ε-Lapachone (SEQ ID NO:11)

To a solution of 544.9 mg (5.323×10$^{-4}$ mol) of Lys(Nε-Cl-Cbz)-Leu-Gln-Leu-β-Lapachone-(SEQ ID NO:9) TFA salt and 164.2 mg 5.325×10$^{-4}$ mol) of morpholino-Ser(OBn) in 2.15 mL of DMF was added 86.2 mg (6.379×10$^{-4}$ mol) of 1-hydroxybenzotriazole. The mixture was cooled in an ice bath. Then 59 μL (5.366×10$^{-4}$ mol) of N-methylmorpholine were added, followed by 120.7 mg (5.850×10$^{-4}$ mol) of DCC. The reaction mixture was stirred in the ice bath for 30 min and at room temperature for 5.5 hr. The reaction mixture was then diluted with CHCl$_3$ and filtered. The filtrate was washed with 5% citric acid (4×30 mL), with saturated NaHCO$_3$ (4×30 mL), with saturated NaCl (30 mL), dried with MgSO$_4$, and evaporated to dryness. Purification by column chromatography on silica gel with 7% MeOH in CHCl$_3$ afforded 515.8 mg (81%) of peptide as an orange glassy solid: R$_f$=0.17 (7% MeOH in CHCl$_3$), 0.36 (10% MeOH in CHCl$_3$); $^1$H NMR (250 MHz, DMSO-d$_6$, TMS) δ 8.22 (br d, J=7 Hz, NH), 8.18 (br d, J=7 Hz, NH), 8.0-7.9 (m, 2H (1 quinone-H+1 NH)), 7.9-7.7 (m, 3H (2 quinone-H+1 NH)), 7.7-7.6 (m, 1H), 7.5-7.4 (m, 2H), 7.4-7.2 (m, 8H (2 Cl—Ph—H+5 Ph—H+1 NH)), 7.20 (br s, NH), 6.78 (br s, NH), 6.60 (br d, J=7 Hz, NH), 5.1-5.0 (m, 4H), 4.50 (s, 2H), 4.4-4.3 (m, 1H), 4.3-4.1 (m, 4H), 3.7-3.6 (m, 2H), 3.6-3.5 (m, 4H), 3.3-3.2 (m, 4H), 3.0-2.9 (m, 2H), 2.8-2.6 (m, 1H), 2.5-2.4 (m, 1H), 2.1-2.0 (m, 2H), 1.9-1.4 (m, 14H), 1.46 (s, 1.5H), 1.42 (s, 1.5 H), 1.41 (s, 1.5H), 1.39 (s, 1.5H), 0.9-0.7 (m, 9H), 0.72 (d, J=5.4 Hz, 1.5H), 0.70 (d, J=5.3 Hz, 1.5H); $^{13}$C NMR (52 MHz, DMSO-d$_6$, TMS) δ 178.7, 177.8, 177.7, 173.6, 171.6, 171.5, 171.4, 171.3, 171.3, 170.8, 170.8, 159.9, 159.7, 157.3, 155.7, 138.2, 135.0, 134.5, 132.2, 131.5, 131.4, 131.0, 130.9, 129.9, 129.8, 129.5, 129.1, 128.1, 127.9, 127.8, 127.4, 127.3, 127.2, 123.8, 109.8, 109.6, 79.5, 79.3, 71.9, 69.6, 69.5, 65.8, 62.4, 54.6, 52.7, 51.7, 51.0, 50.5, 50.4, 43.9, 31.3, 31.3, 29.0, 27.8, 27.7, 24.2, 24.2, 24.1, 24.0, 22.9, 22.5, 22.5, 22.0, 21.8, 21.6, 21.4, 21.2.

Morpholino-Ser-Lys-Leu-Gln-Leu-β-Lapachone (SEQ ID NO:12) (SL-11154)

To a solution of 486.8 mg (4.057×10$^{-4}$ mol) of morpholino-Ser(OBn)-Lys(Nε-Cl-Cbz)-Leu-Gln-Leu-β-Lapachone (SEQ ID NO:11) in 9 mL of MeOH/CHCl$_3$=1:9 was added 180.5 mg 10% Pd/C. Then two drops of HCl were added. The reaction mixture was placed under an atmosphere of H$_2$ (balloon) and stirred at room temperature for 15.5 hr. Removal of catalyst by filtration and evaporation of solvent afforded a light brown solid. The material was dissolved in 12 mL of MeOH/CHCl$_{3=1:9}$, and stirred at room temperature for 1 hr while bubbling air through the solution. Evaporation of solvent afforded an orange glassy solid. Column chromatography on silica gel with 20-30% MeOH in CHCl$_3$ yielded 52.8 mg (14%) of material as an orange solid. The material was further purified by prep HPLC: R$_f$=0.06 (20% MeOH in CHCl$_3$).

Morpholino-Ser-Lys-Leu-Gln-β-Ala-β-Lapachone (SEQ ID NO:12) (SL-11147) (depicted below) is synthesized in an analogous manner to morpholino-Ser-Lys-Leu-Gln-β-Ala-β-Lapachone, except that the initial coupling of Boc-Leu to 3-hydroxy-β-lapachone (SEQ ID NO:8) is replaced with coupling of Boc-β-Ala to 3-hydroxy-β-lapachone

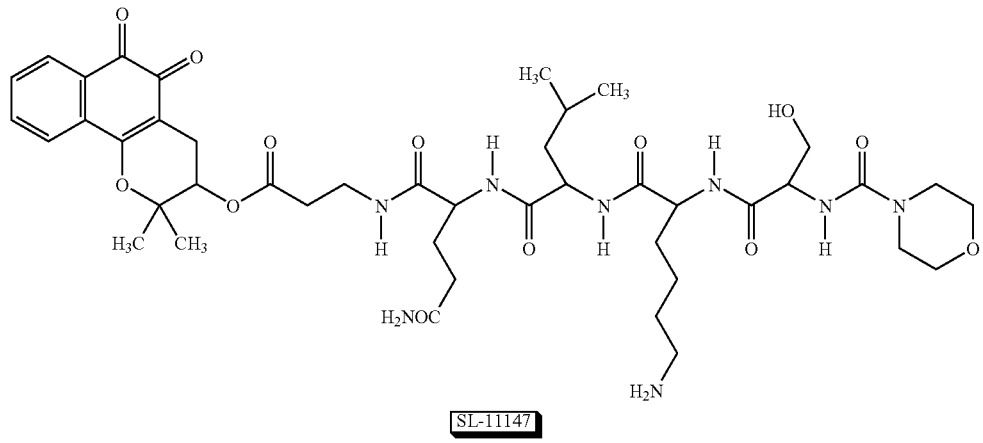

SEQ ID NO:8

Example 3

In Vitro Testing of the Efficacy of Novel Polyamine Analog Conjugates Against Tumor Cell Lines The experiments described below are designed to evaluate newly synthesized polyamine analog conjugates described above against cultured human prostate carcinoma cell lines LNCaP and PC-3 for their effects on cell growth, cell-cycle regulation and polyamine regulatory responses. Analogs conjugated to a PSA-recognized polypeptide moiety are evaluated against LNCaP cells, which are high in PSA expression, and PC-3 cells, which are deficient in PSA expression. Polyamine analog conjugates useful in the present invention demonstrate specific killing in vitro of cells expressing PSA, but not cells not expressing PSA (or a lesser extent of killing).

Model Systems and Biochemical/Cellular Assays

On the basis of the rationale built around the unique nature of polyamine metabolism in the prostate gland, these experiments focus primarily, but not exclusively, on human prostatic carcinoma, more particularly, on two variably differentiated cell lines capable of growing in culture as well as in vivo in athymic nude mice. While PC-82 and LNCaP cells are high in PSA, PC-3 cells show low PSA levels. The in vivo nude mice xenograft studies are carried out with the PC-82 cell line. Growth conditions for PC-82 cells in nude mouse xenograft are well-established. Denmeade et al. (1997). It is also noted that PC-82 cell line is one of the very few human prostate cancer cell lines that produces PSA when grown in xenograft. The LNCaP cell line is a well-differentiated prostate carcinoma originating from a primary tumor which is androgen-responsive, synthesizes polyamines and expresses characteristic prostate specific antigen. Horoszewicz et al. (1983) *Cancer Res.* 43:1809-1818. The PC-3 carcinoma originated from a bone metastasis and is poorly differentiated and prone to metastasis. Kaighn et al. (1979) *Invest. Urol.* 17:16-23. Culturing and treatment of prostatic carcinoma cell lines, cell cycle and apoptosis determinations based on flow cytometry; enzyme assays including ODC, SAMDC and SSAT activities; and high pressure liquid chromatography detection and quantitation of natural polyamines and polyamine analogs are described in the art, for example, Mi et al. (1998) *Prostate* 34:51-60; Kramer et al. (1997) *Cancer Res.* 57:5521-27; and Kramer et al. (1995) *J. Biol. Chem.* 270:2124-2132.

General Strategy for Analog Evaluation

Polyamine analogs are evaluated in human prostate carcinoma cell cultures for their effects on cell growth and polyamine-related metabolism. Analysis begins with $IC_{50}$ determinations based on dose-response curves ranging from 0.1 to 1000 µM performed at 72 hr. From these studies, conditions are defined which produce about 50% growth inhibition and used to: (a) follow time-dependence of growth inhibition for up to 6 days, with particular attention to decreases in cell number, which may indicate drug-induced cell death; (b) characterize analog effects on cell cycle progression and apoptosis using flow cytometry (analysis to be performed on attached and detached cells); (c) examine analog effects on polyamine metabolic parameters, including the biosynthetic enzymes ODC, SAMDC, the catabolic enzyme SSAT and polyamine pools themselves. Analog effects are normalized to intracellular concentrations (by HPLC analysis), which also provide an indication of their relative ability to penetrate cells. Marked differences in analog uptake are further characterized by studying analog ability to utilize and regulate the polyamine transporter, as assessed by competition studies using radiolabeled spermidine, as previously described in Mi et al. (1998).

As shown in Table 2 and FIGS. 1-32, several novel conformationally restricted polyamine analogs were tested for anti-proliferative properties against cancer cells. Table 2 illustrates the concentration in µM of the various novel polyamine analogs needed for 50% growth inhibition ($ID_{50}$) values for human cancer cell lines LNCaP, PC-3, DuPro (all three human prostate cancer cell lines), HT-29 (colon cancer cell line), A549 (lung cancer cell line), MCF7 (breast cancer cell line), and U251 MG-NCI (brain cancer cell line). FIGS. 1-32 show a representative plot of the effects of some of these novel analogs on the growth of human tumor cell lines, as determined by MTT (methyl thiazol tetrazolium) assay; known anti-proliferative polyamine analogs BE-333, BE-343, BE-444, and BE-4444 were used for, comparative purposes.

Cell Lines and Media

Human breast cancer cell line MCF7 was grown in Richter's Improved Modified Eagle's Medium supplemented with 10% fetal bovine serum (FBS) and 2.2 g/L sodium bicarbonate. Human brain tumor cell line U251 MG-NCI was grown in Dulbecco's Modified Eagle's Medium supplemented with 10% FBS. Human lung cancer cell line A549 was grown in Ham's F-12K medium (Cellgro, Mediatech, Inc., VA), supplemented with 10% FBS and 2 mM L-glutamine. Human colon cancer cell line HT29 was cultured in McCoy's 5A medium (Gibco, BRL, Gaithersburg, Md.) supplemented with 10% FBS. Human prostate cancer cell lines PC-3, LNCAP and DuPro were grown in RPMI 1640 Medium (Cellgro, Mediatech, Inc., VA) supplemented with 10% FBS. Another human prostate cancer cell line DU145 was grown in Dulbecco's Modified Eagle's Medium (Gibco, BRL, Gaithersburg, Md.) supplemented with 5% FBS. The A549, MCF7, PC3, LNCAP and DuPro cell lines were cultured in 100 units/mL penicillin and 100 μg/mL streptomycin. HT29 and U251MG cell lines were grown in 50 μg/mL gentamycin (Gibco, BRL, Gaithersburg, Md.). DU145 cell line was maintained in 1% antibitic-antimycotic solution (Sigma, St. Louis, Mo.). The cell cultures were maintained at 37° C. in 5% $CO_2$/95% humidified air. DuPro cells were obtained from M. Eileen Dolan, University of Chicago. All other cells are available from the American Type Culture Collection, Rockville, Md.

MTT Assay

A conventional MTT assay was used to evaluate percent cell survival. Exponentially growing monolayer cells were plated in 96-well plates at a density of 500 cells per well and allowed to grow for 24 hours. Serial dilutions of the drugs were added to the wells. Six days after drug treatment, 25 μl of MTT solution (5 mg/ml) was added to each well and incubated for 4 hours at 37° C. Then 100 μl of lysis buffer (20% sodium dodecyl sulfate, 50% DMF, and 0.8% acetic acid, pH 4.7) was added to each well and incubated for an additional 22 hours. A microplate reader ("EMAX"-brand, Molecular Devices, Sunnyvale, Calif.) set at 570 nm was used to determine the optical density of the cultures. Results are expressed as a ratio of the optical density in drug-treated wells to the optical density in wells treated with vehicle only.

As shown in Table 2, several polyamine analogs were tested for anti-proliferative properties against prostate cancer cells. Table 2 illustrates the concentration of the various novel polyamine analogs needed for 50% growth inhibition ($ID_{50}$) values for human prostate cancer cell lines PC-3, DU-145 and DuPro, and other tumor cell lines. FIGS. 1-32 show representative plots of the effects of some of these novel analogs on the growth of human prostate tumor cell lines. Additional data on polyamines useful in the invention is provided in Reddy et al. (1998) *J. Med. Chem.* 41:4723-32.

TABLE 2

|  | PC-3 | DU-145 | DUPRO | HT-29 | A549 | MCF7 | U251MG |
| --- | --- | --- | --- | --- | --- | --- | --- |
| BE-4444 | 0.54 | 0.07 | 0.2 | 0.8 | 0.4 | >31.25 | NT |
| SL-11029 | 24.5 | 0.32 | NT | >31.25 | >31.25 | >31.25 | >31.25 |
| SL-11090 | >31.25 | >31.25 | NT | >31.25 | >31.25 | >31.25 | >31.25 |
| SL-11091 | >31.25 | 1.33 | NT | >31.25 | >31.25 | >31.25 | >31.25 |
| SL-11092 | >31.25 | 1.7 | NT | >31.25 | >31.25 | >31.25 | >31.25 |
| SL-11093 | 14.3 | 0.01 | 0.06 | 0.40 | 0.26 | 0.66 | NT |
| SL-11094 | >31.25 | 12.6 | NT | 28.8 | >31.25 | >31.25 | >31.25 |
| SL-11098 | 1.4 | 0.018 | 0.08 | 0.40 | 0.51 | >31.25 | 0.10 |
| SL-11099 | 2.5 | 0.014 | 0.08 | 1.00 | 0.65 | 26.3 | 0.11 |
| SL-11100 | 4.7 | 0.021 | 0.29 | 2.00 | 2.20 | >31.25 | 0.22 |
| SL-11101 | 7.7 | 0.218 | 0.85 | 5.20 | 0.15 | >31.25 | 1.70 |
| SL-11102 | >31.25 | 0.027 | 0.15 | 0.73 | 12.40 | >31.25 | 0.15 |
| SL-11103 | >31.25 | 2.8 | NT | 29.4 | >31.25 | >31.25 | 9.50 |
| SL-11104 | >31.25 | 9.4 | NT | 25.8 | 0.43 | >31.25 | 14.71 |
| SL-11105 | >31.25 | 1.6 | >31.25 | 25.2 | >31.25 | >31.25 | 25.9 |
| SL-11108 | 2.2 | 0.13 | 0.98 | 2.00 | >31.25 | >31.25 | 2.00 |
| SL-11114 | 0.70 | 0.135 | 0.64 | 3.6 | >31.25 | NT | NT |
| SL-11118 | 1.65 | 0.05 | 0.25 | 0.98 | 0.21 | NT | NT |
| SL-11119 | >31.25 | 0.08 | 0.44 | 0.97 | NT | NT | NT |
| SL-11121 | 0.52 | 0.08 | 0.40 | 0.80 | >31.25 | 17.0 | NT |
| SL-11122 | >31.25 | 0.80 | 0.56 | 0.80 | >31.25 | >31.25 | NT |
| SL-11123 | >31.25 | 0.51 | >31.25 | 10.42 | >31.25 | >31.25 | NT |
| SL-11124 | >31.25 | >31.25 | >31.25 | >31.25 | >31.25 | >31.25 | NT |
| SL-11126 | 0.20 | 0.51 | 1.10 | 1.50 | >31.25 | 0.70 | NT |
| SL-11127 | >31.25 | 0.22 | 1.3 | 2.91 | NT | NT | NT |
| SL-11128 | 0.50 | 0.14 | 1.25 | 1.35 | NT | NT | NT |
| SL-11129 | 1.70 | 0.32 | NT | NT | NT | NT | NT |
| SL-11130 | >31.25 | 0.43 | NT | NT | NT | NT | NT |

NT indicates not tested.

Most of the tested compounds inhibited growth of at least one prostatic cancer cell line. From these data, we concluded that bis-ethylated polyamine analogs up to a certain degree of rigidity in the aliphatic backbone can exhibit marked cytotoxicity in several prostate tumor cell lines in culture.

As shown in FIGS. 57-59, polyamine alcohol SL-11141 and its corresponding peptide conjugate SL-11155 (see Table 1 for the structures of these two compounds) display effectiveness against tumor cell lines in vitro. This illustrates the ability of the peptide conjugates to function as effective prodrugs.

Example 4

Cell Culture and Drug Testing Protocol for Quinones

Cell Culture: The human lung adenocarcinoma cell line, A549, and human prostatic cancer cell line, DUPRO, were a gift from Dr. M. Eileen Dolan, University of Chicago, Department of Medicine. A549 was grown in Ham's F-12K medium (Fisher Scientific, Itasca, Ill.) supplemented with 10% fetal bovine serum and 2 mM L-glutamine. DUPRO was grown in RPMI-1640 supplemented with 10% fetal bovine serum. The human colon carcinoma cell line, HT29, and the human breast carcinoma cell line, MCF7, were obtained from the American Type Culture Collection, Rockville, Md. HT29 cells were grown in McCoy's 5A medium (Gibco, BRL, Gaithersburg, Md.) supplemented with 10% fetal bovine serum. MCF7 cells were grown in Richter's Improved Modified Eagle's medium supplemented with 10% fetal bovine serum and 2.2 g/L sodium bicarbonate. The human prostate adenocarcinoma cell lines, LNCAP, PC-3 and DU145, were gifts from Dr. George Wilding, University of Wisconsin Comprehensive Cancer Center and the Department of Medicine, and were grown in Dulbecco's Modified Eagle's medium supplemented with a 5% fetal bovine serum. The malignant glioma cell line, U251MG NCI was obtained from the brain tumor tissue bank at the University of California, San Francisco Department of Neurosurgery, and was grown in Dulbecco's Modified Eagle's medium supplemented wth 10% fetal bovine serum. DUPRO, A549 and MCF7 cells were grown in 100 units/mL penicillin and 100 µg/mL streptomycin. HT29 and U251MG NCI cells were grown in 50 µg/mL gentamycin. LNCAP, PC-3 and DU145 cells were maintained in 1% antibiotic antimycotic solution (Sigma, St. Louis, Mo.). All cell cultures were maintained at 37° C. in 5% $CO_2$/95% humidified air.

MTT assay. Exponentially growing monolayer cells were plated in 96 well plates at a density of 500 cells/well and allowed to grow for 24 h. Serially diluted drug solutions were added such that the final drug concentrations in the treatment media were between 0 and 35 µM. Cells were incubated with drug at either 4 hr or 72 hr. After 4 hr and 72 hr treatment, drugs were removed, fresh media (without) drug (100 uL) was added and cells were incubated for 6 days. After six days, 25 µL of a Dulbecco's phosphate-buffered saline solution containing 5 mg/mL of MTT (Thiazolyl blue) (Sigma) was added to each well and incubated for 4 h at 37° C. Then 100 µL of lysis buffer (20% sodium dodecyl sulfate, 50% N,N-dimethylformamide and 0.8% acetic acid, pH 4.7) was added to each well and incubated for an additional 22 h. A microplate reader (E max, Molecular Devices, Sunnyvale, Calif.) set at 570 nm was used to determine the optical density. Results were plotted as a ratio of the optical density in drug treated wells to the optical density in wells treated with vehicle alone. Plotting and estimation of $ID_{50}$ values were accomplished with manufacturer supplied software. The data is presented below in Tables 3, 4, 5 and 6.

TABLE 3
ID$_{50}$ (μM) Values of Quinones in Various Cultured Human Prostate Tumor Cell Lines Determined by the MTT Assay
| Quinones | Structures of Quinones | ID$_{50}$ (μM) of different prostate cells | | |
|---|---|---|---|---|
| | | PC-3 | DUPRO | DU145 LNCAP |
| SL-11051 | 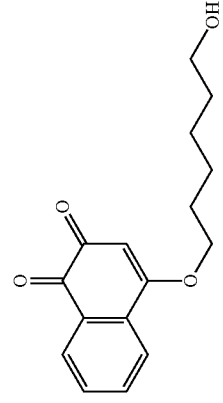 | 17.11 | 19.3 | 11.16 |
| SL-11059 | 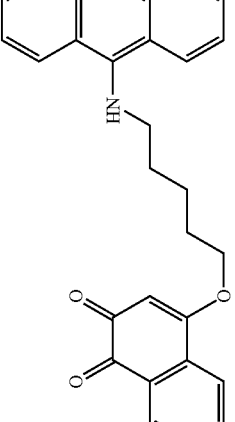 | 4.3 | | |
| SL-11062 | 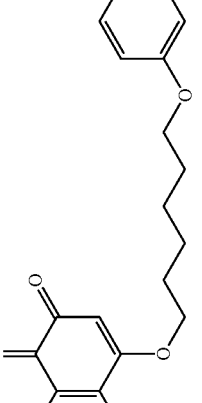 | 1.71 | | |

TABLE 3-continued
ID$_{50}$ (μM) Values of Quinones in Various Cultured Human Prostate Tumor Cell Lines Determined by the MTT Assay
| Quinones | Structures of Quinones | ID$_{50}$ (μM) of different prostate cells | | |
|---|---|---|---|---|
| | | PC-3 | DUPRO | DU145 LNCAP |
| SL-11064 | 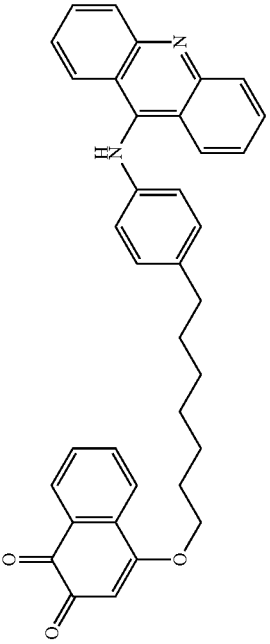 | 0.7 | 2.2 | 0.13 |
| SL-11065 | 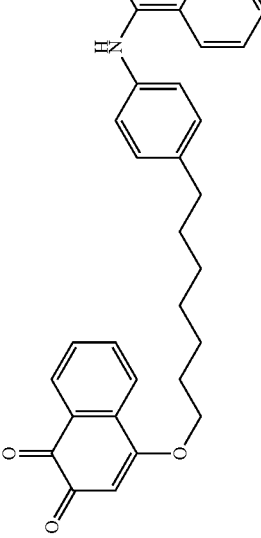 | 1.4 | | |
| SL-11066 | 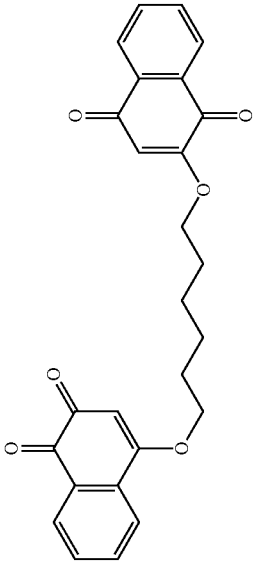 | >31.25 | | |

TABLE 3-continued

ID$_{50}$ (μM) Values of Quinones in Various Cultured Human Prostate Tumor Cell Lines Determined by the MTT Assay

| Quinones | Structures of Quinones | ID$_{50}$ (μM) of different prostate cells | | |
|---|---|---|---|---|
| | | PC-3 | DUPRO DU145 | LNCAP |
| SL-11067 | | 0.25 | | |
| SL-11068 | | 1.5 | | |
| SL-11074 | | 4.6 | | |

TABLE 3-continued
ID$_{50}$ (μM) Values of Quinones in Various Cultured Human Prostate Tumor Cell Lines Determined by the MTT Assay
| Quinones | Structures of Quinones | ID$_{50}$ (μM) of different prostate cells | | |
|---|---|---|---|---|
| | | PC-3 | DUPRO DU145 | LNCAP |
| SL-11075 | 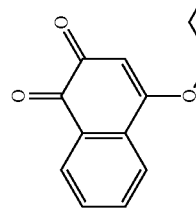 | 2.0 | | |
| SL-11076 | 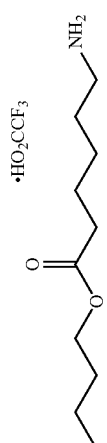 | 1.8 | | |
| SL-11078 | 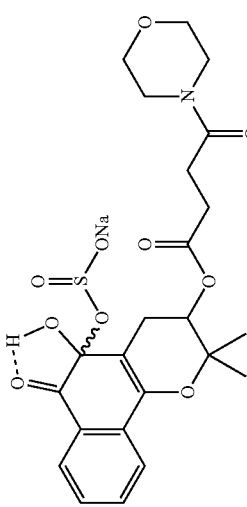 | 18.4 | | |
| SL-11079 | 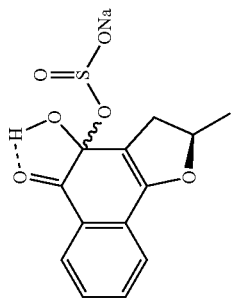 | 22.5 | | |

TABLE 3-continued

ID$_{50}$ (μM) Values of Quinones in Various Cultured Human Prostate Tumor Cell Lines Determined by the MTT Assay

| Quinones | Structures of Quinones | ID$_{50}$ (μM) of different prostate cells | | |
|---|---|---|---|---|
| | | PC-3 | DUPRO DU145 | LNCAP |
| SL-11080 | | 7.3 | | |
| SL-11081 | | 5.6 | | |
| SL-11082 | | 5.4 | | |

TABLE 3-continued

ID$_{50}$ (μM) Values of Quinones in Various Cultured Human Prostate Tumor Cell Lines Determined by the MTT Assay

| Quinones | Structures of Quinones | ID$_{50}$ (μM) of different prostate cells | | |
|---|---|---|---|---|
| | | PC-3 | DUPRO DU145 | LNCAP |
| SL-11083 | | 5.2 | | |
| SL-11084 | | 5.9 | | |
| SL-11085 | | >31.25 | | |

TABLE 3-continued

ID$_{50}$ (μM) Values of Quinones in Various Cultured Human Prostate Tumor Cell Lines Determined by the MTT Assay

| Quinones | Structures of Quinones | ID$_{50}$ (μM) of different prostate cells | | |
| --- | --- | --- | --- | --- |
| | | PC-3 | DUPRO DU145 | LNCAP |
| SL-11087 | | 2.4 | | |
| SL-11088 | | >31.25 | | |
| SL-11089 | | 11.03 | | |

TABLE 3-continued

ID$_{50}$ (μM) Values of Quinones in Various Cultured Human Prostate Tumor Cell Lines Determined by the MTT Assay

| Quinones | Structures of Quinones | ID$_{50}$ (μM) of different prostate cells | | |
|---|---|---|---|---|
| | | PC-3 | DUPRO DU145 | LNCAP |
| SL-11095 | | 4.2 | | |
| SL-11096 | | 3.6 | | |
| SL-11106 | | >31.25 | | |

TABLE 3-continued

ID$_{50}$ (μM) Values of Quinones in Various Cultured Human Prostate Tumor Cell Lines Determined by the MTT Assay

| Quinones | Structures of Quinones | ID$_{50}$ (μM) of different prostate cells | | |
|---|---|---|---|---|
| | | PC-3 | DUPRO | DU145 | LNCAP |
| SL-11107 | | 4.3 | >31.25 | 17.2 | |
| SL-11112 | | >31.25 | 27.9 > 31. | 22.9 | |
| SL-11113 | | 27.9 | >31.25 | 29.2 | |

TABLE 3-continued
ID$_{50}$ (μM) Values of Quinones in Various Cultured Human Prostate Tumor Cell Lines Determined by the MTT Assay
| Quinones | Structures of Quinones | ID$_{50}$ (μM) of different prostate cells | | |
|---|---|---|---|---|
| | | PC-3 | DUPRO | DU145 LNCAP |
| SL-11120 | 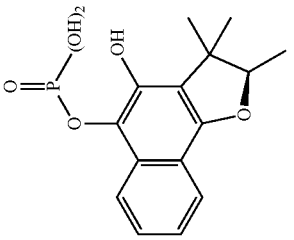 | 6.4 | 13.1 | 3.8 |
| SL-11125 | 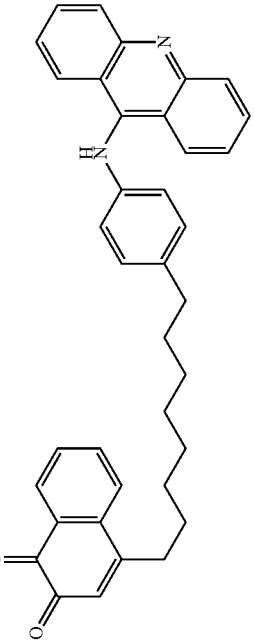 | 5.9 | 7.9 | 0.13 |

TABLE 3-continued

ID$_{50}$ (μM) Values of Quinones in Various Cultured Human Prostate Tumor Cell Lines Determined by the MTT Assay

| Quinones | Structures of Quinones | ID$_{50}$ (μM) of different prostate cells | | |
|---|---|---|---|---|
| | | PC-3 | DUPRO | DU145 | LNCAP |
| SL-11145 | (structure shown) | 1.97 (4 hr)<br>0.51 (6 days) | | 0.7 (4 hr)<br>0.8 (6 days) | |
| SL-11147<br>SEQ ID<br>NO:8 | (structure shown) | 6.3 (4 hr)<br>1.24 (72 hr) | | | 28.08 (4 hr)<br>2.01 (72 hr) |

TABLE 3-continued
ID$_{50}$ (µM) Values of Quinones in Various Cultured Human Prostate Tumor Cell Lines Determined by the MTT Assay
| | | ID$_{50}$ (µM) of different prostate cells | | |
| --- | --- | --- | --- | --- |
| Quinones | Structures of Quinones | PC-3 | DUPRO DU145 | LNCAP |
| SL-11148 | 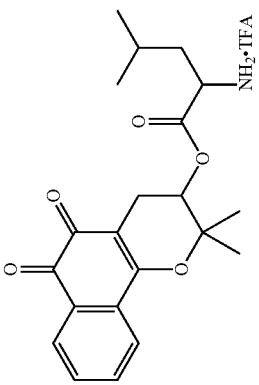 | 6.3 | | 1.84 |

TABLE 4

ID$_{50}$ (µM) Values of Quinones in Various Cultured Human Tumor Cell Lines Determined by the MTT Assay

| Quinones | Structures of Quinones | ID$_{50}$ (µM) of different Tumor cells | | | |
|---|---|---|---|---|---|
| | | Lung A549 | Colon HT-29 | Breast MCF7 | Brain U251-MG |
| SL-11051 | | 17.23 | 20.02 | | |
| SL-11052 | | 26.88 | | | |
| SL-11053 | | 7.39 | 2.8 | | |
| SL-11054 | | >31.25 | >31.25 | | |

TABLE 4-continued
ID$_{50}$ (μM) Values of Quinones in Various Cultured Human Tumor Cell Lines Determined by the MTT Assay
| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11056 |  $X = $ , $n = 4$ | >31.25 | >31.25 | >31.25 | >31.25 |
| SL-11059 | 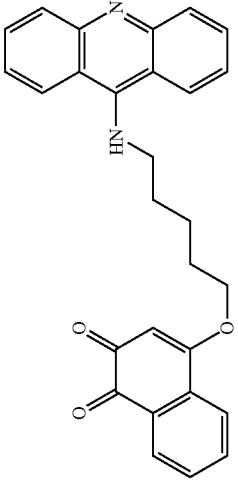 | 15.0 | 10.12 | | |
| SL-11060 | 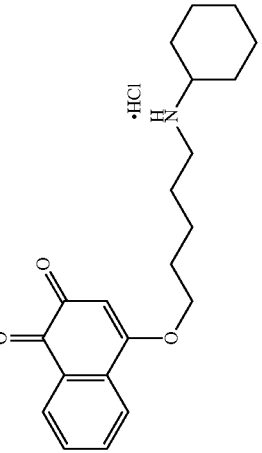 | >31.25 | >31.25 | 17.23 | >31.25 |

TABLE 4-continued

ID$_{50}$ (μM) Values of Quinones in Various Cultured Human Tumor Cell Lines Determined by the MTT Assay

| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11062 | | 18.64 | | | |
| SL-11064 | | 9.3 | | | |
| SL-11065 | | 2.13 | | | |

TABLE 4-continued

ID$_{50}$ (μM) Values of Quinones in Various Cultured Human Tumor Cell Lines Determined by the MTT Assay

| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11066 | | >31.25 | | | |
| SL-11067 | | >31.25 | 0.53 | | |
| SL-11068 | | 24.0 | | | |

TABLE 4-continued
ID$_{50}$ (μM) Values of Quinones in Various Cultured Human Tumor Cell Lines Determined by the MTT Assay
| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11074 | 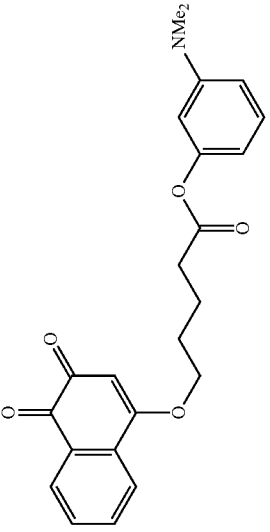 | | | | |
| SL-11075 | 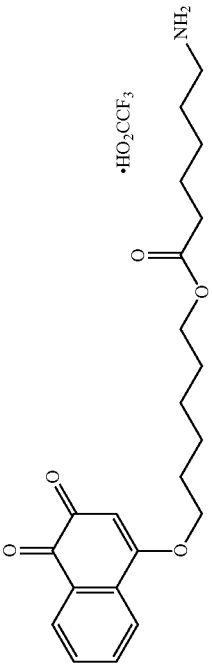 | 1.8 | 1.7 | | 10.24 |
| SL-11076 | 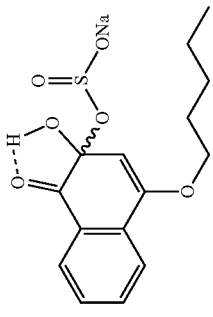 | | | | |

TABLE 4-continued

ID$_{50}$ (μM) Values of Quinones in Various Cultured Human Tumor Cell Lines Determined by the MTT Assay

| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11078 | | 18.9 | 19.3 | 30.85 | |
| SL-11079 | | | | | |
| SL-11080 | | | | | |

TABLE 4-continued

ID$_{50}$ (μM) Values of Quinones in Various Cultured Human Tumor Cell Lines Determined by the MTT Assay

| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11081 | | | | | |
| SL-11082 | | | | | |
| SL-11083 | | | | | |

TABLE 4-continued

ID$_{50}$ (μM) Values of Quinones in Various Cultured Human Tumor Cell Lines Determined by the MTT Assay

| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11084 | | | | | |
| SL-11085 | | | | | |
| SL-11087 | | 19.8 | 6.05 | 4.0 | |

TABLE 4-continued
ID$_{50}$ (μM) Values of Quinones in Various Cultured Human Tumor Cell Lines Determined by the MTT Assay
| Quinones | Structures of Quinones | ID$_{50}$ (μM) of different Tumor cells | | | |
| --- | --- | --- | --- | --- | --- |
| | | Lung A549 | Colon HT-29 | Breast MCF7 | Brain U251-MG |
| SL-11088 | 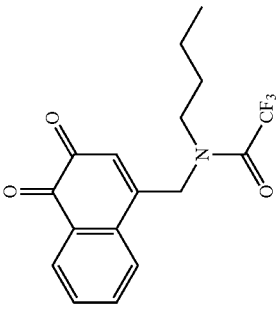 | >31.25 | >31.25 | >31.25 | |
| SL-11089 | 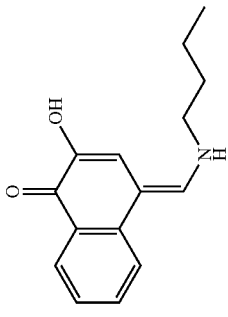 | | | >31.25 | |
| SL-11095 | 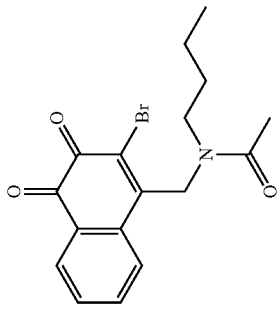 | >31.25 | 22.1 | 20.6 | |

TABLE 4-continued

ID$_{50}$ (µM) Values of Quinones in Various Cultured Human Tumor Cell Lines Determined by the MTT Assay

| Quinones | Structures of Quinones | ID$_{50}$ (µM) of different Tumor cells | | | |
|---|---|---|---|---|---|
| | | Lung A549 | Colon HT-29 | Breast MCF7 | Brain U251-MG |
| SL-11096 | | 17.4 | 3.4 | 3.8 | |
| SL-11106 | | >31.25 | | | |
| SL-11107 | | >31.25 | | | |

TABLE 4-continued

ID$_{50}$ (μM) Values of Quinones in Various Cultured Human Tumor Cell Lines Determined by the MTT Assay

| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11112 | | | | | |
| SL-11113 | | | | | |
| SL-11120 | | 26.7 | 20.9 | 4.1 | |

TABLE 4-continued
ID$_{50}$ (μM) Values of Quinones in Various Cultured Human Tumor Cell Lines Determined by the MTT Assay
| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11125 | 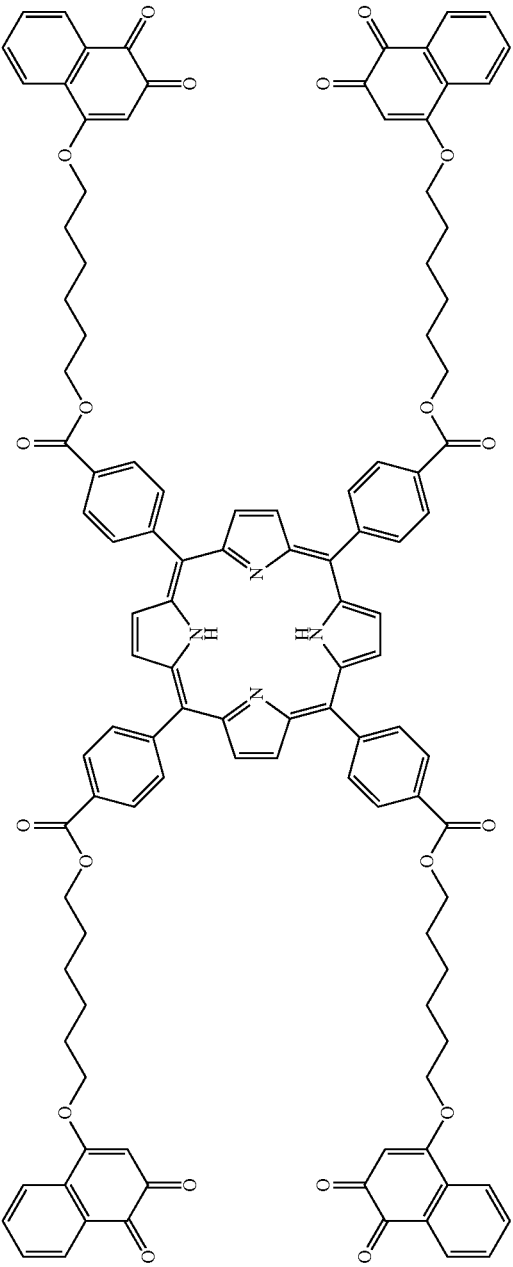 | 27.97 | 5.7 | 5.1 | |
| SL-11145 | 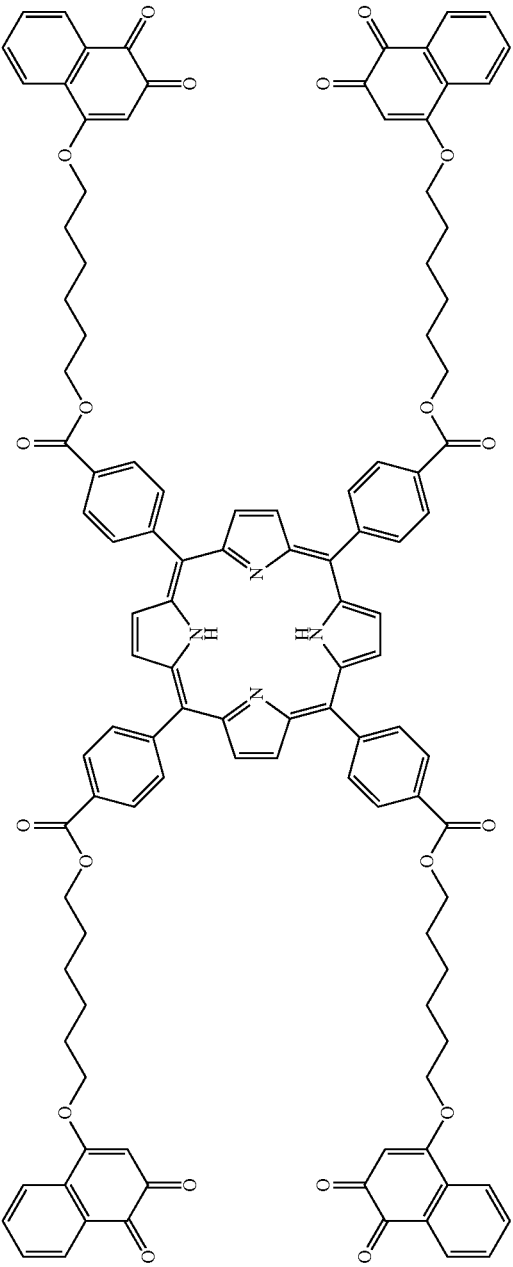 | 2.4 (4hr) 1.0 (6 days) | | | |

TABLE 4-continued
ID$_{50}$ (μM) Values of Quinones in Various Cultured Human Tumor Cell Lines Determined by the MTT Assay
| Quinones | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11147 SEQ ID NO:8 | 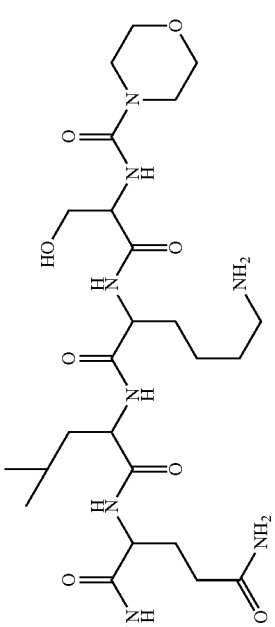 | | | | |
| SL-11148 | 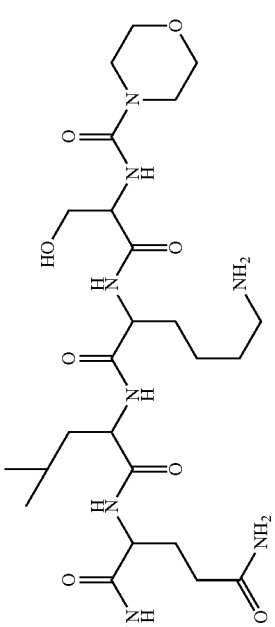 | | | | |

TABLE 5

ID₅₀ (μM) Value(s) of Non-Quinone Structure in A Cultured Human Prostate Tumor Cell Line Determined by the MTT Assay

| | | $ID_{50}$ (μM) of different prostate cells | | | |
|---|---|---|---|---|---|
| Designation | Structures of Compound | PC-3 | DUPRO | DU145 | LNCAP |
| SL-11063 | [structure] | >31.25 | | | |

TABLE 6

ID₅₀ (μM) Values of Selected Non-Quinone Compounds in Various Cultured Humans Tumor Cell Lines Determined by the MTT Assay

| | | $ID_{50}$ (μM) of different Tumor Cells | | | |
|---|---|---|---|---|---|
| Designation | Structures of Non-Quinone Compounds | Lung A549 | Colon HT-29 | Breast MCF7 | Brain U251-MG |
| SL-11055 | [structure] | >31.25 | >31.25 | >31.25 | >31.25 |
| SL-11058 | [structure] | | | | >31.25 |
| SL-11063 | [structure] | | >31.25 | | |

Example 5

In Vivo Testing of Anti-tumor Activity of Polyamine Analog Conjugates

Strategy and Interpretation of Data for Polyamine Analog-PSA Peptide Conjugates

In evaluating polyamine analog conjugates, their in vitro anti-proliferative activity against LNCAP cells, which express PSA, relative to PC-3, which do not, is determined. The cell line PC-82 expresses even higher PSA levels, but does not grow in vitro and is therefore used only for in vivo analysis. Those conjugates demonstrating differential anti-proliferative activity (based on IC₅₀ determinations) toward LNCaP cells, can be chosen for further development.

Analog conjugates found to have potent or mechanism-based anti-proliferative activity in vitro towards cultured prostatic carcinoma cells are evaluated in in vivo model systems, namely LNCaP and PC-82 prostate carcinoma xenografts, both of which express PSA. Because the conjugate could be rapidly cleared from the circulation, it may be necessary to intensify the treatment schedule to two or three times daily. In addition to assessing anti-tumor activity, as described above, free analog levels in tumor and normal tissues are determined. In the event that meaningful anti-tumor activity is observed, these same conjugates are used to treat PC-3 prostate carcinoma xenografts, which do not express PSA. These experiments are designed to confirm the specificity of drug action, since it is expected that the activity against such tumors which do not express PSA, such as PC-3, will be markedly diminished. As above, these studies are augmented by determinations of free analog levels in tumor.

The first goal is to determine the relative toxicity of the analogs in non-tumor-bearing DBA/2 mice. Groups of three animals each are injected intraperitoneally with increasing concentrations of an analog, beginning at 10 mg/kg. Toxicity as indicated by morbidity is closely monitored over the first 24 hr. The polyamine analog, BE-333 is used as an internal standard in these studies, since a data base has already been established regarding acute toxicity via a single dose treatment relative to chronic toxicity via a daily×5 d schedule. Thus, in the case of new analogs, single dose toxicity relative to BE-333 is used to project the range of doses to be used on a daily×5 d schedule.

After the highest tolerated dosage on a daily×5 d schedule is deduced, antitumor activity is determined. Typically, PC-3 tumors are subcutaneously implanted into nude athymic mice by trocar and allowed to reach 100-200 mm$^3$ before initiating treatment by intraperitoneal injection daily×5 d. The LNCaP tumor requires suspension in Matrigel (Microbiological Assoc.) prior to implantation, after which it grows at approximately a 4-day doubling time. Most conjugates are given in a range between 10 and 200 mg/kg. Conjugates are evaluated at three treatment dosages with 10-15 animals per group (a minimum of three from each are used for pharmacodynamic studies, described below). Mice are monitored and weighed twice weekly to determine tumor size and toxicity. Tumor size is determined by multi-directional measurement from which volume in mm$^3$ is calculated. Tumors are followed until median tumor volume of each group reaches 1500 mm$^3$ (i.e., 20% of body weight), at which time the animals are sacrificed. Although the initial anti-tumor studies focuses on a daily×5 d schedule, constant infusion can be performed via Alzet pump delivery for 5 days since this schedule dramatically improves the anti-tumor activity of BE-333 against A549 human large cell hung carcinoma. Sharma et al. (1997) *Clin. Cancer Res.* 3:1239-1244.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of the formula:

and all pharmaceutically-suitable salts and stereoisomers thereof.

2. A composition of matter comprising a compound of claim 1 and a pharmaceutically acceptable excipient.

3. A compound of the formula:

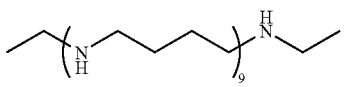

and all pharmaceutically-suitable salts thereof.

4. A composition of matter comprising a compound of claim 3 and a pharmaceutically acceptable excipient.

5. A compound of the formula:

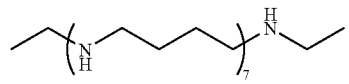

and all pharmaceutically-suitable salts thereof.

6. A composition of matter comprising a compound of claim 5 and a pharmaceutically acceptable excipient.

* * * * *